US007939546B2

(12) United States Patent
Phiasivongsa et al.

(10) Patent No.: US 7,939,546 B2
(45) Date of Patent: May 10, 2011

(54) QUINOLINE DERIVATIVES FOR MODULATING DNA METHYLATION

(75) Inventors: Pasit Phiasivongsa, Brentwood, CA (US); Sanjeev G. Redkar, Hayward, CA (US); Swarna Gamage, Mt Roskill (NZ); Darby Brooke, Waterview (NZ); William Denny, Pakuranga (NZ); David J. Bearss, Cedar Hills, UT (US); Hariprasad Vankayalapati, Draper, UT (US); Yong Xu, Midvale, UT (US); Krzysztof Swierczek, West Jordan, UT (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 12/422,067

(22) Filed: Apr. 10, 2009

(65) Prior Publication Data
US 2009/0285772 A1 Nov. 19, 2009

Related U.S. Application Data

(63) Continuation-in-part of application No. 11/959,181, filed on Dec. 18, 2007, now Pat. No. 7,790,746, which is a continuation-in-part of application No. 11/871,762, filed on Oct. 12, 2007, now abandoned.

(51) Int. Cl.
*A61K 31/47* (2006.01)
(52) U.S. Cl. ......... 514/313; 546/161; 546/242; 548/541
(58) Field of Classification Search .................. 514/313; 546/161, 242; 548/541
See application file for complete search history.

(56) References Cited

U.S. PATENT DOCUMENTS
2009/0099106 A1  4/2009 Phiasivongsa et al.

FOREIGN PATENT DOCUMENTS
WO  WO 2005/118572 A1  12/2005
WO  WO2008046085 A2  4/2008

OTHER PUBLICATIONS

Atwell and Cain, "Potential Antitumor Agents. 13. Bisquaternary Salts," J Med Chem 16(6):673-678, 1973.
Carducci et al., "Phenylbutyrate (PB) for Refractory Solid Tumors: Phase I Clinical and Pharmacologic Evaluation of Intravenous and Oral PB," Anticancer Research 17:3972-3973, 1997.
Chuang et al., "Comparison of biological effects of non-nucleoside DNA methylation inhibitors versus 5-aza-2'-deoxycytidine," Mol Cancer Ther 4(10):1515-1520, Oct. 2005.
Darkin-Rattray et al., "Apicidin: A novel antiprotozoal agent that inhibits parasite histone deacetylase," Proc Natl Acad Sci USA 93:13143-13147, Nov. 1996.
Denny et al., "Potential Antitumor Agents. 29. Quantitative Structure-Activity Relationships for the Antileukemic Bisquatemary Ammonium Heterocycles," J Med Chem 22(2):134-150, 1979.
Egger et al., "Epigenetics in human disease and prospects for epigenetic therapy," Nature 429:457-463, May 27, 2004.
Glick et al., "Hybrid Polar Histone Deacetylase Inhibitor Induces Apoptosis and CD95/CD95 Ligand Expression in Human Neuroblastoma," Cancer Research 59:4392-4399, Sep. 1, 1999.
Godert et al., "An improved synthesis of psammaplin A," Bioorganic & Medicinal Chemistry Letters 16:3330-3333, 2006.
Kijima et al., "Trapoxin, an Antitumor Cyclic Tetrapeptide, Is an Irreversible Inhibitor of Mammalian Histone Deacetylase," J Biol Chem 268(30):22429-22435, Oct. 25, 1993.
Kwon et al., "Depudecin induces morphological reversion of transformed fibroblasts via the inhibition of histone deacetylase," Proc Natl Acad Sci USA 95:3356-3361, Mar. 1998.
Leone et al., "Inhibitors of DNA methylation in the treatment of hematological malignancies and MDS," Clinical Immunology 109:89-102, 2003.
Leupin et al., "NMR Studies of the Complex between the Decadeoxynucleotide d-(GCATTAATGC)2 and a Minor-Groove-Binding Drug," Biochemistry 25(20):5902-5910, 1986.
Newmark et al., "Butyrate as a differentiating agent: pharmacokinetics, analogues and current status," Cancer Letters 78:1-5, 1994.
Piña et al., "Psammaplins from the Sponge Pseudoceratina purpurea: Inhibition of Both Histone Deacetylase and DNA Methyltransferase," J Org Chem 68(10):3866-3873, 2003.
Plowman and Adamson, "Initial Studies on the Disposition of Quinolinium Dibromide (NSC-176319) in Mice and Rats," Pharmacology 17:61-68, 1978.
Saito et al., "A synthetic inhibitor of histone deacetylase, MS-27-275, with marked in vivo antitumor activity against human tumors," Proc Natl Acad Sci USA 96:4592-4597, Apr. 1999.
Squire et al., "Minor groove binding of a bis-quaternary ammonium compound: the crystal structure of SN 7167 bound to d(CGCGAAT-TCGCG)2," Nucleic Acids Research 25(20):4072-4078, 1997.
Tsuji et al., "A New Antifungal Antibiotic, Trichostatin," J Antibiotics 29(1):1-6, Jan. 1976.
Yoshida et al., "Potent and Specific Inhibition of Mammalian Histone Deacetylase Both in Vivo and in Vitro by Trichostatin A," J Biol Chem 265(28):17174-17179, Oct. 5, 1990.
Zhou et al., "Zebularine: A Novel DNA Methylation Inhibitor that Forms a Covalent Complex with DNA Methyltransferases," J Mol Biol 321:591-599, 2002.

*Primary Examiner* — James O Wilson
*Assistant Examiner* — Douglas M Willis
(74) *Attorney, Agent, or Firm* — Seed IP Law Group PLLC

(57) ABSTRACT

Quinoline derivatives, particularly 4-(4-(4-(quinolin-4-ylamino)benzamido)phenylthio)pyrrolidine-2-carboxylic acid; 3-(4-(4-(quinolin-4-ylamino)benzamido)phenylthio) pyrrolidine; N-(4-(piperidin-4-ylthio)phenyl)-4-(quinolin-4-ylamino)-benzamide; and N-(4-(piperidin-3-ylthio)phenyl)-4-(quinolin-4-ylamino)-benzamide, or a physiologically acceptable salt thereof, are provided. Such quinoline derivatives can be used for modulation of DNA methylation, such as effective inhibition of methylation of cytosine at the C-5 position, for example via selective inhibition of DNA methyltransferase DNMT1. Methods for synthesizing numerous 4-anilinoquinoline derivatives and for modulating DNA methylation are provided. Also provided are methods for formulating and administering these compounds or compositions to treat conditions such as cancer and hematological disorders.

17 Claims, 1 Drawing Sheet

QUINOLINE DERIVATIVES FOR MODULATING DNA METHYLATION

CROSS-REFERENCE TO RELATED APPLICATION

This application is a continuation-in-part of U.S. application Ser. No. 11/959,181, filed Dec. 18, 2007, which is a continuation-in-part of U.S. application Ser. No. 11/871,762 filed Oct. 12, 2007, both of which applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 670095_420C2_SEQUENCE_LISTING.txt. The text file is 4 KB, was created on Jul. 1, 2009, and is being submitted electronically via EFS-Web.

BACKGROUND

1. Technical Field

The present invention relates to compounds, compositions, formulations, kits, methods of use, and manufacture of quinoline derivatives, and more particularly to 4-anilinoquinoline derivatives as inhibitors of DNA methylation enzymes, modulators of DNA methylation and therapeutic agents for preventing or treating diseases associated with aberrant DNA methylation such as cancer and hematological malignancy.

2. Description of the Related Art

Methylation at the C-5 position of cytosine residues in 5'-m$^5$CpG-3' sequences plays a major role in gene expression by the silencing of genes (Smith, A. F. A. *Curr. Opin. Genet. Devel.*, 1999, 9, 657). The major enzyme responsible for the maintenance of these methylation patterns during replication is the DNA methyltransferase DNMT1 (Siedlecki et al., *Biochem .Biophys. Res. Comm.*, 2003, 306, 558). DNA methylation is the cause of a number of inherited disease syndromes, and can also have a major role in the development of human cancer. It is the most frequent molecular change in hematopoietic neoplasms (Egger et al., *Nature*, 2004, 429, 457), and is likely involved in other tumor types; for example, a percentage of patients with sporadic colorectal cancers show methylation and silencing of the gene encoding MLH1 (Kane et al., *Cancer Res.*, 1997, 57, 808).

The most widely-explored inhibitors of DNMT1 are suicide inhibitors such as azacitidine (Vidaza®) and decitabine (Dacogen®), antimetabolites that incorporate into DNA in place of cytosine, and irreversibly trap the enzyme (Egger et al., *Nature*, 2004, 429, 457; Zhou et al., *J. Mol. Biol.*, 2002, 321, 599). Both compounds are now used clinically for the treatment of myelodysplastic syndromes and lymphoproliferative diseases, but do possess considerable toxicity (Leone et al., *Clin. Immunol.*, 2003, 109, 89). Presumably this is due to incorporation of 5-azacytidine into the DNA. Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting the carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine (Juttermann et al., *Proc. Natl. Acad. Sci. USA*, 1994, 91, 11797). By specifically inhibiting DNMT1, the enzyme required for maintenance methylation, the aberrant methylation of the tumor suppressor genes can be prevented.

Only a few other small-molecule inhibitors of DNA methylation have been described, including the psammaplin sponge metabolites (Piña et al., *J. Org. Chem.*, 2003, 68, 3866), which are potent direct inhibitors of DNA methyltransferases but are less effective in cellular assays (Godert et al., *Bioorg. Med. Chem. Lett.*, 2006, 16, 3330). Other non-nucleoside demethylating agents such as (−)-epigallocatechin-3-gallate, hydralazine, and procainamide were also shown to be far less effective in reactivating genes than decitabine (Chuang et al., *Mol. Cancer. Ther.*, 2005, 4, 1515).

Thus, there still exists a need to develop effective modulators of DNA methylation which can be used in the prevention or treatment of diseases associated with aberrant DNA methylation such as cancer and hematological malignancy.

BRIEF SUMMARY

In one aspect, the present invention provides a compound of formula (I), or a physiologically acceptable salt or a phosphate prodrug, or a carboxylic acid or aminoacid ester prodrug thereof,

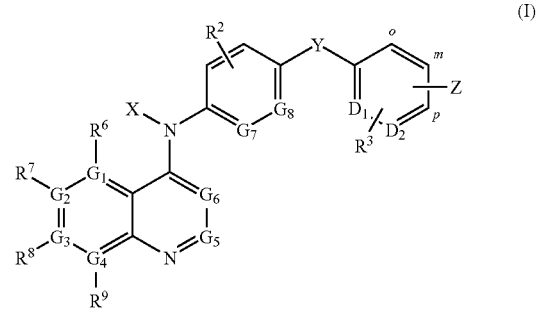

(I)

wherein $G_1$, $G_2$, $G_3$, and $G_4$ are each independently C, N, or N+ (where an $R^6$-$R^9$ is attached to N); $G_5$ and $G_6$ are each independently CH or N; $G_7$ and $G_8$ are each independently CH, C (where an $R^2$ is attached to C), N, or N+ (where an $R^2$ is attached to N), $D_1$ and $D_2$ are each separately CH, C (where $R^3$ attached to C), N, or N+ (where an $R^3$ is attached to N).

$R^6$, $R^7$, $R^8$, and $R^9$ are each separately H, halogen, $CF_3$, $OCF_3$, CN, $CONHR^4$, $CONR^4R^5$, $SO_2Me$, $SO_2NHR^4$, $SO_2NR^4R^5$, $NHCOR^4$, $NHR^4$, $NR^4R^5$, $OR^4$, $NO_2$, or $CH_2R^4$, wherein $R^4$ and $R^5$ are each independently H, lower $C_1$-$C_6$ alkyl or cycloalkyl optionally substituted with amino, hydroxyl, methoxy, —CN, —COOH or $SO_2NH_2$ groups, or with one or more oxygen, sulfur or nitrogen atoms as part of the cycloalkyl structure which may represent morpholine, pyrrolidine, piperidine, pyrrolidine, thiomorpholine, imidazole or 4-methylpiperazine, or may be substitution of a —CH= ring carbon by —N=, $R^2$ and $R^3$ are each independently H, $NHR^4$, $NR^4R^5$, $OR^4$, $NO_2$ or $CH_2R^4$, wherein $R^4$ and $R^5$ are defined as above, X may be H or $C_1$-$C_6$ alkyl optionally substituted with amino, hydroxyl or methoxy groups, or with one or more oxygen or nitrogen atoms as part of a cycloalkyl structure which may represent azetidine, pyrrolidine, piperidine, piperazine, or morpholine;

Y may be CONR$^4$, NR$^4$CO, O, S(O)$_n$ [n=0 to 2], (CH$_2$)$_k$ [k=1 to 6], —CH=CH—, NR$^4$, or a direct link between the two aromatic rings (i.e., a C—C bond between the two aromatic rings), wherein R$^4$ and R$^5$ are defined as above;

o, m and p represent positions of attachment of the moiety Z;

Z may be one of the groups Q1-Q43 represented in formula (II);

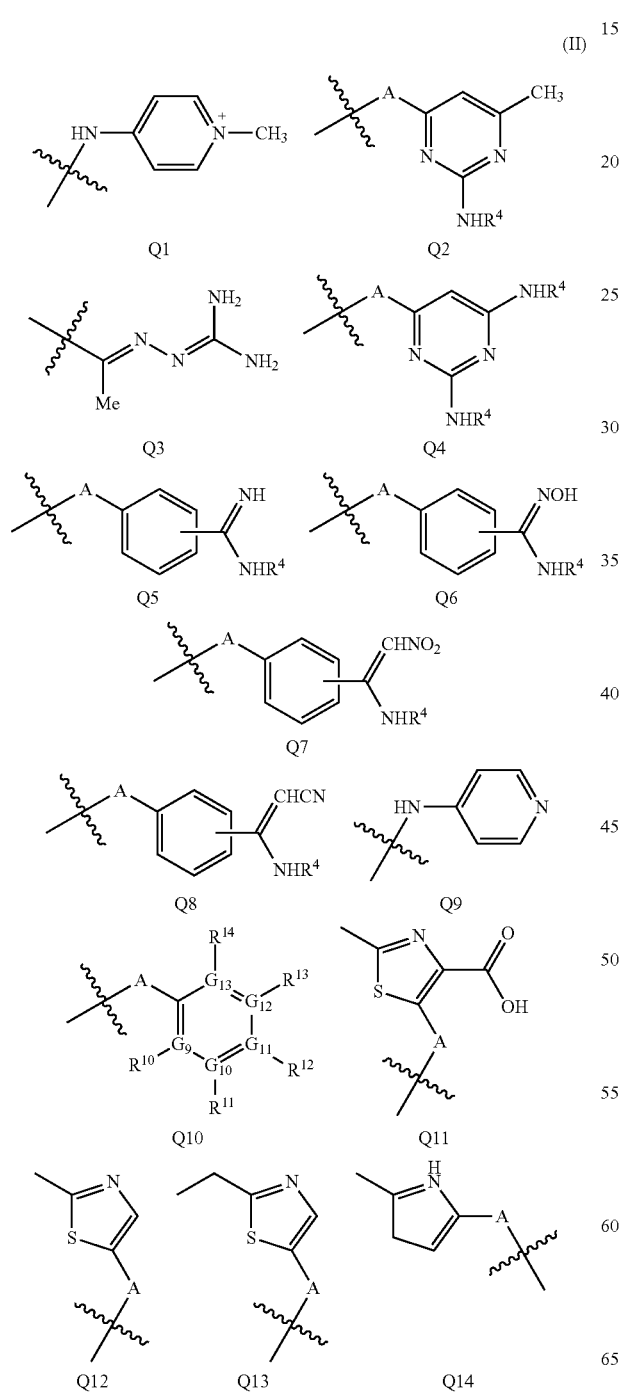

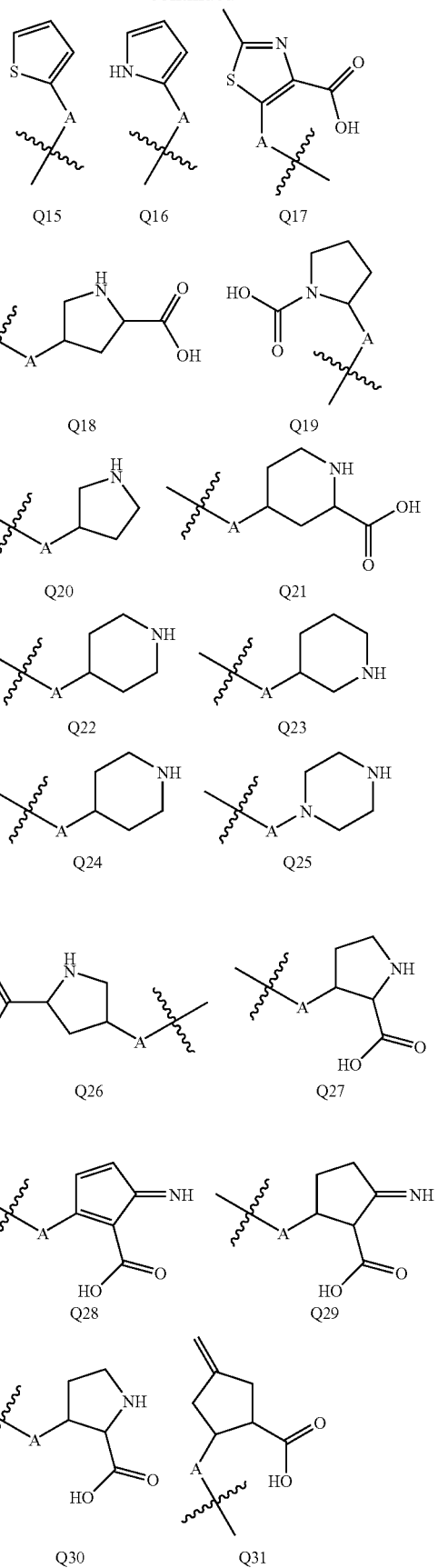

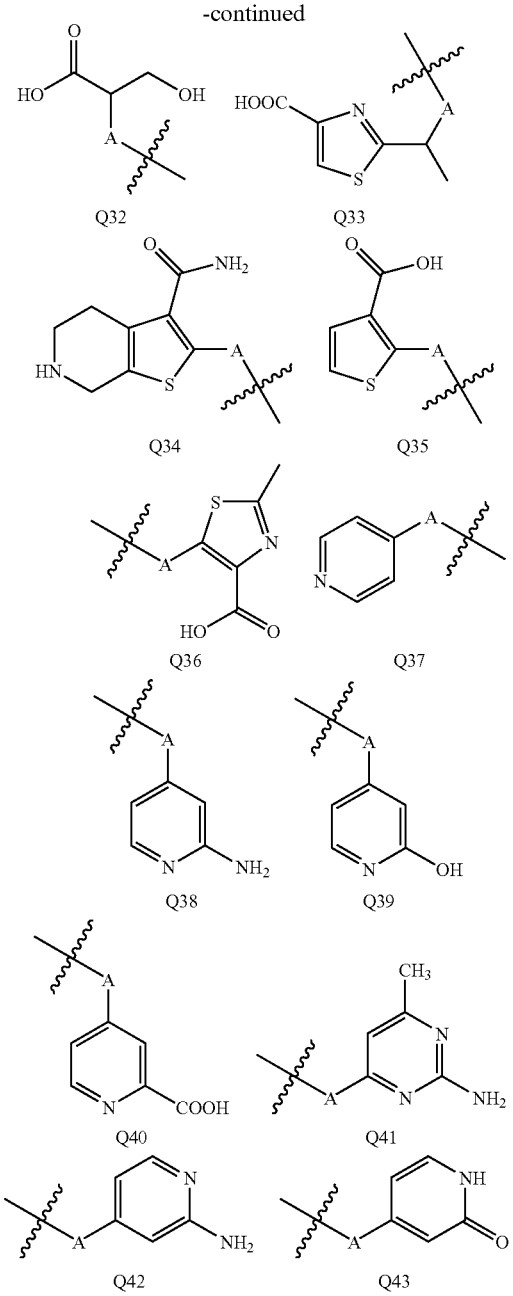

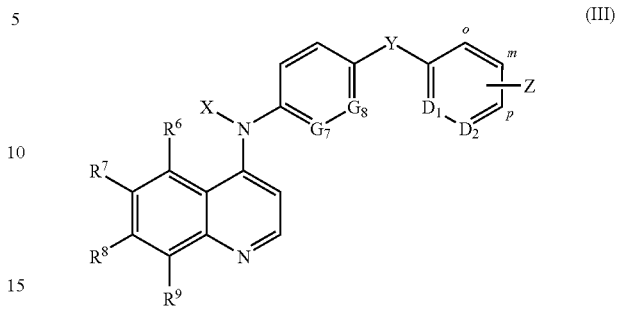

wherein A is O, S(O)$_w$ [w=0 to 2] or NR$^4$ where R$^4$ is defined as above,

G$_9$-G$_{13}$ are each independently C, N, or N+ (where an R$^{10}$-R$^{13}$ is attached to N); but at least three of G$_9$-G$_{13}$ are C; and R$^{10}$, R$^{11}$, R$^{12}$, R$^{13}$, and R$^{14}$ are each separately H, halogen, alkyl, CF$_3$, OCF$_3$, CN, CONHR$^4$, CONR$^4$R$^5$, SO$_2$Me, SO$_2$NHR$^4$, SO$_2$NR$^4$R$^5$, NHCOR$^4$, NHR$^4$, NR$^4$R$^5$, OR$^4$, NO$_2$ or CH$_2$R$^4$, wherein R$^4$ and R$^5$ are as defined above.

It is appreciated that compounds of Formula (I) may occur in different geometric and enantiomeric forms, and that both pure forms and mixtures of these separate isomers are included, and any physiologically functional salt derivatives or phosphate or carboxylic acid or amino acid ester prodrugs thereof.

In another aspect, the invention provides a compound of formula (III), or a pharmaceutically acceptable salt, a phosphate prodrug, or a carboxylic acid or amino acid ester prodrug thereof, wherein R$^6$, R$^7$, R$^8$, and R$^9$ are each separately H, halogen, CF$_3$, OCF$_3$, CN, CONHR$^4$, CONR$^4$R$^5$, SO$_2$Me, SO$_2$NHR$^4$, SO$_2$NR$^4$R$^5$, NHCOR$^4$, NHR$^4$, NR$^4$R$^5$, OR$^4$, NO$_2$ or CH$_2$R$^4$, wherein R$^4$ and R$^5$ are each independently H, C$_1$-C$_6$ alkyl, or cycloalkyl that is optionally substituted with one or more amino, hydroxyl, methoxy, —CN, —COOH or —SO$_2$NH$_2$ groups;

X is H, or C$_1$-C$_6$ alkyl that is optionally substituted with one or more amino, hydroxyl or methoxy groups;

Y is CONR$^4$, NR$^4$CO, O, S(O), (n=0 to 2), (CH$_2$)$_k$ (k=1 to 6), —CH═CH—, or NR$^4$, where R$^4$ and R$^5$ are defined as above;

G$_7$ and G$_8$ are each independently CH or N,

D$_1$ and D$_2$ are each independently CH or N, o, m and p represent positions of attachment of the moiety Z;

Z is one of the groups Q1-Q43 represented in formula (JJ) above, wherein,

A is O, S(O)$_w$ [w=0 to 2] or NR$^4$, where R$^4$ is defined as above;

G$_9$-G$_{13}$ are each independently C, N, or N+ (where an R$^{10}$-R$^{13}$ is attached to N), but at least three of G$_9$-G$_{13}$ are C, R$^{10}$, R$^{11}$, R$^{12}$, R$^{13}$, and R$^{14}$ are each separately H, halogen, alkyl, CF$_3$, OCF$_3$, CN, CONHR$^4$, CONR$^4$R$^5$, SO$_2$Me, SO$_2$NHR$^4$, SO$_2$NR$^4$R$^5$, NHCOR$^4$, NHR$^4$, NR$^4$R$^5$, OR$^4$, NO$_2$ or CH$_2$R$^4$, and wherein R$^4$ and R$^5$ are as defined above.

In a yet another aspect the invention provides a method for treating or preventing a disease associated with aberrant DNA methylation, such as cancer, including the step of administering a compound of formula (I) or (III) or its salts or prodrugs, wherein R$^2$-R$^{14}$, G$_1$-G$_{13}$, o, m, p, X, Y, Z, and A, are defined as above, respectively for each formula.

Preferably, the subject in need of treatment or prevention of such a disease is in need of some reduction in the function/activity of the maintenance methylase DNMT1, preferably at least 25%, more preferably at least 50%, and most preferably at least 75%, reduction of such function/activity. It is envisaged that at least 25% reduction in DNA methylase activity may be beneficial.

The method may also include co-administering one or more therapeutic agents and/or therapies. It is preferred that the method of therapy further includes the step of administering one or more chemotherapeutic or biologic therapeutic agents to, or radiating the subject before, during or after the administration of the compound of formula (I) or (III) or its salts or prodrugs as defined above.

While these compounds will typically be used in disease prevention or treatment of human subjects, they can be used to treat or prevent diseases in other mammals, such as warm blooded animal subjects (e.g., other primates, farm animals such as cattle, and sports animals and pets such as horses, dogs, and cats).

In yet another aspect the present invention provides a pharmaceutical composition comprising a compound of formula (I) or (III) or its salts or prodrugs as defined above, and a pharmaceutically acceptable excipient, adjuvant, carrier, buffer or stabiliser.

In yet another aspect the present invention provides a method for synthesizing or manufacturing a compound of formula (I) or (III) or its salts or prodrugs as defined above. Examples of such a method are illustrated in Schemes 1-6 below.

In yet another aspect the present invention provides a method for manufacture of a medicament comprising a compound of formula (I) or (III) or its salts or prodrugs as defined above for administration to a subject.

Examples of some preferred compound of Formula (I) is listed in Table 1 below, wherein $R^2$, $R^3$ and $R^4$ are H, and A is NH.

TABLE 1

SOME PREFERRED COMPOUNDS OF THE PRESENT INVENTION.

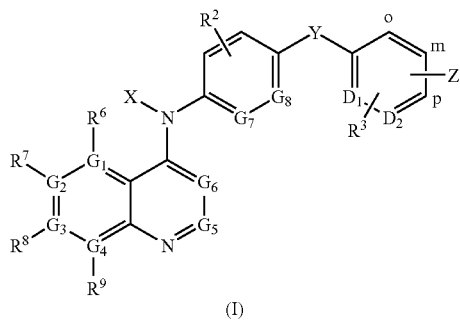

(I)

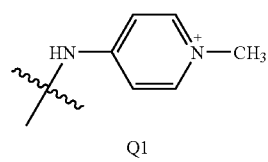

Q1

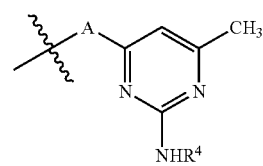

Q2

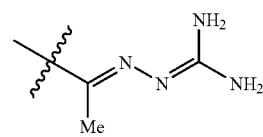

Q3

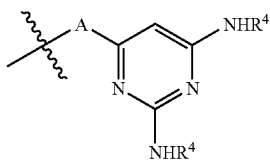

Q4

($R^2$, $R^3$ and $R^4$ are H, $D_1$ and $D_2$ are CH, X is H, and A is NH)

| $R^6$—$R^9$* | Y | attach | Z | $G_5$ | $G_6$ | $G_1$ | $G_2$ | $G_3$ | $G_4$ | $G_7$ | $G_8$ |
|---|---|---|---|---|---|---|---|---|---|---|---|
| — | CONH | m | Q1 | CH | CH | C | C | C | C | CH | CH |
| — | CONH | m | Q1 | N | CH | C | C | C | C | CH | CH |
| — | CONH | m | Q1 | CH | N | C | C | C | C | CH | CH |
| — | CONH | m | Q1 | CH | CH | N | C | C | C | CH | CH |
| — | CONH | m | Q1 | CH | CH | C | N | C | C | CH | CH |
| — | CONH | m | Q1 | CH | CH | C | C | N | C | CH | CH |

TABLE 1-continued

SOME PREFERRED COMPOUNDS OF THE PRESENT INVENTION.

| | | | | | | | | | | | |
|---|---|---|---|---|---|---|---|---|---|---|---|
| — | CONH | m | Q1 | CH | CH | C | C | C | N | CH | CH |
| — | CONH | m | Q1 | CH | CH | C | C | C | C | N | CH |
| — | CONH | m | Q1 | CH | CH | C | C | C | C | CH | N |
| — | CONH | p | Q1 | CH | CH | C | C | C | C | CH | CH |
| — | CONH | p | Q1 | N | CH | C | C | C | C | CH | CH |
| — | CONH | p | Q1 | CH | N | C | C | C | C | CH | CH |
| — | CONH | p | Q1 | CH | CH | N | C | C | C | CH | CH |
| — | CONH | p | Q1 | CH | CH | C | N | C | C | CH | CH |
| — | CONH | p | Q1 | CH | CH | C | C | N | C | CH | CH |
| — | CONH | p | Q1 | CH | CH | C | C | C | N | CH | CH |
| — | CONH | p | Q1 | CH | CH | C | C | C | C | N | CH |
| — | CONH | p | Q1 | CH | CH | C | C | C | C | CH | N |
| — | NHCO | m | Q1 | CH | CH | C | C | C | C | CH | CH |
| — | NHCO | p | Q1 | CH | CH | C | C | C | C | CH | CH |
| — | CONH | p | Q2 | CH | CH | C | C | C | C | CH | CH |
| — | CONH | p | Q2 | N | CH | C | C | C | C | CH | CH |
| — | CONH | p | Q2 | CH | N | C | C | C | C | CH | CH |
| — | CONH | p | Q2 | CH | CH | N | C | C | C | CH | CH |
| — | CONH | p | Q2 | CH | CH | C | N | C | C | CH | CH |
| — | CONH | p | Q2 | CH | CH | C | C | N | C | CH | CH |
| — | CONH | p | Q2 | CH | CH | C | C | C | N | CH | CH |
| — | CONH | p | Q2 | CH | CH | C | C | C | C | N | CH |
| — | CONH | p | Q2 | CH | CH | C | C | C | C | CH | N |
| — | CONH | p | Q3 | CH | CH | C | C | C | C | CH | CH |
| — | CONH | p | Q4 | CH | CH | C | C | C | C | CH | CH |
| — | CONH | p | Q4 | N | CH | C | C | C | C | CH | CH |
| — | CONH | p | Q4 | CH | N | C | C | C | C | CH | CH |
| — | CONH | p | Q4 | CH | CH | N | C | C | C | CH | CH |
| — | CONH | p | Q4 | CH | CH | C | N | C | C | CH | CH |
| — | CONH | p | Q4 | CH | CH | C | C | N | C | CH | CH |
| — | CONH | p | Q4 | CH | CH | C | C | C | N | CH | CH |
| — | CONH | p | Q4 | CH | CH | C | C | C | C | N | CH |
| — | CONH | p | Q4 | CH | CH | C | C | C | C | CH | N |
| — | CONH | m | Q2 | CH | CH | C | C | C | C | CH | CH |
| — | CONH | m | Q2 | N | CH | C | C | C | C | CH | CH |
| — | CONH | m | Q2 | CH | N | C | C | C | C | CH | CH |
| — | CONH | m | Q2 | CH | CH | N | C | C | C | CH | CH |
| — | CONH | m | Q2 | CH | CH | C | N | C | C | CH | CH |
| — | CONH | m | Q2 | CH | CH | C | C | N | C | CH | CH |
| — | CONH | m | Q2 | CH | CH | C | C | C | N | CH | CH |
| — | CONH | m | Q2 | CH | CH | C | C | C | C | N | CH |
| — | CONH | m | Q2 | CH | CH | C | C | C | C | CH | N |
| — | CONH | m | Q3 | CH | CH | C | C | C | C | CH | CH |
| — | CONH | m | Q4 | CH | CH | C | C | C | C | CH | CH |
| — | CONH | m | Q4 | N | CH | C | C | C | C | CH | CH |
| — | CONH | m | Q4 | CH | N | C | C | C | C | CH | CH |
| — | CONH | m | Q4 | CH | CH | N | C | C | C | CH | CH |
| — | CONH | m | Q4 | CH | CH | C | N | C | C | CH | CH |
| — | CONH | m | Q4 | CH | CH | C | C | N | C | CH | CH |
| — | CONH | m | Q4 | CH | CH | C | C | C | N | CH | CH |
| — | CONH | m | Q2 | CH | CH | C | C | C | C | N | CH |
| — | CONH | m | Q2 | CH | CH | C | C | C | C | CH | N |
| $R^7 = NO_2$ | CONH | m | Q2 | CH | CH | C | C | C | C | CH | CH |
| $R^7 = NO_2$ | CONH | p | Q2 | CH | CH | C | C | C | C | CH | CH |
| $R^7 = NO_2$ | NHCO | p | Q2 | CH | CH | C | C | C | C | CH | CH |
| $R^7 = NH_2$ | CONH | m | Q1 | CH | CH | C | C | C | C | CH | CH |
| $R^7 = NH_2$ | CONH | p | Q1 | CH | CH | C | C | C | C | CH | CH |
| $R^7 = NH_2$ | NHCO | m | Q1 | CH | CH | C | C | C | C | CH | CH |
| $R^7 = NH_2$ | NHCO | p | Q1 | CH | CH | C | C | C | C | CH | CH |
| $R^7 = NH_2$ | CONH | m | Q2 | CH | CH | C | C | C | C | CH | CH |
| $R^7 = NH_2$ | CONH | p | Q2 | CH | CH | C | C | C | C | CH | CH |
| $R^7 = NH_2$ | NHCO | m | Q2 | CH | CH | C | C | C | C | CH | CH |
| $R^7 = NH_2$ | NHCO | p | Q2 | CH | CH | C | C | C | C | CH | CH |
| $R^7 = NH_2$ | CONH | m | Q4 | CH | CH | C | C | C | C | CH | CH |
| $R^7 = NH_2$ | CONH | p | Q4 | CH | CH | C | C | C | C | CH | CH |
| $R^7 = NH_2$ | NHCO | m | Q4 | CH | CH | C | C | C | C | CH | CH |
| $R^7 = NH_2$ | NHCO | p | Q4 | CH | CH | C | C | C | C | CH | CH |
| $R^7 = NH_2$ | CONH | m | Q2 | N | CH | C | C | C | C | CH | CH |
| $R^7 = NH_2$ | CONH | p | Q2 | N | CH | C | C | C | C | CH | CH |
| $R^7 = NH_2$ | NHCO | m | Q2 | N | CH | C | C | C | C | CH | CH |
| $R^7 = NH_2$ | NHCO | p | Q2 | N | CH | C | C | C | C | CH | CH |
| $R^7 = NH_2$ | CONH | m | Q2 | CH | N | C | C | C | C | CH | CH |
| $R^7 = NH_2$ | CONH | p | Q2 | CH | N | C | C | C | C | CH | CH |
| $R^7 = NH_2$ | NHCO | m | Q2 | CH | N | C | C | C | C | CH | CH |
| $R^7 = NH_2$ | NHCO | p | Q2 | CH | N | C | C | C | C | CH | CH |
| $R^7 = NH_2$ | CONH | m | Q2 | CH | CH | N | C | C | C | CH | CH |
| $R^7 = NH_2$ | CONH | p | Q2 | CH | CH | N | C | C | C | CH | CH |
| $R^7 = NH_2$ | NHCO | m | Q2 | CH | CH | N | C | C | C | CH | CH |

TABLE 1-continued

SOME PREFERRED COMPOUNDS OF THE PRESENT INVENTION.

| | | | | | | | | | | | |
|---|---|---|---|---|---|---|---|---|---|---|---|
| $R^7 = NH_2$ | NHCO | p | Q2 | CH | CH | N | C | C | C | CH | CH |
| $R^7 = NH_2$ | CONH | m | Q2 | CH | CH | C | C | N | C | CH | CH |
| $R^7 = NH_2$ | CONH | p | Q2 | CH | CH | C | C | N | C | CH | CH |
| $R^7 = NH_2$ | NHCO | m | Q2 | CH | CH | C | C | N | C | CH | CH |
| $R^7 = NH_2$ | NHCO | p | Q2 | CH | CH | C | C | N | C | CH | CH |
| $R^7 = NH_2$ | CONH | m | Q2 | CH | CH | C | C | C | N | CH | CH |
| $R^7 = NH_2$ | CONH | p | Q2 | CH | CH | C | C | C | N | CH | CH |
| $R^7 = NH_2$ | NHCO | m | Q2 | CH | CH | C | C | C | N | CH | CH |
| $R^7 = NH_2$ | NHCO | p | Q2 | CH | CH | C | C | C | N | CH | CH |
| $R^7 = NH_2$ | CONH | m | Q2 | CH | CH | C | C | C | C | N | CH |
| $R^7 = NH_2$ | CONH | p | Q2 | CH | CH | C | C | C | C | N | CH |
| $R^7 = NH_2$ | NHCO | m | Q2 | CH | CH | C | C | C | C | N | CH |
| $R^7 = NH_2$ | NHCO | p | Q2 | CH | CH | C | C | C | C | N | CH |
| $R^7 = NH_2$ | CONH | m | Q2 | CH | CH | C | C | C | C | CH | N |
| $R^7 = NH_2$ | CONH | p | Q2 | CH | CH | C | C | C | C | CH | N |
| $R^7 = NH_2$ | NHCO | m | Q2 | CH | CH | C | C | C | C | CH | N |
| $R^7 = NH_2$ | NHCO | p | Q2 | CH | CH | C | C | C | C | CH | N |
| $R^7 = NH_2$ | CONH | m | Q3 | CH | CH | C | C | C | C | CH | CH |
| $R^7 = NH_2$ | CONH | p | Q3 | CH | CH | C | C | C | C | CH | CH |
| $R^7 = NH_2$ | NHCO | m | Q3 | CH | CH | C | C | C | C | CH | CH |
| $R^7 = NH_2$ | NHCO | p | Q3 | CH | CH | C | C | C | C | CH | CH |
| $R^7 = NMe_2$ | CONH | p | Q1 | CH | CH | C | C | C | C | CH | CH |
| $R^7 = NMe_2$ | CONH | m | Q1 | CH | CH | C | C | C | C | CH | CH |
| $R^7 = NMe_2$ | NHCO | p | Q1 | CH | CH | C | C | C | C | CH | CH |
| $R^7 = NMe_2$ | NHCO | m | Q1 | CH | CH | C | C | C | C | CH | CH |
| $R^7 = NMe_2$ | CONH | p | Q2 | CH | CH | C | C | C | C | CH | CH |
| $R^7 = NMe_2$ | CONH | m | Q2 | CH | CH | C | C | C | C | CH | CH |
| $R^7 = NMe_2$ | NHCO | p | Q2 | CH | CH | C | C | C | C | CH | CH |
| $R^7 = NMe_2$ | NHCO | m | Q2 | CH | CH | C | C | C | C | CH | CH |
| $R^7 = NMe_2$ | CONH | p | Q3 | CH | CH | C | C | C | C | CH | CH |
| $R^7 = NMe_2$ | CONH | m | Q3 | CH | CH | C | C | C | C | CH | CH |
| $R^7 = NMe_2$ | NHCO | p | Q3 | CH | CH | C | C | C | C | CH | CH |
| $R^7 = NMe_2$ | NHCO | m | Q3 | CH | CH | C | C | C | C | CH | CH |
| $R^8 = NO_2$ | CONH | m | Q1 | CH | CH | C | C | C | C | CH | CH |
| $R^8 = NO_2$ | CONH | p | Q1 | CH | CH | C | C | C | C | CH | CH |
| $R^8 = NO_2$ | NHCO | m | Q1 | CH | CH | C | C | C | C | CH | CH |
| $R^8 = NO_2$ | NHCO | p | Q1 | CH | CH | C | C | C | C | CH | CH |
| $R^8 = NO_2$ | CONH | m | Q2 | CH | CH | C | C | C | C | CH | CH |
| $R^8 = NO_2$ | CONH | p | Q2 | CH | CH | C | C | C | C | CH | CH |
| $R^8 = NO_2$ | NHCO | m | Q2 | CH | CH | C | C | C | C | CH | CH |
| $R^8 = NO_2$ | NHCO | p | Q2 | CH | CH | C | C | C | C | CH | CH |
| $R^8 = NO_2$ | CONH | m | Q3 | CH | CH | C | C | C | C | CH | CH |
| $R^8 = NO_2$ | CONH | p | Q3 | CH | CH | C | C | C | C | CH | CH |
| $R^8 = NO_2$ | NHCO | m | Q3 | CH | CH | C | C | C | C | CH | CH |
| $R^8 = NO_2$ | NHCO | p | Q3 | CH | CH | C | C | C | C | CH | CH |
| $R^8 = NH_2$ | CONH | m | Q1 | CH | CH | C | C | C | C | CH | CH |
| $R^8 = NH_2$ | CONH | p | Q1 | CH | CH | C | C | C | C | CH | CH |
| $R^8 = NH_2$ | NHCO | m | Q1 | CH | CH | C | C | C | C | CH | CH |
| $R^8 = NH_2$ | NHCO | p | Q1 | CH | CH | C | C | C | C | CH | CH |
| $R^8 = NH_2$ | CONH | m | Q2 | CH | CH | C | C | C | C | CH | CH |
| $R^8 = NH_2$ | CONH | p | Q2 | CH | CH | C | C | C | C | CH | CH |
| $R^8 = NH_2$ | NHCO | m | Q2 | CH | CH | C | C | C | C | CH | CH |
| $R^8 = NH_2$ | NHCO | p | Q2 | CH | CH | C | C | C | C | CH | CH |
| $R^8 = NH_2$ | CONH | m | Q2 | N | CH | C | C | C | C | CH | CH |
| $R^8 = NH_2$ | CONH | p | Q2 | N | CH | C | C | C | C | CH | CH |
| $R^8 = NH_2$ | NHCO | m | Q2 | N | CH | C | C | C | C | CH | CH |
| $R^8 = NH_2$ | NHCO | p | Q2 | N | CH | C | C | C | C | CH | CH |
| $R^8 = NH_2$ | CONH | m | Q2 | CH | N | C | C | C | C | CH | CH |
| $R^8 = NH_2$ | CONH | p | Q2 | CH | N | C | C | C | C | CH | CH |
| $R^8 = NH_2$ | NHCO | m | Q2 | CH | N | C | C | C | C | CH | CH |
| $R^8 = NH_2$ | NHCO | p | Q2 | CH | N | C | C | C | C | CH | CH |
| $R^8 = NH_2$ | CONH | m | Q2 | CH | CH | N | C | C | C | CH | CH |
| $R^8 = NH_2$ | CONH | p | Q2 | CH | CH | N | C | C | C | CH | CH |
| $R^8 = NH_2$ | NHCO | m | Q2 | CH | CH | N | C | C | C | CH | CH |
| $R^8 = NH_2$ | NHCO | p | Q2 | CH | CH | N | C | C | C | CH | CH |
| $R^8 = NH_2$ | CONH | m | Q2 | CH | CH | C | N | C | C | CH | CH |
| $R^8 = NH_2$ | CONH | p | Q2 | CH | CH | C | N | C | C | CH | CH |
| $R^8 = NH_2$ | NHCO | m | Q2 | CH | CH | C | N | C | C | CH | CH |
| $R^8 = NH_2$ | NHCO | p | Q2 | CH | CH | C | N | C | C | CH | CH |
| $R^8 = NH_2$ | CONH | m | Q2 | CH | CH | C | C | N | C | CH | CH |
| $R^8 = NH_2$ | CONH | p | Q2 | CH | CH | C | C | N | C | CH | CH |
| $R^8 = NH_2$ | NHCO | m | Q2 | CH | CH | C | C | N | C | CH | CH |
| $R^8 = NH_2$ | NHCO | p | Q2 | CH | CH | C | C | N | C | CH | CH |
| $R^8 = NH_2$ | CONH | m | Q2 | CH | CH | C | C | C | N | CH | CH |
| $R^8 = NH_2$ | CONH | p | Q2 | CH | CH | C | C | C | N | CH | CH |
| $R^8 = NH_2$ | NHCO | m | Q2 | CH | CH | C | C | C | N | CH | CH |
| $R^8 = NH_2$ | NHCO | p | Q2 | CH | CH | C | C | C | N | CH | CH |
| $R^8 = NH_2$ | CONH | m | Q2 | CH | CH | C | C | C | C | N | CH |
| $R^8 = NH_2$ | CONH | p | Q2 | CH | CH | C | C | C | C | N | CH |
| $R^8 = NH_2$ | NHCO | m | Q2 | CH | CH | C | C | C | C | N | CH |
| $R^8 = NH_2$ | NHCO | p | Q2 | CH | CH | C | C | C | C | N | CH |
| $R^8 = NH_2$ | CONH | m | Q2 | CH | CH | C | C | C | C | CH | N |

TABLE 1-continued

SOME PREFERRED COMPOUNDS OF THE PRESENT INVENTION.

| | | | | | | | | | | | | |
|---|---|---|---|---|---|---|---|---|---|---|---|---|
| $R^8 = NH_2$ | CONH | p | Q2 | CH | CH | C | C | C | C | CH | N |
| $R^8 = NH_2$ | NHCO | m | Q2 | CH | CH | C | C | C | C | CH | N |
| $R^8 = NH_2$ | NHCO | p | Q2 | CH | CH | C | C | C | C | CH | N |
| $R^8 = NH_2$ | CONH | m | Q2 | CH | N | C | C | C | C | CH | N |
| $R^8 = NH_2$ | CONH | p | Q2 | CH | N | C | C | C | C | CH | N |
| $R^8 = NH_2$ | NHCO | m | Q2 | CH | N | C | C | C | C | CH | N |
| $R^8 = NH_2$ | NHCO | p | Q2 | CH | N | C | C | C | C | CH | N |
| $R^8 = NH_2$ | CONH | m | Q3 | CH | CH | N | C | C | C | CH | CH |
| $R^8 = NH_2$ | CONH | p | Q3 | CH | CH | N | C | C | C | CH | CH |
| $R^8 = NH_2$ | NHCO | m | Q3 | CH | CH | N | C | C | C | CH | CH |
| $R^8 = NH_2$ | NHCO | p | Q3 | CH | CH | N | C | C | C | CH | CH |
| $R^8 = NMe_2$ | CONH | m | Q1 | CH | CH | C | C | C | C | CH | CH |
| $R^8 = NMe_2$ | CONH | p | Q1 | CH | CH | C | C | C | C | CH | CH |
| $R^8 = NMe_2$ | CONH | m | Q2 | CH | CH | C | C | C | C | CH | CH |
| $R^8 = NMe_2$ | CONH | p | Q2 | CH | CH | C | C | C | C | CH | CH |
| $R^8 = NMe_2$ | CONH | m | Q3 | CH | CH | C | C | C | C | CH | CH |
| $R^8 = NMe_2$ | CONH | p | Q3 | CH | CH | C | C | C | C | CH | CH |
| $R^8 = NMe_2$ | NHCO | m | Q1 | CH | CH | C | C | C | C | CH | CH |
| $R^8 = NMe_2$ | NHCO | p | Q1 | CH | CH | C | C | C | C | CH | CH |
| $R^8 = NMe_2$ | NHCO | m | Q2 | CH | CH | C | C | C | C | CH | CH |
| $R^8 = NMe_2$ | NHCO | p | Q2 | CH | CH | C | C | C | C | CH | CH |
| $R^8 = NMe_2$ | NHCO | m | Q3 | CH | CH | C | C | C | C | CH | CH |
| $R^8 = NMe_2$ | NHCO | p | Q3 | CH | CH | C | C | C | C | CH | CH |

*If not specified, $R^6$-$R^9$ = H

It is to be recognized that certain compounds of the present invention may exist in one or more different enantiomeric or diastereomeric forms. It is to be understood that the enantiomeric or diastereomeric forms are included in the above aspects of the invention.

The term pharmacologically acceptable salt used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like and potassium carbonate sodium or potassium hydroxide ammonia, triethylamine, triethanolamine and the like.

In some embodiments of the invention, the salt of the compound of formula (I) or (III) is formed with an acid selected from the group consisting of hydrochloric acid, hydrobromic acid, sulfuric acid, phosphoric acid, carboxylic, sulfonic, sulfo or phospho acids, acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, amino acid, glutamic acid, aspartic acid, phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexyl-sulfamic acid, and ascorbic acid. In some embodiments, the salt is a sodium, calcium, lithium, potassium, ammonium, or trialkylammonium salt.

In some preferred embodiments, Z is Q1, Q2, Q3, Q4, Q9, or Q10. In some preferred embodiments, the compound is a structure of formula (III), $R^6$, $R^7$, $R^8$, and $R^9$ are each H; X is H; Y is CONH or NHCO; Z is Q2 or Q9; A is NH, and Z is attached at the m or p position. In some preferred embodiments, the compound is a structure of formula (III), $R^6$, $R^7$, $R^8$, and $R^9$ are each H; X is H; Y is CONH, Z is Q2; A is NH; and Z is attached at the p position. In some preferred embodiments, the compound is a structure of formula (III), $R^6$, $R^7$, $R^8$, and $R^9$ are each H; X is H; Y is CONH; Z is Q9; A is NH; and Z is attached at the p position. In some preferred embodiments, the compound is a structure of formula (III), $R^6$, $R^7$, $R^8$, and $R^9$ are each H; X is H; Y is CONH or NHCO; Z is Q2; A is NH, and Z is attached at the m position. In some preferred embodiments, the compound is a structure of formula (III), $R^6$, $R^8$, and $R^9$ are each H; $R^7$ is $NMe_2$; X is H; Y is CONH or NHCO; Z is Q2; A is NH, and Z is attached at the m position. In some preferred embodiments, the compound is a structure of formula (III), $R^6$, $R^8$, and $R^9$ are each H; $R^7$ is Cl; X is H; Y is CONH; Z is Q2; A is NH, and Z is attached at the p position. In some preferred embodiments, the compound is a structure of formula (III), $R^6$, $R^7$, $R^8$, and $R^9$ are separately H, F, or Cl. In some embodiments, Z is Q9, Q39 or Q42. In other more specific embodiments, the compound is a structure of formula (III), $R^6$, $R^7$, $R^8$, and $R^9$ are each H; X is H; Y is CONH or NHCO; Z is Q9, Q39 or Q42; A is S; w is 0; and Z is attached at the m or p position. In other specific embodiments, the compound is a structure of formula (III), $R^6$, $R^7$, $R^8$, and $R^9$ are each H; X is H; Y is CONH, Z is Q9; A is S; w is 0; and Z is attached at the p position. In other specific embodiments, the compound is a structure of formula (III), $R^6$, $R^7$, $R^8$, and $R^9$ are each H; X is H; Y is CONH; Z is Q39; A is S; w is 0; and Z is attached at the p position. In yet other specific embodiments, the compound is a structure of formula (III), $R^6$, $R^7$, $R^8$, and $R^9$ are each H; X is H; Y is CONH; Z is Q42; A is S; w is 0; and Z is attached at the p position.

One aspect of the invention is a pharmaceutical composition comprising a compound, salt, or prodrug of formula (I) or (III) or its salts or prodrugs as defined above, and a pharmaceutically-acceptable carrier. In some embodiments of the pharmaceutical composition, the compound, salt, or prodrug is in solid form. In some embodiments the pharmaceutical composition is in an oral dosage form. In some embodiments the pharmaceutical composition is in an injectable dosage form. In some embodiments the pharmaceutical composition is in a topical dosage form.

One aspect of the invention is a method for inhibiting DNA methylation in a cell, comprising: contacting the cell with the compound of formula (I) or (III) or its salts or prodrugs as defined above, such that DNA methylation activity of the cell is inhibited.

One aspect of the invention is a method for inhibiting DNA methylation in a cell, comprising: contacting the cell with the compound of formula (I) or (III) or its salts or prodrugs as defined above, such that DNA methylransferase activity in the cell is inhibited. In some embodiments, the activity of DNA methyltransferase activity is inhibited via degradation of DNA methyltransferase DNMT1. In some embodiments, the step of contacting includes contacting the cell with a biologically effective amount of the compound of formula (I) or (III) or its salts or prodrugs as defined above, such that at least 50% of the activity of DNA methyltransferase DNMT1 in the cell is inhibited. In some embodiments, the step of contacting includes contacting the cell with a biologically effective amount of the compound of formula (I) or (III) or its salts or prodrugs as defined above, such that at least 25% of the activity of DNA methyltransferase DNMT1 in the cell is inhibited.

One aspect of the invention is a method for restoring activity of a DNA methylation-suppressed gene in a cell, comprising: contacting a cell with a biologically effective amount of the compound of formula (I) or (III) or its salts or prodrugs as defined above, such that activity of the DNA methylation-suppressed gene is elevated by at least 25% relative to that in the absence of the compound, salt, or prodrug. In some embodiments, the step of contacting includes contacting the cell with a biologically effective amount of the compound of formula (I) or (III) or its salts or prodrugs as defined above, such that transcriptional activity or levels of transcript of the DNA-methylation-suppressed gene is elevated by at least 25%. In some embodiments, the DNA methylation-suppressed gene is selected from the group consisting of 14-3-3 Sigma, ABL1 (P1), ABO, APC, AR (Androgen Receptor), BLT1 (Leukotriene B4 Receptor), BRCA1, CALCA (Calcitonin), CASP8 (CASPASE 8), Caveolin 1, CD44, CFTR, COX2, CSPG2 (Versican), CX26 (Connexin 26), Cyclin A1, DBCCR1, ECAD (E-cadherin), Endothelin Receptor B, EPHA3, EPO (Erythropoietin), ER (Estrogen Receptor), FHIT, GPC3 (Glypican 3), GST-pi, H19, H-Cadherin (CDH13), γ-globin, HIC1, hMLH1, HOXA5, IGF2 (Insulin-Like Growth Factor II), IGFBP7, IRF7, LKB1, LRP-2 (Megalin), MDGI (Mammary-derived growth inhibitor), MDR1, MDR3 (PGY3), MGMT (O6 methyl guanine methyl transferase), MUC2, MYOD1, N33, NEP (Neutral Endopeptidase 24.1)/CALLA, NIS (sodium-iodide symporter gene), P14/ARF, P15 (CDKN2B), P16 (CDKN2A), P27KIP1, p57 KIP2, PAX6, PgR (Progesterone Receptor), RAR-Beta2, RASSF1, RB1 (Retinoblastoma), TERT, TESTIN, TGFBR1, THBS1 (Thrombospondin-1), TIMP3, TLS3 (T-Plastin), Urokinase (uPA), VHL (Von-Hippell Lindau), WT1, and Z02 (Zona Occludens 2). The website of M. D. Anderson Cancer Center provides detailed information on these tumor suppressor genes. See the website at www.mdanderson.org/departments/methylation/dIndex.cfm?pn=D02B3250-57D7-4F61-88358636A8073A08, which is herein incorporated by reference.

One aspect of the invention is a method for treating a patient suffering from a disease associated with aberrant DNA methylation, comprising: administering to the patient a pharmaceutical composition comprising a therapeutically-effective amount of the compound of formula (I) or (III) or its salts or prodrugs as defined above and a pharmaceutically-acceptable carrier. In some embodiments, the pharmaceutical composition is administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally. In some embodiments, the pharmaceutical composition is administered orally. In some embodiments, the method further involves administering to the patient a second therapeutic agent in combination with the pharmaceutical composition. In some embodiments, the second therapeutic agent is decitabine or azacitidine. In some embodiments the second therapeutic agent is selected from the group consisting of histone deacylase inhibitors, antibiotic agents, alkylating agents, retinoids, hormonal agents, plant-derived agents, biologic agents, interleukins, interferons, cytokines, immuno-modulating agents, and monoclonal antibodies. In some embodiments, the histone deacylase inhibitor is selected from the group consisting of trichostatin A, suberoylanilide hydroxamic acid, oxamflatin, suberic bishydroxamic acid, m-carboxy-cinnamic acid bishydroxamic acid, pyroxamide, trapoxin A, apicidin, depsipeptide, N-(2-amimophenyl)-4-[N-(pyridin-3-ylmethoxycarbonyl) aminomethyl]benzamide, butyric acid, phenylbutyrate and arginine butyrate.

In some embodiments, the disease associated with aberrant DNA methylation is selected from the group consisting of hematological disorders, benign tumor and cancer. In some embodiments the hematological disorder is selected from the group consisting of acute myeloid leukemia, acute promyelocytic leukemia, acute lymphoblastic leukemia, chronic myelogenous leukemia, myelodysplastic syndromes, and sickle cell anemia. In some embodiments, the disease is cancer and is selected from group consisting of breast cancer, skin cancer, bone cancer, prostate cancer, liver cancer, lung cancer, non-small cell lung cancer, brain cancer, cancer of the larynx, gall bladder, pancreas, rectum, parathyroid, thyroid, adrenal, neural tissue, head and neck, colon, stomach, bronchi, and kidney cancer, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic sarcoma, malignant hypercalcemia, renal cell tumor, polycythermia vera, adenocarcinoma, glioblastoma multiforma, leukemias, lymphomas, malignant melanomas, and epidermoid carcinomas.

In yet another aspect the present invention provides a method for inhibiting DNA methylation in a cell, comprising: contacting the cell with the compound of formula (I) or (III) or its salts or prodrugs as defined above, such that DNA methylation activity of the cell is inhibited, preferably by at least 25%, more preferably by at least 50%, relative to the DNA methylation activity prior to the administration of the compound.

In yet another aspect the present invention provides a method for selectively inhibiting activity of DNA methyltransferase DNMT1 in a cell, comprising: contacting a cell with the compound of the present invention, such that activity of DNA methyltransferase DNMT1 in the cell is inhibited more than that of DNA methyltransferase DNMT3a or DNMT3b.

According to the method, the activity of DNA methyltransferase DNMT1 is inhibited via degradation of DNA methyltransferase DNMT1.

According to the method, the step of contacting includes contacting the cell with a biologically effective amount of the compound of present invention, such that at least 50% of the activity of DNA methyltransferase DNMT1 in the cell is inhibited.

According to the method, the step of contacting includes contacting the cell with a biologically effective amount of the compound of the present invention, such that at least 25% of the activity of DNA methyltransferase DNMT1 in the cell is inhibited.

In yet another aspect the present invention provides a method for restoring activity of a DNA methylation-suppressed gene in a cell, comprising: contacting a cell with a biologically effective amount of the compound of the present invention, such that activity of the DNA methylation-suppressed gene is elevated by at least 25%, preferably at least 50%, relative to that in the absence of the compound. The activity of the DNA methylation-suppressed gene includes but is not limited to transcriptional activity of the methylation-suppressed gene.

In yet another aspect the present invention provides a method for treating a patient suffering from a disease associated with aberrant DNA methylation, comprising: administering to the patient a pharmaceutical composition comprising a therapeutically-effective amount of the compound of formula (I) or (III) or its salts or prodrugs as defined above and a pharmaceutically-acceptable carrier.

According to the method, the pharmaceutical composition is administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

According to the method, the method further comprises: administering to the patient a second therapeutic agent in combination with the pharmaceutical composition.

According to the method, the second therapeutic agent may be decitabine or azacitidine.

According to the method, the second therapeutic agent may be selected from the group consisting of histone deacylase inhibitor, antibiotic agents, alkylating agents, retinoids, hormonal agents, plant-derived agents, biologic agents, interleukins, interferons, cytokines, immuno-modulating agents, and monoclonal antibodies.

According to the method, the disease associated with aberrant DNA methylation is selected from the group consisting of hematological disorders, benign tumor and cancer.

Examples of cancer include but are not limited to acute myeloid leukemia, acute promyelocytic leukemia, acute lymphoblastic leukemia, chronic myelogenous leukemia, myelodysplastic syndromes, and sickle cell anemia.

Examples of the hematological disorder include but are not limited to breast cancer, skin cancer, bone cancer, prostate cancer, liver cancer, lung cancer, non-small cell lung cancer, brain cancer, cancer of the larynx, gall bladder, pancreas, rectum, parathyroid, thyroid, adrenal, neural tissue, head and neck, colon, stomach, bronchi, and kidney cancer, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic sarcoma, malignant hypercalcemia, renal cell tumor, polycythermia vera, adenocarcinoma, glioblastoma multiforma, leukemias, lymphomas, malignant melanomas, and epidermoid carcinomas.

Further aspects of the present invention will become apparent from the following description given by way of example only and with reference to the accompanying synthetic schemes.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Figure 1:
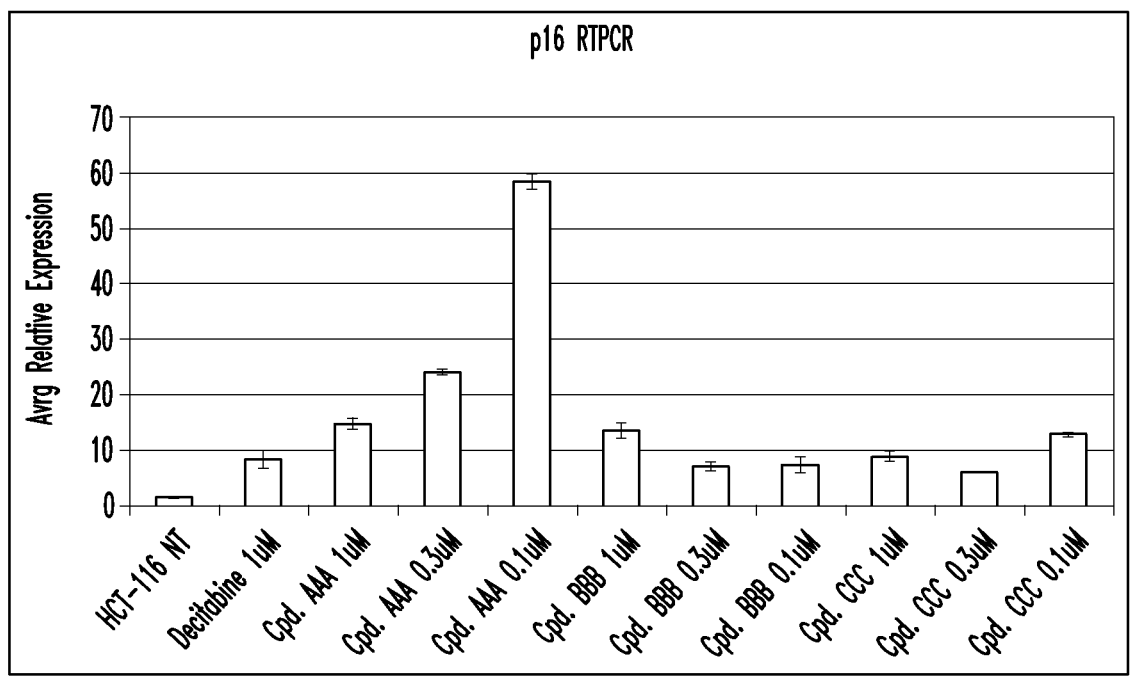
FIG. 1 illustrates the increase of RNA expression levels of p16 by representative compounds of this invention at different concentrations.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention provides compounds, compositions, formulations, kits, methods of use, and manufacture of quinoline derivatives, and more particularly to 4-anilinoquinoline derivatives as inhibitors of DNA methylation enzymes, modulators of DNA methylation and therapeutic agents for preventing or treating diseases associated with aberrant DNA methylation such as cancer and hematological malignancy.

We have unexpectedly found that a series of 4-anilinoquinolines (e.g., compounds of Formula (I) or Formula (III)) specifically inhibit the cellular functions of the DNA methyltransferase DNMT1 via selective degradation of DNMT1. In contrast, previously 4-anilinoquinolinium bis-quaternary salts have been shown to bind in the DNA minor groove (Leupin et al., *Biochemistry*, 1986, 25, 5902; Squire et al., *Nucleic Acids Res.*, 1997, 25, 4072). These have been shown to be cytotoxic, and were originally developed as anticancer drugs (Atwell & Cain, *J. Med. Chem.*, 1973, 16, 673; Denny et al., *J. Med. Chem.*, 1979,22, 134), but the example (NSC 176319) considered for clinical trial was found to be too toxic (Plowman & Adamson, *Pharmacol.*, 1978, 17, 61).

While not wishing to be bound to the exact mechanism of action of the compounds of present invention, we believe that the inventive 4-anilinoquinoline derivatives, in comparison with 4-anilinoquinolinium bis-quaternary salts in the art, should be more specific in the inhibition of DNMT1 and/or in the inhibition of DNA methylation in the cell due to their fewer charged substitutes or the replacement of the quaternary quinolinium and/or the pyridinium functional groups with ones with lower pKa values. Thus, the compounds of present invention should have reduced cytotoxicity and more specifically modulate DNA methylation activity in the cell.

1. Methods for Preparing Compounds of the Invention

The compounds of the invention can be prepared by the methods shown in Schemes 1-6 below, and given in the detailed examples.

In Scheme 1, compounds where Y is CONH and Z is Q1 in Formula (I) can be prepared by reaction of 4-(pyridyl)pyridinium with nitroanilines (2), reduction of these with H2/Pd to amines (3), then reaction of these with 4-nitrobenzoic acid to gave amides (6), which can be quaternised (for example, with MeOTs) to give pyridinium compounds (7). Reduction of these with Fe dust/HCl gives amines (8), which can be coupled with 4-chloroquinolines, and if necessary further processed, to give compounds of Formula (I).

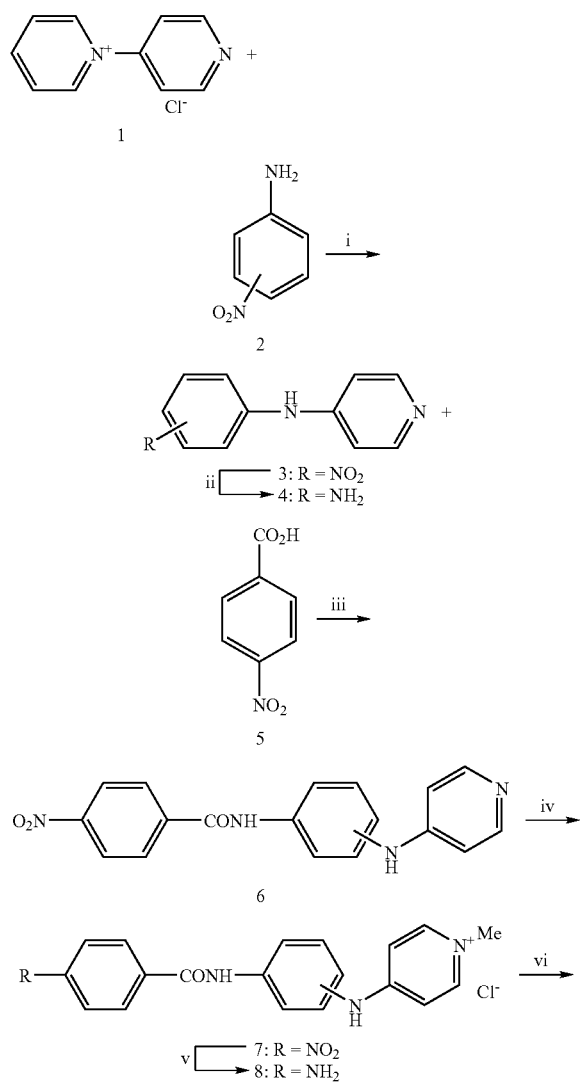

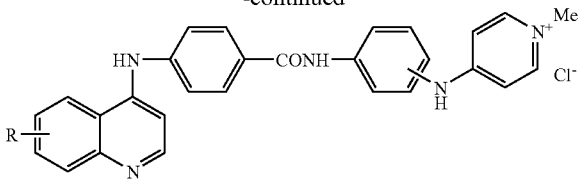

Compounds of formula (I);
R($R^6$—$R^9$) = H, $NO_2$, $NH_2$, $NMe_2$ (i) TsOH/180° C.; (ii) $H_2$/Pd/C/MeOH; (iii) 5/$SOCl_2$/reflux, then 4/pyridine/dioxane; (iv) DMF/MeOTs/20° C., then ion exchange, (v) Fe dust/EtOH/$H_2O$; (vi) 4-chloroquinolines/MeOH/cat. HCl/reflux.

In Scheme 2, compounds where Y is NHCO and Z is Q1 in Formula (I) can be prepared by reacting N-acetylaminobenzoic acids (9) with 4-nitroaniline using coupling reagents such as EDCI or CDI to give amides (10), which can be hydrolysed with dilute HCl in 1,4-dioxane to amines (11). These can be reacted with 4-pyridyl pyridiniumchloride to give amines (12). Quaternisation of these as above (for example, with MeOTs) gives pyridinium compounds (13), which can be reduced to amines (14) and then coupled with 4-chloroquinolines as before, and if necessary further processed, to give compounds of Formula (I).

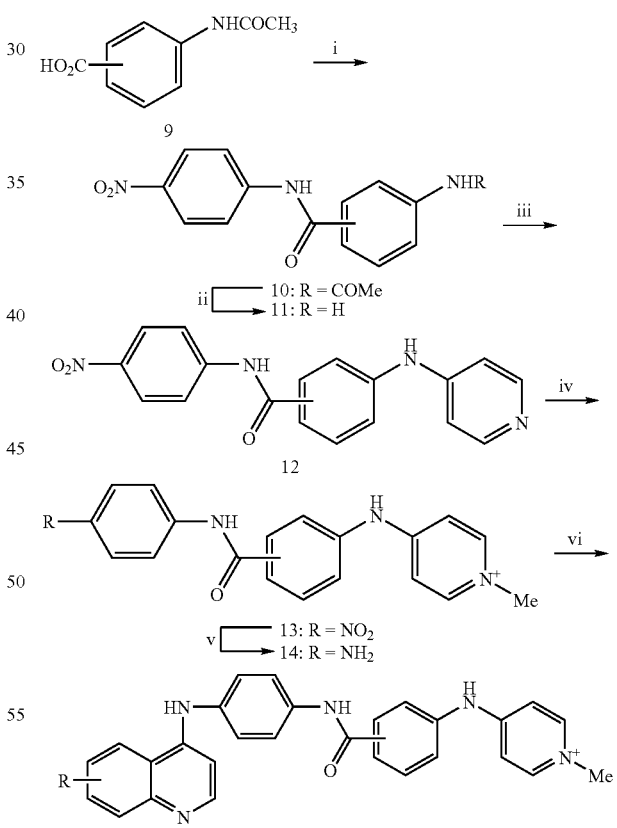

compounds of formula (I):
R ($R^6$—$R^9$) = H, $NO_2$, $NH_2$, $NMe_2$ (i) EDCI/DMF/DMAP/ 4-nitroaniline; (ii) HCl/dioxane/reflux (iii) p-TsOH/4-pyridylpyridinium chloride/180° C.; (iv) DMF/MeOTs; (i) Fe dust/EtOH/$H_2O$/$H^+$/then ion exchange; (vi) 4-chloroquinolines/EtOH/$H_2O$/$H^+$/reflux In Scheme 3, compounds where Y is NHCO and Z is Q3 in Formula (I) can be prepared by coupling of 4-chloroquinolines (15) and 4-acetylaminoaniline (16) to give anilinoquinolines (17), and deblocking these to give anilinoquinolines (18). Reaction of acetylbenzoic acids (19) with aminoguanidine gives guanylhydrazones (20), and these are coupled with anilinoquinolines (18) using EDCI or some other coupling reagent to give compounds of Formula I.

which are hydrolysed to amines (23) then reacted with 2-amino-6-chloro-4-methylpyrimidine to give compounds of Formula I.

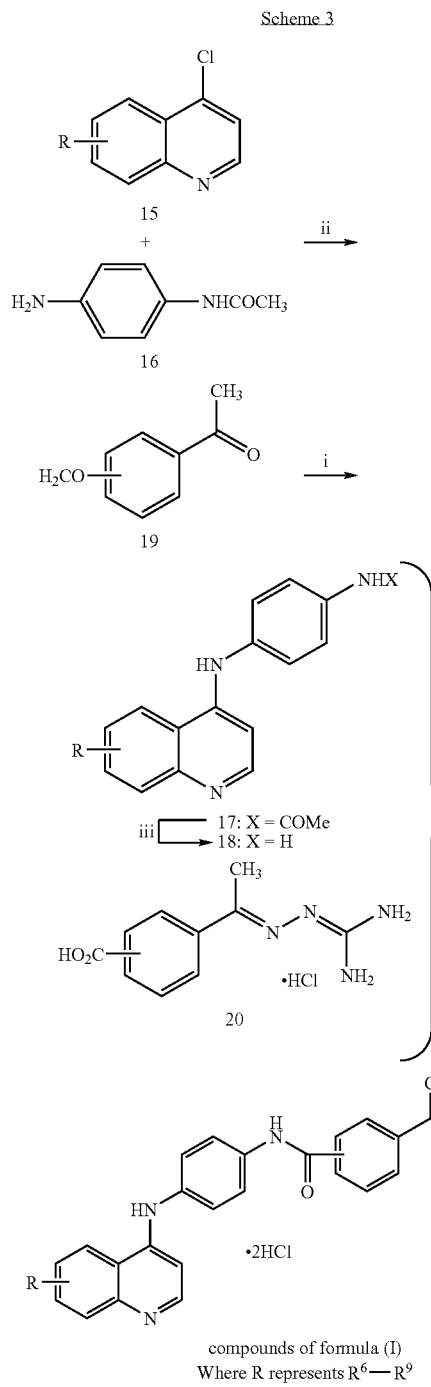

(i) 2-Aminoguanidine/MeOH/c. HCl/reflux; (ii) EtOH/H$_2$O(2:1)/c. HCl/reflux; (iii) 2N HCl/EtOH/reflux; (iv) EDCI/DMAP/DMF/RT

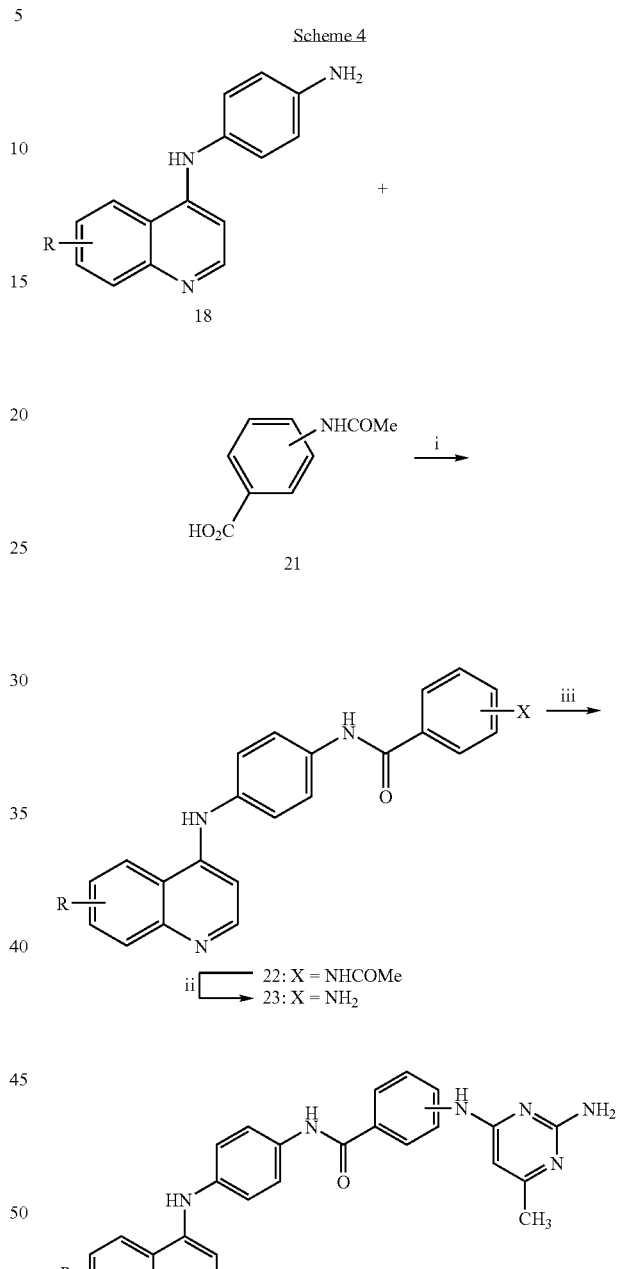

compounds of Formula (I)
Where R represents R$^6$—R$^9$
(i) EDCI/DMAP/DMF/RT; (ii) 1,4-dioxane/HCl reflux; (iii) 2-amino-6-chloro-4-methylpyrimidine/2-ethoxyethanol/H$^+$/reflux In Scheme 4, compounds where Y is NHCO and Z is Q2 in Formula (I) can be prepared by coupling 4-anilinoquinolines (18) with N-acetylbenzoic acids (21) to give amides (22), In Scheme 5, compounds where Y is CONH and Z is Q3 in Formula (I) can be prepared by reaction of nitroacetophenones (24) with aminoguanidine, followed by reduction of the product guanylhydrazones with Fe/HCl (25) to give the amines (26). These are reacted with 4-nitrobenzoyl chloride, and the product amides (27) are again reduced to the amines (28). Coupling of these with 4-chloroquinolines then gives the compounds of Formula I.

Scheme 5

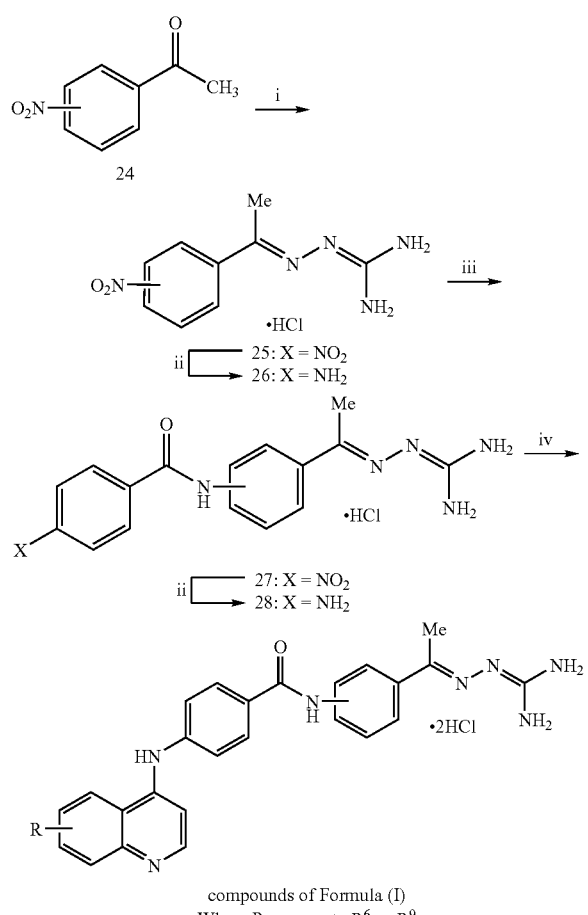

compounds of Formula (I)
Where R represents $R^6$—$R^9$ (i) Aminoguanidine/MeOH/.c. HCl/reflux; (ii) Fe dust/EtOH/H2O/cat HCl/reflux; (iii) 4-nitrobenzoyl chloride/pyridine/dioxane/reflux; (iv) 4-Chloroquinilones/EtOH/cat. HCl/reflux.

In Scheme 6, compounds where Y is CONH and Z is Q2 in Formula (I) can be prepared by coupling nitroanilines (2) with 2-amino-6-chloro-4-methylpyrimidine, and reduction of the resulting products (27) with Fe/HCl to give amines (28). Coupling of these with 4-nitrobenzoyl chloride, and reduction of the products (29) as before gave the amines (30). These were coupled with 4-chloroquinolines as above to give compounds of formula (I).

Scheme 6

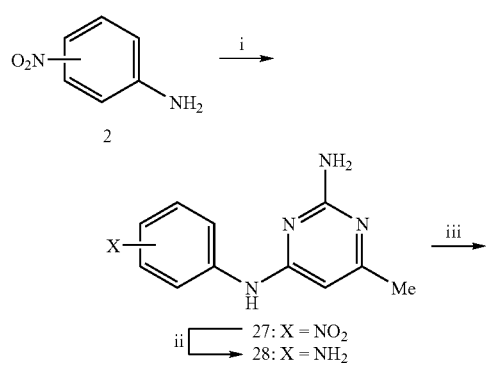

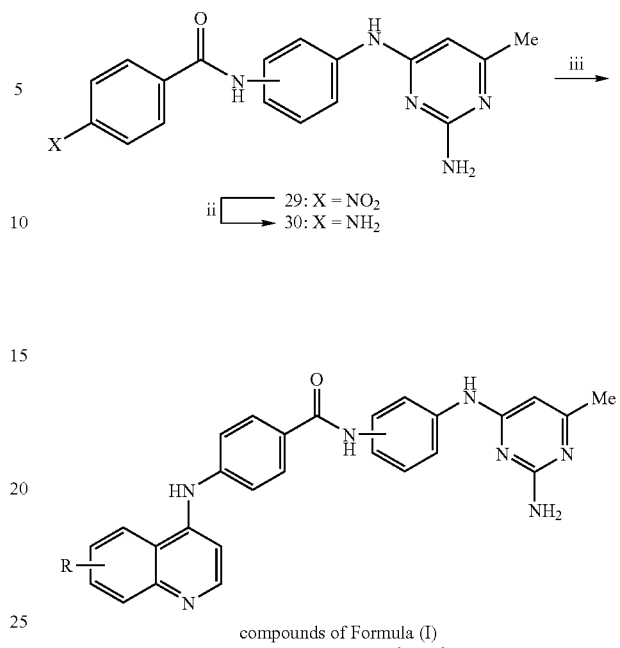

compounds of Formula (I)
Where R represents $R^6$—$R^9$ (i) 2-amino-6-chloro-4-methylpyrimidine/2-ethoxyethanol, c.HCl, reflux; (ii) Fe/2:1 EtOH:H2O, 2% v/v AcOH/reflux, (iii) 4-nitrobenzoyl chloride/pyridine, dioxane,/~50° C.; (iv) 4-chloroquinolines/1:2 EtOH:H2O/cat. c.HCl/reflux.

Compounds of Formula (I), where A is S, can be prepared according to Scheme 7. An appropriately substituted thiol where X is either $NO_2$ (31) or $NH_2$ (32) can be reacted with a chloro Q derivative (33), wherein 33 represents any of Q1-Q43 wherein A (or the bond at the point of connection in the case of Q3) is replaced with Cl, to obtain compounds of structure 34 (X=$NO_2$) or 35 (X=$NH_2$). Compounds of structure 34 can be reduced with an appropriate reducing agent, for example iron and hydrochloric acid, to produce compounds of structure 35. Reaction of an appropriately substituted benzoyl chloride (36) with compounds of structure 35 yields compounds of structure 37. Reduction of compounds of structure 37 with an appropriate reducing agent, for example iron and hydrochloric acid, produces compounds of structure 38. Reaction of compounds of structure 38 with an appropriately substituted 4-chloroquinoline (39) then yields compounds of structure (I) wherein Q represents any of Q1-Q43 and w is 0. Further oxidation with an appropriate oxidant, for example meta-chloroperbenzoic acid), yields compounds of structure (I) wherein Q represents and of Q1-Q43 and w is 1 or 2.

Scheme 7

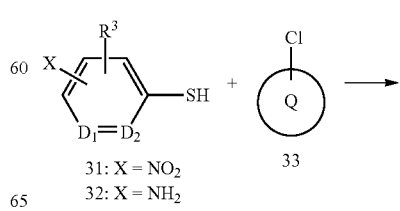

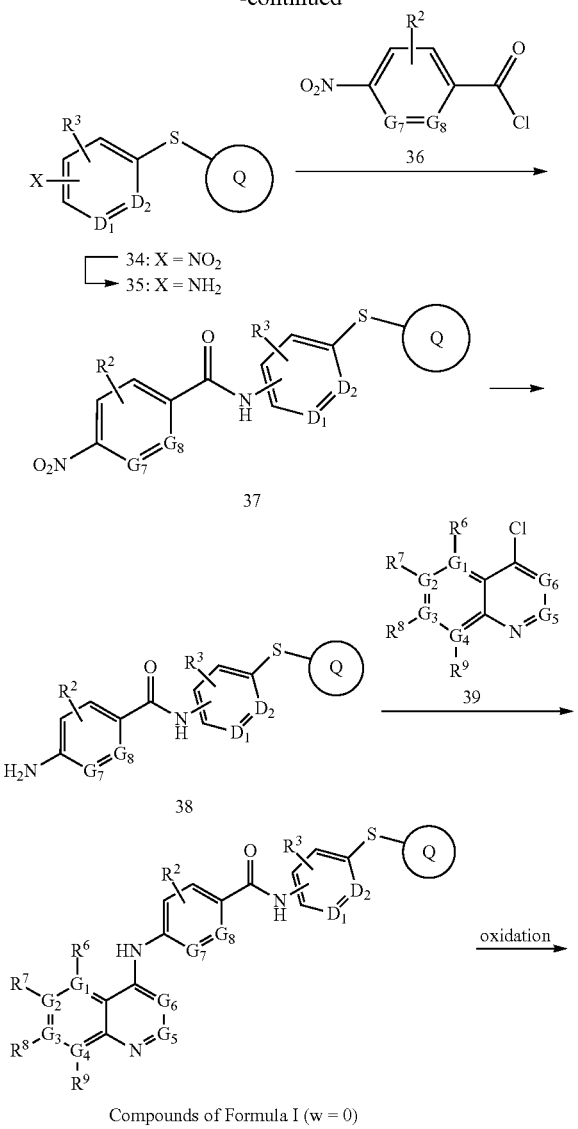

Compounds of Formula I (w = 0)

Compounds of Formula I (w = 1 or 2)

The quinoline derivatives of the present invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the quinoline derivatives of the invention may be prepared by forming one or more ester bond with any of the hydroxyl groups in the compounds using an organic compound containing a carboxyl group, or as SATE [(S-acetyl-2-thioethyl) phosphate) derivatives according to the methods disclosed in WO 93/2451, or in WO 94/26764 and U.S. Pat. No. 5,770,713.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Thus, 4-anilinoquinolinium bisquaternary salts are preferably excluded.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" includes a pharmaceutically acceptable salt of an acid form of one of the components of the compositions of the invention. These include organic or inorganic acid salts of the amines. Suitable pharmaceutically acceptable salts are well known to those skilled in the art and include basic salts of a variety of inorganic and organic acids, such as, for example, with inorganic acids, for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

The invention also embraces isolated compounds. An isolated compound refers to a compound which represents at least 10%, preferably 20%, more preferably 50% and most preferably 80% of the compound present in the mixture, and exhibits a detectable (i.e., statistically significant) inhibitory activity of DNA methylation directly or indirectly when tested in biological assays such as the combined bisulfite restriction analysis or COBRA (Xiong, Z.; Laird, P. W. *Nucleic Acids Res.* 1997, 25, 2532-2534), radiolabeled methyl incorporation assay (Francis, K. T.; Thompson, R. W.; Krumdieck, C. L. *Am. J. Clin. Nutr.* 1977, 30, 2028-2032), and the DNMT assays described in Ghoshal et al (2005) 11:4727-41 and in the EXAMPLE section below. Preferably, the compounds of the present invention selectively inhibit activity of DNMT1 relative to DNMT3a and DNMT3b.

2. Pharmaceutical Formulations of the Present Invention

According to the present invention, the compounds of the present invention can be formulated into pharmaceutically acceptable compositions for treating various diseases and conditions.

The pharmaceutically-acceptable compositions of the present invention comprise one or more compounds of the invention in association with one or more nontoxic, pharmaceutically-acceptable carriers and/or diluents and/or adjuvants and/or excipients, collectively referred to herein as "carrier" materials, and if desired other active ingredients.

The compounds of the present invention are administered by any route, preferably in the form of a pharmaceutical composition adapted to such a route, as illustrated below and are dependent on the condition being treated. The compounds and compositions can be, for example, administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by a catheter or stent), subcutaneously, intraadiposally, intraarticularly, or intrathecally.

The pharmaceutical formulation may optionally further include an excipient added in an amount sufficient to enhance the stability of the composition, maintain the product in solution, or prevent side effects (e.g., potential ulceration, vascular irritation or extravasation) associated with the administration of the inventive formulation. Examples of excipients include, but are not limited to, mannitol, sorbitol, lactose, dextrose, cyclodextrin such as, $\alpha$-, $\beta$-, and $\gamma$-cyclodextrin, and modified, amorphous cyclodextrin such as hydroxypropyl-, hydroxyethyl-, glucosyl-, maltosyl-, maltotriosyl-, carboxyamidomethyl-, carboxymethyl-, sulfobutylether-, and diethylamino-substituted $\alpha$, $\beta$-, and $\gamma$-cyclodextrin. Cyclodextrins such as Encapsin® from Janssen Pharmaceuticals or equivalent may be used for this purpose.

For oral administration, the pharmaceutical compositions can be in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery.

The pharmaceutical compositions can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

3. Methods for Administrating Inventive Compounds/Compositions

The compounds or formulations of the present invention can be administered by any route, preferably in the form of a pharmaceutical composition adapted to such a route, as illustrated below and are dependent on the condition being treated. The compounds or formulations can be, for example, administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or co-administered in slow release dosage forms.

The compounds and/or compositions of this invention may be administered or co-administered in any conventional dosage form. Co-administration in the context of this invention is defined to mean the administration of more than one therapeutic agent in the course of a coordinated treatment to achieve an improved clinical outcome. Such co-administration may also be coextensive, that is, occurring during overlapping periods of time.

The inventive compound or the composition containing the inventive compound may be administered into a host such as a patient at a dose of 0.1-1000 mg/m$^2$, optionally 1-200 mg/m$^2$, optionally 1-50 mg/m$^2$, optionally 1-40 mg/m$^2$, optionally 1-30 mg/m$^2$, optionally 1-20 mg/m$^2$, or optionally 5-30 mg/m$^2$.

The pharmaceutical formulations may be co-administered in any conventional form with one or more member selected from the group comprising infusion fluids, therapeutic compounds, nutritious fluids, anti-microbial fluids, buffering and stabilizing agents.

Patients may receive the pharmaceutical formulations intravenously. The preferred route of administration is by intravenous infusion. Optionally, the pharmaceutical formulations of the current invention may be infused directly, without prior reconstitution.

Patients may be infused with the pharmaceutical formulations for 1, 2, 3, 4, 5 or more hours, as a result of the enhanced stability of the formulations. Prolonged periods of infusion enable flexible schedules of administration of therapeutic formulations.

Alternatively or in addition, speed and volume of the infusion can be regulated according to the patient's needs. The regulation of the infusion of the pharmaceutical formulations can be performed according to existing protocols.

The pharmaceutical formulations may be co-infused in any conventional form with one or more member selected from the group comprising infusion fluids, therapeutic compounds, nutritious fluids, anti-microbial fluids, buffering and stabilizing agents. Optionally, therapeutic components including, but are not limited to, anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies, may be co-infused with the inventive formulations.

Co-infusion in the context of this invention is defined to mean the infusion of more than one therapeutic agent in a course of coordinated treatment to achieve an improved clinical outcome. Such co-infusion may be simultaneous, overlapping, or sequential. In one particular example, co-infusion of the pharmaceutical formulations and infusion fluids may be performed through Y-type connector.

The pharmacokinetics and metabolism of intravenously administered the pharmaceutical formulations resemble the pharmacokinetics and metabolism of intravenously administered the inventive compound.

4. Combination Therapy with Inventive Pharmaceutical Compositions

The compounds or pharmaceutical formulations of the present invention may be used in conjunction with a cytidine analog, such as 5-aza-2'-deoxycytidine (decitabine), and 5-aza-cytidine (azacitidine).

Decitabine is an antagonist of its related natural nucleoside, deoxycytidine. The only structural difference between these two compounds is the presence of a nitrogen at position 5 of the cytosine ring in decitabine as compared to a carbon at this position for deoxycytidine.

Decitabine possesses multiple pharmacological characteristics. At a molecular level, it is S-phase dependent for incorporation into DNA. At a cellular level, decitabine can induce cell differentiation and exert hematological toxicity.

The most prominent function of decitabine is its ability to specifically and potently inhibit DNA methylation. As described above for methylation of cytosine in CpG islands as an example, methylation of cytosine to 5-methylcytosine occurs at the level of DNA. Inside the cell, decitabine is first converted into its active form, the phosphorylated 5-aza-deoxycytidine, by deoxycytidine kinase which is primarily synthesized during the S phase of the cell cycle. The affinity of decitabine for the catalytical site of deoxycytidine kinase is similar to the natural substrate, deoxycytidine. After conversion to its triphosphate form by deoxycytidine kinase, decitabine is incorporated into replicating DNA at a rate similar to that of the natural substrate, dCTP. Bouchard and Momparler (1983) *Mol. Pharmacol.* 24:109-114.

Incorporation of decitabine into the DNA strand has a hypomethylation effect. Each class of differentiated cells has its own distinct methylation pattern. After chromosomal duplication, in order to conserve this pattern of methylation, the 5-methylcytosine on the parental strand serves to direct methylation on the complementary daughter DNA strand. Substituting carbon at the 5 position of the cytosine for a nitrogen interferes with this normal process of DNA methylation. The replacement of 5-methylcytosine with decitabine at a specific site of methylation produces an irreversible inactivation of DNA methyltransferase, presumably due to formation of a covalent bond between the enzyme and decitabine. Juttermann et al. (1994) *Proc. Natl. Acad. Sci. USA* 91:11797-11801. By specifically inhibiting DNA methyltransferase, the enzyme required for methylation, the aberrant methylation of the tumor suppressor genes can be prevented.

The compounds or pharmaceutical formulations of the present invention may be used in conjunction with inhibitors of histone deacetylase (HDAC) to further modulate transcription of genes, e.g., to reestablish transcription of genes silenced by hypermethylation and acetylation of histones, in a synergistic manner.

The compounds or pharmaceutical formulations of the present invention may be used in conjunction with inhibitors of histone deacetylase (HDAC) to further modulate transcription of genes, e.g., to reestablish transcription of genes silenced by hypermethylation and acetylation of histones, in a synergistic manner.

HDAC plays important roles in transcription silencing of genes. The amount of acetylation on the histones is controlled by the opposing activities of two types of enzymes, histone acetyl transferase (HATs) and histone deacetylases (HDACs). Substrates for these enzymes include e-amino groups of lysine residues located in the amino-terminal tails of the histones H3, H4, H2A, and H2B. These amino acid residues are acetylated by HATs and deacetylated by HDACs. With the removal of the acetyl groups from the histone lysine by HDACs, a positive charge is restored to the lysine residue, thereby condensing the structure of nucleosome and silencing the genes contained within. Thus, to activate these genes silenced by deacetylase of histones, the activity of HDACs should be inhibited. With the inhibition of HDAC, histones are acetylated and the DNA that is tightly wrapped around a deacetylated histone core relaxes. The opening of DNA conformation leads to expression of specific genes.

In addition to deacetylation of histones, HDACs may also regulated gene expression by deacetylating transcription factors, such as p53 (a tumor suppressor gene), GATA-1, TFIIE, and TFIIF. Gu and Roeder (1997) *Cell* 90:595-606 (p53); and Boyes et al. (1998) *Nature* 396:594-598 (GATA-1). HDACs also participate in cell cycle regulation, for example, by transcription repression which is mediated by RB tumor suppressor proteins recruiting HDACs. Brehm et al. (1998) *Nature* 391:597-601. Thus, inhibition of HDACs should activate expression of tumor suppressor genes such as p53 and RB and as a result promote cell growth arrest, differentiation and apoptosis induced by these genes.

As described above, aberrant transcriptional silencing of a number of genes, such as tumor suppressor genes, is directly related to pathogenesis of cancer and other diseases. Methylation of cytosine residues in DNA and removal of acetyl groups from histones are the two primary mechanisms for gene silencing. Due to methylation and/or histone deacetylase of cancer-related genes, expression of these genes is suppressed or completely silenced. Meanwhile, expression of these genes is required for induction of growth arrest, differentiation, and/or apoptotic cell death of transformed cells. Inaction of these genes in the transformed cells leads to uncontrolled proliferation of these cells, which eventually results in cancer.

By combining the inventive compounds/compositions with HDAC inhibitors, genes required for induction of growth arrest, differentiation and cell death of transformed cells can be reactivated effectively. The inventive compounds/compositions inhibit methylation of DNA for the genes, especially in the regulatory region, thus resulting in activation of transcription of the gene. Meanwhile, HDAC inhibitors inhibit deacetylase of the histones in the nucleosomal core of the gene, thus resulting in net increase of the acetylation of histones, which, in turn, activates transcription of the gene. By exploiting these two complementary mechanisms, the combination therapy may reestablish gene transcription more effectively and, ideally, in a synergistic manner. A combination therapy having synergistic effects should require a less amount of each inhibitor than it being used alone, thus reducing potential side effects associated systemic administration of high dosages of the inhibitors and improving therapeutic index.

Many anticancer agents exert their anti-cancer effects by triggering signal transduction cascades involving proteins encoded by these tumor suppressor genes. With insufficient expression of these genes in cancer cells, the anti-cancer effects of these anti-neoplastic agents may be severely reduced or completely eradicated. Through reactivation or re-expression of these genes that are epigenetically silenced by DNA methylation and histone deacetylase, the intrinsic defense mechanisms of the body are mobilized to combat the disease by restoration of the tumor-suppressing functions to cancer cells in response to signals sent by the anti-cancer agent administered. Such stimulation of the intrinsic tumor suppressing functions of the body should lead to the requirement of lower dosage of the anticancer agent, thus resulting in a higher therapeutic index (i.e., greater efficacy and lower toxicity) of the agent.

Inhibitors of HDACs include, but are not limited to, the following structural classes: 1) hydroxamic acids, 2) cyclic peptides, 3) benzamides, and 4) short-chain fatty acids.

Examples of hydroxamic acids and hydroxamic acid derivatives, but are not limited to, trichostatin A (TSA), suberoylanilide hydroxamic acid (SAHA), oxamflatin, suberic bishydroxamic acid (SBHA), m-carboxy-cinnamic acid bishydroxamic acid (CBHA), and pyroxamide. TSA was isolated as an antifungal antibiotic (Tsuji et al (1976) *J. Antibiot* (Tokyo) 29:1-6) and found to be a potent inhibitor of mammalian HDAC (Yoshida et al. (1990) *J. Biol. Chem.* 265: 17174-17179). The finding that TSA-resistant cell lines have an altered HDAC evidences that this enzyme is an important target for TSA. Other hydroxamic acid-based HDAC inhibitors, SAHA, SBHA, and CBHA are synthetic compounds that are able to inhibit HDAC at micromolar concentration or lower in vitro or in vivo. Glick et al. (1999) *Cancer Res.* 59:4392-4399. These hydroxamic acid-based HDAC inhibitors all possess an essential structural feature: a polar hydroxamic terminal linked through a hydrophobic methylene spacer (e.g., 6 carbon at length) to another polar site which is attached to a terminal hydrophobic moiety (e.g., benzene ring). Compounds developed having such essential features also fall within the scope of the hydroxamic acids that may be used as HDAC inhibitors.

Cyclic peptides used as HDAC inhibitors are mainly cyclic tetrapeptides. Examples of cyclic peptides include, but are not limited to, trapoxin A, apicidin and FR901228. Trapoxin A is a cyclic tetrapeptide that contains a 2-amino-8-oxo-9,10-epoxy-decanoyl (AOE) moiety. Kijima et al. (1993) *J. Biol. Chem.* 268:22429-22435. Apicidin is a fungal metabolite that exhibits potent, broad-spectrum antiprotozoal activity and inhibits HDAC activity at nanomolar concentrations. Darkin-Rattray et al. (1996) *Proc. Natl. Acad. Sci. USA.* 93; 13143-13147. FR901228 is a depsipeptide that is isolated from *Chromobacterium violaceum*, and has been shown to inhibit HDAC activity at micromolar concentrations.

Examples of benzamides include but are not limited to MS-27-275. Saito et al. (1990) *Proc. Natl. Acad. Sci. USA.* 96:4592-4597. Examples of short-chain fatty acids include but are not limited to butyrates (e.g., butyric acid, arginine butyrate and phenylbutyrate (PB)). Newmark et al. (1994) *Cancer Lett.* 78:1-5; and Carducci et al. (1997) *Anticancer Res.* 17:3972-3973. In addition, depudecin which has been shown to inhibit HDAC at micromolar concentrations (Kwon et al. (1998) *Proc. Natl. Acad. Sci. USA.* 95:3356-3361) also falls within the scope of histone deacetylase inhibitor of the present invention.

The compounds or pharmaceutical formulations of the present invention may also be used in conjunction with other therapeutic components including but not limiting to antineoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies.

In one embodiment, an alkylating agent is used in combination with and/or added to the inventive compound/formulation. Examples of alkylating agents include, but are not limited to bischloroethylamines (nitrogen mustards, e.g., chlorambucil, cyclophosphamide, ifosfamide, mechlorethamine, melphalan, uracil mustard), aziridines (e.g., thiotepa), alkyl alkone sulfonates (e.g., busulfan), nitrosoureas (e.g., carmustine, lomustine, streptozocin), non-classic alkylating agents (altretamine, dacarbazine, and procarbazine), platinum compounds (carboplastin and cisplatin).

In another embodiment, cisplatin, carboplatin or cyclophosphamide is used in combination with and/or added to the inventive compound/formulation.

In another embodiment, a member of the retinoids superfamily is used in combination with and/or added to the inventive compound/formulation. Retinoids are a family of structurally and functionally related molecules that are derived or related to vitamin A (all-trans-retinol). Examples of retinoid include, but are not limited to, all-trans-retinol, all-trans-retinoic acid (tretinoin), 13-cis retinoic acid (isotretinoin) and 9-cis-retinoic acid.

In yet another embodiment, a hormonal agent is used in combination with and/or added to the inventive compound/formulation. Examples of such a hormonal agent are synthetic estrogens (e.g., diethylstibestrol), antiestrogens (e.g., tamoxifen, toremifene, fluoxymesterol and raloxifene), anti-androgens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

In yet another embodiment, a plant-derived agent is used in combination with and/or added to the inventive compound/formulation. Examples of plant-derived agents include, but are not limited to, vinca alkaloids (e.g., vincristine, vinblastine, vindesine, vinzolidine and vinorelbine), camptothecin (20(S)-camptothecin, 9-nitro-20(S)-camptothecin, and 9-amino-20(S)-camptothecin), podophyllotoxins (e.g., etoposide (VP-16) and teniposide (VM-26)), and taxanes (e.g., paclitaxel and docetaxel).

In yet another embodiment, a biologic agent is used in combination with and/or added to the inventive compound/formulation, such as immuno-modulating proteins such as cytokines, monoclonal antibodies against tumor antigens, tumor suppressor genes, and cancer vaccines.

Examples of interleukins that may be used in combination with and/or added to the inventive compound/formulation include, but are not limited to, interleukin 2 (IL-2), and interleukin 4 (IL-4), interleukin 12 (IL-12). Examples of interferons that may be used in conjunction with decitabine-glycerin formulations include, but are not limited to, interferon α, interferon β (fibroblast interferon) and interferon γ (fibroblast interferon). Examples of such cytokines include, but are not limited to erythropoietin (epoietin), granulocyte-CSF (filgrastim), and granulocyte, macrophage-CSF (sargramostim). Immuno-modulating agents other than cytokines include, but are not limited to bacillus Calmette-Guerin, levamisole, and octreotide.

Example of monoclonal antibodies against tumor antigens that can be used in conjunction with the inventive formulations include, but are not limited to, HERCEPTIN® (Trastuzumab), RITUXAN® (Rituximab), MYLOTARG® (anti-CD33 antibody), and CAMPATH® (anti-CD52 antibody).

In yet another embodiment, a kinase inhibitor is used in combination with and/or added to the inventive compound/formulation for treating diseases associated with abnormal kinase activity.

In one variation, the tyrosine kinase inhibitor is imatanib mesylate (e.g., Gleevec®). Imatanib mesylate is a protein tyrosine kinase inhibitor that inhibits the Bcr-Abl tyrosine kinase created by the Philadelphia chromosome abnormality in CML. Imatanib mesylate achieves this inhibitory result through binding to the adenosine triphosphate-binding site of the Bcr-Abl tyrosine kinase, which prevents phosphorylation of substrates and related malignant transformation. Through inhibition of this kinase, it is believed that imatinib mesylate inhibits cell proliferation and induces apoptosis. T. Schindler et al (2000) *Science* 289:1938-1942.

In another variation, the kinase is a serine/threonine kinase such as a Raf kinase; and the kinase inhibitor is BAY 43-9006.

In yet another variation, the kinase is a protein kinase such as a Raf-mitogen-activated protein kinase (MEK) and protein kinase B (Akt) kinase.

In yet another variation, the kinase is an extracellular signal-regulated kinase (ERK). Examples of the inhibitor of ERK include but are not limited to PD98059, PD184352, and U0126.

In yet another variation, the kinase is a phosphatidylinositol 3'-kinase (PI3K). Examples of the inhibitor of PI3K include but are not limited to LY294002.

In a particular variation, the kinase is a tyrosine kinase. The tyrosine kinase may be a receptor tyrosine kinase and non-receptor tyrosine kinase.

Examples of the receptor tyrosine kinase include, but are not limited to, epidermal growth factor receptor family (EGFR), platelet-derived growth factor receptor (PDGFR) family, vascular endothelial growth factor receptor (VEGFR) family, nerve growth factor receptor (NGFR) family, fibroblast growth factor receptor family (FGFR) insulin receptor family, ephrin receptor family, Met family, and Ror family.

Examples of the epidermal growth factor receptor family include, but are not limited to, HER1, HER2/neu, HER3, and HER4.

Examples of the inhibitors of epidermal growth factor receptor family include, but are not limited to, HERCEPTIN®, ZD1839 (IRESSA®), PD168393, CI1033, IMC-C225, EKB-569, and inhibitors binding covalently to Cys residues of the receptor tyrosine kinase.

Examples of diseases associated with abnormal activity of the epidermal growth factor receptor family, include, but are not limited to, epithelial tumor, carcinoma, carcinoma of upper aerodigestive tract, lung cancer, and non-small cell lung cancer.

Examples of the vascular endothelial growth factor receptor family include, but are not limited to, VEGFR1, VEGFR2, and VEGFR3.

An example of the inhibitor of the vascular endothelial growth factor receptor family includes, but is not limited to, SU6668.

Examples of the disease associated with abnormal activity of the vascular endothelial growth factor receptor family include, but are not limited to, solid and metastasis-prone tumors.

Examples of the nerve growth factor receptor family include, but are not limited to, trk, trkB and trkC.

Examples of the inhibitors of the nerve growth factor receptor family include, but are not limited to, CEP-701, CEP-751, and indocarbazole compound.

Examples of the diseases associated with abnormal activity of the nerve growth factor receptor family include, but are not limited to, prostate, colon, papillary and thyroid cancers, neuromas and osteoblastomas.

Examples of the Met family include, but are not limited to, Met, TPR-Met, Ron, c-Sea, and v-Sea.

Examples of disease associated with activity of the receptor tyrosine kinase from Met family include, but are not limited to, invasively in-growing tumor, carcinoma, papillary carcinoma of thyroid gland, colon, carcinoma, renal carcinoma, pancreatic carcinoma, ovarian carcinoma, head and neck squamous carcinoma.

Examples of the non-receptor tyrosine kinase include, but are not limited to, c-kit family, Src family, Fes family, JAK family, Fak family, Btk family, Syk/ZAP-70 family, and Abl family.

Examples of the non-receptor tyrosine kinases from the Src family include, but are not limited to, Src, c-Src, v-Src, Yes, c-Yes, v-Yes, Fyn, Lyn, Lck, Blk, Hck, Fgr, c-Fgr, v-Fgr, p56lck, Tk1, Csk, and Ctk.

Examples of the inhibitors of the non-receptor tyrosine kinase from the Src family include, but are not limited to, SU101 CGP 57418B.

Examples of the diseases associated with activity of the non-receptor tyrosine kinase from the Src family include, but are not limited to, breast cancer, carcinoma, myeloma, leukemia, and neuroblastoma.

Examples of the non-receptor tyrosine kinases from the Fes family include, but are not limited to, c-fes/fps, v-fps/fes, p94-c-fes-related protein, and Fer.

Examples of the diseases associated with activity of the non-receptor tyrosine kinase from the Fes family include, but are not limited to, tumor of mesenchymal origin and tumor of hematopoietic origin.

Examples of the non-receptor tyrosine kinases from the JAK family include, but are not limited to, Jak1, Jak2, Tyk2, and Jak3.

Examples of the inhibitors of the non-receptor tyrosine kinase from the JAK family include, but are not limited to, tyrphostin, member of CIS/SOCS/Jab family, synthetic component AG490, dimethoxyquinazoline compound, 4-(phenyl)-amino-6,7-dimethoxyquinazoline, 4-(4'-hydroxyphenyl)-amino-6,7-dimethoxyquinazoline, 4-(3'-bromo-4'-hydroxylphenyl)-amino-6,7-dimethoxyquinazoline, and 4-(3',5'-dibromo-4'-hydroxylphenyl)-amino-6,7-dimethoxyquinazoline.

Examples of the diseases associated with activity of the non-receptor tyrosine kinase from JAK family include, but are not limited to, tumor of mesenchymal origin and tumor of hematopoietic origin.

Examples of the non-receptor tyrosine kinases from the Fak family include, but are not limited to, Fak and CAK.beta./Pyk2/RAFTK.

Examples of the inhibitors of the non-receptor tyrosine kinases from the Fak family include, but are not limited to, a dominant negative mutant S1034-FRNK; a metabolite FTY720 from *Isaria sinclarii*, and FAK antisense oligonucleotide ISIS 15421.

Examples of the diseases associated with abnormal activity of the non-receptor tyrosine kinases from Fak family include, but are not limited to, human carcinoma, metastasis-prone tumor, and tumor of hematopoietic origin.

Examples of the non-receptor tyrosine kinase from the Btk family include, but are not limited to, Btk/Atk, Itk/Emt/Tsk, Bmx/Etk, and Itk, Tec, Bmx, and Rlk.

Examples of the inhibitors of the non-receptor tyrosine kinases from Btk family include, but are not limited to, alpha-cyano-beta-hydroxy-beta-met-hyl-N-(2,5-dibromophenyl) propenamide.

Examples of the diseases associated with abnormal activity of the non-receptor tyrosine kinase from the Btk family include, but are not limited to, B-lineage leukemia and lymphoma.

Examples of the non-receptor tyrosine kinases from the Syk/ZAP-70 family include, but are not limited to, Syk and ZAP-70.

Examples of the inhibitors of the non-receptor tyrosine kinases from the Syk/ZAP-70 family include, but are not limited to, piceatannol, 3,4-dimethyl-10-(3-aminopropyl)-9-acridone oxalate, acridone-related compound, Lys-Leu-Ile-Leu-Phe-Leu-Leu-Leu [SEQ ID NO: 1) peptide, and peptide containing Lys-Leu-Ile-Leu-Phe-Leu-Leu-Leu motif.

Examples of the diseases associated with abnormal activity of the non-receptor tyrosine kinases from the Syk/ZAP-70 family include, but are not limited to, benign breast cancer, breast cancer, and tumor of mesenchymal origin.

5. Indications for Compounds or Pharmaceutical Compositions of the Present Invention The pharmaceutical formulations according to the present invention may be used to treat a wide variety of diseases, preferably those associated with aberrant DNA methylation.

Preferable indications that may be treated using the pharmaceutical formulations of the present invention include those often involving undesirable or uncontrolled cell proliferation. Such indications include benign tumors, various types of cancers such as primary tumors and tumor metastasis, restenosis (e.g., coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancer or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomymater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may also be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In another embodiment, the pharmaceutical formulations of the present invention may be used for treating diseases associated with undesired or abnormal angiogenesis. The method comprises administering to a patient suffering from undesired or abnormal angiogenesis the pharmaceutical formulations of the present invention alone, or in combination with anti-neoplastic agent whose activity as an anti-neoplastic agent in vivo is adversely affected by high levels of DNA methylation. The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the pharmaceutical formulations of the present invention may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment, the pharmaceutical formulations of the present invention may be used for treating chronic inflammatory diseases associated with abnormal angiogenesis. The method comprises administering to a patient suffering from a chronic inflammatory disease associated with abnormal angiogenesis the pharmaceutical formulations of the present invention alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the pharmaceutical formulations of the present invention should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the pharmaceutical formulations of the present invention alone or in conjunction with other anti-RA agents may prevent the formation of new blood vessels necessary to maintain the chronic inflammation and provide the RA patient relief from the symptoms.

In yet another embodiment, the pharmaceutical formulations of the present invention may be used for treating diseases associated with abnormal hemoglobin synthesis. The method comprises administering the pharmaceutical formulations of the present invention to a patient suffering from disease associated with abnormal hemoglobin synthesis. Decitabine containing formulations stimulate fetal hemoglobin synthesis because the mechanism of incorporation into DNA is associated with DNA hypomethylation. Examples of diseases associated with abnormal hemoglobin synthesis include, but are not limited to, sickle cell anemia and β-thalassemia.

In yet another embodiment, the pharmaceutical formulations of the present invention may be used to control intracellular gene expression. The method comprises administering the pharmaceutical formulations of the present invention to a patient suffering from disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

Gene activation facilitated by the pharmaceutical formulations of the present invention may induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Although exemplary embodiments of the present invention have been described and depicted, it will be apparent to the artisan of ordinary skill that a number of changes, modifications, or alterations to the invention as described herein may be made, none of which depart from the spirit of the present invention. All such changes, modifications, and alterations should therefore be seen as within the scope of the present invention.

EXAMPLES

The following examples are representative of the invention, and provide detailed methods for preparing the compounds of the invention. In these examples, elemental analyses were carried out in the Microchemical Laboratory, University of Otago, Dunedin, NZ. Melting points were determined on an Electrothermal 2300 Melting Point Apparatus. NMR spectra were obtained on a Bruker Avance-400 spectrometer at 400 MHz for $^1$H and 100 MHz for 13C spectra, referenced to Me4Si. Mass spectra were determined on a VG-70SE mass spectrometer using an ionizing potential of 70 eV at a nominal resolution of 1000. High-resolution spectra were obtained at nominal resolutions of 3000, 5000, or 10000 as appropriate. All spectra were obtained as electron impact (EI) using PFK as the reference unless otherwise stated. Column chromatography was carried out on silica gel, (Merck 230-400 mesh) unless otherwise stated.

Example A

Preparation of 1-methyl-4-(3-{[4-(4-quinolinylamino)benzoyl]amino}anilino)pyridinium chloride (Cpd. A)

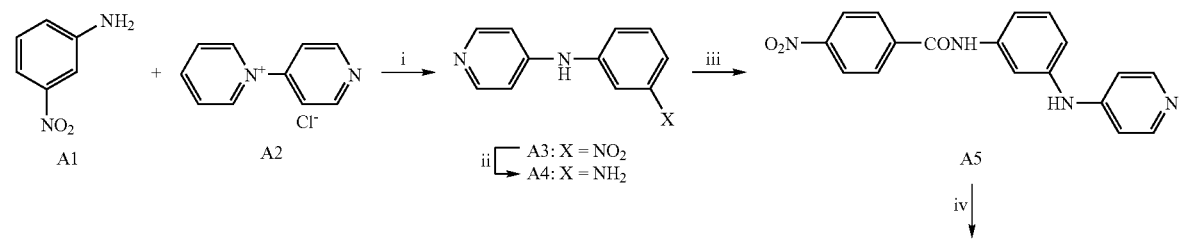

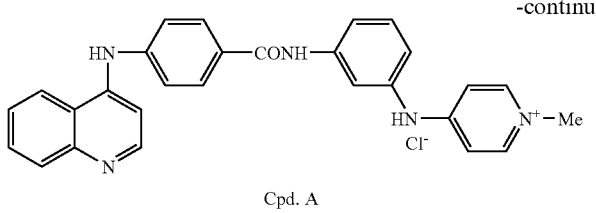

Cpd. A

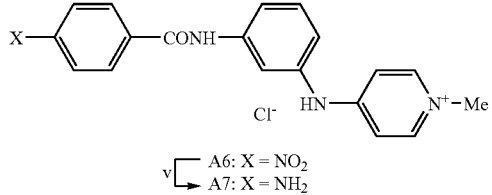

A6: X = NO₂
A7: X = NH₂

(i) TsOH/180° C.; (ii) H₂/Pd/C/MeOH; (iii) 4-nitrobenzoyl chloride/pyridine/dioxane; (iv) DMF/MeOTs/20° C., then ion-exchange; (v) Fe dust/EtOH/H₂O; (vi) 4-chloroquinoline/MeOH/cat. HCl/reflux.

N-(3-Nitrophenyl)-4-pyridinamine (A3). A suspension of p-toluenesulfonic acid monohydrate (17.4 g, 0.126 mol) in benzene was azeotroped for 10 h. Phenol (50g) was added and the mixture was azeotroped for 2 h, then 4-pyridylpyridinium chloride (26.6 g, 0.138 mmol) and 3-nitroaniline (17.4 g, 0.126 mmol) was added and the mixture was azeotroped for 3 h. Benzene was removed under reduced pressure and the resulting black residue was heated to 180° C. for 1 h. The reaction mixture was cooled to 20° C., and 4N NaOH (150 mL) was added. The mixture was stirred for 30 min, and then diluted with water (2 L). This mixture was stirred in $CH_2Cl_2$ (1 L) and the resulting precipitate was filtered and washed with more $CH_2Cl_2$. The solid was recrystallized from MeOH/$H_2O$ to give A3 (11.9 g), as a yellow solid: mp (MeOH/$H_2O$) 182-184° C. Further material was recovered from $CH_2Cl_2$ washes, by drying over $Na_2SO_4$ and evaporation to dryness. The residue was dissolved in $CH_2Cl_2$ (100 mL) and hexanes (200 mL) were added, and the mixture was stirred for 16 h. The resulting precipitate was filtered and washed with ether to remove any unreacted 3-nitroaniline, and the solid was crystallized from MeOH/$H_2O$ to give additional A3 (3.2 g; total yield 15.7 g, 58%); $^1$H NMR [$(CD_3)_2SO$] δ 9.28 (s, 1H, NH), 8.31-8.29 (m, 2 H, H-2,6), 7.95 (t, J=2.1 Hz, 1 H, H-2'), 7.82-7.79 (m, 1 H, H-4'), 7.65-7.57 (m, 2 H, H-5', H-6'), 7.03-7.02 (m, 2 H, H-3, H-5), $^{13}$C NMR [$(CD_3)_2SO$] δ150.5 (2×C), 148.8, 148.6, 142.2, 130.8, 124.8, 116.2, 112.7, 110.2 (2×C); Analysis calc. for $C_{11}H_9N_3O_2$: C, 61.4; H, 4.2; N, 19.5; found, C, 64.5; H, 4.3; N. 19.7%.

$N^1$-(4-Pyridinyl)-1,3-benzenediamine (A4). A suspension of compound A3 (7.26 g, 33.7 mmol) and 10% Pd/C in MeOH was hydrogenated for 2 h, filtered through a pad of Celite, and solvent evaporated. The residue was recrystallized from MeOH/$H_2O$ to give A4 as a pale yellow powder (5.43 g, 83%): mp (MeOH/$H_2O$) 170-171° C. $^1$H NMR [$(CD_3)_2SO$] δ8.48 (bs, 1 H, NH), 8.14-8.12 (m, 2 H, H-2'&6'), 6.96 (t, J=7.9 Hz, 1 H, H-5), 6.86-6.84 (m, 2 H, H-3' & 6'), 6.43 (t, J=2.0 Hz, 1 H, H-2), 6.32 (dd, J=7.8, 1.3H, 1 H, H-6), 6.26 (dd, J=7.8, 1.5 Hz, 1 H, H-4) 5.07 (br s, 2 H, $NH_2$); HRMS ($EI^+$) calc. for $C_{11}H_{11}N_3$ ($M^+$) m/z 185.0953, found 185.0945; Anal. calc. for $C_{11}H_{11}N_3 \cdot 0.125 H_2O$: C, 70.5; H, 6.1; N, 22.5; found, C, 70.6; H, 6.0; N, 22.7%.

N-(4-Nitrophenyl)-3-(4-pyridinylamino)benzamide (A5). 4-Nitrobenzoic acid (4.3 g, 16.36 mmol) was suspended in $SOCl_2$ (30 mL), 2 drops of DMF were added, and the mixture was refluxed for 1 h (until a clear solution was obtained). The reaction mixture was cooled to room temperature and excess $SOCl_2$ was removed under vacuum. The resulting residue was dissolved in 1,4-dioxane and added to a suspension of A4 (3.0 g, 16.20 mmol) in 1,4-dioxane (300 mL) containing pyridine (8 mL). The reaction mixture was stirred 16 h at 50° C., and the solvent was then evaporated. The residue was stirred in dilute aqueous ammonia, and the resulting precipitate was filtered and crystallized from MeOH to give A5 (5.3 g, 79%): mp (MeOH) 219-222° C.; $^1$H NMR [$(CD_3)_2SO$] δ10.63 (s, 1 H, NH), 9.04 (s, 1 H, NH), 8.37 (d, J=8.9 Hz, 2 H, ArH), 8.24-8.18 (m, 4 H, ArH), 7.81 (bs, 1 H, ArH), 7.45 (d, J=8.5 Hz, 1 H, ArH), 7.34 (t, J=8.0 Hz, 1 H, ArH), 6.99-6.95 (m, 3 H, ArH), $^{13}$C NMR [$(CD_3)_2SO$] δ 166.9, 164.0, 150.3, 149.4 (2×C), 149.1, 140.5, 139.6, 129.5 (2×C), 129.2, 123.5 (2×C), 123.4, 115.8, 114.6, 111.6, 109; HRMS ($FAB^+$) calc. for $Cs_8H_{15}N_4O_3$ ($M^{+1}$) m/z 335.1144, found 335.1154.

1-Methyl-4-{3-[(4-nitroanilino)carbonyl]anilino}pyridinium chloride (A6). To a solution of A5 (507 mg, 1.51 mmol) in DMF (2 mL) was added methyl-p-toluene sulfonate (3 mL), and the reaction mixture was stirred at room temperature for 20 h. Solvent was removed under reduced pressure, and the residue re-dissolved in MeOH. This solution was evaporated to dryness, and the residue crystallized from MeOH/EtOAc to give A6 as a tosylate salt (530 mg, 67%). This was converted to a chloride salt by ion-exchange, as follows. $AG^R$ 1-$X_4$ resin 200-400 chloride form (7g) was washed with water and packed in a column. Tosylate A6 (530 mg) was stirred in pre-washed resin (2g), and the resulting slurry was loaded onto the column. The column was then eluted with water, and fractions containing the compound were combined and evaporated to dryness. The residue was azeotroped with MeOH (3×20 mL), and finally reprecipitated from MeOH/EtOAc to give A6 as the chloride salt (317 mg 54%): mp (MeOH/EtOAc) 295-298° C. $^1$H NMR [$(CD_3)_2SO$] δ10.82 (s, 1 H, NH), 10.76 (s, 1 H, NH), 8.38 (d, J=8.9 Hz, 2 H, ArH), 8.31 (d, J=7.5 Hz, 2 H, ArH), 8.21 (d, J=8.9 Hz, 2 H, ArH), 7.96 (t, J=1.9 Hz, 1H, ArH), 7.64 (dd, J=8.7, 1.1 Hz, 1 H, ArH), 7.50 (t, J=5.4 Hz, 1 H, ArH), 7.22 (d, J=7.6 Hz, 2 H, ArH), 7.11 (dd, J=7.9, 1.3 Hz, 1 H, ArH), 3.97 (s, 3 H, $N^+CH_3$); HRMS ($FAB^+$) calc. for $C_{19}H_{17}N_4O_3$ ($M^{+1}$) m/z 349.1301, found 349.1303.

4-{3-[(4-Ammoniobenzoyl)amino]anilino}-1-methylpyridinium dichloride (A7). A6 (1.57 g, 4.08 mmol) was dissolved in 5:1 $H_2O$:EtOH (62 mL), Fe dust was added (1.1 g), and the resulting suspension was refluxed with vigorous stirring for 5 h. The hot reaction mixture was filtered through a pad of Celite, and the Celite pad was washed with hot EtOH. The combined EtOH fractions were evaporated to dryness, and the residue extracted with warm water. This solution was evaporated to dryness, and the residue was dried by azeotroping with methanol (3×30 mL). The residue was dissolved in MeOH (20 mL), methanolic HCl (1.25 M, 5 mL) was added, and the solution was stirred for 30 min. The solution was evaporated to dryness, and the residue dried by azeotroping with MeOH (3×30 mL). The residue was finally crystallized from MeOH/EtOAc to give A7 (913 mg, 63%) as a white solid: mp (MeOH/EtOAc) 269-273° C.; $^1$H NMR [$(CD_3)_2SO$] δ10.76 (s, 1 H, NH), 10.05 (s, 1 H, NH), 8.29 (d, J=7.4 Hz, 2 H, ArH), 7.95 (t, J=1.9 Hz, 1 H, ArH), 7.78 (d, J=8.7 Hz, 2 H, ArH), 7.60 (dd, J=8.7, 1.1 Hz, 1 H, ArH), 7.60 (t, J=8.1 Hz, 1 H ArH), 7.20 (d, J=7.5 Hz, 2 H, ArH), 7.00 (dd, J=7.9, 1.4 Hz, 1H, ArH), 6.72 (d, J=8.6 Hz, 2 H, ArH), 3.96 (s, 3H, $N^+CH_3$) the signal for $NH_2$ was not observed; HRMS ($FAB^+$)

calc. for $C_{19}H_{19}N_4O$ (M$^+$) m/z 319.1559, found 319.1562. Analysis CRL11720 calc.CHN for $C_{19}H_{20}N_4Cl_2O$: C, 58.3; H, 5.4; N, 14.3; found, C, 58.7; H, 5.3; N, 14.5%.

1-Methyl-4-(3-{[4-(4-quinolinylamino)benzoyl]amino}anilino)-pyridinium chloride (Cpd. A). To a suspension of A7 (200 mg, 0.51 mmol) in MeOH (20 mL) was added 4-chloroquinoline (100 mg, 0.61 mmol), and the mixture was heated at reflux for 1 h (until a clear solution was obtained). A drop of c.HCl was then added, and refluxing was continued for a further 20 h. The reaction mixture was evaporated to dryness, and the residue was dissolved in MeOH (10 mL). EtOAc (50 mL) was then added, and the MeOH was boiled off. The resulting precipitate was filtered, washed with EtOAc, and crystallized from MeOH/EtOAc to give Cpd. A (214 mg, 81%) as a pale yellow solid: mp 253-257° C.; $^1$H NMR [(CD$_3$)$_2$SO] δ11.07 (br, 1 H, NH), 10.79 (s, 1 H, NH), 10.60 (s, 1 H, NH), 8.84 (d, J=13.5 Hz, 1 H, ArH), 8.61 (d, J=6.9 Hz, 1 H, ArH), 8.31 (d, J=7.4 Hz, 2H, ArH), 8.18 (d, J=8.6 Hz, 2H, ArH), 8.12-8.04 (m, 2 H, ArH), 7.99 (br s, 1 H, ArH), 7.84 (t, J=7.2 Hz, 1H, ArH), 7.68 (d, J=8.5 Hz, 2 H, ArH), 7.49 (t, J=8.1 Hz, 1 H, ArH), 7.23 (d, J=7.5 Hz, 2 H, ArH), 7.10 (br d, J=7.8 Hz, 1 H, ArH), 7.01 (d, J=6.7 Hz, 1 H, ArH), 3.98 (s, 3 H, N$^+$CH$_3$; $^{13}$C NMR [(CD$_3$)$_2$SO] δ164.8, 154.6, 154.3, 144.2, 142.8, 140.5, 140.3, 138.3, 137.3, 133.8, 132.5, 129.8, 129.4 (2×C), 127.0, 124.4 (2×C), 124.1, 120.2, 118.0, 117.9, 117.5, 114.5, 109.2, 100.3, 44.6, enhancement of two of the carbon signals was difficult to observe; HRMS (FAB$^+$) calc. For $C_{28}H_{24}N_5O$ 446.1981, found 446.1975; Anal. Calc.CHN for $C_{28}H_{25}Cl_2N_5O$. 2.25H$_2$O: C, 60.2; H, 5.3; N, 12.5; found, C, 60.1; H, 5.3; N, 12.5%.

Example B

Preparation of 1-methyl-4-(4-(4-(quinolin-4-ylamino)benzamido)phenylamino)pyridinium chloride hydrochloride (Cpd. B)

added, and the resulting mixture was refluxed under Dean-Stark conditions for approximately 2 h, until evolution of H$_2$O ceased. After this time, benzene was removed under reduced pressure, and the resulting black residue heated to 180° C. for 2 h. The residue was then cooled to room temperature, and basified thoroughly by addition of 4 N aqueous NaOH. The resulting solution was diluted with H$_2$O and CH$_2$Cl$_2$, and stirred for 2 h at room temperature. The resulting suspension was filtered through a pad of Celite to give a first batch of nitroaniline B3 (0.22 g) as a fine yellow solid. The filtrate was diluted with MeOH, re-basified with 4 N NaOH, and then extracted with EtOAc (×4). The combined organic extracts were washed with H$_2$O (×1), brine, and dried over MgSO$_4$. Solvent was removed under reduced pressure to afford a second batch of B3 (55g); $^1$H NMR [(CD$_3$)$_2$SO]: δ 7.16 (dd, J=4.76, 1.60 Hz, 2H, ArH), 7.33 (ddd, J=10.37, 5.32, 3.23 Hz, 2H, ArH), 8.18 (ddd, J=10.37, 5.32, 3.23 Hz, 2H, ArH), 8.38 (dd, J=4.72, 1.56 Hz, 2H, ArH), 9.71 (br s, Ar—NH—Ar). LCMS (APCI$^+$): 216 (100%).

N$^1$-(4-Pyridinyl)-1,4-benzenediamine (B4). Nitroaniline B3 (~55.00 g, ~0.26 mol) was brought to reflux in 2:1 EtOH:H$_2$O (500 mL), and then Fe dust (56.96 g, 1.02 mmol) and glacial acetic acid (10 mL) were added. The resulting mixture was refluxed for 30 min, and then cooled to room temperature. The reaction mixture was basified by addition of aqueous NH$_3$, and filtered to remove solids. Solvent was removed under reduced pressure to give B4 as a fluffy, crystalline magenta solid (28.49 g, 54% from B1); $^1$H NMR [(CD$_3$)$_2$SO]: δ 4.99 (br s, 2H, Ar—NH$_2$), 6.58 (m, 4H, ArH), 6.86 (ddd, J=9.66, 4.99, 3.04 Hz, 2H, ArH), 8.03 (d, J=6.28 Hz, 2H, ArH), 8.24 (s, 1H, Ar—NH—Ar). LCMS (APCI$^+$): 186 (100%).

N-(4-Nitrophenyl)-4-(4-pyridinylamino)benzamide (B5). To a solution of B4 (10.07 g, 54.37 mmol) in dry pyridine (21.90 mL, 271.82 mmol) was added a solution of 4-nitrobenzoyl chloride (10.09 g, 54.37 mmol) in dry dioxane (100 mL),

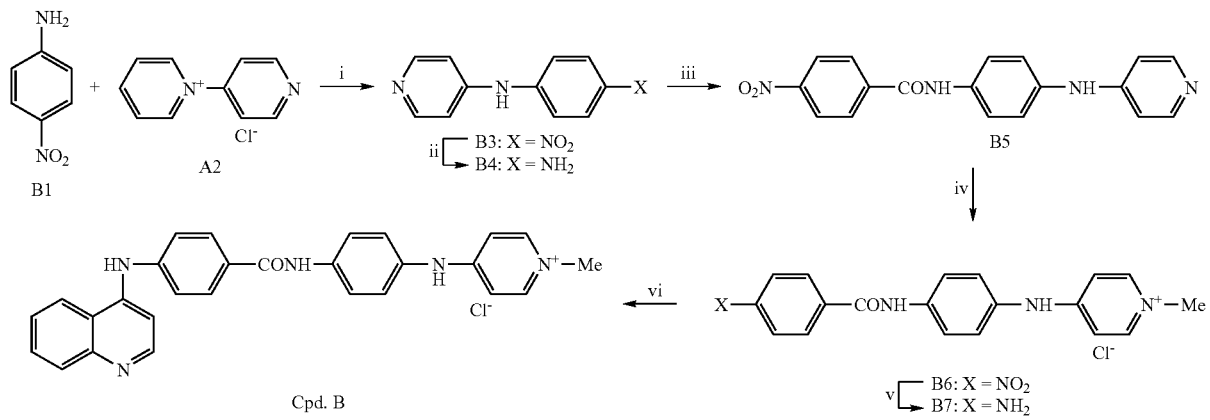

(i) TsOH/180° C.; (ii) H$_2$/Pd/C/MeOH; (iii) 4-nitrobenzoyl chloride/pyridine/dioxane; (iv) DMF/MeOTs/20° C., then ion exchange; (v) Fe dust/EtOH/H$_2$O; (vi) 4-chloroquinoline/MeOH/cat. HCl/reflux.

N-4-Nitrophenyl)-4-pyridinamine (B3). 4-Toluenesulfonic acid (53.80 g, 0.28 mol) was dissolved in benzene (200 mL), and the resulting solution refluxed under Dean-Stark conditions for approximately 96 h, until evolution of H$_2$O ceased. To this solution was added phenol (112.25 g, 1.19 mol), and the resulting mixture refluxed under Dean-Stark conditions for approximately 1 h, until evolution of H$_2$O ceased. After this time, 1-(4-pyridyl)-pyridinium chloride (59.95 g, 0.31 mol) (A2) and 4-nitroaniline (B1) were and the resulting mixture was heated at 50° C. for 2 h. After this time, the reaction mixture was cooled to room temperature and basified by addition of aqueous NH$_3$. The resulting precipitate was collected by filtration to give a first batch of amide B5 (3.47 g, 19%) as an amorphous orange-yellow solid. The filtrate was extracted with EtOAc (×4), and the combined organic extracts were washed with brine, and then evaporated to dryness to give a mixture of B4 and B5 (ca. 1:1 by $^1$H NMR). Re-treatment of this mixture with 4-nitrobenzoyl chloride at 50° C. for 12 h gave a further 4g of B5; $^1$H NMR [(CD$_3$)$_2$SO]: δ 6.86 (dd, J=4.82, 1.60 Hz, 2H, ArH), 7.21 (dt, J=9.86, 5.02, 3.00 Hz, 2H, ArH), 7.76 (d, J=8.84, 2H, ArH), 8.18 (m, 4H, ArH), 8.37 (ddd, J=9.23, 4.33, 2.34 Hz, 2H, ArH), 8.73 (s, 1H, ArNHAr), 10.52 (s, 1H, ArC(O)N-HAr). LCMS (APCI$^+$): 335 (100%).

1-Methyl-4-{4-[(4-nitroanilino)carbonyl] anilino}pyridinium chloride (B6). o a solution of amide B5 (5.62 g, 16.82 mmol) in dry DMF (110 mL) was added methyl tosylate (33.00 mL, 218.68 mmol), and the resulting mixture was stirred at room temperature for 12 h. After this time, the reaction mixture was filtered through a pad of Celite to give a first batch of the tosylate salt of 11 as an amorphous bright yellow solid (7.57 g, 86%). The filtrate was concentrated under reduced pressure until a precipitate formed, and this was collected by filtration through a pad of Celite to give a second batch of the tosylate salt of B6 (0.72 g, 8%). $^1$H NMR [(CD$_3$)$_2$SO]: δ 2.29 (s, 3H, $^-$O(O)$_2$SPhCH$_3$), 3.96 (s, 3H, R$_2$N$^{+-}$CH$_3$), 7.10 (m, 4H, O(O)$_2$SArHCH$_3$), 7.35 (d, J=8.84 Hz, 2H, ArH), 7.47 (d, J=8.08 Hz, 2H, ArH), 7.91 (d, J=8.86, 2H, ArH), 8.20 (dd, J=6.94, 1.94, ArH), 8.26 (d, J=7.45 Hz, 2H, ArH), 8.39 (m, 2H, ArH), 10.42 (s, 1H, ArNHAr), 10.70 (s, 1H, ArNHAr). (APCI$^+$): 349 (100%).

To a suspension of the tosylate salt of B6 (8.30 g, 15.97 mmol) in MeOH (~200 mL), was added ion-exchange resin (67g, pre-washed with H$_2$O) [1-X$_4$, BioRad AG, 200-400 chloride form]. The resulting suspension was loaded onto a column of more ion-exchange resin (70g, pre-washed with H$_2$O), and the column was eluted with MeOH. Solvent was removed under reduced pressure to afford chloride salt of B6 (6.47 g, 91%) as an amorphous yellow solid; $^1$H NMR [(CD$_3$)$_2$ SO]: δ 3.95 (s, 3H, R$_2$N$^{+-}$CH$_3$), 7.10 (m, 2H, ArH), 7.35 (d, J=7.93 Hz, 2H, ArH), 7.91 (d, J=8.52 Hz, 2H, ArH), 8.22 (m, 4H, ArH), 8.39 (d, J=8.76 Hz, 2H, ArH), 10.50 (br s, 1H, ArNHAr), 10.72 (s, 1H, ArNHAr). LCMS (APCI$^+$): 349 (100%).

4-{4-[(4-Ammoniobenzoyl)amino]anilino}-1-methylpyridinium dichloride (B7). To a refluxing suspension of amide B6 (6.47 g, 16.81 mmol) in 2:1 EtOH:H$_2$O (600 mL) were sequentially added Fe dust (3.76 g, 67.24 mmol) and glacial acetic acid (12 mL). The resulting mixture was refluxed for 2 h, and the hot reaction mixture was then filtered through a pad of Celite. Solvent was removed under reduced pressure, and the residue was re-dissolved in MeOH, and solvent again removed under reduced pressure. This latter process was repeated twice more, with a few drops of methanolic HCl (~4M) added in the final re-dissolution. Solvent was removed under reduced pressure, and the residue was recrystallized from MeOH:EtOAc to give amine B8 (6.35 g) as a khaki green-white solid, which was used without purification. $^1$H NMR [(CD$_3$)$_2$SO]: δ 3.94 (s, 3H, R$_2$N$^{+-}$CH$_3$), 6.85 (d, J=8.26 Hz, 2H, ArH), 7.12 (d, J=7.12 Hz, 2h, ArH), 7.29 (m, 2H, ArH), 7.83 (d, J=8.64 Hz, 2H, ArH), 7.89 (m, 2H, ArH), 8.24 (d, J=7.42 Hz, 2H, ArH), 10.10 (s, 1H, ArNHAr, 10.73 (s, 1H, ArH). LCMS (APCI$^+$): 319 (100%).

1-Methyl-4-[4-({4-[(6-nitro-4-quinolinyl)amino] benzoyl}amino)anilino]pyridinium chloride (Cpd. B). 4-Chloroquinoline (89 mg, 0.55 mmol) and 3 drops of cHCl were sequentially added to a solution of amine B7 (214 mg, 0.55 mmol) in dry MeOH (19 mL), and the resulting mixture was then refluxed for 31 h. After this time, solvent was removed under reduced pressure, and the resulting residue dried via two MeOH-azeotrope cycles. The residue was crystallized twice from MeOH:EtOAc, and then further purified by preparative HPLC, to afford Cpd. B as an amorphous yellow solid (68 mg, 24%). $^1$H NMR [(CD$_3$)$_2$SO]: 3.96 [s, 3H, ArN$^+$CH$_3$], 7.00 [d, J=6.92 Hz, 1H, ArH], 7.14 [d, J=7.29 Hz, 2H, ArH], 7.35 [d, J=8.86 Hz, 2H, ArH], 7.69 [d, J=8.58 Hz, 2H, ArH], 7.85 [t, J=15.42, 7.71 Hz, 1H, ArH], 7.96 [d, J=8.86, 2H, ArH], 8.07 [t, J=15.42, 7.71 Hz, 1H, ArH], 8.13 [d, J=7.76 Hz, 1H, ArH], 8.20 [d, J=8.58 Hz, 2H, ArH], 8.26 [d, J=7.39 Hz, 2H, ArH], 8.61 [d, J=6.92 Hz, 1H, ArH], 8.88 [d, J=8.43 Hz, 1H, ArH], 10.58 [s, 1H, ArNHAr], 10.76 [s, 1H, ArNHAr], 11.16 [s, 1H, ArC(O)NHAr], 14.81 [br s, quinoline-N$^+$H]. LCMS (APCI$^+$): 447 (100%). HPLC: 99.7%.

Example C

Preparation of 4-[4-({3-[(1-methyl-4-pyridiniumyl) amino]benzoyl}amino)anilino]quinolinium dichloride (Cpd. C)

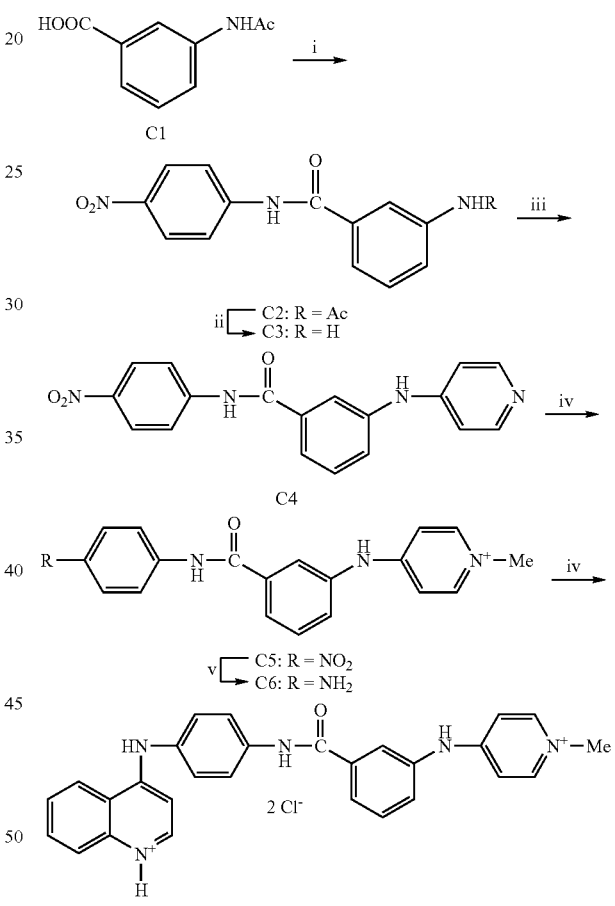

Cpd. C

Reagents: (i) CDI/DMF/55° C. 1 h, then 4-nitroaniline/DMAP/150° C.;
(ii) p-TsOH; (iii) pyridylpyridiniumchloride/180° C.; (iv) DMF/MeOTs;
(v) Fe dust/EtOH/H$_2$O/H$^+$/then ion exchange; (vi) 4-chloroquinoline/EtOH/H$_2$O/H$^+$/reflux.

(Acetylamino)-N-(4-nitrophenyl)benzamide (C2). A mixture of 3-acetamidobenzoic acid (C1) (5.30 g, 29.58 mmol) and CDI (5.75 g, 35.50 mmol, 1.2 equivalent) in N-methylpyrrolidinone (20 mL) was heated at 55-60° C. for 2 h. 4-Nitroaniline (6.13 g, 44.37 mmol, 1.5 equivalent) was then added and the mixture was heated to 140° C. for 4 h, then poured into water (400 mL) and stirred for 18 h. The resulting precipitate was filtered and washed sequentially with water and CH$_2$Cl$_2$ and then crystallized from MeOH to give C2

(4.84 g; 55%) as a yellow solid; mp (MeOH) 259-261° C.; $^1$H NMR [(CD$_3$)$_2$SO] δ 10.80 (s, 1 H, NH), 10.15 (s, 1 H, NH), 8.29 (m, 2 H, H-3 & H-5), 8.12 (t, J=1.8 Hz, 1 H, H-2), 7.84 (br dd, J=8.1, 1.2 Hz, 1 H, H-6), 7.65 (td, J=7.8, 2.5 Hz, 1 H, H-4), 7.48 (t, J=7.9 Hz, 1 H, H-5), 2.08 (s, 3H, COCH$_3$); Anal. Calc. For C$_{15}$H$_{13}$N$_3$O$_4$: C, 60.2; H, 4.4; N, 14.0; found C, 60.4; H, 4.6; N, 14.1%.

3-Amino-N-(4-nitrophenyl)benzamide (C3). Compound C2 (4.25 g, 15.9 mmol) was suspended in 1,4-dioxane (100 mL), dilute HCl (15 mL c.HCl+85 mL H$_2$O) was added, and the mixture was refluxed for 6 h (until TLC in 6% MeOH: CH$_2$Cl$_2$ showed complete consumption of starting material). The reaction mixture was then cooled to 20° C. and the solvent was evaporated to dryness. The resulting residue was stirred in dilute aqueous NH$_3$, then filtered, washed with water, oven-dried and crystallized from MeOH to give amine C3 (2.75 g, 67%); mp (MeOH) 229-232° C.; $^1$H NMR [(CD$_3$)$_2$ SO] δ10.63 (s, 1 H, CONH), 8.27-8.22 (m, 2 H, H-3'&H-5'), 8.06-8.02 (m, 2 H, H-2'&H-6'), 7.18 (t, J=7.7 Hz, 1 H, H-5), 7.12-7.08 (m, 2 H, H-2&H-6), 6.80-6.78 (m, 1 H, H-4), 5.38 (s, 2 H, NH$_2$); HRMS (FAB$^+$) calc. for C$_{13}$H$_{11}$N$_3$O$_3$ (M$^{+1}$) m/z 258.0879, found 258.0875; Anal. Calc. for C$_{13}$H$_{11}$N$_3$O$_3$: C, 60.7; H, 4.3; N, 16.3; found C, 60.7; H, 4.4; N, 16.6%.

N-(4-Nitrophenyl)-3-(4-pyridinylamino)benzamide (C4). Para-toluenesulfonic acid (2 g, 10.49 mmol) was azeotroped with benzene (250 mL) for 2 h. Pyridylpyridinium chloride (3.3 g), compound C3 (2.7 g, 10.49 mmol) and N-methylpyrrolidinone (10 mL) were then added, and the mixture azeotroped at 130° C. for 2 h. Solvent was boiled off, and the resulting dark brown mixture was heated at 180° C. for 1 h, and then cooled about 50° C. and diluted with water. The mixture was stirred at room temperature for 2 h, and the resulting precipitate was filtered and washed sequentially with water, dilute aqueous NH$_3$ and CH$_2$Cl$_2$. The solid was then crystallized from MeOH, filtered, and washed with MeOH and CH$_2$Cl$_2$ to give C4 (1.92 g, 55%); $^1$H NMR [(CD$_3$)$_2$SO] δ10.79 (s, 1 H, CONH), 9.00 (s, 1 H, NH), 8.29-8.22 (m, 4 H, H-3',5'& py H-2,6)), 8.08-8.04 (m, 2 H, H-2', 6'), 7.76 (t, J=1.8 Hz, 1 H, H-2), 7.63 (t d, J=8.0, 1.3 Hz, 1H, H-6), 7.52 (t, J=7.8 Hz, 1 H, H-5), 7.46-7.43 (m, 1 H, H-4), 6.98-6.97 (m, 2 H, py H-3&5).

1-Methyl-4-{3-[(4-nitroanilino)carbonyl]anilino}pyridinium 4-methylbenzenesulfonate (C5). Compound C4 (1.92 g, 5.73 mmol) was suspended in DMF (10 mL), methyl-p-toluenesulfonate (15 mL) was added, and the mixture was stirred at room temperature for 18 h. Solvent was removed under reduced pressure and the residue was dissolved in warm MeOH (10 mL), then diluted with EtOAc. Some of the MeOH was boiled off, and the solution was then refrigerated for 18 h. The resulting precipitate was filtered, and washed with EtOAc to give essentially pure C5 (2.90 g, 97%), which was used without further purification. $^1$H NMR [(CD$_3$)$_2$SO] δ10.85 (s, 1 H, CONH), 10.60 (s, 1 H, NH), 8.33-8.27 (m, 4 H, H-3',5' & py H-2,6), 8.08-8.30 (m, 2 H, H-2',6'), 7.94-7.89 (m, 2 H, H-2" 4"), 7.69 (t, J=7.9 Hz, 1 H, H-5"), 7.60-7.57 (m, 1 H, H-6"), 7.48-7.45 (m, 2 H, H-3, 5), 7.22 (d, J=7.5 Hz, 2 H, p-tol H-2,6), 7.20 (d, J=8.1 Hz, 2 H, p-tol H-3,5), 3.99 (s, 3 H, N$^+$CH$_3$), 1.99 (s, 3 H, CH$_3$).

4-{3-[(4-aminoanilino)carbonyl]anilino}-1-methylpyridinium chloride (C6). Compound C5 (1.59 g, 3.06 mmol) was dissolved in ~6:1 EtOH:H$_2$O (46 mL), Fe dust (885 mg) was added, and the resulting suspension brought to reflux. Two drops of c.HCl were added, and refluxing was continued for 1 h. (until TLC with the top phase of 5:4:1 mixture of n-BuOH: H$_2$O:CH$_3$CO$_2$H showed complete consumption of starting material). The reaction mixture was diluted with EtOH (100 mL) and brought to reflux. The hot reaction mixture was filtered through a pad of Celite, and the top layer of the Celite pad was boiled with more EtOH and filtered (this procedure was repeated three times to ensure complete extraction of product from iron residues). The combined EtOH extracts were evaporated to dryness, and the residue was extracted with hot water, and filtered through a pad of Celite. The filtrate was concentrated to a smaller volume, and then stirred in pre-washed ion-exchange resin (55g). The resulting slurry was loaded onto a column packed with pre-washed ion-exchange resin and eluted with water. Fractions containing product were combined and evaporated to dryness, and the residue was azeotroped several times with EtOH. The residue was dissolved in a small volume of MeOH, methanolic HCl (1.25 M, 1 mL) was added, and the solution stirred for 10 min. The solution was diluted with EtOAc, and the resulting precipitate filtered and then crystallized from MeOH/EtOAc to give C6 (873 mg, 80%); mp (MeOH/EtOAc)>300° C.; $^1$H NMR [(CD$_3$)$_2$SO] δ10.77 (br s, 1 H, NH), 9.95 (s, 1 H, NH), 8.41 (br d, J=5.5 Hz, 2 H, Py H-2,6), 7.87-7.84 (m, 2 H, H-2,4), 7.61 (t, J=7.8 Hz, 1 H, H-5), 7.49 (br d, J=7.8 Hz, 1 H, H-6), 7.37 (d, J=8.7 Hz, 2 H, H-2',6'), 7.21 (br d, J=4.6 Hz, 2 H py H-3,5), 6.55 (d, J=8.8 Hz, 2 H, H-3',5'), 4.93 (s, 2 H, NH$_2$), 3.97 (s, 3 H, N$^+$CH$_3$).

4-[4-({3-[(1-Methyl-4-pyridiniumyl)amino]benzoyl}amino)anilino] quinolinium dichloride (Cpd. C). Compound C6 (100 mg, 0.28 mmol) was dissolved in EtOH (10 mL) and H$_2$O (5 mL) by heating. 4-Chloroquinoline (60 mg, 0.36 mmol) and 3 drops of c.HCl were added, and the mixture refluxed for 18 h (until TLC with the top phase of 5:4:1 mixture of n-BuOH:H$_2$O:CH$_3$CO$_2$H showed complete consumption of starting amine). The reaction mixture was then diluted with EtOAc, boiled for a few minutes and then allowed to cool to room temperature. The resulting precipitate was filtered and crystallized from MeOH/EtOAc to give Cpd. C (64 mg, 63%); mp (MeOH, EtOAc)>300° C.; $^1$H NMR [(CD$_3$)$_2$SO] δ14.49 (br, 1 H, N$^+$H), 11.01 (s, 1 H, NH), 11.78 (br, 1 H, NH), 10.64 (s, 1 H, NH), 8.77 (d, J=8.5 Hz, 1 H, ArH), 8.57 (d, J=6.5 Hz, 1 H, ArH), 8.32 (d, J=7.5 Hz, 2H, ArH), 8.06-7.92 (m, 6 H, ArH), 7.53 (t, J=7.7 Hz, 1 H, ArH), 7.70-7.65 (m, 1 H, ArH), 7.48 (d, J=8.8 Hz, 2 H, ArH), 7.29 (d, J=7.5 Hz, 2 H, ArH), 6.79 (d, J=6.8 Hz, 1 H, ArH), 3.98 (s, 3 H, N$^+$CH$_3$).

Example D

Preparation of 4-[4-({4-[(1-methyl-4-pyridiniumyl)amino]benzoyl}amino)anilino]quinolinium dichloride (Cpd. D)

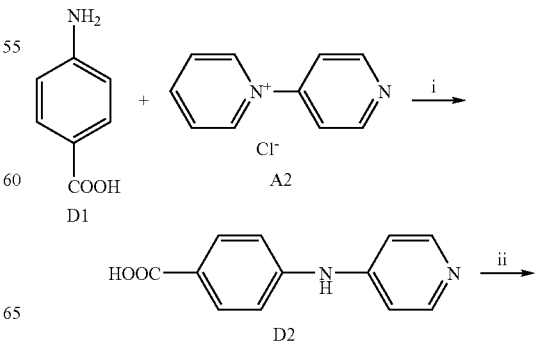

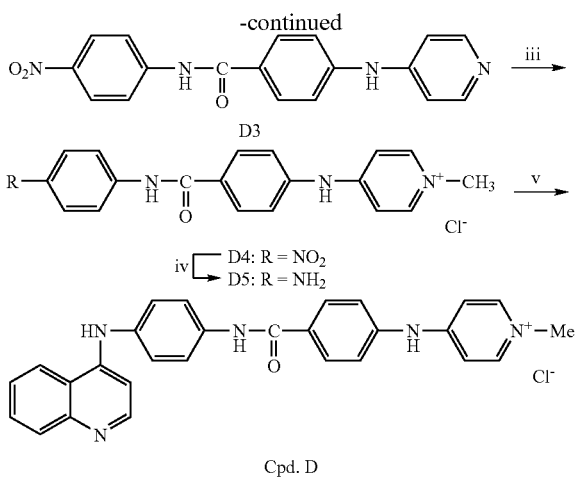

(i) TsOH/180° C.; (ii) SOCl₂, then 4-nitroaniline/pyridine; (iii) EDMF/MeOTs/20° C., then ion exchange; (iv) Fe dust/EtOH/trace HCl; (v) 4-chloroquinoline/EtOH/H2O/H+/reflux.

4-(4-Pyridinylamino)benzoic acid (D2). Para-toluenesulfonic acid (17.4 g, 0.126 mol) was azeotroped with benzene (300 mL) for 5 h. 4-Pyridylpyridinium chloride (26.6 g, 0.138 mol), 4-aminobenzoic acid (D1) (17.3 g, 0.126 mol) and N-methylpyrrolidinone (40 mL) were then added, and the mixture was azeotroped at 110° C. for 1 h in an oil bath. Benzene was evaporated at 130° C., and the temperature was then increased to 180° C. for 1.5 h. The reaction mixture was then cooled to room temperature and diluted with brine. The resulting mixture was warmed to obtain a precipitate, which was filtered and then oven-dried at 110° C. The solid was then extracted into boiling ethanol (5×150 mL), and the combined EtOH extracts were evaporated to dryness. The resulting residue was stirred in dilute aqueous NH₃, and the resulting precipitate was filtered. Further product was obtained by neutralizing the filtrate with glacial AcOH, and filtering the resulting precipitate. Crude product batches were combined and crystallized from H₂O to give D2 (8.8 g, 32%): mp (H₂O) 333-336° C.; $^1$H NMR [(CD3)₂SO] δ12.05 (br., 1 H, COOH), 9.17 (s, 1 H, NH), 8.28-8.27 (m, 2 H, ArH), 7.90-7.86 (m, 2 H, ArH), 7.26-7.23 (m, 2 H, ArH), 7.05-7.03 (m, 2 H, ArH), $^{13}$C NMR [(CD₃SO)₂] δ 166.8, 150.2 (2×C), 148.6, 145.0, 130.9 (2×C), 123.4, 117.32 ((2×C), 110.6 (2×C); LCMS 215+ve.

N-(4-nitrophenyl)-4-(4-pyridinylamino)benzamide (D3). Compound D2 (172 mg, 0.80 mmol) was refluxed in SOCl₂ (5 mL) containing a catalytic amount of DMF for 1 h (until a clear solution was obtained). The reaction mixture was cooled to room temperature and excess SOCl₂ was removed under vacuum. Dioxane (10 mL) was added to the residue, and then removed under vacuum. The residue was cooled in a dry ice-acetone bath, p-nitroaniline (112 mg, 0.81 mmol) and pyridine (1.3 mL) were added, followed by Et₃N (0.3 mL), and the mixture was stirred at room temperature for 20 min, and then refluxed for 1 h. The reaction mixture was cooled to room temperature and diluted with H₂O, and then basified with aqueous NH₃ and stirred for 30 min. The resulting precipitate was filtered, and washed sequentially with water, hexane and CH₂Cl₂. The crude product was dissolved in MeOH and then adsorbed onto silica gel, and the resulting adsorbate chromatographed on silica gel, eluting with 0-10% MeOH:CH₂Cl₂, to give D3 (85 mg, 32%); mp 298-302° C. (MeOH); $^1$H NMR [(CD₃)₂SO] δ 10.64 (s, 1 H, NH), 9.21 (s, 1 H, NH), 8.30-8.24 (m, 4 H, ArH), 8.09-8.05 (m, 2 H, ArH), 8.00-7.98 (m, 2 H, ArH), 7.34-7.31 (m, 2 H, ArH), 7.07-7.05 (d, m, 2 H, ArH);LCMS 235+ve.

1-Methyl-4-{4-[(4-nitroanilino)carbonyl]anilino}pyridinium chloride (D4). Compound D3 (80 mg, 0.24 mmol) was dissolved in DMF (0.8 mL), methyl-p-toluenesulphonate (0.5 mL) was added, and the mixture was stirred at room temperature for 18 h. Solvent was evaporated under reduced pressure, and the residue was dissolved in MeOH (1 mL), and then diluted with EtOAc (50 mL). The precipitate which formed upon cooling was filtered and then crystallized from MeOH/EtOAc to give D5 (119 mg) as the tosylate salt. This was converted to the chloride salt by ion-exchange, as follows. AG$^R$ 1-X₄ resin 200-400 chloride form (3g) was washed with water and packed in a column. Tosylate D5 (119 mg) was stirred in pre-washed resin (1g), and the resulting slurry was loaded onto the column. The column was then eluted with 50% MeOH:H₂O, and fractions containing the compound were combined and evaporated to dryness. The residue was azeotroped with MeOH (3×20 mL), and finally reprecipitated from MeOH/EtOAc to give D4 as the chloride salt (82 mg, 88%); mp (MeOH/EtOAc); $^1$H NMR [(CD₃)₂SO] δ11.00 (s, 1 H, NH), 10.87 (s, 1 H, NH), 8.37 (d, J=7.3 Hz, 2 H ArH), 8.30-8.26 (m, 2 H, ArH), 8.15-8.08 (m, 4 H, ArH), 7.52 (d, J=8.6 Hz, 2 H, ArH), 7.33 (d, J=7.2 Hz, 2 H, ArH), 4.01 (s, 3 H, N⁺CH₃); LCMS 349+ve.

4-{4-[(4-Aminoanilino)carbonyl]anilino}-1-methylpyridinium chloride (D5). Compound D4 (295 mg, 0.77 mmol) was dissolved in ~5:1 EtOH:H₂O (12 mL), and Fe dust (209 mg)was added. The mixture was vigorously stirred and refluxed for 4 h, and then filtered hot through a pad of Celite. The Celite was washed with boiling EtOH, and EtOH fractions were combined and evaporated to dryness. The residue was extracted into hot water, and filtered through Celite, and then evaporated to dryness. The residue was azeotroped with MeOH (3×20 mL), and then dissolved in MeOH (10 mL). Methanolic HCl (1.25 M, 5 mL) was added, and the solution stirred for 10 min. Solvent was removed under reduced pressure, and the residue was crystallized from MeOH/EtOAc to give D5 (218 mg, 80%); mp (MeOH/EtOAc); $^1$H NMR [(CD₃)₂SO] δ11.13 (s, 1 H, NH), 10.44 (s, 1 H, NH), 9.88 (br, 2 H, NH₂), 8.36 (d, J=7.5 Hz, 2 H, ArH), 8.12 (d, J=8.6 Hz, 2 H, ArH), 7.86 (d, J=8.8 Hz, 2 H, ArH), 7.50 (d, J=8.8 Hz, 2 H, ArH), 7.32 (d, J=8.6 Hz, 2 H, ArH), 7.32 (d, J=7.5 Hz, 2 H, ArH), 7.30 (d, J=8.7 Hz, 2 H, ArH), 4.00 (s, 3 H, N⁺CH₃); LCMS 319+ve 4-[4-({4-[(1-Methyl-4-pyridiniumyl)amino]benzoyl}amino)anilino] quinolinium dichloride (Cpd. D). Compound D5 (100 mg, 0.28 mmol) was dissolved in EtOH (10 mL) and H₂O (5 mL) by heating. 4-Chloroquinoline (60 mg, 0.36 mmol) and c.HCl (3 drops) were added, and the reaction mixture was refluxed for 18 h (until TLC with the top phase of 5:4:1 mixture of n-BuOH:H₂O:CH₃CO₂H showed complete consumption of starting amine). The reaction mixture was diluted with EtOAc, refluxed for a few minutes, and then allowed to cool. The resulting precipitate was filtered and crystallized from MeOH/EtOAc to give Cpd. D (88 mg, 63%); mp (MeOH, EtOAc)>300° C.; $^1$H NMR [(CD₃)₂SO] δ14.38 (br, 1 H, N⁺H), 11.04 (s, 1 H, NH), 10.84 (br, 1 H, NH), 10.53 (s, 1 H, NH), 8.76 (d, J=8.6 Hz, 1 H, ArH), 8.58 (d, J=6.7 Hz, 1 H, ArH), 8.37 (d, J=7.5 Hz, 2 H, ArH), 8.14 (d, J=8.7 Hz, 2 H, ArH), 8.06-8.01 (m, 4 H, ArH), 7.83-7.79 (m 1 H, ArH), 7.53-7.48 (m, 4 H, ArH), 7.33 (d, J=7.6 Hz, 2 H, ArH), 6.79 (d, J=6.9 Hz, 1 H, ArH), 4.00 (s, 3 H, N⁺CH₃).

Example E

Preparation of N-(4-(2-amino-6-methylpyrimidin-4-ylamino)phenyl)-4-(quinolin-4-ylamino)benzamide hydrochloride (Cpd. E)

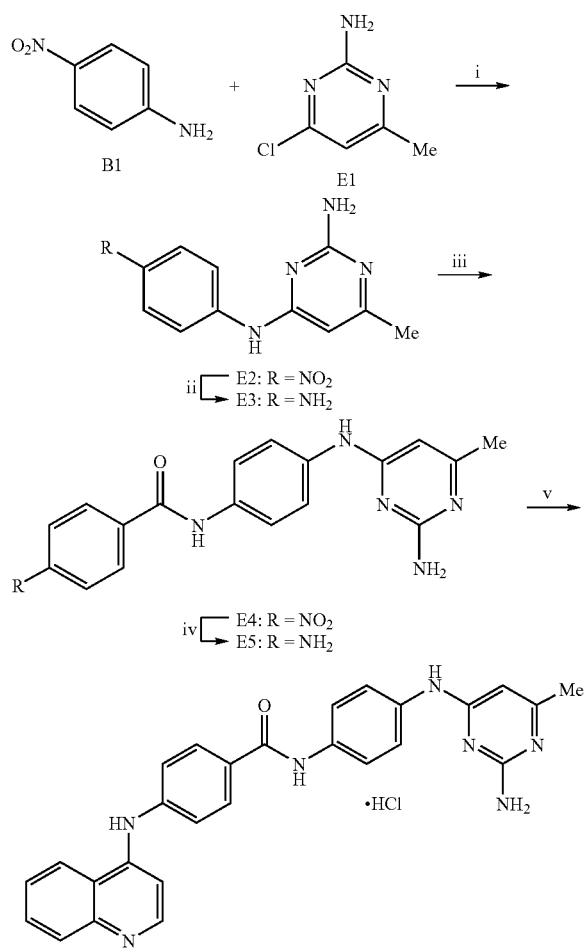

Cpd. E
(i) 2-ethoxyethanol/c.HCl/reflux/30 min 14 h; (ii) Fe, 2:1 EtOH/H₂O, 2% v/v AcOH/relux/1.5 h;
(iii) 4-nitorbenzoyl chloride/pyridine/dioxane/50° C./5 d; (iv) Fe/2:1 EtOH/H₂O/cat. c.HCl; (v) MeOH/cat. c.HCl/relux/30 h 6-Methyl-$N^4$-(4-nitrophenyl)pyrimidine-2,4-diamine (E2). 4-Nitroaniline (B1) [9.22 g, 0.07 mol] and 2-amino-4-chloro-6-methylpyrimidine (E1) (9.30 g, 0.07 mol) were dissolved in 2-ethoxyethanol (330 mL). To the resulting solution were added a few drops of c.HCl, and the resulting mixture was refluxed for 30 min, and then allowed to cool to room temperature overnight. After this time, the reaction mixture was filtered, and the resulting solid was basified by addition of aqueous ammonia solution, and then crystallized from H₂O: EtOH to afford amine E2 as an amorphous bright-yellow solid (7.33 g). Concentration of the filtrate, followed by basification and reprecipitation as before, afforded a further quantity (0.78 g, overall yield 51%). $^1$H NMR [(CD$_3$)$_2$SO]: 2.14 [s, 3H, ArCH$_3$], 6.00 [s, 1H, ArNH$_2$], 6.37 [s, 2H, ArNH$_2$], 8.00 [ddd, J=10.24, 5.05, 2.96 Hz, 2H, ArH], 8.12 [ddd, J=10.24, 4.95, 2.90 Hz, 2H, ArH], 9.75 [s, 1H, ArH]. LCMS (APCI$^+$): 246 (100%).

$N^4$-(4-Aminophenyl)-6-methylpyrimidine-2,4-diamine (E3). To a refluxing suspension of amine E2 (5.46 g, 0.02 mol) in 2:1 EtOH:H₂O (100 mL) were sequentially added Fe dust (4.97 g, 0.09 mol) and AcOH (2 mL, 2% v/v), and the resulting dark brown suspension was refluxed for ~14 h. After this time, the hot reaction mixture was filtered through a pad of Celite, and solvent was removed under reduced pressure. The resulting residue was extracted with hot water, and the resulting aqueous suspension filtered through a pad of Celite. Solvent was removed under reduced pressure, and the residue extracted again with hot water. The resulting aqueous suspension was filtered through a pad of Celite. Solvent was removed to afford amine E3 as a brown-white crystalline solid (4.85 g, quantitative). $^1$H NMR [CD$_3$)$_2$SO]: 2.01 [s, 3H, ArCH$_3$], 5.68 [s, 1H, ArNHAr], 5.88 [br s, 2H, ArNH$_2$], 6.51 [ddd, J=9.67, 4.85, 2.94 Hz, 2H, ArH], 7.14 [d, J=8.52 Hz, 2H, ArH], 8.35 [s, 1H, ArH]. LCMS (APCI$^+$): 216 (100%).

N-[4-(2-Amino-6-methylpyrimidin-4-ylamino)phenyl]-4-nitrobenzamide (E4). 4-Nitrobenzoyl chloride (11.00 g, 0.06 mol) and dry pyridine (9.08 mL, 0.11 mol) were sequentially added to a solution of amine E3 (4.85 g, 0.02 mol) in dry dioxane (200 mL), and the resulting solution heated at ~50° C. for 5 d. After this time, the reaction mixture was cooled to room temperature, and then basified by addition of aqueous ammonia solution. The resulting suspension was filtered through a pad of Celite to afford amide E4 as an amorphous yellow solid (3.40 g, 41%). $^1$H NMR [(CD$_3$)$_2$SO]: 2.09 [s, 3H, ArCH$_3$], 5.87 [s, 1H, ArNHAr], 6.08 [br s, 6.08, ArNH$_2$], 7.68 [m, 4H, ArH], 8.18 [d, J=8.80 Hz, 2H, ArH], 8.36 [d, J=8.80 Hz, 2H, ArH], 8.95 [s, 1H, ArH], 10.45 [s, 1H, ArC(O)NHAr]. LCMS (APCI$^+$): 365 (100%).

4-Amino-N-[4-(2-amino-6-methylpyrimidin-4-ylamino)phenyl]benzamide hydrochloride (E5). To a refluxing suspension of amide E4 (2.10 g, 5.77 mmol) in 2:1 EtOH:H₂O (100 mL) were sequentially added Fe dust (1.29 g, 23.09 mol) and c.HCl (1-2 mL), and the resulting mixture was refluxed for 24 h. After this time, the hot reaction mixture was filtered through a pad of Celite, and solvent was removed under reduced pressure. The resulting residue was crystallized from MeOH:EtOAc to afford amine E5 (in two batches) as a cream-coloured amorphous solid (1.94 g, 90%). $^1$H NMR [(CD$_3$)$_2$SO]): 2.27 [s, 3H, ArCH$_3$], 6.16 [br s, 2H, ArNH$_2$], 6.75 [d, J=8.36 Hz, 2H, ArNH$_2$], 7.74 [m, 8H, ArH], 9.90 [br s, 1H ArH], 10.55 [br s, 1H, ArNHAr], 12.58 [br s, 1H, ArC(O)NH]. LCMS (APCI$^+$): 335 (100%).

N-(4-(2-Amino-6-methylpyrimidin-4-ylamino)phenyl)-4-(quinolin-4-ylamino)benzamide hydrochloride (Cpd. E). To solution of amine E5 (267 mg, 0.720 mmol) in ~1:1:1 MeOH:EtOH:H₂O were sequentially added 4-chloroquinoline (1.06 g, 6.48 mmol) and 3 drops of cHCl, and the resulting mixture was refluxed for ~24 h. After this time, solvent was removed under reduced pressure, and the resulting residue dried via two MeOH-azeotrope cycles. The residue was re-precipitated from MeOH/EtOAc, and then further purified by preparative HPLC, to afford Cpd. E as an amorphous yellow solid (16 mg, 4%). $^1$H NMR [(CD$_3$)$_2$SO]: 1.91 [s, 3H, ArCH$_3$], 6.11 [s, 1H, ArH], 7.02 [d, J=6.77 Hz, 1H, ArH], 7.65 [d, J=8.55 Hz, 2H, ArH], 7.71 [br s, 2H, ArNH$_2$], 7.84 [m, 4H, ArH], 8.04 [m, 2H, ArH], 8.15 [d, J=8.55 Hz, 2H, ArH], 8.63 [d, J=6.77 Hz, 1H, ArH], 8.70 [d, J=8.50 Hz, 1H, ArH], 10.38 [s, 2H, ArNHAr & ArH], 10.77 [br s, 1H, ArN- HAr], 13.10 [v v br s, 2H, ArC(O)NHAr & quinoline-N⁺H]. LCMS (APCI⁺): 463 (100%). HPLC: 95.7%.

Example F

Preparation of 1-methyl-4-(3-{[4-(6-nitro-4-quinolinylamino)benzoyl]amino}anilino)pyridinium chloride (Cpd. F)

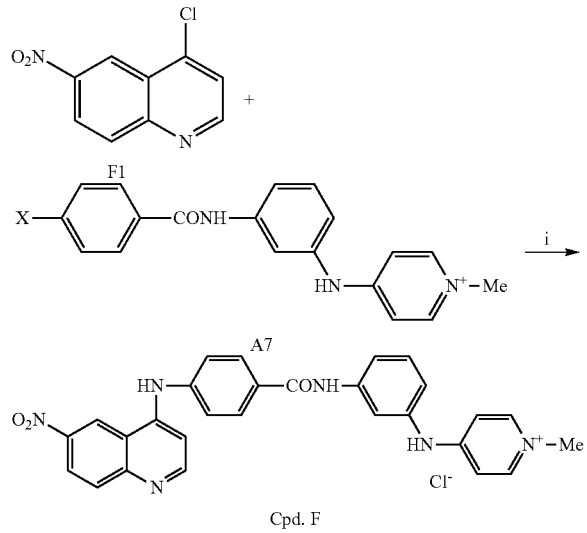

Cpd. F (i) MeOH/cat. HCl/relux.

Coupling of A7 with 4-chloro-6-nitroquinoline (F1) [Simpson & Wright, *J. Chem. Soc.,* 1948, 1707] as above gave Cpd. F in 97% yield: mp 273-277° C.; ¹H NMR [(CD₃)₂SO] δ11.33 (br, 1 H, NH), 10.70 (s, 1 H, NH), 10.60 (s, 1 H, NH), 8.72-8.69 (m, 2H, ArH), 8.31 (d, J=7.4 Hz, 2 H, ArH), 8.24 (d, J=9.3 Hz, 1 H, ArH), 8.18 (d, J=8.5 Hz, 2 H, ArH), 7.98 (br s, 1 H, ArH), 7.68-7.65 (m, 3 H, ArH), 7.49 (t, J=8.1 Hz, 1 H, ArH), 7.21 (d, J=7.5 Hz, 2 H, ArH), 7.12-7.01 (m, 2 H, ArH), 4.02 (s, 3 H, N⁺CH₃); HRMS (FAB) calc. for C₂₈H₂₃N₆O₃ (M⁺) m/z 491.1832, found 491.1822.

Example G

Preparation of 1-methyl-4-(4-(4-(6-nitroquinolin-4-ylamino)benzamido)phenylamino)pyridinium chloride hydrochloride (Cpd. G)

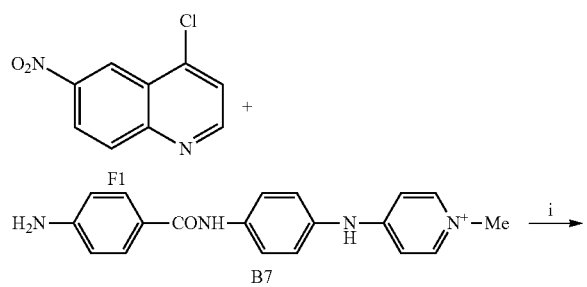

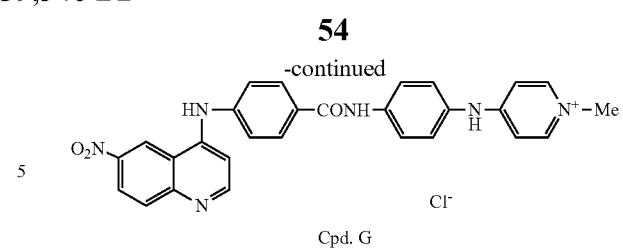

Cpd. G (i) MeOH/cat. HCl/relux.

To a suspension of amide B7 (2.09 g, 5.32 mmol) in dry MeOH (100 mL) were sequentially added 4-chloro-6-nitroquinoline (F1) [1.11g, 5.32 mmol] and a few drops of concentrated HCl, and the resultant mixture was refluxed for 12 h. After this time, solvent was removed under reduced pressure, and the residue was re-suspended in 1:1 MeOH:EtOAc. This mixture was heated to remove MeOH, and then cooled, and the resulting precipitate collected by filtration. This solid was recrystallized from MeOH:EtOH to give nitroquinoline Cpd. G (2.48 g, 89%) as an amorphous yellow solid; ¹H NMR [(CD₃)₂SO]: δ 3.96 (s, 3H, R₂N⁺⁻CH₃), 7.12 (m, 3H, ArH), 7.35 (d, J=8.81 Hz, 2H, ArH), 7.68 (d, J=8.51 Hz, 2H, ArH), 7.96 (d, J=8.81 Hz, 2H ArH), 8.24 (m, 5H, ArH), 8.72 (m, 2H, ArH), 9.83 (d, J=1.69 Hz, 1H, ArH), 10.56 (s, 1H, ArNHAr), 10.67 (s, 1H, ArNHAr), 11.48 (br s, 1H, ArNHAr). LCMS (APCI⁺): 492 (20%).

Example H

Preparation of N-(4-(2-amino-6-methylpyrimidin-4-ylamino)phenyl)-4-(6-nitroquinolin-4-ylamino)benzamide hydrochloride (Cpd. H)

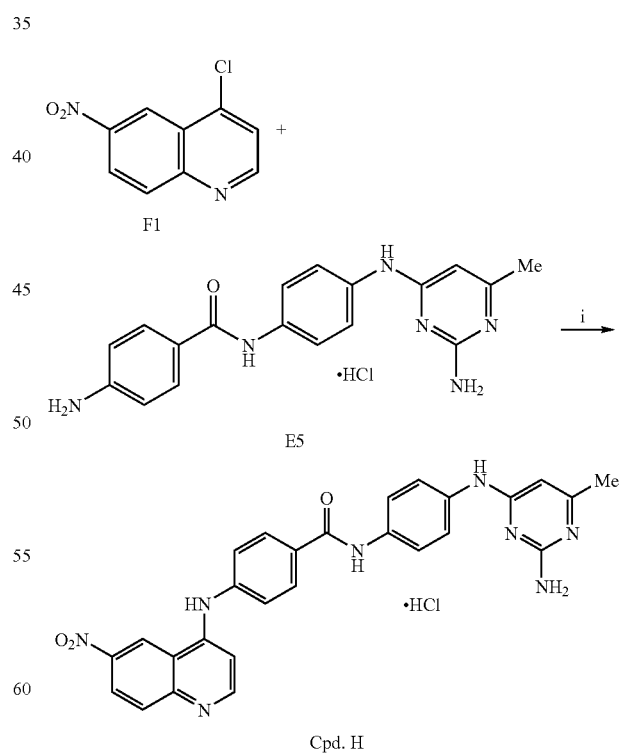

Cpd. H (i) MeOH, cat. c.HCl, 2.5 d

N-[4-(2-Amino-6-methylpyrimidin-4-ylamino)phenyl]-4-(6-nitroquinolin-4-ylamino)benzamide hydrochloride (Cpd. H). To a solution of amine E5 (304 mg, 0.82 mmol) in dry MeOH (30 mL) were sequentially added 4-chloro-6-nitroquinoline (F1) (171 mg, 0.82 mmol) and c.HCl (1-2 drops), and the resulting mixture was refluxed for ~12 h. MS and TLC analysis after this time showed some F1 was still present in the reaction mixture, so further aliquots of E5 (171 mg, 0.82 mmol) and c.HCl (1-2 drops) were added at 12 h and 24 h. Solvent was then removed from the reaction mixture, and the resulting residue dissolved in MeOH, and then re-concentrated under reduced pressure. The residue was subjected to a further MeOH azeotrope cycle, and the resulting residue was then reprecipitated from MeOH:Et$_2$O to afford Cpd. H as an amorphous yellow solid (383 mg, 86%). $^1$H NMR (400 MHz, DMSO): 2.28 [s, 3H, ArCH$_3$], 6.18 [br s, 1H, ArH], 7.11 [d, J=6.59 Hz, 1H, ArH], 7.65 Hz [d, J=8.52 Hz, 2H, ArH], 7.81 [m, 5H, ArH & ArNH$_2$], 8.17 [d, J=8.52 Hz, 2H, ArH], 8.25 [d, J=9.30 Hz, 1H, ArH], 8.69 [m, 2H, ArH], 9.77 [s, 1H, ArH], 10.42 [s, 1H, ArH], 10.62 [br s, 1H, ArNHAr], 11.20 [v br s, 1H, ArNHAr], 12.63 [v br s, 1H, ArC(O)NH]. LCMS (APCI$^+$): 508 (100%). HPLC: 98.5%.

Example I

Preparation of (E)-N-[4-{1-([diaminomethylene]hydrazono)ethyl}phenyl]-4-(6-nitroquinolin-4-ylamino)benzamide hydrochloride (Cpd. I)

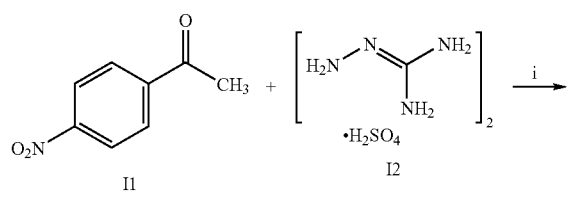

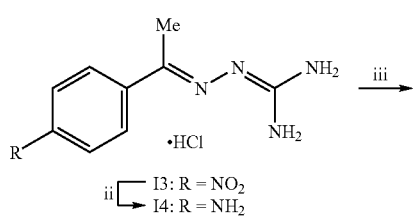

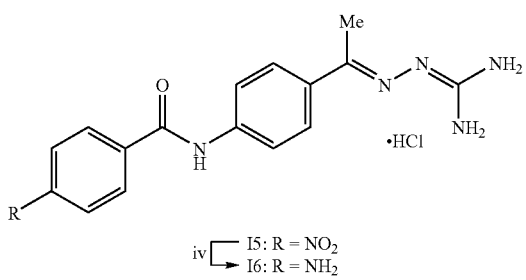

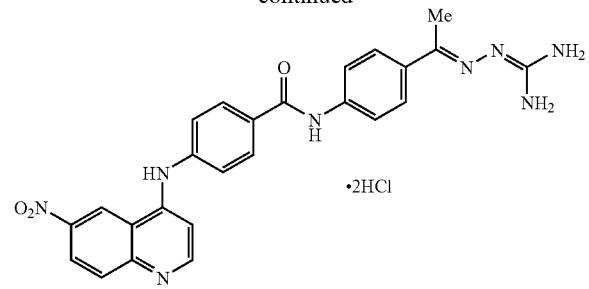

Cpd. I (i) MeO/ c.HCl/ reflux 1 ; (ii) Fe dust/2:1 EtO/:H$_2$O/cat. c.HCl/reflux/14 h; (iii) 4-nitrobenzoyl chloride/pyridine, dioxane, reflux, 2 h; (iv) Fe dust/2:1 EtOH/H$_2$O/reflux/1.5 h; (v) 4-chloro-6-nitroquinoline/EtOH/cat. c.HCl/reflux/65 h.

(E)-N-[4-(1-{Diaminomethylene}hydrazono)ethyl]-4-nitrobenzene hydrochloride (I3). 4-Nitroacetophenone (I1) (49.95 g, 0.30 mol), aminoguanidine sulfate (I2) (51.77 g, 0.20 mol), and c.HCl (10 mL, 0.33 mol) were combined in MeOH (600 mL), and the resulting mixture refluxed for 1 h, and then allowed to cool to room temperature overnight. After this time, solvent was removed under reduced pressure, and the residue collected by filtration. The resulting solid was washed sequentially with MeOH and hexanes to afford diamine I3 as an amorphous white solid (88.19 g, quantitative), which was used without further purification. $^1$H NMR [CD$_3$)$_2$SO): 2.36 [s, 3H ArC(CH$_3$)=N—], 7.72 [br s, 4H, =C(NH$_2$)$_2$], 8.23 [m. 5H, ArH], 10.42 [v br s, 1.5H]. LCMS (APCI$^+$): 222 (100%).

(E)-N-[4-(1-{Diaminomethylene}hydrazono)ethyl]-4-benzamine dihydrochloride (I4). Fe dust (35.00 g, 0.62 mol) and c.HCl (4 mL) were sequentially added to a refluxing suspension of diamine I3 (40.00 g, 0.16 mmol) in 2:1 EtOH:H$_2$O (200 mL), and the resulting yellow suspension was refluxed for 14 h. After this time, the hot reaction mixture was filtered through a pad of Celite, and solvent was removed under reduced pressure to afford triamine I4 as a dark brown resinous glass (34.93 g, 85%). This material was used without further purification. $^1$H NMR [CD$_3$)$_2$SO): 2.20 [s, 3H ArC(CH$_3$)=N—], 5.48 [br s, 2H, ArNH$_2$], 5.54 [d, J=7.98 Hz, 2H, ArH], 7.58 [v br s, 4H, =C(NH$_2$)$_2$], 7.63 [d, J=7.98 Hz, ArH], 10.83 [br s, 1H, =N$^+$(H)—N=]. LCMS (APCI$^+$): 192 (100%).

(E)-N-[4-(1-{[Diaminomethylene]hydrazono}ethyl)phenyl]-4-nitrobenzamide hydrochloride (I5). 4-Nitrobenzoyl chloride (16.01 g, 86.26 mmol) was added to a solution of triamine I4 (8.59 g, 32.51 mmol) and dry pyridine (13.09 mL, 162.53 mmol) in dry dioxane (300 mL), and the resulting suspension was refluxed for 2 h, and then allowed to cool room temperature overnight. After this time, the reaction mixture was filtered to afford a solid which was crystallized from MeOH-EtOAc to afford three batches of amide I5 as an amorphous cream-pale yellow solid (total 3.50 g, 29%). $^1$H NMR [CD$_3$)$_2$SO): 2.34 [s, 3H, ArC(CH$_3$)=N—], 7.73 [br s, 4H, =C(NH$_2$)$_2$], 7.87 [d, J=8.89 Hz, 2H, ArH], 8.01 [d, J=8.89 Hz, 2H, ArH], 8.22 [ddd, J=2.28, 4.27, 9.19 Hz, 2H, ArH], 8.38 [ddd, J=2.28, 4.27, 9.19 Hz, 2H, ArH], 10.73 [s, 1H, =N$^+$(H)—N=], 11.02 [s, 1H, ArC(O)NHAr]. LCMS (APCI$^+$): 341 (100%).

(E)-N-[4-(1-{[Diaminomethylene]hydrazono}ethyl)phenyl]-4-aminobenzamide dihydrochloride (I6). Fe dust (0.06 g, 1.05 mmol) was added to a refluxing suspension of amide I5 (0.10 g, 0.26 mmol) in 2:1 EtOH/H$_2$O (100 mL), and the resulting black suspension was refluxed for 1.5 h. After this time, the hot reaction mixture was filtered through a pad of Celite, and solvent was removed under reduced pressure. The residue was dried via two MeOH-azeotrope cycles, and then re-dissolved in MeOH. This solution was acidified with a few drops of methanolic HCl, and then diluted with EtOAc. The resulting suspension was filtered to afford an amorphous tan solid, which was re-dissolved in MeOH. Solvent was removed under reduced pressure, and the residue re-dissolved in hot H$_2$O. The resulting suspension was filtered through a pad of Celite (with a small volume of cold MeOH), and solvent was removed under reduced pressure. The residue was re-precipitated from MeOH-EtOAc to afford amine I6 as an amorphous yellow solid (0.36 g, quantitative). $^1$H NMR [(CD$_3$)$_2$SO]:2.25 [s, 3H, ArC(CH$_3$)=N—], 5.74 [s, 2H, ArNH$_2$], 6.40 {v br s, 4H, =C(NH$_2$)$_2$], 6.60 [d, J=8.66 Hz, 2H, ArH], 7.77 [m, 6H, ArH], 9.81 [s, 1H, ArC(O)NHAr].

(E)-N-[4-{1-([Diaminomethylene] hydrazono) ethyl}phenyl]-4-(6-nitroquinolin-4-ylamino)benzamide hydrochloride (Cpd. I). To a suspension of amine I6 (~100 mg based on I5, 0.26 mmol) in dry EtOH (60 mL) were sequentially added 4-chloro-6-nitroquinoline (220 mg, 1.04 mmol) and c.HCl (3 drops), and the resulting mixture refluxed for 64 h. After this time, the reaction mixture was filtered to afford a yellow solid, which was crystallized from MeOH—HCl: EtOAc to afford Cpd. I as an amorphous bright yellow solid (113 mg, 84%). $^1$H NMR [(CD$_3$)$_2$SO]: 2.36 [s, 3H, ArC(CH$_3$)=N—], 7.09 [d, J=6.95 Hz, 1H ArH], 7.69 [d, J=8.62 Hz, ArH], 7.77 [br s, 4H, =C(NH$_2$)$_2$], 7.91 [d, J=8.92 Hz, 2H, ArH], 8.00 [d, J=8.92 Hz, 2H, ArH], 8.21 [d, J=8.62 Hz, 2H, ArH], 8.31 [d, J=9.32 Hz, 2H, ArH], 8.70 [d, J=6.95 Hz, 1H, ArH], 8.74 [dd, J=9.32, 2.29 Hz, 1H, ArH], 9.86 [s, 1H, ArH], 10.55 [s, 1H, ArNHAr], 11.41 [s, 1H, ArC(O)NHAr], 11.60 [br s, 1H, 1H, =N$^+$(H)—N=]. LCMS (APCI$^+$): 484 (100%). HPLC: 97.1%.

Example J

Preparation of 4-[4-({3-[(1-methyl-4-pyridiniumyl) amino]benzoyl}amino)anilino]-6-nitroquinolinium dichloride (Cpd. J)

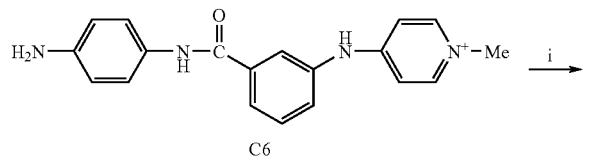

C6

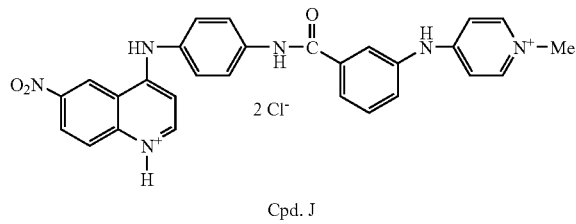

Cpd. J (i) 4-chloro-6-nitroquinoline/EtOH/H$_2$O/H$^+$/reflux.

Compound C6 (100 mg, 0.28 mmol) was dissolved in EtOH (10 mL) and H$_2$O (5 mL) by heating. 4-Chloro-6-nitroquinoline (F1) (75 mg, 0.36 mmol) and c.HCl (3 drops) were added, and the reaction mixture was refluxed for 18 h. (until TLC with the top phase of 5:4:1 mixture of n-BuOH: H$_2$O:AcOH showed complete consumption of starting amine). The reaction mixture was diluted with EtOAc, refluxed for a few minutes, and allowed to cool. The resulting precipitate was filtered and crystallized from MeOH/EtOAc to give Cpd. J (148 mg, 94%); mp (MeOH, EtOAc)>300° C.; $^1$H NMR [(CD$_3$)$_2$SO]: 614.90 (br 1 H, N$^+$H), 11.36 (br, 1 H, NH), 10.93 (s, 1 H, NH), 10.65 (s, 1 H, NH), 9.81 (d, J=2.2 Hz, 1 H, H-5), 8.71 (dd, J=9.3, 2.3 Hz, 1 H, H-7), 8.60 (d, J=7.0 Hz, 1 H, H-8), 8.33 (d, J=7.5 Hz, 2 H, py H-2,6), 8.22 (d, J=9.5 Hz, 1 H, H-2), 8.02 (d, J=8.9 Hz, 2 H, ArH), 7.81-7.92 (m, 2 H, ArH), 7.68 (t, J=7.8 Hz, 1 H, ArH), 7.58 (dd, J=8.6, 1.3 Hz, 1 H, ArH), 7.50 (d, J=7.0 Hz, 2 H, ArH), 7.28 (d, J=7.5 Hz, 2 H, ArH), 6.91 (d, J=7.0 Hz, 1 H, ArH), 3.98 (s, 3 H, N$^+$CH$_3$).

Example K

Preparation of 4-[3-({4-[(6-ammonio-4-quinolinyl) amino]benzoyl}amino)anilino]-1-methylpyridinium dichloride (Cpd. K)

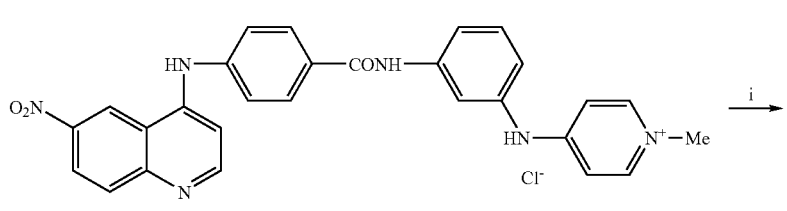

Cpd. F

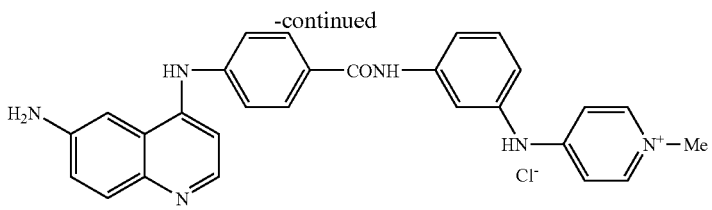

Cpd. K (i) Fe dust/EtOH/H₂O/cat. HCl/reflux.

To a suspension of Cpd. F (200 mg, 0.41 mmol) in ~6:1 EtOH:H₂O (6 mL) was added Fe dust (200 mg), and the resulting suspension was refluxed for 3 h. The hot reaction mixture was filtered through a pad of Celite, and the Celite pad washed with hot EtOH. The EtOH extracts were combined and evaporated to dryness, and the residue extracted into water. The solution was filtered through Celite, and then evaporated to dryness. The residue was azeotroped with methanol (3×30 mL), and then dissolved in MeOH (20 mL). Methanolic HCl (1.25 M, 1 mL) was added, and the solution stirred for 30 min. The solution was evaporated to dryness, and the residue crystallized from MeOH/EtOAc to give Cpd. K (160 mg, 80%): mp, (MeOH/EtOAc) 270-274° C.; $^1$H NMR [(CD₃)₂SO] δ14.50 (br, 1 H, N⁺H), 10.80 (s, 1 H, NH), 10.57 (s, 1 H, NH), 10.36 (s, 1 H, NH), 8.31 (d, J=7.5 Hz, 3 H, ArH), 8.15 (d, J=8.6 Hz, 2 H, ArH), 7.99 (t, J=1.9 Hz, 1 H, ArH), 7.85 (d, J=9.1 Hz, 1 H, ArH), 7.68 (br d, J=9.2 Hz, 1 H, ArH), 7.62 (d, J=8.6 Hz, 2 H, ArH), 7.51-7.12 (m, 3 H, ArH), 7.23 (d, J=7.6 Hz, 2 H, ArH), 7.09 (dd, J=7.9, 2.8 Hz, 1 H, ArH), 6.95 (d, J=6.7 Hz, 1 H, ArH), 3.96 (s, 3 H, N⁺CH₃), the signal for NH₂ was not observed. HRMS (FAB⁺) calc for $C_{28}H_{25}N_6O$ (M⁺¹) m/z 461.2090, found 461.2108; Anal. calc.CHN for $C_{28}H_{27}N_6Cl_3O \cdot 0.25H_2O$: C, 58.6; H, 4.8; N, 14.6; found, C, 58.5; H, 4.8; N, 14.5%.

Example L

Preparation of 4-[4-({4-[(6-ammonio-4-quinolinyl)amino]benzoyl}amino)anilino]-1-methylpyridinium dichloride (Cpd. L)

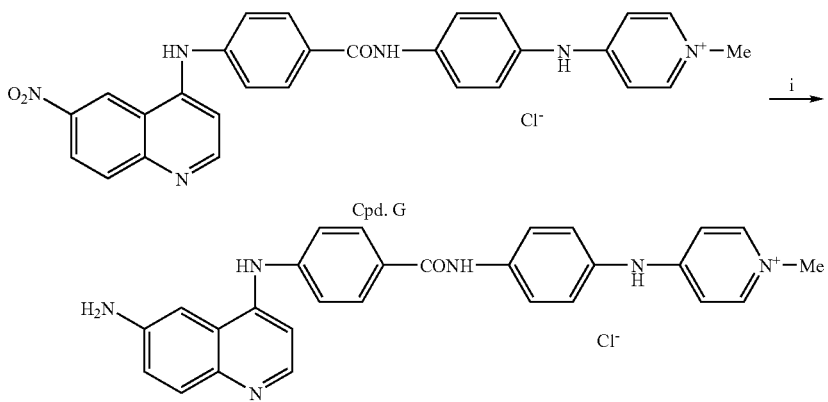

(i) Fe dust/EtOH/H₂O/cat. HCl/reflux.

To a refluxing suspension of Cpd. G (150 mg, 0.28 mmol) in 2:1 EtOH:H₂O (50 mL) was added Fe dust (60 mg, 1.13 mmol), and the resulting mixture was refluxed overnight. After this time, the hot reaction mixture was filtered through a pad of Celite, and solvent was again removed under reduced pressure. The residue was re-dissolved in MeOH, and solvent was removed under reduced pressure. This latter process was repeated twice more, and the residue was then recrystallized from HCl-MeOH:Et₂O to give Cpd. L (33 mg, 22%) as an amorphous yellow-brown solid. $^1$H NMR [(CD₃)₂SO]: δ 3.95 (s, 3H, R₂N⁺⁻CH₃), 6.94 (d, J=6.67 Hz, 1H, ArH), 7.13 (d, J=7.36 Hz, 2H, ArH), 7.34 (d, J=8.85 Hz, 2H, ArH), 7.43 (dd, J=9.06, 2.17 Hz, 1H, ArH), 7.45 (d, J=1.97 Hz, 1H, ArH), 7.62 (d, J=8.61 Hz, 2H, ArH), 7.85 (d, J=9.06 Hz, 1H, ArH), 7.95 (d, J=8.86 Hz, 1H, ArH), 8.15 (d, J=8.59 Hz, 2H, ArH), 8.26 (d, J=7.39 Hz, 2H, ArH), 8.32 (t, J=6.11 Hz, 1H, ArH), 10.35 (s, 1H, ArNHAr), 10.51 (s, 1H, ArNHAr), 10.69 (s, 1H, ArNHAr), 14.49 (br s, 1H, quinolone-N⁺—H) [NH₂ signal not observed]. LCMS (APCI⁺): 462 (100%). HPLC: 97%.

Example M

Preparation of 6-amino-4-[4-({3-[(1-methyl-4-pyridiniumyl)amino]benzoyl}amino)anilino]quinolinium dichloride (Cpd. M)

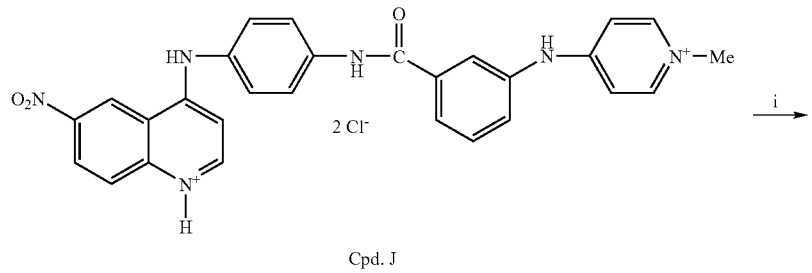

Cpd. J

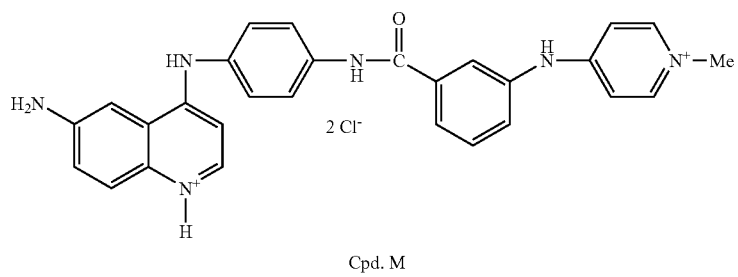

Cpd. M (i) Fe dust/EtOH/H₂O/cat. HCl/reflux

To a vigorously stirred suspension of compound Cpd. J (80 mg, 0.15 mmol) in 5:1 EtOH/H₂O (5 mL) was added Fe dust (43 mg), and the mixture was brought to reflux. Two drops of c.HCl were then added, and refluxing continued for a further 2 h (until TLC with the top phase of 5:4:1 mixture of n-BuOH:H₂O:AcOH showed complete consumption of starting material). The reaction mixture was diluted with EtOH (100 mL) and brought to reflux, and the hot mixture was filtered through a pad of Celite. The top residue of the Celite pad was extracted three further times with hot EtOH to ensure the complete extraction of the amine. The EtOH fractions were combined and evaporated to dryness, and the residue was extracted with hot water. The solution was evaporated to dryness, and azeotroped several times with EtOH. The resulting residue was dissolved in a small amount of MeOH, methanolic HCl (1.25 M, 1 mL) was added, and the solution was stirred for 10 min. The solution was then diluted with EtOAc, and then some of the MeOH was evaporated. The resulting precipitate was filtered and crystallized from MeOH/EtOAc to give Cpd. M (56 mg, 70%); mp>310° C. ¹H NMR [(CD₃)₂SO] δ 14.5 (br, 1 H, N⁺H), 11.22 (s, 1 H, NH), 10.59 (s, 1 H, NH), 9.55 (br, 1 H, NH), 8.32 (d, J=7.2 Hz, 2 H, ArH), 8.18 (d, J=6.1 Hz, 1 H, ArH), 7.95-7.91 (m, 4 H, ArH), 7.76 (d, J=8.8 Hz, 1 H, ArH), 7.66 (t, J=5.6 Hz, 1 H, ArH), 8.07 (d, J=8.4 Hz, 1 H, ArH), 7.40-7.37 (m, 3 H, ArH), 7.33-7.29 (m, 3 H, ArH), 6.71 (d, J=6.2 Hz, 1 H, ArH), 5.75 (br S, 2 H, NH₂), 3.98 (s, 3 H, N⁺CH₃)

Example N

Preparation of 4-[4-({4-[(6-amino-4-quinolinyl)amino]anilino}carbonyl)anilino]-1-methylpyridinium chloride (Cpd. N)

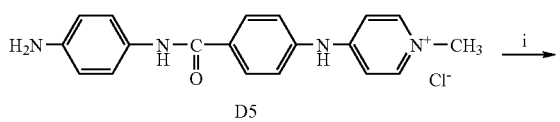

D5

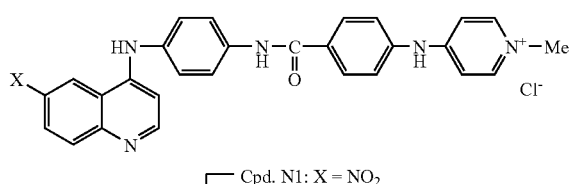

Cpd. N1: X = NO₂
Cpd. N:  X = NH₂

(i) 4-chloro-6-nitroquinoline/EtOH/H₂O/H+/reflux; (ii) Fe dust/EtOH/H₂O/cat. HCl/reflux.

1-Methyl-4-[4-({4-[(6-nitro-4-quinolinyl)amino]anilino}carbonyl)-anilino]pyridinium chloride (N1). To a suspension of 4-chloro-6-nitroquinoline (70 mg, 0.33 mmol)

in MeOH (10 mL) was added compound D5 (100 mg, 0.28 mmol), and the mixture was stirred at 20° C. for 1 h (until a clear solution obtained). A drop of c.HCl was then added, and refluxing was continued for a further 20 h. TLC analysis (eluting with the top phase of a 5:4:1 mixture of n-BuOH: H₂O:AcOH) showed some D5 remained, so more 4-chloro-6-nitroquinoline (35 mg, 0.16 mmol) was added and refluxing was continued for a further 4 h. The reaction mixture was then diluted with EtOAc and the resulted precipitate was filtered and washed sequentially with EtOAc, CH₂Cl₂ and diisopropylether, and finally crystallized from MeOH EtOAc to give Cpd. N1 (111 mg, 75%), mp (MeOH/EtOAc)>300° C.; ¹H NMR [(CD₃)₂SO] δ14.50 (br, 1 H, N⁺H); 11,42, (br s, 1 H, NH), 8.37 (d, J=7.5 Hz, 2 H, ArH), 8.22 (t, J=6.6 Hz, 1 H, ArH), 8.14 (d, J=8.6 Hz, 2 H, ArH), 7.98 (d, J=8.9 Hz, 2 H, ArH), 7.79 (d, J=9.1 Hz, 1 H, ArH), 7.52-7.59 (m, 3 H, ArH), 7.44-7.40 (m, 3 H, ArH), 7.43 (d, J=7.6 Hz, 2 H, ArH), 6.67 (d, J=6.8 Hz, 1 H, ArH), 4.01 (s, 3 H, N⁺CH₃) partial signal for the N⁺H₃ was observed. LCMS 461+ve.

Example O

Preparation of 4-[4-({4-[(6-dimethylammonio-4-quinolinyl)amino]benzoyl}amino)-anilino]-1-methylpyridinium dichloride (Cpd. O)

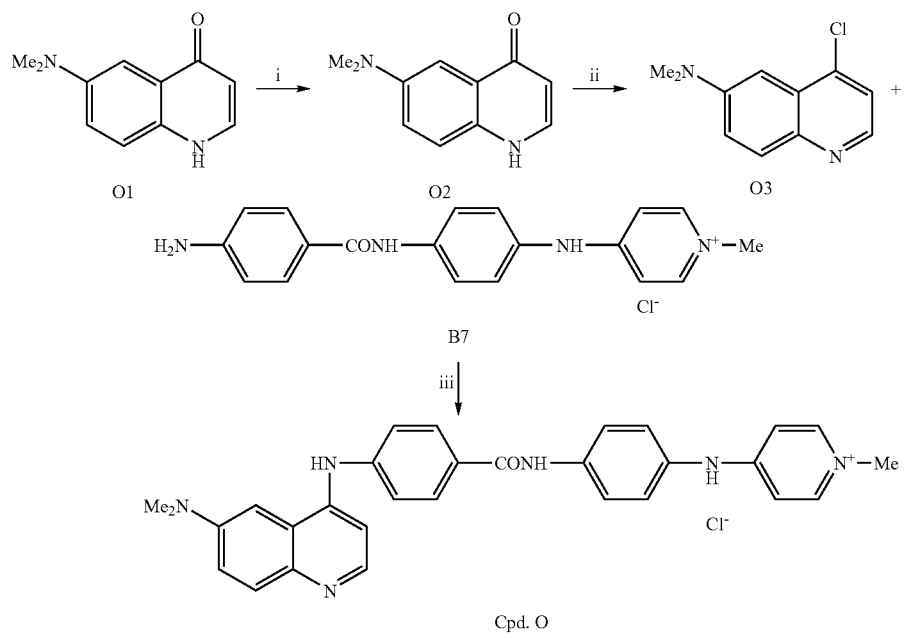

(i) HCHO/NaBH₃CN/EtOH/HCl; (ii) POCl₃;
(iii) MeOH/cat. HCl/reflux.

NH), 11.10 (s, 1 H, NH), 10.58 (s, 1 H, NH), 9.82 (d, J=2.1 Hz, 1 H, ArH), 8.72 (dd, J=9.3, 2.2 Hz, 1 H, ArH), 8.60 (d, J=7.0 Hz, 1 H, ArH), 8.42 (d, J=7.4 Hz, 2 H, ArH), 8.24 (d, J=8.6 Hz, 1 H, ArH), 8.15 (d, J=8.6 Hz, 2 H, ArH), 8.04 (d, J=8.8 Hz, 2 H, ArH), 7.51 (t, J=8.3 Hz, 4 H, ArH), 7.34 (d, J=7.5 Hz, 2 H, ArH), 6.91 (d, J=7.0 Hz, 1 H, ArH), 4.01 (s, 3 H, N⁺CH₃); LCMS 489+ve.

4-[4-({4-[(6-Amino-4-quinolinyl)amino]anilino}carbonyl)anilino]-1-methylpyridinium chloride (Cpd. N). To a solution of compound N1 (102 mg, 0.19 mmol) in ~5:1 EtOH:H₂O (3 mL) was added Fe dust (53 mg) and a drop of AcOH, and the resulting suspension vigorously stirred and refluxed for 3 h. The hot reaction mixture was filtered through Celite, and the Celite pad washed with more hot EtOH. The EtOH fractions were combined and evaporated to dryness, and the residue extracted into hot water. This solution was filtered through Celite and then evaporated to dryness. The residue was azeotroped with MeOH (3×20 mL), and then dissolved in MeOH (10 mL). Methanolic HCl (1.25 M, 2 mL) was added, and the solution stirred for 10 min. The solvent was evaporated to dryness, and the residue crystallized with MeOH/EtOAc to give Cpd. N (92 mg, 96%) mp (MeOH/EtOAc) ¹H NMR (CD₃)₂SO] δ14.17 (d, J=5.8 Hz, 1H NH), 11.11 (s, 1 H, NH), 10.52 (s, 1 H, NH), 10.21 (s, 1 H, To a solution of 6-amino-4-quinolone (O1) (112 mg, 0.71 mmol) and aqueous formaldehyde (40% w/v, 1.6 mL, 21.2 mmol) in EtOH (10 mL) were sequentially added NaBH₃CN (335 mg, 5.67 mmol) and 1N HCl (2.8 mL, 2.8 mmol), and the resulting bright yellow suspension was stirred at room temperature for 15 minutes. After this time, solvent was removed under reduced pressure, and the residue then dried by two MeOH azeotrope cycles. The residue was resuspended in MeOH and filtered through Celite, and solvent was removed under reduced pressure. The residue was crystallized from MeOH:EtOAc to give 6-dimethylamino-4-quinolone (O₂) (80 mg, 60%) as an amorphous tan solid; ¹H NMR [(CD₃)₂SO] δ2.93 [s, 6H, ArN(CH₃)₂], 5.90 [d, J=7.00 Hz, 1H, ArH], 7.13 [br s, ArOH], 7.24 [m, 2H, ArH], 7.45 [dd, J=7.41, 2.29 Hz, 1H, ArH], 7.74 [d, J=7.00 Hz, 1H, ArH]. LCMS (APCI⁺): 189 (100%). R_f=0.48 (10% MeOH:CH₂Cl₂).

Quinolone O2 (80 mg, 0.43 mmol) was refluxed in POCl₃ (10 mL) for 1 h. After this time, excess POCl₃ was removed under reduced pressure, and the residue was dissolved in CH₂Cl₂, cooled to 0° C., and treated with aqueous ammonia. The resulting mixture was extracted with CH₂Cl₂ (×3). The combined organic extracts were washed sequentially with H₂O (×1) and brine (×1), and then dried over MgSO₄. Solvent was removed under reduced pressure to give 6-dimethylamino-4-chloroquinoline (O3) (70 mg, 80%) as a bright yellow oil [Riegel et al., *J. Am. Chem. Soc.*, 1946, 68, 1264]. $^1$H NMR [(CD$_3$)$_2$SO] δ3.10 [s, 6H, ArN(CH$_3$)$_2$], 6.96 [d, J=2.85 Hz, 1H, ArH], 7.74 [dd, J=9.36, 2.85 Hz, 1H, ArH], 7.57 [d, J=4.69 Hz, 1H, ArH], 7.90 [d, J=9.36 Hz, 1H, ArH], 8.46 Hz [d, J=4.69 Hz, 1H, ArH]. LCMS (APCI$^+$): 207 (100%), 209 (40%). R$_f$=0.73 (10% MeOH:CH$_2$Cl$_2$).

To a solution of amine B7 (260 mg, 0.65 mmol) dissolved in 1:2 EtOH:H$_2$O (6 mL) were sequentially added cHCl (0.19 mL, 6.34 mmol) and O3 (140 mg, 0.70 mmol). The resulting mixture was refluxed for 72 h (reaction progress followed by TLC, eluting with the top phase of a 5:4:1 mixture of n-BuOH:H$_2$O:AcOH; R$_f$=0.30-0.40, bright yellow spot at 365 nm). After this time, solvent was removed under reduced pressure. The residue was re-dissolved in MeOH, and solvent was again removed under reduced pressure. This latter process was repeated once more, and the residue was crystallized twice from MeOH:EtOAc to afford Cpd. O (163 mg, 45%) as an amorphous yellow solid. $^1$H NMR [(CD$_3$)$_2$SO] δ3.06 (s, 6H, Ar(CH$_3$)$_2$), 3.93 (s, 3H, R$_2$N$^{+-}$CH$_3$), 7.07 (d, J=6.58 Hz, 2H, ArH), 7.12 (d, J=4.98 Hz, 1H, ArH), 7.22 (d, J=2.43 Hz, 1H, ArH), 7.30 (d, J=8.70 Hz, 2H, ArH), 7.42 (m, 3H, ArH), 7.78 (d, J=9.28 Hz, ArH), 7.92 (d, J=10.75 Hz, 2H, ArH), 8.01 (d, J=8.64 Hz, 1H, ArH), 8.19 (d, J=6.93 Hz, 2H, ArH), 8.32 (d, J=4.90 Hz, 1H, ArH), 8.50 (br s, 1H, —NH—), 8.91 (s, 1H, —NH—), 10.28 (s, 1H, —NH—), 10.80 (v br s, 1H, —NH—). LCMS (APCI$^+$): 490 (100%). HPLC: 95%.

Example P

Preparation of N-[4-(2-amino-6-methylpyrimidin-4-ylamino)phenyl]-4-(6-(dimethylamino)quinolin-4-ylamino)benzamide hydrochloride (Cpd. P)

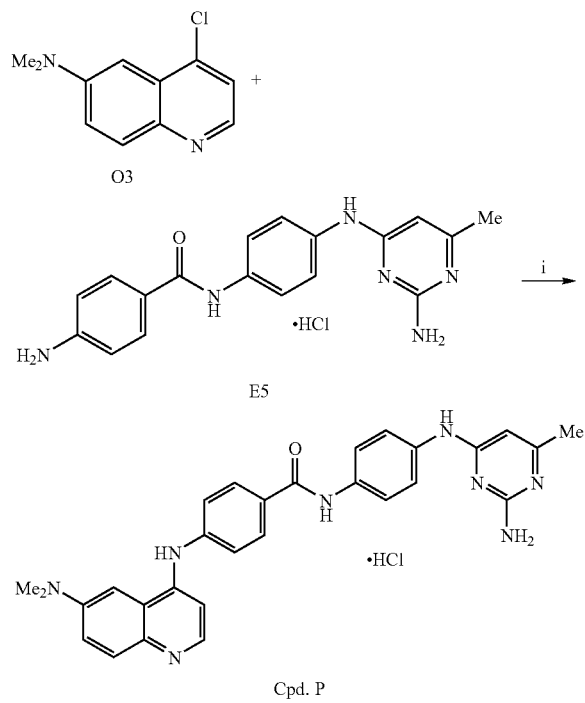

(i) MeOH, cat. c.HCl, 2.5 d

To a solution of amide E5 (228 mg, 0.62 mmol) in 1:2 EtOH:H$_2$O (20 mL) were sequentially added c.HCl (0.17 mL, 5.61 mmol) and 4-chloro-6-dimethylaminoquinoline (O3) (140 mg, 0.68 mmol), and the resulting mixture was refluxed for ~12 h. MS and TLC analysis (eluting with the top phase of a 5:4:1 mixture of n-BuOH:H$_2$O:AcOH) after this time showed some starting material still present in the reaction mixture, thus more O3 (140 mg, 0.68 mmol) was added. After a further few hours refluxing, TLC showed the reaction was complete, and thus solvent was removed under reduced pressure. The residue was crystallized from MeOH:EtOAc to afford Cpd. P as an (extremely fine) amorphous yellow solid (170 mg, 51%). $^1$H NMR [(CD$_3$)$_2$SO] δ2.28 [s, 3H], 3.15 [s, 6H, ArN(CH$_3$)$_2$], 6.21 [br s, 1 H, ArH], 6.89 [d, J=6.71 Hz, 1 H, ArH], 7.65 [m, 5 H, ArH], 7.82 [m, 4 H, ArH & ArNH$_2$], 7.96 [d, J=9.39 Hz, 1 H, ArH], 8.18 [d, J=8.57 Hz, 2 H, ArH], 8.35 [t, J=12.38, 6.19 Hz, 1 H, ArH], 10.44 [br s, 1 H, ArH], 10.65 [br s, 1 H, ArNHAr], 10.71 [s, 1 H, ArNHAr], 12.75 [br s, 1 H, ArC(O)NH], 14.56 [d, J=4.10 Hz, 1 H, quinolinyl N$^+$H]. LCMS (APCI$^+$): 506 (100%). HPLC: 97.6%.

Example Q

Preparation of 6-(dimethylamino)-4-[4-({3-[(1-methyl-4-pyridiniumyl)amino]anilino}carbonyl)anilino]quinolinium dichloride (Cpd. Q)

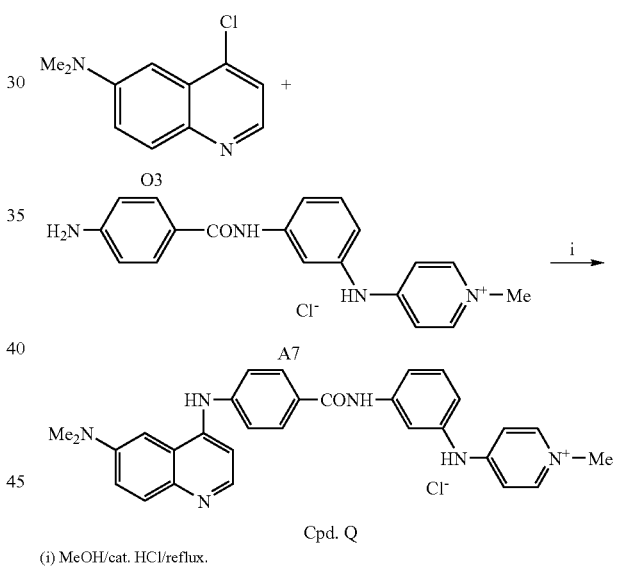

(i) MeOH/cat. HCl/reflux.

Amine A7 (100 mg, 0.28 mmol) was dissolved in EtOH (20 mL) and H$_2$O (10 mL) by heating. 4-Chloro-6-dimethylaminoquinoline (O3) (70 mg, 0.33 mmol) and c.HCl (3 drops) were then added, and the mixture was refluxed for 3 d. (until TLC with the top phase of 5:4:1 mixture of n-BuOH:H$_2$O:AcOH showed complete consumption of starting amine). The reaction mixture was evaporated to dryness, and the residue azeotroped with EtOH. The residue was dissolved in a small volume of MeOH, which was then diluted with EtOAc. The resulting precipitate was filtered and crystallized from MeOH/EtOAc to give 163 mg of crude product, which was purified by preparative HPLC to give Cpd. Q (70 mg, 45%); mp (MeOH/EtOAc), >300° C.; $^1$H NMR [(CD$_3$)$_2$SO] δ14.38 (br, 1 H, N$^+$H), 10.71 (s, 1 H, NH), 10.56 (s, 1 H, NH), 10.52 (s, 1 H, NH), 8.36 (d, J=6.7 Hz, 1 H, ArH), 8.31 (d, J=7.3 Hz, 2 H, ArH), 8.18 (d, J=8.6 Hz, 2 H, ArH), 7.99 (brs, 1 H, ArH), 7.92 (d, J=9.4 Hz, 1 H, ArH), 7.69-7.64 (m, 4 H, ArH), 7.54 (d, J=2.3 Hz, 1 H, ArH), 7.49 (t, J=8.1 Hz, 1 H, ArH), 7.21 (d, J=7.4 Hz, 2 H, ArH), 7.08 (d, J=7.9 Hz, 1 H, ArH), 6.91 (d, J=6.7 Hz, 1 H, ArH), 3.98 (s, 3 H, N⁺CH₃), 3.14 [s, 6 H, N(CH₃)₂].

Example R

Preparation of 1-methyl-4-[3-({4-[(7-nitro-4-quinolinyl)amino]benzoyl}amino)anilino]pyridinium chloride (Cpd. R)

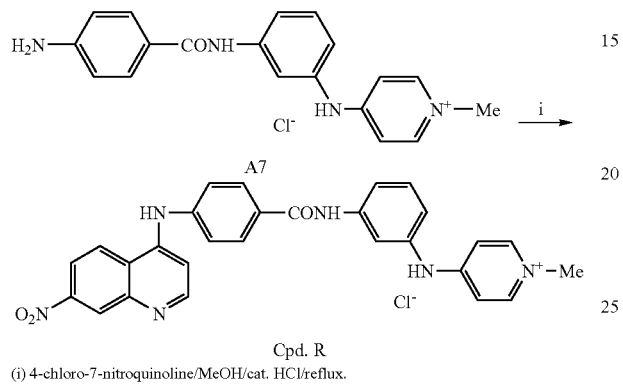

Cpd. R
(i) 4-chloro-7-nitroquinoline/MeOH/cat. HCl/reflux.

Coupling of A7 with 4-chloro-7-nitro quinoline (Ruchelman et al. *Biorg. Med. Chem.* 2004, 12, 3731) gave Cpd. R in 89% yield; mp (MeOH/EtOAC), 302-306° C. (dec); ¹H NMR [(CD₃)₂SO] δ 11.50 (br, 1 H, NH), 10.74 (s, 1 H, NH), 10.58 (s, 1 H, NH), 9.04 (d, J=9.3 Hz, 1 H, ArH), 8.90 (d, J=2.3 Hz, 1 H, ArH), 8.77 (d, J=6.7 Hz, 1 H, ArH), 8.51 (dd, J=9.3, 4.5 Hz, 1 H, ArH), 8.31 (d, J=7.4 Hz, 2 H, ArH), 8.18 (d, J=8.6 Hz, 2 H, ArH), 7.98 (t, J=1.9 Hz, 1 H, ArH), 7.70 (d, J=8.6 Hz, 3 H, ArH), 7.49 (t, J=8.1 Hz, 1 H, ArH), 7.22 (d, J=7.6 Hz, 2 H, ArH), 7.15 (d, J=6.7 Hz, 1 H, ArH), 7.09 (br d, J=7.8 Hz, 1 H, ArH), 3.96 (s, 3 H, N⁺CH₃); HRMS (FAB⁺) calc. for C₂₈H₂₄N₆O₃ (M⁺¹) m/z 491.1832, found 491.1825.

Example S

Preparation of 1-methyl-4-[4-(4-{7-nitroquinolin-4-ylamino}benzamido)-phenylamino]pyridinium dichloride (Cpd. S)

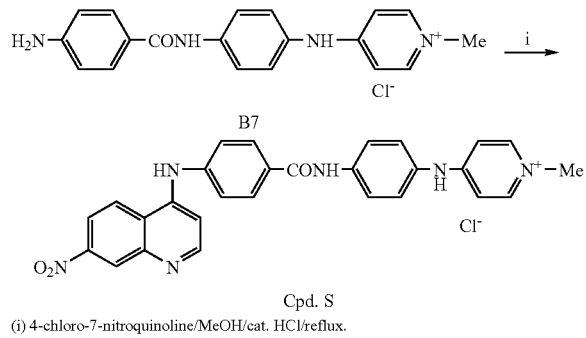

Cpd. S
(i) 4-chloro-7-nitroquinoline/MeOH/cat. HCl/reflux.

To a solution of amine B7 (1.46 g, 3.73 mmol) in dry MeOH (20 mL) were sequentially added 4-chloro-7-nitroquinoline (S1) (0.78 g, 3.73 mmol) and two drops of c.HCl, and the resulting mixture was refluxed for 4 h. After this time, the temperature was reduced to ~40° C. and heating was continued for a further 65 h. After this time, solvent was removed under reduced pressure. The residue was re-dissolved in MeOH, and solvent was again removed under reduced pressure. This latter process was repeated once more, and the residue was then re-precipitated twice from MeOH:Et₂O. Finally, a portion of the solid thus obtained was re-precipitated from MeOH:EtOAc to afford Cpd. S as an amorphous yellow-orange solid (0.070g, 3%). ¹H NMR [(CD₃)₂SO]: 3.96 [s, 3H, R₂N⁺CH₃], 7.14 [m, 3H, ArH], 7.35 [d, J=8.85 Hz, 2H, ArH], 7.68 [d, J=8.57 Hz, 2H, ArH], 7.96 [d, J=8.85 Hz, 2H, ArH], 8.18 [d, J=8.57 Hz, 2H, ArH], 8.26 [d, J=7.37 Hz, 2H, ArH], 8.50 [dd, J=9.28, 2.23 Hz, 1H, ArH], 8.77 [d, J=6.65 Hz, 1H, ArH], 8.94 [d, J=2.23 Hz, 1H, ArH], 9.08 [d, J=9.28 Hz, 1H, ArH], 10.55 [s, 1H, ArNHAr], 10.71 [s, 1H, ArNHAr], 11.21 [br s, 1H, ArC(O)NHAr], 11.21 [v v br s, 1H, quinoline-N⁺H]; LCMS (APCI⁺): 492 (100%), 493 (30%). HPLC: 98.1%.

Example T

Preparation of 4-[4-({3-[(1-methyl-4-pyridiniumyl)amino]benzoyl}amino)anilino]-7-nitroquinolinium dichloride (Cpd. T)

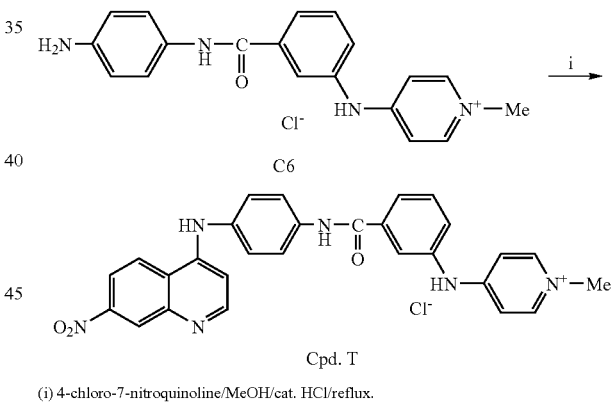

Cpd. T
(i) 4-chloro-7-nitroquinoline/MeOH/cat. HCl/reflux.

Compound C6 (92 mg, 0.25 mmol) was dissolved in EtOH (10 mL) and H₂O (5 mL) by heating. 4-Chloro-7-nitroquinoline (65 mg, 0.31 mmol) and c.HCl (3 drops) were then added and the mixture was refluxed for 18 h. (until TLC with the top phase of 5:4:1 mixture of n-BuOH:H₂O:AcOH showed complete consumption of starting amine). The reaction mixture was then diluted with EtOAc, refluxed for a few minutes, and allowed to cool. The resulting precipitate was filtered and crystallized twice from MeOH/EtOAc to give Cpd. T (104 mg, 71%); mp (MeOH, EtOAc)>300° C.; ¹H NMR [(CD₃)₂SO] δ14.80 (br 1 H, N⁺H), 10.89 (br, 2 H, 2×NH), 10.60 (s, 1 H, NH), 8.96 (d, J=9.0 Hz, 1 H, ArH), 8.84 (bs, 1 H, ArH), 8.67 (d, J=6.5 Hz, 1 H, ArH), 8.32 (d, J=7.3 Hz, 2 H, ArH), 8.0-7.91 (m, 4 H, ArH), 7.68 (t, J=7.8 Hz, 1 H, ArH), 7.57 (d, J=9.4 Hz, 1 H, ArH), 7.49 (d, J=8.7 Hz, 2 H, ArH), 7.29 (d, J=7.4 Hz, 2 H, ArH), 6.94 (d, J=6.6 Hz, 1 H, ArH), 3.99 (s, 3 H, N$^+$CH$_3$). HRMS (FAB$^+$) calc. for C$_{28}$H$_{23}$N$_6$O$_3$ (M$^{+1}$) m/z 491.1832, found 491.1830.

Example U

Preparation of 4-[4-({4-[(1-methyl-4-pyridiniumyl)amino]benzoyl}amino)anilino]-7-nitroquinolinium dichloride (Cpd. U)

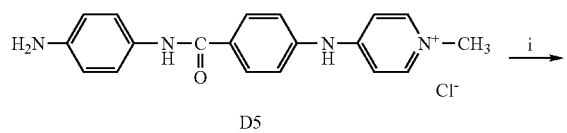

D5

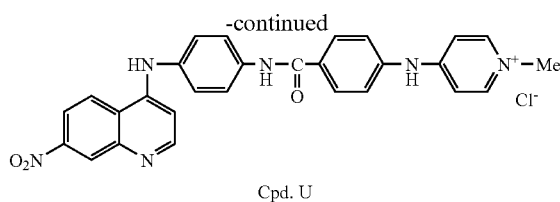

Cpd. U
(i) 4-chloro-7-nitroquinoline/EtOH/H$_2$O/H+/reflux.

Compound D5 (100 mg, 0.28 mmol) was dissolved in EtOH (20 mL) and H$_2$O (10 mL) by heating. 4-Chloro-7-nitroquinoline (70 mg, 0.33 mmol) and c.HCl (3 drops) were then added and the reaction mixture was refluxed for 18 h. (until TLC with the top phase of 5:4:1 mixture of n-BuOH:H$_2$O:AcOH showed complete consumption of starting amine). The reaction mixture was then diluted with EtOAc, refluxed for a few minutes, and allowed to cool. The resulting precipitate was filtered and crystallized twice from MeOH/EtOAc to give Cpd. U (99 mg, 63%); mp (MeOH/EtOAc) 268° C. (dec); $^1$H NMR [(CD$_3$)$_2$SO] δ10.93 (brs, 2 H, 2×NH), 10.53 (s, 1 H, NH), 8.94 (d, J=9.2 Hz, 1H, ArH), 8.85 (bs, 1 H, ArH), 8.67 (d, J=6.7 Hz, 1 H, ArH), 8.49 (d, J=9.2 Hz, 1 H, ArH), 8.37 (d, J=7.5 Hz, 2 H, ArH), 8.13 (d, J=8.6 Hz, 2 H, ArH), 8.51 (d, J=8.8 Hz, 2 H, ArH), 7.50 (t, J=8.7 Hz, 4H, ArH), 7.31 (d, J=7.5 Hz, 2 H, ArH), 6.94 (d, J=6.8 Hz, 1 H, ArH), 4.02 (s, 3 H, N$^+$CH$_3$). APCI$^+$ve 461.

Example V

Preparation of Preparation of 4-[3-({4-[(7-ammonio-4-quinolinyl)amino]benzoyl}amino)anilino]-1-methylpyridinium dichloride (Cpd. V)

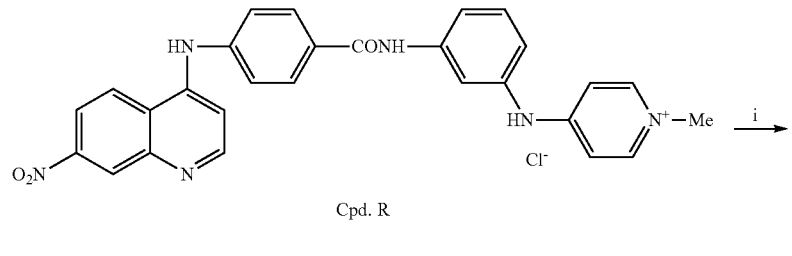

Cpd. R

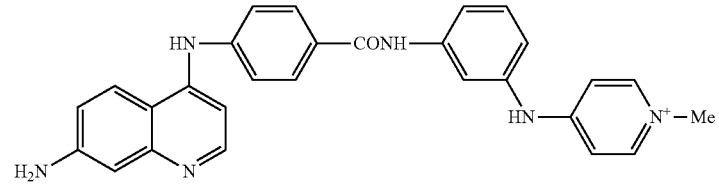

Cpd. V
(i) Fe dust/EtOH/H$_2$O/reflux

Fe dust reduction of Cpd. R as above gave Cpd. V in 83% yield: mp 281-285° C.; $^1$H NMR [(CD$_3$)$_2$SO] δ13.73 (br, 1 H, NH), 10.79 (s, 1 H, NH), 10.56 (s, 1 H, NH), 10.53 (br s, 1 H, NH), 8.41 (d, J=9.3 Hz, 1 H, ArH), 8.31 (d, J=7.4 Hz, 2 H, ArH), 8.24 (d, J=7.0 Hz, 1 H, ArH), 8.14 (d, J=8.6 Hz, 2 H, ArH), 7.98 (t, J=1.9 Hz, 1 H, ArH), 7.67 (br d, J=9.2 Hz, 1 H, ArH), 7.59 (d, J=8.6 Hz, 2 H, ArH), 7.48 (t, J=8.1 Hz, 1 H, ArH), 7.23 (d, J=7.5 Hz, 2 H, ArH), 7.10-7.06 (m, 2 H, ArH), 6.86 (d, J=2.1 Hz, 1 H, ArH), 6.76 (br s, 2 H, NH$_2$), 6.68 (d, J=7.0 Hz, 1 H, ArH), 3.98 (s, 3 H, N$^+$CH$_3$); HRMS (FAB$^+$) calc. for C$_{28}$H$_{25}$N$_6$O (M$^+$) m/z 461.2090, found 461.2108; Anal. calc. for C$_{28}$H$_{26}$N$_6$ClO$_3$. 1.25H$_2$O: C, 60.5; H, 5.2; N, 15.1; Cl, 12.8; found, C, 60.6; H, 5.2; N, 15.0; Cl, 13.0%.

Example W

Preparation of 1-methyl-4-[4-(4-{7-aminoquinolin-4-ylamino}benzamido)-phenylamino]pyridinium dichloride (Cpd. W)

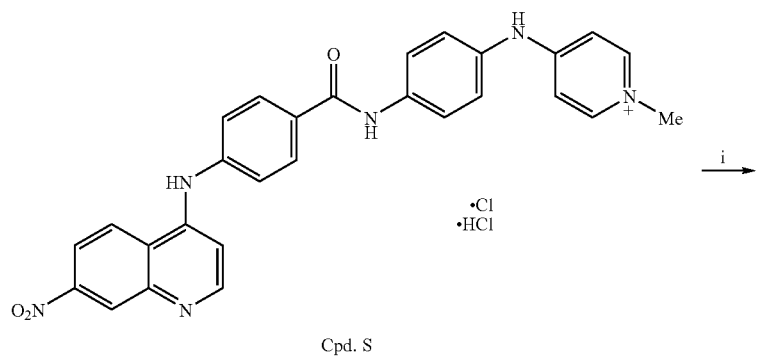

Cpd. S

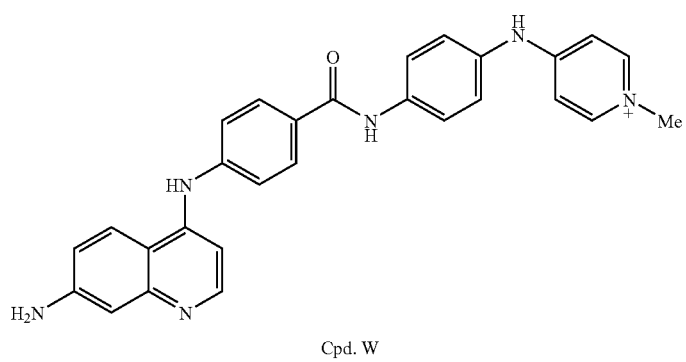

Cpd. W (i) Fe dust, 2:1 EtOH:H$_2$O, reflux.

To a refluxing suspension of Cpd. S (40 mg, 0.07 mmol) in 2:1 EtOH:H$_2$O (50 mL) was added Fe dust (15 mg, 0.28 mmol), and the resulting mixture was refluxed for a few hours until complete. After this time, the hot reaction mixture was filtered through a pad of Celite, and solvent was removed under reduced pressure. The residue was dried via three MeOH-azeotrope cycles, and finally recrystallized from HCl-MeOH:EtOAc to give Cpd. W (34 mg, 90%) as an amorphous yellow solid; mp (MeOH, EtOAc)>280° C.; $^1$H NMR [(CD$_3$)$_2$SO]: 3.95 (s, 3H, R$_2$N$^+$CH$_3$), 6.67 (d, J=7.00 Hz, 1H, ArH), 6.92 (d, J=2.13 Hz, 1H, ArH), 7.07 (dd, J=9.38, 2.13 Hz, 1H, ArH), 7.18 (br d, J=6.45 Hz, 2H, ArNH$_2$), 7.34 (d, J=8.89 Hz, 2H, ArH), 7.60 (d, J=8.60 Hz, 2H, ArH), 7.97 (d, J=8.89 Hz, ArH), 8.16 (d, J=8.60 Hz, 2H ArH), 8.22 (t, J=6.66 Hz, 1H, ArH), 8.27 (d, J=7.49 Hz, 2H, ArH), 8.51 (d, J=9.39 Hz, 1H, ArH), 10.58 (s, 1H, ArNHAr), 10.71 (s, 1H, ArNHAr), 11.00 (s, 1H, ArC(O)NHAr), 14.08 (d, J=6.09 Hz, 1H, quinoline-N$^+$—H); LCMS (APCI$^+$): 462 (100%); HPLC: 96.1%.

Example X

Preparation of 7-amino-4-[4-({3-[(1-methyl-4-pyridiniumyl)amino]benzoyl}amino)anilino]quinolinium dichloride (Cpd. X)

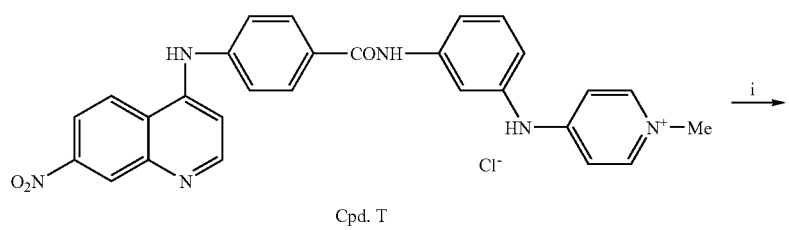

Cpd. T

-continued

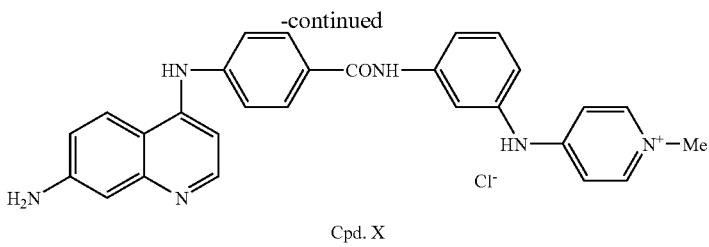

Cpd. X (i) Fe dust/EtOH/H₂O/reflux

To a vigorously stirred suspension of compound Cpd. T (107 mg, 0.19 mmol) in 5:1 EtOH:H₂O (5 mL) was added Fe dust (43 mg), and the mixture was brought to reflux. Two drops of c.HCl were added, and refluxing was continued for 2 h (until TLC with the top phase of 5:4:1 mixture of n-BuOH:H₂O:AcOH showed complete consumption of starting material). The reaction mixture was then diluted with EtOH (100 mL), and brought to reflux. The hot mixture was filtered through a pad of Celite, and the top layer of the Celite pad extracted three times with hot EtOH to ensure complete extraction of the amine. The combined ethanol extracts were evaporated to dryness, and the residue was extracted with hot H₂O. The solution was evaporated to dryness, and azeotroped several times with EtOH. The resulting residue was dissolved in a small volume of MeOH, methanolic HCl was added (1.25 M, 1 mL), and the solution was stirred for 10 min. The solution was diluted with EtOAc, and some of the MeOH was evaporated. The resulting precipitate was filtered and crystallized from MeOH/EtOAc to give Cpd. X (99 mg, 98%); mp (MeOH/EtOAc >300° C.; ¹H NMR [(CD₃)₂SO] δ13.48 (s, 1H, N⁺H), 10.98 (s, 1 H, NH), 10.59 (s, 1 H, NH), 10.32 (s, 1 H, NH), 8.36-8.31 (m, 3 H, ArH), 8.14 (d, J=7.0 Hz, 1 H, ArH), 8.00-7.91 (m, 4 H, ArH), 7.67 (t, J=7.7 Hz, 1 H, ArH), 7.57 (d, J=7.4 H, 1 H, ArH), 7.40 (d, J=8.6 Hz, 2 H, ArH), 7.02 (d, J=9.2 Hz, 1 H, ArH), 6.82 (bs, 1 H, ArH), 6.66 (brs, 2 H, NH₂), 6.43 (d, J=6.9 Hz, 1 H, ArH), 3.99 (s, 3 H, N⁺CH₃).

HRMS (FAB⁺) calc. for $C_{28}H_{25}N_6O$ (M⁺¹) m/z 461.2090, found 461.2085.

Example Y

Preparation of 4-[4-({4-[(7-amino-4-quinolinyl)amino]anilino}carbonyl)anilino]-1-methylpyridinium chloride (Cpd. Y)

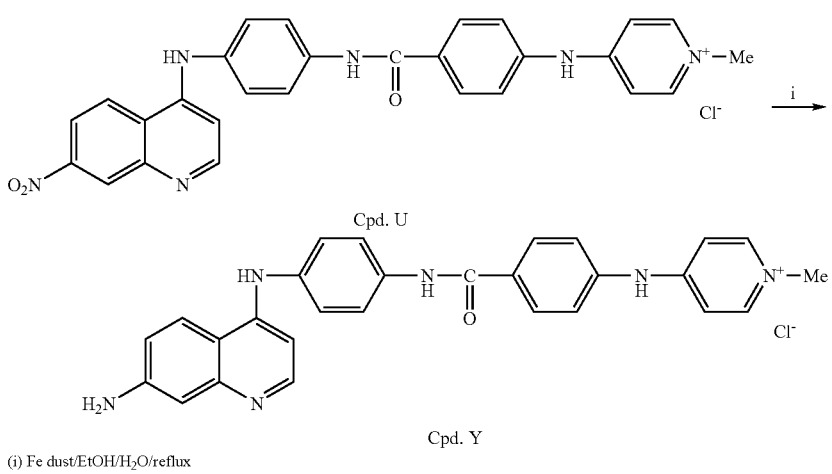

Cpd. U

Cpd. Y (i) Fe dust/EtOH/H₂O/reflux

To a suspension of Cpd. U (101 mg, 0.19 mmol) in-5:1 EtOH:H₂O (3 mL) was added Fe dust (53 mg), followed by a drop of AcOH. The resulting suspension was vigorously stirred and refluxed for 3 h. The hot reaction mixture was filtered through Celite, and the Celite pad was washed with hot EtOH. The combined EtOH extracts were evaporated to dryness and the residue extracted into hot water. The solution was filtered through Celite, and then evaporated to dryness. The residue was azeotroped with MeOH (3×20 mL), and then dissolved in MeOH (10 mL). Methanolic HCl (1.25 M, 2 mL) was added, and the solution stirred for 10 min. The solution was then evaporated to dryness, and the residue crystallized from MeOH/EtOAc to give compound Cpd. Y (55 mg, 58%) mp (MeOH/EtOAc) 290-295° C.; ¹H NMR (CD₃)₂SO] δ13.44 (br, 1 H, N⁺H), 11.04 (s, 1 H, NH), 10.50 (s, 1H, NH), 10.31 (s, 1 H, NH), 8.38-8.33 (m, 3 H, ArH), 8.15-8.11 (m, 3 H, ArH), 7.97 (d, J=8.9 Hz, 2 H, ArH), 7.51 (d, J=8.7 Hz, 2 H, ArH), 7.41 (d, J=9.9 Hz, 2 H, ArH), 7.33 (d, J=7.5 Hz, 2 H, ArH), 7.03 (dd, J=9.2, 2.1 Hz, 1 H, ArH), 6.81 (d, J=2.2 Hz, 1 H, ArH), 6.67 (bs, 2 H, NH₂), 6.44 (d, J=7.1 Hz, 1 H, ArH), 4.01 (s, 3 H, N⁺CH₃); LCMS 461+ve.

Example Z

Preparation of 7-(dimethylamino)-4-[4-({3-[(1-methyl-4-pyridiniumyl)amino]anilino}carbonyl)anilino]quinolinium dichloride (Cpd. Z)

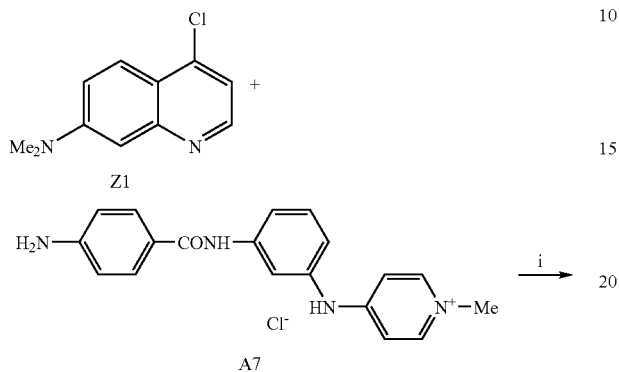

(i) EtOH/H₂O/cat. HCl/reflux.

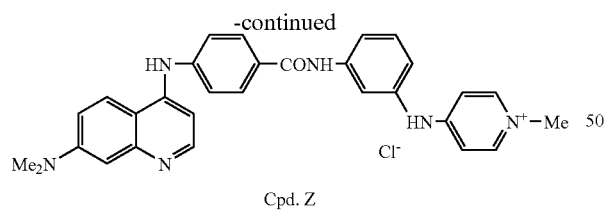

(i) EtOH/H₂O/cat. HCl/reflux.

4-Chloro-7-dimethylaminoquinoline (Z1) [Konishi et al., WO 9611187 A1] (70 mg, 0.34 mmol) was added to a solution of A7 (100 mg, 0.28 mmol) in EtOH (20 ml) and H₂O (10 mL) then c.HCl (0.25 mL, 9 eq) was added and refluxed for 2 days. Mass spectrum of a sample of the reaction mixture showed A7 still present, so more 4-chloro-7-dimethylaminoquinoline (35 mg, 0.17 mmol) was added and refluxed continued for a further 5 days. The reaction mixture was then evaporated to dryness. The residue was dissolved in a small volume of MeOH diluted with EtOAc. The resulting precipitate was filtered, and crystallized from MeOH/EtOAc to give crude product (160 mg), which was purified by preparative HPLC (fraction with mass of 489+ve was evaporated to dryness, and the residue dissolved in EtOH/H₂O 2:1 (5 mL), diluted with EtOAc, and the resulting precipitate filtered) to give Cpd. Z (20 mg 13%). This was 90% clean by HPLC; MP (MeOH EtOAc) 285-289° C. (dec); 1 H NMR [(CD3)₂SO] δ13.47 (br, 1 H, N⁺H) 10.54 (s, 1 H, NH), 10.51 (s, 1 H, NH), 10.49 (s, 1 H, NH), 8.44 (d, J=9.7 Hz, 1 H, ArH), 8.35-8.30 (m, 3 H, ArH) 8.13 (d, J=8.6 Hz, 2 H, ArH), 7.98 (t, J=1.9 Hz, 1 H, ArH), 7.63-7.58 (m, 3 H, ArH), 7.49 (t, J=8.1 Hz, 1 H, ArH), 7.40 (dd, J=9.6, 2.5 Hz, 1 H, ArH), 7.18 (d, J=7.5 Hz, 2 H, ArH), 7.09 (dd, J=7.7, 1.3 Hz, 1 H, ArH), 6.81 (d, J=2.5 Hz, 1 H, ArH), 6.71 (d, J=7.0 Hz, 1 H, ArH), 3.98 (s, 3 H, N⁺CH₃), 3.16 (s, 6H, NMe₂); Mass APCI⁺ve 489.

Example AA

Preparation of 4-[4-({4-[(7-dimethylamino)quinolin-4-ylamino)benzamido)-phenylamino)-1-methylpyridinium dichloride (Cpd. AA)

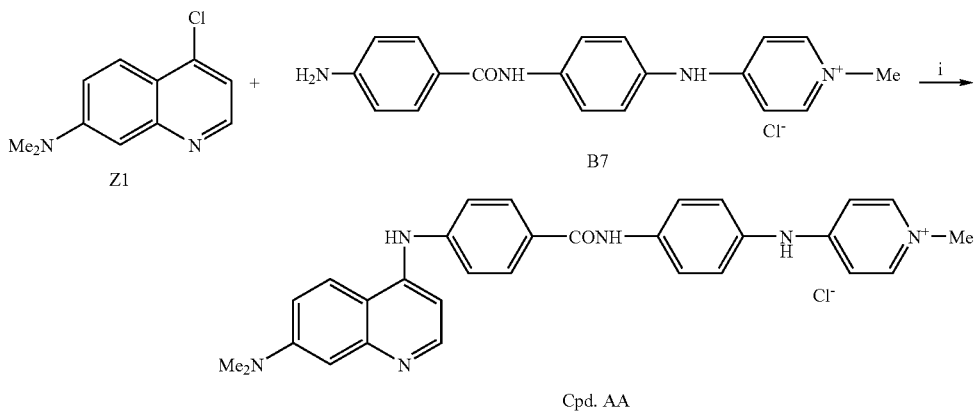

To a solution of amine B7 (311 mg, 0.79 mmol) dissolved in 1:2 EtOH:H₂O (3 mL) were sequentially added c.HCl (0.22 mL, 0.72 mmol) and 4-chloro-7-dimethylaminoquinoline (Z1) (175 mg, 0.85 mmol). The resulting mixture was refluxed for 30 h (reaction progress followed by TLC, eluting with the top phase of a 5:4:1 mixture of n-BuOH:H₂O:AcOH; $R_f$=0.30-0.40, bright yellow spot at 365 nm). After this time, solvent was removed under reduced pressure. The residue was re-dissolved in MeOH, and solvent was again removed under reduced pressure. This latter process was repeated once more, and the residue was crystallized thrice from MeOH: EtOAc to afford Cpd. AA as an amorphous yellow solid (93 mg, 21%). ¹H NMR [CD₃)₂SO]: 3.15 [s, 6H, ArN(CH₃)₂], 3.96 [s, 3H, ArN⁺—CH₃], 6.72 [d, J=7.00 Hz, 1H, ArH], 6.91 [d, J=2.36 Hz, 1H ArH], 7.14 [d, J=7.40 Hz, 2H, ArH], 7.36 [m, 3H, ArH], 7.62 [d, J=8.53 Hz, 2H, ArH], 7.95 [d, J=8.89 Hz, 2H, ArH], 8.16 [d, J=8.53 Hz, 2H, ArH], 8.26 [d, J=7.40 Hz, 2H, ArH], 8.32 [d, J=7.00 Hz, 1H, ArH], 8.57 [d, J=9.59 Hz, 1H, ArH], 10.53 [s, 1H, —NH—], 10.70 [s, 1H, —NH—], 10.75 [s, 1H, —NH—], 13.85 [br s, 1H, Ar—N⁺H]. LCMS (APCI⁺): 490 (100%), 491 (20%). HPLC: 96.7%.

Example BB

Preparation of N-[4-(2-amino-6-methylpyrimidin-4-ylamino)phenyl]-4-(7-(dimethylamino)quinolin-4-ylamino)benzamide hydrochloride (Cpd. BB)

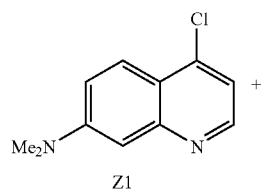
Z1

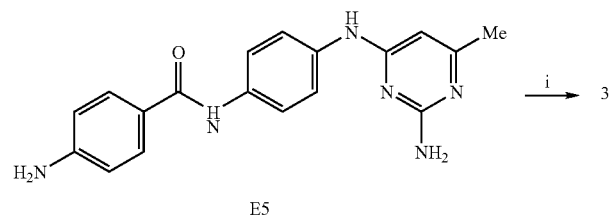
E5

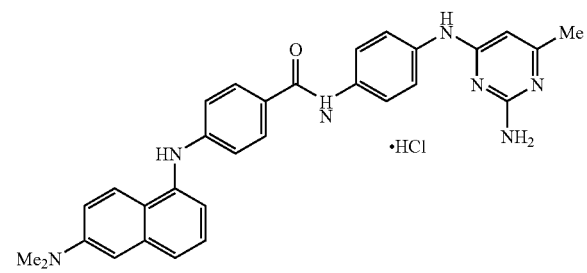
Cpd. BB (i) EtOH/H$_2$O/cat. HCl/reflux.

To a solution of amide E5 (306 mg, 0.83 mmol) in 1:2 EtOH:H$_2$O (10 mL) were sequentially added c.HCl (0.23 mL) and 4-chloro-7-dimethylamino-quinoline (Z1) (188 mg, 0.91 mmol), and the resulting mixture was refluxed for 20 h. After this time [when MS and TLC analysis (5:4:1 n-BuOH:H$_2$O:CH$_3$CO$_2$H) of the reaction mixture suggested the remaining small quantity of E5 was degrading], the reaction mixture was filtered, and the resulting solid washed sequentially with EtOAc and hexanes, to furnish Cpd. BB as an amorphous lemon-yellow solid (199 mg, 45%). $^1$H NMR [(CD$_3$)$_2$SO]: 2.28 [s, 3H, ArCH$_3$], 3.15 [s, 6H, ArN(CH$_3$)$_2$], 6.18 [br s, 1H, ArH], 6.70 [d, J=7.02 Hz, 1H, ArH], 6.88 [d, J=2.46 Hz, 1H, ArH], 7.38 [dd, J=9.62, 2.46 Hz, 1H, ArH], 7.61 [d, J=8.60, 2H, ArH & ArNH$_2$], 8.14 [d, J=8.60 Hz, 2H, ArH], 8.31 [d, J=7.02 Hz, 1H, ArH], 8.55 [d, J=9.71 Hz, 1H, ArH], 10.41 [br s, 1H, ArH], 10.65 [m, 2H, ArNHAr & ArNHAr], 12.68 [v br s, 1H, ArC(O)NH], 13.77 [v br s, 1H, quinolinyl N⁺H]. LCMS (APCI⁺): 506 (100%). HPLC: 96.6%.

Example CC

Preparation of 7-(dimethylamino)-4-[4-({3-[(1-methyl-4-pyridiniumyl)amino]benzoyl}amino)aniline]quinolinium dichloride (Cpd. CC)

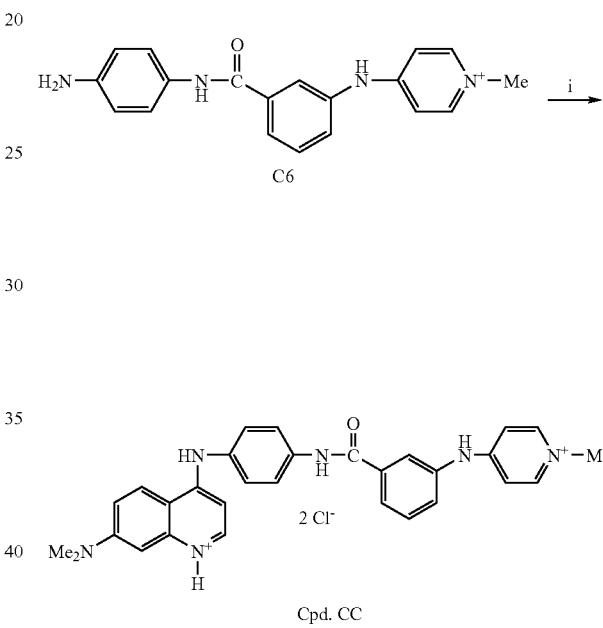
Cpd. CC (i) 4-chloro-7-(dimethylamino)quinoline/EtOH/H$_2$O/H⁺/reflux.

4-Chloro-7-dimethylaminoquinoline (Z1) (71 mg, 0.34 mmol) and c.HCl (0.3 mL, 9 eq) were sequentially added to a solution of C6 (104 mg, 0.0.29 mmol) in EtOH (10 ml) and H$_2$O (5 mL), and the mixture was refluxed for 4 days. The reaction mixture was then diluted with EtOAc (150 mL), refluxed, and then cooled to room temperature. The resulting precipitate was filtered, and then dissolved in a small volume of MeOH. The solution was diluted with EtOAc, and the resulting precipitate filtered, and then purified by preparative HPLC to give Cpd. CC (13 mg, 8%): mp (MeOH/EtOAc) 188° C. (dec); $^1$H NMR [(CD$_3$)$_2$SO] δ13.22 (bd, J=5.7 Hz, 1 H, N⁺H), 10.61 (s, 1 H, NH), 10.51 (s, 1 H, NH), 10.38 (s, 1 H, NH), 8.42 (d, J=9.7 Hz, 1 H, ArH), 8.32 (d, J=7.5 Hz, 2 H, ArH), 8.23 (t, J=6.7 Hz, 1 H, ArH), 7.96-7.92 (m, 3 H, ArH), 7.88 (t, J=1.8 Hz, 1 H, ArH), 7.69 (t, J=7.9 Hz, 1 H, ArH), 7.58 (dd, J=8.0, 1.4 Hz, 1 H, ArH), 7.43 (d, J=8.9 Hz, 2 H, ArH), 7.34 (dd, J=9.6, 2.6 Hz, 1 H, ArH), 7.21 (d, J=7.5 Hz, 2 H, ArH), 6.77 (d, J=2.5 Hz, 1 H, ArH), 6.48 (d, J=7.1 Hz, 1 H, ArH), 3.99 (s, 3 H, N⁺CH$_3$), 3.15 [s, 6 H, N(CH$_3$)$_2$]. Mass APCI⁺ve 489.

Example DD

Preparation of 7-(dimethylamino)-4-[4-[4-({4-[(1-methyl-4-pyridiniumyl)amino]benzoyl}amino)aniline] quinolinium dichloride (Cpd. DD)

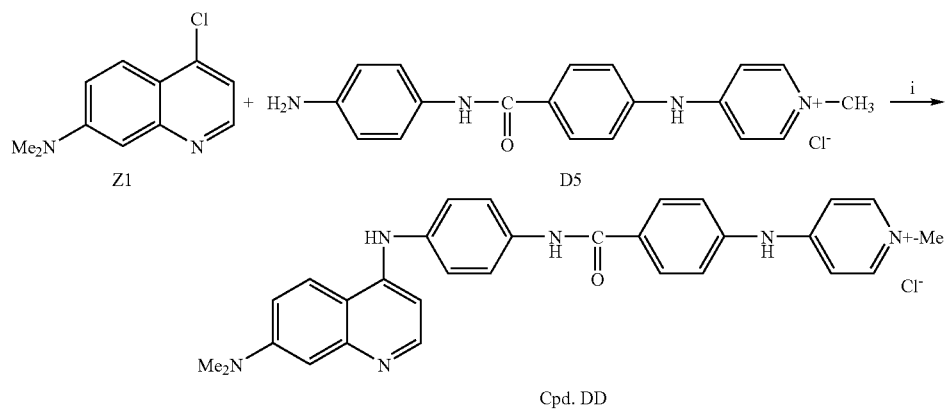

(i) EtOH/H₂O/cat•HCl/reflux.

4-Chloro-7-dimethylaminoquinoline (Z1) (140 mg, 0.62 mmol) and c.HCl (0.3 mL, 9 eq) were sequentially added to a solution of D5 (110 mg, 0.31 mmol) in EtOH (20 ml) and H₂O (10 mL), and the mixture was refluxed for 4 d. The reaction mixture was diluted with EtOAc (150 mL), refluxed, and then cooled to room temperature. The resulting precipitate was filtered, and then dissolved in a small volume of MeOH, which was then diluted with EtOAc. The resulting precipitate was filtered to give crude product, which was purified by preparative HPLC to give Cpd. DD (47 mg, 27%) HPLC 99.9%; mp (MeOH/EtOAc) 198-200° C.; 1 HNMR [(CD$_3$)$_2$SO] δ13.26 (br, 1 H, N⁺H), 10.71 (s, 1 H, NH), 10.46 (s, 1 H, NH), 10.37 (brs, 1 H, NH), 8.43 (d, J=9.6 Hz, 1 H, ArH), 8.37 (d, J=7.4 Hz, 2 H, ArH), 8.23 (d, J=7.0 Hz, 1 H, ArH), 8.11 (d, J=8.6 Hz, 2 H, ArH), 7.96 (d, J=8.8 Hz, 2 H, ArH), 7.50 (d, J=8.6 Hz, 2 H, ArH), 7.43 (d, J=8.8 Hz, 2 H, ArH), 7.34 (dd, J=9.6, 2.4 Hz, 1 H, ArH), 7.28 (d, J=7.5 Hz, 2 H, ArH), 6.78 (d, J=2.4 Hz, 1 H, ArH), 6.49 (d, J=7.0 Hz, 1 H, ArH), 4.01 (s, 3 H, N⁺CH$_3$), 3.14 [s, 6 H, N(CH$_3$)$_2$]. Mass APCI⁺ve 489.

TABLE 2

EXEMPLARY COMPOUNDS OF THE INVENTION

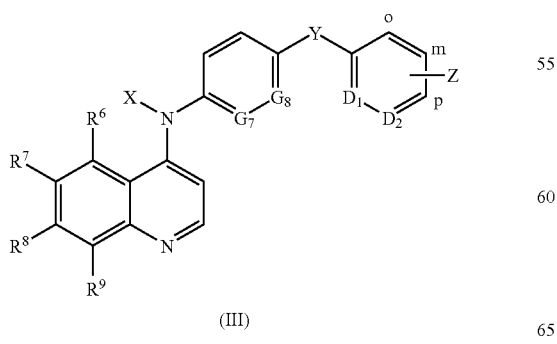

(III)

TABLE 2-continued

EXEMPLARY COMPOUNDS OF THE INVENTION

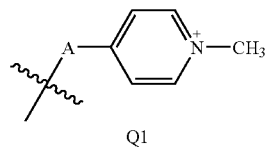

Q1

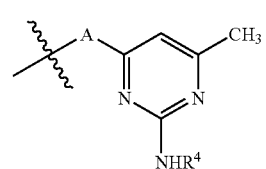

Q2

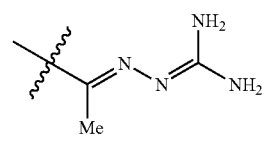

Q3

TABLE 2-continued

EXEMPLARY COMPOUNDS OF THE INVENTION

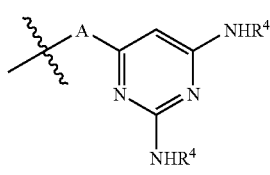

Q4

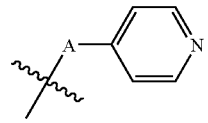

Q9

For the entries in Table 2, $R^4$ is H, A is NH, and X is H. Unless specified, $R^6$-$R^9$ are H. Unless specified, G7, G8, D1, and D2 are CH.

| Cpd. | $R^6$-$R^9$ | Y | attach | Z | mp | Formula | HPLC (%) | Anal |
|---|---|---|---|---|---|---|---|---|
| A | — | CONH | m | Q1 | 253-257 | $C_{28}H_{27}N_5OCl_2$ | 99.7 | C, H, N |
| V | $R^8 = NH_2$ | CONH | m | Q1 | 281-285 | $C_{28}H_{26}N_6OCl_2$ | 99.9 | C, H, N |
| K | $R^7 = NH_2$ | CONH | m | Q1 | 270-274 | $C_{28}H_{26}N_6OCl_2$ | 97.9 | C, H, N |
| L | $R^7 = NH_2$ | CONH | p | Q1 | 262-266 | $C_{28}H_{26}N_6OCl_2$ | 99.3 | LRMS |
| O | $R^7 = NMe_2$ | CONH | p | Q1 | 242-246 | $C_{30}H_{30}N_6OCl_2$ | 96.4 | LRMS |
| N | $R^7 = NH_2$ | NHCO | p | Q1 | >300 | $C_{28}H_{26}N_6OCl_2$ | 97.6 | LRMS |
| F | $R^7 = NO_2$ | CONH | m | Q1 | 273-277 | $C_{28}H_{24}Cl_2N_6O_3$ | 97.0 | HRMS |
| R | $R^8 = NO_2$ | CONH | m | Q1 | 303(dec.) | $C_{28}H_{24}Cl_2N_6O_3$ | 96.0 | HRMS |
| Y | $R^8 = NH_2$ | NHCO | p | Q1 | 290-295 | $C_{28}H_{26}N_6Ocl_2$ | 97.0 | HRMS |
| S | $R^8 = NO_2$ | CONH | p | Q1 | 265(dec.) | $C_{28}H_{24}Cl_2N_6O_3$ | 98.1 | LRMS |
| AA | $R^8 = NMe_2$ | CONH | p | Q1 | 242-245 | $C_{30}H_{30}Cl_2N_6O$ | 97.6 | LRMS |
| J | $R^7 = NO_2$ | NHCO | m | Q1 | >300 | $C_{28}H_{24}N_6Cl_2O_3$ | 98.5 | HRMS |
| T | $R^8 = NO_2$ | NHCO | m | Q1 | >300 | $C_{28}H_{24}N_6Cl_2O_3$ | 97.7 | HRMS |
| D | — | NHCO | p | Q1 | >300 | $C_{28}H_{25}NCl_2N_5O$ | 96.6 | HRMS |
| C | — | NHCO | m | Q1 | >300 | $C_{28}H_{25}NCl_2N_5O$ | 97.5 | HRMS |
| U | $R^8 = NO_2$ | NHCO | p | Q1 | 268 dec | $C_{28}H_{24}N_6Cl_2O_3$ | 96.6 | LRMS |
| M | $R^7 = NH_2$ | NHCO | m | Q1 | >310 | $C_{28}H_{26}N_6OCl_2$ | 96.0 | HRMS |
| X | $R^8 = NH_2$ | NHCO | m | Q1 | >300 | $C_{28}H_{26}N_6OCl_2$ | 95.8 | HRMS |
| BB | $R^8 = NMe_2$ | CONH | p | Q2 | 272-275 | $C_{29}H_{29}ClN_8O$ | 96.6 | HRMS |
| EEE7 | $R^7 = NMe_2$ | CONH | p | Q2 | 260-265 | $C_{29}H_{29}ClN_8O$ | 97.6 | LRMS |
| H | $R^7 = NO_2$ | CONH | p | Q2 | 301-305 | $C_{27}H_{23}ClN_8O_3$ | 98.5 | LRMS |
| Q | $R^7 = NMe_2$ | CONH | m | Q1 | >300 | $C_{30}H_{30}Cl_2N_6O$ | 97.8 | LRMS |
| Z | $R^8 = NMe_2$ | CONH | m | Q1 | 285-289 | $C_{30}H_{30}Cl_2N_6O$ | 90.0 | HRMS |
| B | — | CONH | p | Q1 | >300 | $C_{28}H_{25}Cl_2N_5O$ | 99.7 | LRMS |
| DD | $R^8 = NMe_2$ | NHCO | p | Q1 | 198-200 | $C_{30}H_{30}Cl_2N_6O$ | 99.9 | HRMS |
| CC | $R^8 = NMe_2$ | NHCO | m | Q1 | 188 dec | $C_{30}H_{30}Cl_2N_6O$ | 98.5 | HRMS |
| E | — | CONH | p | Q2 | 189-192 | $C_{27}H_{24}ClN_7O$ | 95.7 | LRMS |
| I | $R^7 = NO_2$ | CONH | p | Q3 | >300 | $C_{25}H_{23}ClN_8O$ | 97.1 | LRMS |
| G | $R^7 = NO_2$ | CONH | m | Q1 | 183-187 | $C_{28}H_{24}Cl_2N_6O_3$ | 99.9 | LRMS |
| EE | $R^7 = NMe_2$ | NHCO | m | Q2 | >300 | $C_{29}H_{29}ClN_8O$ | 96.0 | HRMS |
| W | $R^8 = NH_2$ | CONH | p | Q1 | 242-245 | $C_{28}H_{26}Cl_2N_6O$ | 96.1 | HRMS |
| OO2 | $R^7 = NMe_2$ | NHCO | p | Q1 | 156 | $C_{30}H_{30}Cl_2N_6O$ | 97.0 | LRMS |
| NN | $R^7 = NMe_2$ | CONH | p | Q3 | >280 | $C_{27}H_{30}Cl_2N_8O$ | 98.7 | LRMS |
| OO1 | $R^7 = NMe_2$ | NHCO | m | Q1 | 170-173 | $C_{30}H_{30}Cl_2N_6O$ | 98.0 | HRMS |
| QQ | $R^7 = NMe_2$ | NHCO | m | Q3 | >280 | $C_{27}H_{30}Cl_2N_8O$ | 96.0 | HRMS |
| EEE2 | — | CONH | p | Q9 | 171-174 | $C_{27}H_{23}Cl_2N_5O$ | 100.0 | LRMS |
| PP | $R^7 = NMe_2$ | NHCO | p | Q3 | >300 | $C_{27}H_{30}Cl_2N_8O$ | 97.9 | HRMS |
| GG1 | — | NHCO | p | Q2 | >300 | $C_{27}H_{25}Cl_2N_7O$ | 97.7 | HRMS |
| GG2 | $R^8 = NH_2$ | NHCO | p | Q2 | 257-261 | $C_{27}H_{26}Cl_2N_8O$ | 97.8 | HRMS |
| JJ1 | $R^7 = NMe_2$ | CONH | m | Q3 | 278-282 | $C_{27}H_{30}Cl_2N_8O$ | 95.8 | LRMS |
| JJ2 | — | NHCO | m | Q3 | 264-268 | $C_{25}H_{25}Cl_2N_7O$ | 96.4 | LRMS |
| GG3 | $R^7 = NH_2$ | NHCO | p | Q2 | >300 | $C_{27}H_{26}Cl_2N_8O$ | 96.4 | HRMS |
| II | — | CONH | m | Q2 | 251-255 | $C_{27}H_{25}Cl_2N_7O$ | 95.4 | LRMS |
| FF1 | — | NHCO | m | Q2 | >300 | $C_{27}H_{25}Cl_2N_7O$ | 99.5 | HRMS |
| FF2 | — | NHCO | m | Q4 | >300 | $C_{26}H_{24}Cl_2N_8O$ | 99.2 | HRMS |
| LL | $R^7 = Cl$ | CONH | p | Q2 | 250-254 | $C_{27}H_{24}Cl_3N_7O$ | 99.7 | LRMS |
| KK | $R^7, R^8, R^9 = F$ | CONH | p | Q2 | >280 | $C_{27}H_{22}Cl_2F_3N_7O$ | 98.9 | LRMS |
| HH | $R^7 = NMe_2$ | NHCO | p | Q2 | >300 | $C_{29}H_{30}Cl_2N_8O$ | 96.7 | HRMS |
| GG4 | $R^7 = NO_2$ | NHCO | p | Q2 | 295-300 | $C_{27}H_{24}Cl_2N_8O_3$ | 96.4 | HRMS |
| GG5 | $R^8 = NO_2$ | NHCO | p | Q2 | >300 | $C_{27}H_{24}Cl_2N_8O_3$ | 96.6 | HRMS |
| RR1 | $R^7 = NO_2$ | NHCO | m | Q4 | >300 | $C_{26}H_{23}Cl_2N_9O_3$ | 96.0 | HRMS |
| RR2 | $R^7 = NO_2$ | NHCO | m | Q2 | >300 | $C_{27}H_{24}Cl_2N_8O_3$ | 99.0 | HRMS |
| RR3 | $R^7 = NH_2$ | NHCO | m | Q2 | 280-284 | $C_{27}H_{26}Cl_2N_8O$ | 98.0 | LRMS |
| N1 | $R^7 = NO_2$ | NHCO | p | Q1 | >300 | $C_{28}H_{24}Cl_2N_6O_3$ | 97.0 | LRMS |
| SS | $R^7 = NMe_2$ | NHCO | p | Q4 | 283-287 | $C_{28}H_{29}Cl_2N_9O$ | 99.2 | LRMS |
| TT | — | NHCO | p | Q4 | 263-267 | $C_{26}H_{24}Cl_2N_8O$ | 98.3 | LRMS |
| UU | $R^7 = NH_2$ | NHCO | m | Q4 | 250-255 | $C_{26}H_{25}Cl_2N_9O$ | 99.5 | HRMS |
| VV1 | $R^7 = NO_2$ | NHCO | p | Q4 | 260-265 | $C_{26}H_{23}Cl_2N_9O_3$ | 100.0 | HRMS |
| VV2 | $R^7 = NH_2$ | NHCO | p | Q4 | 262-266 | $C_{26}H_{25}Cl_2N_9O$ | 99.7 | HRMS |
| WW | — | CONMe | p | Q9 | 287-292 | $C_{28}H_{25}Cl_2N_5O$ | 96.3 | HRMS |

-continued

| Cpd. | R6-R9 | Y | attach | Z | mp | Formula | HPLC (%) | Anal |
|---|---|---|---|---|---|---|---|---|
| XX* | — | NHCO | p | Q2 | >290 | $C_{26}H_{24}Cl_2N_8O$ | 99.2 | C, H, N |
| YY** | — | NHCO | p | Q2 | >290 | $C_{26}H_{24}Cl_2N_8O$ | 98.9 | C, H, N |
| ZZ*** | — | NHCO | p | Q2 | >295 | $C_{26}H_{24}Cl_2N_8O$ | 100.0 | C, H, N |

*$G_8 = N$;
**$D_2 = N$;
***$D_1 = N$

Example EE

Synthesis of 4-[4-({3-[(2-amino-6-methyl-4-pyrimidinyl)amino]benzoyl}amino)anilino]-6-(dimethylamino)quinolinium chloride (Cpd. EE)

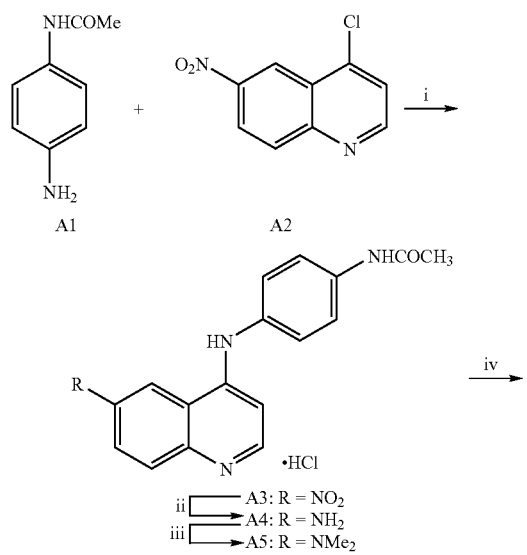

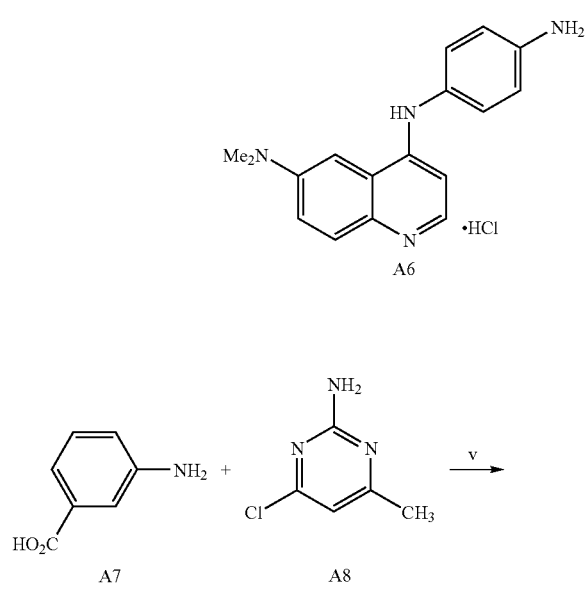

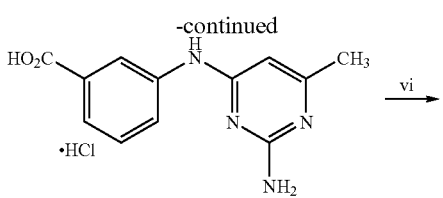

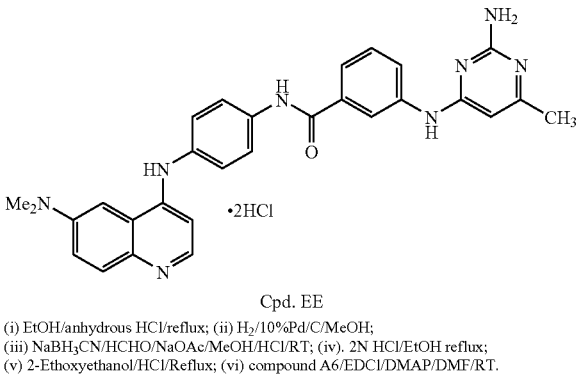

Cpd. EE (i) EtOH/anhydrous HCl/reflux; (ii) $H_2$/10%Pd/C/MeOH;
(iii) $NaBH_3CN$/HCHO/NaOAc/MeOH/HCl/RT; (iv). 2N HCl/EtOH reflux;
(v) 2-Ethoxyethanol/HCl/Reflux; (vi) compound A6/EDCI/DMAP/DMF/RT.

4-[4-(acetylamino)anilino]-6-nitroquinolinium chloride (A3). To a solution of N-(4-aminophenyl)acetamide (A1) (933 mg, 6.2 mmol) in ethanol (30 mL) was added 6-nitro-4-chloroquinoline (A2) (1.08 g, 5.18 mmol) in ethanol (10 mL) followed by a solution of 4N HCl in 1,4-dioxane (1.5 mL). The reaction mixture was refluxed for 30 min, by this time TLC ($SiO_2$/8% MeOH/DCM) showed completion of the reaction. The reaction mixture was diluted with EtOAc and brought to boil, then allowed to cool to 20° C. The resulting precipitate was filtered, washed with EtOAc and recrytallized from MeOH to give A3 (1.79 g, 96%); mp (MeOH)>280° C.; $^1$H NMR [$(CD_3)_2SO$] δ14.59 (br, 1 H, N$^+$H), 11.36 (br, 1 H, NH), 10.24 (s, 1 H, NH), 9.78 (d, J=2.3 Hz, 1 H, ArH), 8.71 (dd, J=9.3, 2.3 Hz, 1 H, ArH), 8.57 (d, J=7.0 Hz, 1 H, ArH), 8.21 (d, J=9.3 Hz, 1 H, ArH), 7.80 (d, J=8.8 Hz, 2 H, ArH), 7.42 (d, J=8.8 Hz, 2 H, ArH), 6.86 (d, J=7.0 Hz, 1 H, ArH), 2.09 (s, 3 H, $COCH_3$), APCI$^+$ve 323.

4-[4-(acetylamino)anilino]-6-aminoquinolinium chloride (A4). To a suspension of (A3 (1.75 g, 4.88 mmol) in MeOH (10 mL) was added 10% Pd/C (0.1 g) and hydrogenated (under 40 psi). for 2 h. The reaction mixture was filtered and washed with more MeOH. The filtrated was concentrated to half the volume, diluted with EtOAc and the rest of the MeOH was evaporated. The Resulting precipitate was filtered washed with more EtOAc and dried to give essentially pure (A4) (1.255 g 78%); mp (MeOH/EtOAc)>280° C.; $^1$H NMR [$(CD_3)_2SO$] δ13.95 (br, 1 H, N$^+$H), 10.14 (s, 1 H, NH), 10.01 (s, 1H, NH), 8.10 (d, J=6.7 Hz, 1 H, ArH), 7.74 (d, J=8.9 Hz, 3 H, ArH), 7.43 (d, J=2.2 Hz, 1 H, ArH), 7.38-7.32 (m, 3 H, ArH), 6.61 (d, J=6.7 Hz, 1 H, ArH), 5.94 (s, 2 H, $NH_2$), 2.08 (s, 3 H, $COCH_3$); APCI+ve 293.

N-(4-{[6-(Dimethylamino)-4-quinolinyl]amino}phenyl) acetamide (A5). To a solution of A4 (1.237 g, 3.76 mmol), in MeOH (50 mL) was added 38% aqueous formaldehyde (8.4 mL, 112.8 mmol, 30 eq), NaBH$_3$CN (2.134 g, 30.08 mmol, 8 eq), NaOAc (526 mg, 6.41 mmol) and 2 drops of c.HCl. The reaction mixture was stirred at 20° C. for 2 h, by this time TLC (SiO$_2$/8% MeOH/DCM/aq NH$_3$) and mass spectrum showed completion of the reaction. Then the reaction mixture was acidified with c.HCl, stirred for 1 h. at 20° C. After this time the reaction mixture was carefully neutralize with aqueous NH$_3$. The MeOH was evaporated under reduced pressure and the aqueous residue was the stirred with aqueous NH$_3$. The resulting precipitate was filtered washed with water to give essentially pure A5 (1.22 g, 91%); This was used without further purification; mp, (MeOH)>280° C.; $^1$H NMR [(CD$_3$)$_2$SO] δ 9.95 (s, 1 H, NH), 8.85 (bs, 1 H, NH), 8.18 (d, J=5.5 Hz, 1 H, ArH), 7.72 (d, J=9.3 Hz, 1 H, ArH), 7.65 (d, J=8.8 Hz, 2 H, ArH), 7.41 (dd, J=9.3, 2.6 Hz, 1 H, ArH), 7.29-7.26 (m, 3 H, ArH), 6.67 (d, J=5.5 Hz, 1 H, ArH), 3.06 [s, 6 H, N(CH$_3$)$_2$], 2.06 (s, 3 H, COCH$_3$), ;APCI$^+$ve 321.

4-(4-aminoanilino)-6-(dimethylamino)quinolinium chloride (A6). To a suspension of A5 in 1,4-dioxane (20 mL) was added 1.5 M aq HCl (5 mL) and the reaction mixture was refluxed for 2 h. The reaction mixture was then diluted with MeOH/EtOAc, brought to boil and allowed to cool to 20° C. The resulting precipitate was filtered, washed with EtOAc and dried to give essentially pure A6 as a pale yellow solid (1.20 g, 100%); mp (MeOH/EtOAc) 152-155; $^1$H NMR [(CD$_3$)$_2$SO] 14.35 (br, 1 H, N$^+$H), 10.50 (br, 2 H, NH$_2$), 8.27 (d, J=6.6 Hz, 1 H, ArH), 7.92 (d, J=9.4 Hz, 1 H, ArH), 7.65 (dd, J=9.5, 2.6 Hz, 1 H, ArH), 7.57 (d, J=2.4 Hz, 1 H, ArH), 7.54 (d, J=8.5 Hz, 2 H, ArH), 7.41 (d, J=8.1 Hz, 2H, ArH), 6.68 (d, J=6.7 Hz, 1 H, ArH), 3.12 (s, 6 H, [N(CH$_3$)$_2$]; APCI$^+$ve 279.

3-[(2-Amino-6-methyl-4-pyrimidinyl)amino]benzoic acid hydrochloride(A9). 3-Amino benzoic acid (A7) (1.02 g, 7.42 mmol) and 2-amino-6-chloro-4-methylpyrimidine (A8) (1.08 g, 7.42 mmol) was dissolved in 2-ethoxyethanol by heating, then a drop of c.HCl was added, refluxed for 1 h. and cool to 20° C. The resulting precipitate was filtered washed with more 2-ethoxy ethanol followed by EtOAc. The solid was recrystallized from MeOH/EtOAc give A9 (1.98 g, 95%) as an off white solid; mp>300° C.; $^1$H NMR [(CD$_3$)$_2$SO] δ12.97 (bs 2 H, NH, and COOH), 10.81 (s, 1 H, NH), 8.22 (bs, 1 H, ArH), 8.03 (s, 1 H, ArH), 7.82 (br, 2 H, NH$_2$), 7.72 (bd, J=7.7 Hz, 1 H, ArH), 7.50 (t, J=7.9 Hz, 1 H, ArH), 6.22 (s, 1 H, ArH); APCI$^+$ve 245.

4-[4-({3-[(2-amino-6-methyl-4-pyrimidinyl)amino]benzoyl}-amino)anilino]-6-(dimethylamino)quinolinium chloride(15) (Cpd. EE). A mixture of 4-(4-aminoanilino)-6-(dimethylamino)quinolinium chloride (A6) (102 mg, 0.32 mmol), A9 (111 mg, 0.32 mmol), and EDCI (151 mg, 0.64 mmol) in DMF (5 mL) was stirred at 20° C. for 5 min. Then DMAP (96 mg, 0.64 mmol) was added and the reaction mixture was stirred at 20° C. for 72 h. The solvent was removed under reduced pressure and residue was diluted with H$_2$O and basified with aqueous NH$_3$. The resulting precipitate was filtered washed with water, and purified by chromatography in SiO$_2$ eluting with a gradient 0-5% DCM/MeOH and 1% aqueous NH$_3$ to give 102 mg 62%. A sample of this (98 mg, 0.19 mmol) was dissolved in MeOH (5 mL) and 4N HCl in 1,4-dioxane (0.3 mL) was added and stirred for 30 min. This was then diluted with EtOAc and the resulting precipitate was filtered and recrystallized from MeOH/EtOAc to give Cpd. EE (107 mg); $^1$H NMR [(CD$_3$)$_2$SO] δ (13.9 br 1H, N$^+$H), 12.9 (br (1H, N$^+$H), 10.58 (s, 2 H, 2×NH), 10.40 (s, 1 H, NH), 8.26 (d, J=6.8 Hz, 1 H, ArH), 8.38 (br 1 H, ArH), 8.06 (bs, 1 H, ArH), 8.00 (d, J=8.9 Hz, 2 H, ArH), 7.89 (d, J=9.4 Hz, 1 H, ArH), 7.75 (bd, J=7.6 Hz, 1 H, ArH), 7.56-7.52 (m, 2 H, ArH), 7.46 (d, J=8.8 Hz, 2 H, ArH), 6.67 (d, J=6.8 Hz, 1 H), 6.19 (s, 1 H, ArH), 3.12 [s, 6 H, (NCH$_3$)$_2$], 2.28 (s, 3 H, CH$_3$), The signal for NH$_2$ was not observed, APCI$^+$ve 505.

Example FF

Preparation of 3-[(2-amino-6-methyl-4-pyrimidinyl) amino]-N-[4-(4-quinolinylamino)phenyl]benzamide dihydrochloride (Cpd. FF1) and related compound (Cpd. FF2)

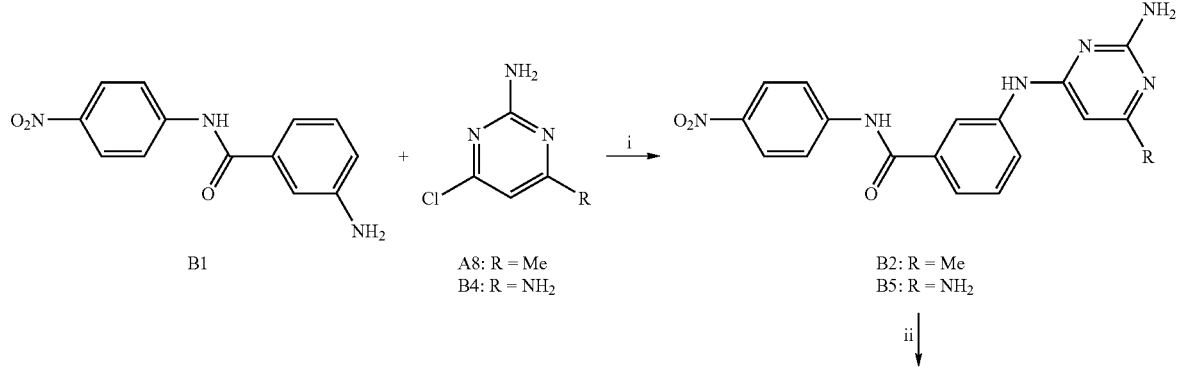

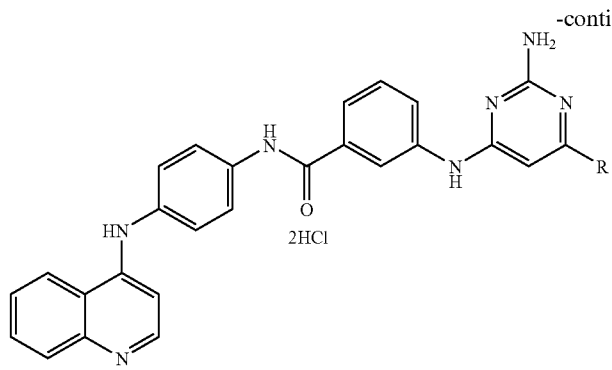

Cpd. FF1: R = Me
Cpd. FF2: R = NH₂

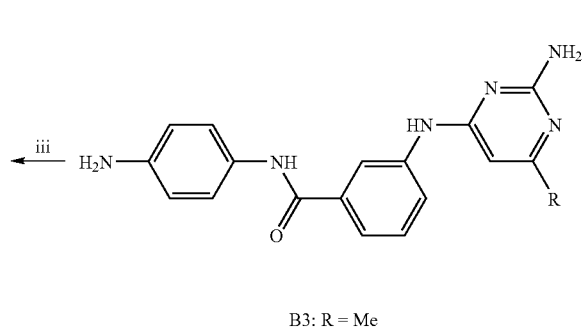

B3: R = Me
B6: R = NH₂

Reagents: (i) 2-ethoxyethanol/H⁺/reflux; (ii) H₂/10%Pd/C/MeOH; (iii) 4-chloroquinoline/EtOH/H₂O/reflux 3-[(2-Amino-6-methyl-4-pyrimidinyl)amino]-N-(4-nitrophenyl)-benzamide hydrochloride (B2). 3-Amino-N-(4-nitrophenyl)benzamide (B1) (1.0 g, 3.89 mmol) and 4-chloro-6-methyl-2-pyrimidinylamine (A8) (569 mg, 3.89 mmol) were dissolved in warm 2-ethoxyethanol. (20 mL). Two drops c.HCl was then added to the reaction mixture and refluxed for 1 h. by this time TLC and mass spec. showed completion of the reaction. The reaction mixture was diluted with ethyl acetate and cooled to 20° C. The resulting precipitate was filtered, washed with more EtOAc and recrystallized from MeOH/EtOAc/Charcoal/Celite to give B2 (1.531 g, 98%); m.p (MeOH/EtOAc)>300° C.; ¹H NMR [(CD₃)₂SO] δ12.86 (br s, 1 H, N⁺H), 10.90 (s, 1 H, NH), 10.80 (br s, 1 H, NH), 8.30-8.26 (m, 2H, ArH), 8.11-8.08 (m, 4 H, ArH), 7.80-7.78 (br m, 3 H, ArH & NH₂), 7.56 (t, J=7.8 Hz, 1 H, ArH), 2.30 (s, 3 H, CH₃); mass APCI⁺ 365.

3-[(2-Amino-6-methyl-4-pyrimidinyl)amino]-N-(4-aminophenyl)-benzamide hydrochloride (B3). To a suspension of compound B2 (1.41 g, 3.51 mmol) in (MeOH) 30 (mL) was added 10% Pd/C (20 mg) and hydrogenated under 45 Hg mm for 5 h. The reaction mixture was filtered through a pad of celite and the filtrate was evaporated to dryness. The residue was dissolved in a small volume of MeOH then 1 ml of 1.25M HCl in MeOH was added, stirred 10 min and evaporated to dryness. The residue was recrystallized from MeOH/EtOAc to give B3 (758 mg, 58%); m.p. (MeOH/EtOAc); ¹H NMR [(CD₃)₂SO] δ12.70 (br, 1 H, NH), 10.83 (br s, 1 H, NH), 10.43 (s, 1 H, NH), 9.70 (v br, 2 H, NH₂), 8.05-7.84 (br m, 2 H, ArH), 7.85-7.75 (m, 4 H, ArH & NH₂), 7.55 (t, J=7.9 Hz, 1 H, ArH), 7.28 (d, J=8.7 Hz, 2 H, ArH), 6.24 (s, 1 H, ArH), 2.30 (s, 3 H, CH₃); mass APCI⁺ 335.

3-[(2-Amino-6-methyl-4-pyrimidinyl)amino]-N-[4-(4-quinolinyl-amino)phenyl]benzamide dihydrochloride (Cpd. FF1). To a solution of compound B3 (150 mg, 0.37 mmol) in EtOH (15 mL) and H₂O (7.5 mL) was added 4-chloroquinoline (73 mg, 0.45 mmol) and stirred until it dissolved, then 2 drops of c.HCl was added. The reaction mixture was refluxed for 20 h, diluted with EtOAc, brought to boil and cool to 20° C. The resulting precipitate was filtered and recrystallized from MeOH/EtOAc/Charcoal/Celite to give Cpd. FF1 (195 mg, 96%) as a yellow solid.; M.P (MeOH/EtOAc)>300° C.; ¹H NMR [(CD₃)₂SO] δ13.72 (v br, 2H , 2×N⁺H), 10.91 (br s, 1 H, NH), 10.96 (br s, 1 H, NH), 10.56 (s, 1 H, HN), 8.79 (d, J=8.5 Hz, 1 H, ArH), 7.50 (d, J=6.9 Hz, 1 H, ArH), 8.14-7.99 (m, 6 H, ArH & NH₂), 7.83 (m, 3 H, ArH), 7.55 (t, J=7.9 Hz, 1 H, ArH), 7.49 (d, J=8.8 Hz, 2 H, ArH), 6.78 (d, J=6.9 Hz, 1 H, ArH), 6.24 (s, 1 H, ArH), 2.30 (s, 3 H, ArH), mass APCI⁺ 476.

3-[(2,6-Diamino-4-pyrimidinyl)amino]-N-(4-nitrophenyl)-benzamide hydrochloride (B5). 3-Amino-N-(4-nitrophenyl)benzamide (B1) (1.07 g, 4.14 mmol) and 4-chloro-2,6-diaminopyrimidine (B4) (569 mg, 3.89 mmol) were dissolved in warm 2-ethoxyethanol (20 mL). Two drops c.HCl was then added to the reaction mixture and refluxed for 20 h., by this time TLC and mass spec showed the completion of the reaction. The reaction mixture was diluted with ethyl acetate and cooled to 20° C. The resulting precipitate was filtered, washed with more EtOAc and recrystallized from MeOH/EtOAc/Charcoal/Celite to give compound B5 (824 mg, 50%), m.p (MeOH/EtOAc)>300° C.; ¹H NMR [(CD₃)₂SO] δ11.57 (br, 1 H, N⁺H), 10.84 (s, 1 H, NH), 9.98 (s, 1 H, NH), 8.30-8.26 (m, 2 H, Ar), 8.10-8.07 (m, 2 H, ArH), 8.06 (br s, 2 H, NH₂), 7.70 (d, J=7.2 Hz, 1 H, ArH), 7.53-7.49 (m, 3 H, ArH), 7.38 (br s, 2 H, NH₂), mass APCI⁺ 366.

N-(4-Aminophenyl)-3-[(2,6-diamino-4-pyrimidinyl)amino]-benzamide hydrochloride (B6). To a suspension of compound B5 (567 mg, 1.41 mmol) in (MeOH) (30 mL) was added 10% Pd/C (20 mg) and hydrogenated under 40 Hg mm for 6 h. The reaction mixture was filtered through a pad of celite and the filtrate was evaporated to dryness. The residue was dissolved in a small volume of MeOH then 1 ml of 1.25M HCl in MeOH was added, stirred 10 min and evaporated to dryness. The residue was recrystallized from MeOH/EtOAc to give B6 (398 mg, 76%); mp (MeOH/EtOAc)>300° C., ¹H NMR [(CD₃)₂SO] δ10.37 (s, 1 H, NH), 9.93 (s, 1 H, NH), 7.92-7.80 (m, 4 H, ArH & NH₂), 7.68 (d, J=7.7 Hz, 1 H, ArH), 7.61 (br s, 2 H, NH₂), 7.49-7.45 (m, 3 H, ArH), 7.24 (br d, J=8.7 Hz, 2 H, ArH), 5.45 (s, 1 H, ArH), mass APCI⁺ 336.

3-[(2,6-Diamino-4-pyrimidinyl)amino]-N-[4-(4-quinolinylamino)-phenyl]benzamide dihydrochloride (Cpd. FF2). To a solution of compound B6 (150 mg, 0.37 mmol) in EtOH (15 mL) and H₂O (7.5 mL) was added 4-chloroquinoline (73 mg, 0.45 mmol) and stirred until it dissolved, then 2 drops of c.HCl was added. The reaction mixture was refluxed for 20 h, diluted with EtOAc, brought to boil and cool to 20° C. The resulting precipitate was filtered and stirred in aqueous NH₃ (20 ml) to convert to free base. This new precipitate was filtered and chromatographed (neutral Al₂O₃, 0-7% DCM/MeOH) to give pure free base of the product. This was then converted to HCl salt by using 1.25 M HCl in MeOH to give Cpd. FF2 (139 mg, 70%); m.p (MeOH/EtOAc)>300° C. ¹H NMR [(CD₃)₂SO] δ14.25 (br, 1 H, N⁺H), 12.00 (br, 1 H, N⁺H), 10.95 (s, 1 H, NH), 10.53 (s, 1 H, NH), 9.93 (s, 1 H, NH), 9.05 (d, J=8.5 Hz, 1 H, ArH), 7.51 (d, J=7.0 Hz, 1 H, ArH), 8.06-8.00 (m, 5 H, ArH), 7.95-7.91 (br m, 2 H, NH$_2$), 7.81 (d d, J=7.6, 1.4 Hz, 1 H, ArH), 7.71 (d, J=7.6 Hz, 1 H, ArH), 7.58 (s, 2 H, NH$_2$), 7.57-7.47 (m, 5 H, ArH), 6.78 (d, J=7.0 Hz, 1 H, ArH), 6.78 (d, J=7.0 Hz, 1 H, ArH), 5.46 (s, 1 H, ArH); HRMS (FAB⁺) calc. for $C_{26}H_{23}N_8O$ (M⁺¹) m/z 463.1995, found 463.1992.

Example GG

Preparation of 4-[(2-amino-6-methyl-4-pyrimidinyl) amino]-N-[4-(4-quinolinylamino)phenyl]benzamide dihydrochloride (Cpd. GG1) and related compounds (Cpd. GG2, CPD, GG3, CPD, GG4, CPD, GG5)

pyrimidinylamine (A8) (416 mg, 2.84 mmol) were dissolved in warm 2-ethoxyethanol (20 mL), two drops c.HCl was then added to the reaction mixture was refluxed for 40 min. by which time TLC and MS showed the completion of the reaction. The reaction mixture was diluted with ethyl acetate and cooled to 20° C. The resulting precipitate was filtered and washed with more EtOAc to give a solid product. This was suspended in MeOH and basified with aqueous NH$_3$ and diluted with water. The resulting precipitate was filtered and dried to give C2 (671 mg). The filtrate was concentrated to give a further 276 mg of C2 (92% overall): mp (MeOH)>300° C.; ¹H NMR [(CD$_3$)$_2$SO] δ10.59 (s, 1 H, NH), 9.37 (s, 1 H, NH), 8.27-8.24 (m, 2 H, ArH), 8.09-8.06 (m, 2 H, ArH), 8.05-7.90 (m, 4 H, ArH), 6.25 (s, 2 H, NH$_2$), 5.96 (s, 1 H, ArH), 2.16 (s, 3 H, CH$_3$); Mass APCI⁺ 365.

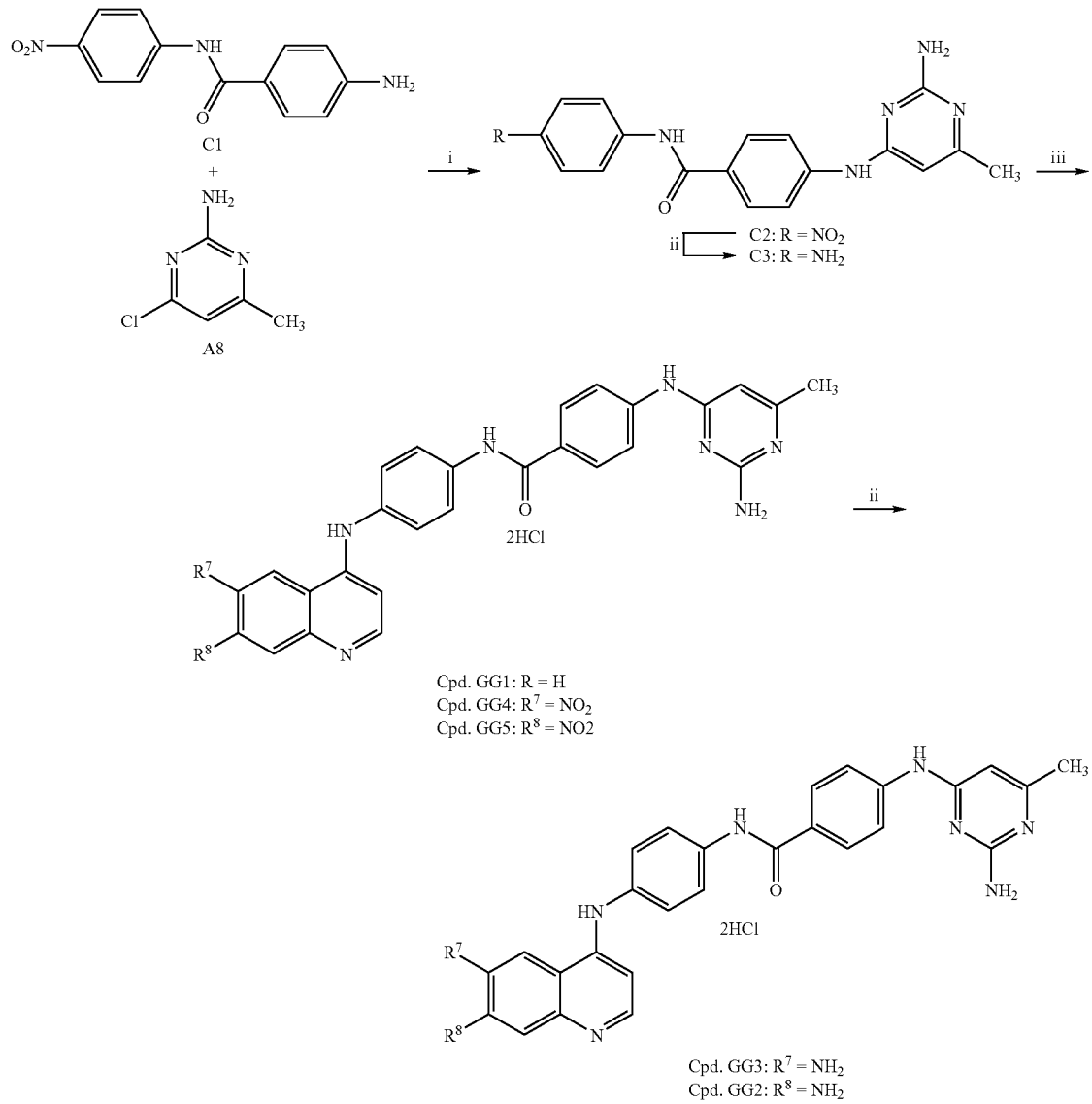

(i) 2-Ethoxyethanol/H⁺/reflux; (ii) H$_2$/10%Pd/C/MeOH; (iii) substituted 4-chloroquinolines/EtOH/H$_2$O/reflux.

4-[(2-Amino-6-methyl-4-pyrimidinyl)amino]-N-(4-nitrophenyl)-benzamide (5). 4-Amino-N-(4-nitrophenyl)benzamide (C1) (730 mg, 2.84 mmol) and 4-chloro-6-methyl-2-

4-[(2-Amino-6-methyl-4-pyrimidinyl)amino]-N-(4-aminophenyl)-benzamide (C3). A suspension of C2 (671 mg, 1.84 mmol) in MeOH (50 mL) was hydrogenated (10% Pd/C 50 mg) at 40 Hg mm. for 3 h. The product was precipitated as a white solid. The reaction mixture was stirred in (MeOH/HCl/H₂O) (100 mL/2 mL/50 mL) and filtered to remove Pd/C residues. The filtrate was evaporated to dryness and crystallized from MeOH/EtOAc to give C3 (740 mg, 99%); M.P. (MeOH/EtOAc)>300° C.; $^1$H NMR [(CD$_3$)$_2$SO] δ10.96 (bs, 1 H, NH), 10.38 (s, 1H NH), 8.02-7.97 (m, 4 H, ArH), 7.86 (d, J=8.8 Hz, 2 H, ArH), 7.30 (d, J=8.8 Hz, 2 H, ArH), 6.30 (d, J=0.6 Hz, 1 H, ArH), 2.33 (s, 3 H, CH$_3$). The signal for 2×NH$_2$ groups were not observed; mass spectrum APCI⁺ 335.

4-[(2-Amino-6-methyl-4-pyrimidinyl)amino]-N-[4-(4-quinolinyl-amino)phenyl]benzamide dihydrochloride (Cpd. GG1). To a solution of C3 (218 mg, 0.54 mmol) in EtOH (20 mL) and H₂O (10 mL) was added 4-chloroquinoline (96 mg, 0.59 mmol) and stirred until it dissolved, then 2 drops of c.HCl was added. The reaction mixture was refluxed for 3 h, diluted with EtOAc, brought to boil and cool to 20° C. The resulting precipitate was filtered and recrystallized from MeOH/EtOAc/Charcoal/Celite to give Cpd. GG1 (259 mg 98%) as a yellow solid.; M.P (MeOH/EtOAc)>300° C.; $^1$H NMR [(CD$_3$)$_2$SO] δ13.75 (br. 2 H, 2×N⁺H), 11.07 (s, 1 H, NH), 10.99 (s, 1 H, NH), 10.52 (s, 1 H, NH), 8.83 (d, J=8.4 Hz, 1 H, ArH), 8.50 (d, J=7.0 Hz, 1 H, ArH), 8.11-7.99 (m, 10 H, ArH & NH$_2$), 7.80 (dt, J=8.0, 1.1 Hz, 1 H, ArH), 7.48 (d, J=8.9 Hz, 2 H, ArH), 6.78 (d, J=7.0 Hz, 1 H, ArH), 6.35 (s, 1 H, ArH), 2.31 (s, 3 H, CH$_3$); $^{13}$C NMR [(CD$_3$)$_2$SO] δ164.8, 161.6, 155.9, 155.0, 153.3, 142.5, 141.4, 138.4, 138.1, 133.7, 132.1, 129.6, 128.5 (2×C), 126.8, 125.8 (2×C), 123.5, 121.4 (2×C), 120.2, 120.1, 116.9, 99.6, 94.3, 18.4, one of the quaternary carbons were difficult to observe; HRMS FAB⁺ calc. for C$_{27}$H$_{25}$N$_7$O (M⁺¹) m/z, 462.2042 found 462.2047.

4-[(2-Amino-6-methyl-4-pyrimidinyl)amino]-N-{4-[(6-nitro-4-quinolinyl)amino]phenyl}benzamide dihydrochloride (Cpd. GG4). To a solution of compound C3 (200 mg, 0.49 mmol) in EtOH (20 mL) and H₂O (10 mL) was added 4-chloro-6-nitroquinoline (113 mg, 0.54 mmol) and stirred until it dissolved, then 2 drops of c.HCl was added. The reaction mixture was refluxed for 3 h., diluted with EtOAc, brought to boil and cool to 20° C. The resulting precipitate was filtered and recrystallized from MeOH/EtOAc/Charcoal/Celite to give Cpd. GG4 (247 mg 87%) as a yellow solid.; M.P (MeOH/EtOAc) 295-300° C.; $^1$H NMR [(CD$_3$)$_2$SO] δ13.50 (br, 2 H, 2×N⁺H), 11.32 (br, 1 H, NH), 11.00 (brs, 1 H, NH), 10.51 (s, 1 H, NH), 9.81 (d, J=2.2 Hz, 1 H, ArH), 8.69 (dd, J=9.3, 2.2 Hz, 1 H, ArH), 8.59 (d, J=6.9 Hz, 1 H, ArH), 8.24 (d, J=9.3 Hz, 1 H, ArH), 8.06-7.98 (m, 7H, ArH & NH$_2$), 7.48 (d, J=8.9 Hz, 2 H, ArH), 6.90 (d, J=6.9 Hz, 1 H, ArH), 6.32 (s, 1 H, ArH), 2.32 (d, J=0.4 Hz, 3 H, CH$_3$); HRMS (FAB⁺) calc. for C$_{27}$H$_{23}$N$_8$O$_3$ (M⁺) m/z 507.1893, found 507.1896.

4-[(2-amino-6-methyl-4-pyrimidinyl)amino]-N-{4-[(6-amino-4-quinolinyl)amino]phenyl}benzamide dihydrochloride (Cpd. GG3). To a suspension of Cpd. GG4 (140 mg, 0.24 mmol) in (MeOH) 30 (mL) was added 10% Pd/C and hydrogenated under 45 Hg mm for 1 h. The reaction mixture was filtered through a pad of celite and the filtrate was evaporated to dryness. The residue was dissolved in a small volume of MeOH then 1 ml of 1.25M HCl in MeOH was added, stirred 10 min and evaporated to dryness. The residue was recrystallized from MeOH/EtOAc to give Cpd. GG3 (107 mg, 81%); m.p. (MeOH/EtOAc)>300° C. $^1$H NMR [(CD$_3$)$_2$SO] δ14.13 (d, J=5.6 Hz, 1 H, N⁺H), 12.95 (s, 1 H, N⁺H), 10.97 (s, 1 H, NH), 10.44, (s, 1 H, NH), 10.20 (s, 1 H, NH), 8.22 (t, J=6.5 Hz, 1 H, ArH), 8.05-7.96 (m, 7 H, ArH), 7.79 (d, J=9.1 Hz, 1 H, ArH), 7.49 (d, J=1.9 Hz, 1 H, ArH), 7.43-7.38 (m, 3 H, ArH), 6.66 (d, J=6.8 Hz, ArH), 6.30 (d, J=0.6 Hz, 3 H, CH$_3$); HRMS (FAB⁺) calc. for C$_{27}$H$_{25}$N$_8$O (M⁺¹) m/z 477.2151, found 477.2153.

4-[(2-Amino-6-methyl-4-pyrimidinyl)amino]-N-{4-[(7-nitro-4-quinolinyl)amino]phenyl}benzamide dihydrochloride (Cpd. GG5). To a solution of C3 (235 mg, 0.58 mmol) in EtOH (20 mL) and H₂O (10 mL) was added 4-chloro-7-nitroquinoline (132 mg, 0.63 mmol) and stirred until it dissolved, then 2 drops of c.HCl was added. The reaction mixture was refluxed for 5 h., diluted with EtOAc, brought to boil and cool to 20° C. The resulting precipitate was filtered and recrystallized from MeOH/EtOAc/Charcoal/Celite to give Cpd. GG5 (317 mg 94%) as a yellow solid.; m.p (MeOH/EtOAc)>300° C.; $^1$H NMR [(CD$_3$)$_2$SO] δ12.9 (br, 1 H, N⁺H), 10.81 (brs, 2H, 2×NH), 10.44 (s, 1 H, NH), 8.93 (d, J=9.3 Hz, 1 H, ArH), 8.81 (d, J=1.9 Hz, 1 H, ArH), 8.66 (d, J=6.6 Hz, 1 H, ArH), 8.46 (d, J=8.9 Hz, 1 H, ArH), 8.05-7.98 (m, 8 H, ArH & NH$_2$), 7.47 (d, J=8.8 Hz, 1 H, ArH), 6.94 (d, J=6.6 Hz, 1 H, ArH), 6.26 (s, 1 H, ArH), 2.32 (s, 3 H, CH$_3$); HRMS (FAB⁺) calc. for C$_{27}$H$_{23}$N$_8$O$_3$ (M⁺¹) m/z 507.1893, found 507.1885.

4-[(2-Amino-6-methyl-4-pyrimidinyl)amino]-N-{4-[(7-amino-4-quinolinyl)amino]phenyl}benzamide dihydrochloride (Cpd. GG2). To a suspension of Cpd. GG5 (150 mg, 0.25 mmol) in (MeOH) 30 (mL) was added 10% Pd/C (20 mg) and hydrogenated under 45 Hg mm for 1 h. The reaction mixture was filtered through a pad of celite and the filtrate was evaporated to dryness. The residue was dissolved in a small volume of MeOH then 1 ml of 1.25M HCl in MeOH was added, stirred 10 min and evaporated to dryness. The residue was recrystallized from MeOH/EtOAc to give Cpd. GG2 (141 mg, 100%), m.p (MeOH/EtOAc) 257-262° C. $^1$H NMR [(CD$_3$)$_2$SO] δ13.45 (br, 2 H, 2×N⁺H), 10.33 (s, 1 H, NH), 10.30 (s, 1 H, NH), 10.00 (br, 1 H, NH), 8.33 (d, J=9.4 Hz, 1 H, ArH), 8.14 (d, J=7.0 Hz, 1 H, ArH), 3.19-7.92 (m, 6 H, ArH), 7.39 (d, J=8.9 Hz, 2 H, ArH), 7.04-7.01 (br m, 3 H, ArH), 6.86 (d, J=2.2 Hz, 1 H, ArH), 6.67 (brs, 2 H, NH$_2$), 6.43 (d, J=7.0 Hz, 1 H, ArH &NH$_2$)), 6.13 (s, 1 H, ArH), 2.22 (s, 3 H, CH$_3$); HRMS (FAB⁺) calc. for C$_{27}$H$_{25}$N$_8$O (M⁺¹) m/z 477.2151, found 477.2153.

Example HH

Preparation of 4-[(2-amino-6-methyl-4-pyrimidinyl)amino]-N-(4-{[6-(dimethylamino)-4-quinolinyl]amino}phenyl)benzamide dihydrochloride (Cpd. HH)

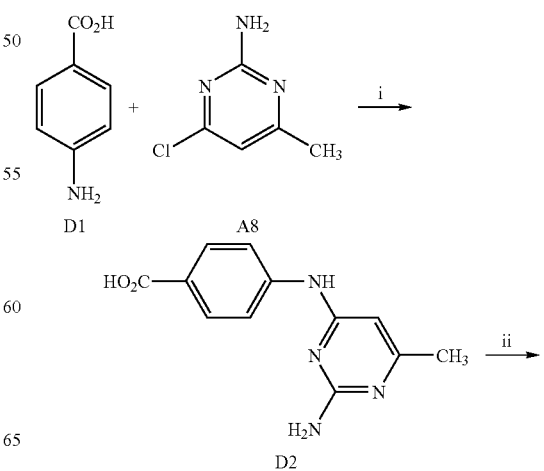

93

-continued

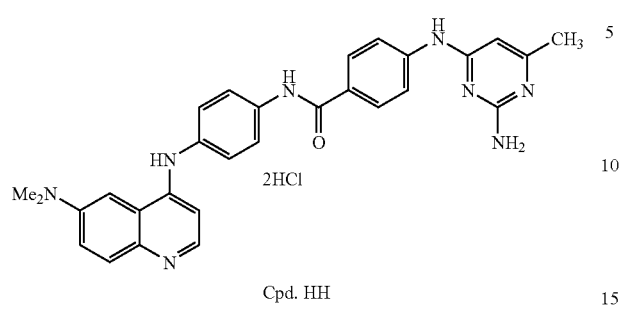

Cpd. HH (i) 2-Ethoxyethanol/H+/reflux; (ii). A3/EDCI/DMAP/N-methylpyrrolidinone

4-[(2-Amino-6-methyl-4-pyrimidinyl)amino]benzoic acid hydrochloride (D2). p-Aminobenzoic acid (D1) (1.48 g, 10.8 mmol) and 4-chloro-6-methyl-2-pyrimidinamine (A8) (1.60 g, 11.9 mmol) was dissolved in warm 2-ethoxyethanol (20 mL), then two drops of c.HCl was added and refluxed for 1 h. The reaction mixture was cooled to 20° C. and the resulting precipitate was filtered washed with more 2-ethoxyethanol and EtOAc. The solid was boiled in MeOH, cooled and filtered washed with more MeOH and dried to give D2 (2.89 g, 95%); m.p. (MeOH)>300° C.; $^1$H NMR [(CD$_3$)$_2$SO] δ12.93 (br, 1 H, N$^+$H or COOH), 12.80 (br, 1 H, N$^+$H or COOH), 10.87 (s, 1 H, NH), 7.92 (s, 6 H, ArH &NH$_2$)), 6.27 (s, 1 H, ArH), 2.32 (s, 3 H, CH$_3$); mass APCI$^+$ 245.

4-[(2-Amino-6-methyl-4-pyrimidinyl)amino]-N-(4-{[6-(dimethylamino)-4-quinolinyl]amino}phenyl)benzamide dihydrochloride (Cpd. HH). Compound D2 (111 mg, 0.4 mmol), EDCI (155 mg, 0.72 mmol) and DMAP (174 mg, 1.44 mmol) in N-methylpyrrolidinone (5 mL) was stirred 5 min at 20° C. N$^4$-(4-Aminophenyl)-N6,N$^6$-dimethyl-4,6-quinolinediamine (100 mg, 0.36 mmol) was then added and the reaction mixture was stirred at 20° C. for 20 h. The reaction mixture was diluted with water and stirred. The resulting precipitate was filtered washed with water and air dried. This solid was dissolved in hot MeOH, boiled with charcoal and filtered through a pad of celite. The filtrate was evaporated to dryness and the resulting residue was dissolved in MeOH (10 mL), 1.25 M HCl in MeOH (1 mL) was added and stirred 10 min. The solvent was evaporated and the residue was recrytallized from MeOH/EtOAc to give Cpd. HH (135 mg, 65%) as a yellow solid; m.p. (MeOH/EtOAc)>300° C.; $^1$H NMR [(CD$_3$)$_2$SO] δ14.10 (br, 1 H, N$^+$H), 12.75 (br, 1 H, N$^+$H), 10.85 (br, 1 H, NH), 10.45 (s, 1 H, NH), 10.40 (s, 1 H, NH), 8.27 (d, J=6.8 Hz, 1 H, ArH), 8.08-7.99 (m, 6 H, ArH), 7.88 (d, J=9.4 Hz, 1 H, ArH), 7.65 (dd, J=9.4, 2.5 Hz, 1 H, ArH), 7.54 (d, J=2.4 Hz, 1 H, ArH), 7.45 (d, J=8.9 Hz, 2 H, ArH), 6.67 (d, J=6.8 Hz, 1 H, ArH), 6.27 (s, 1 H, ArH), 3.12 [s, 6 H, N(CH$_3$)$_2$], 2.32 (s, 3 H, CH$_3$); mass APCI$^+$ 505.

94

Example II

Preparation of N-[3-(2-amino-6-methylpyrimidin-4-ylamino)phenyl]-4-(quinolin-4-ylamino)benzamide Hydrochloride (Cpd. II)

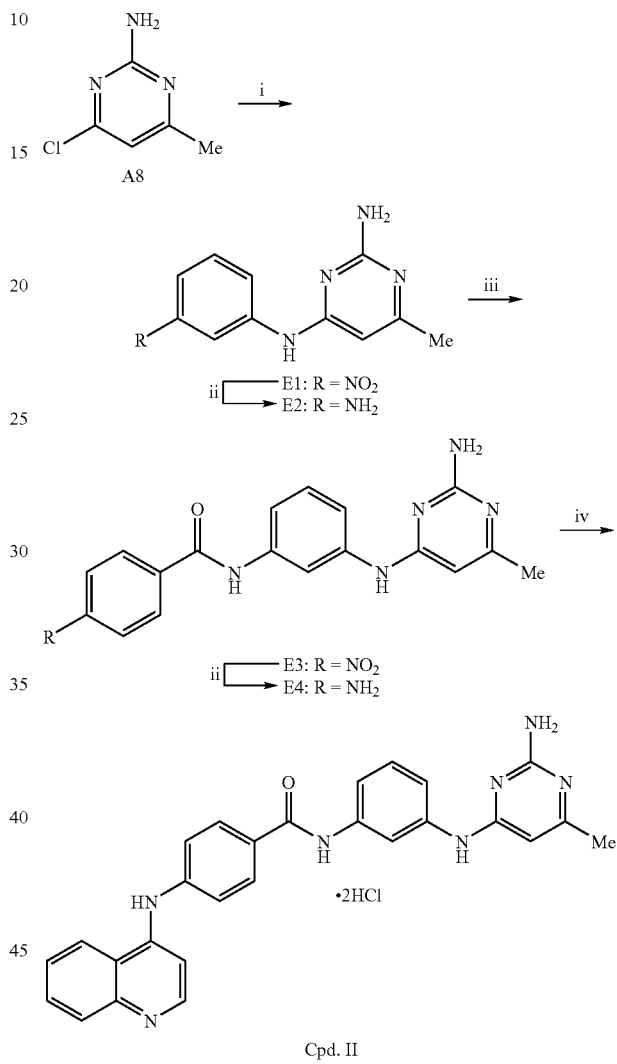

Cpd. II (i) 3-nitroaniline/2-ethoxyethanol/cHCl/reflux; (ii) Fe dust/(2:1) EtOH/H$_2$O, 2% v/v HCl/reflux; (iii) 4-nitrobenzoyl chloride/pyridine/EtOH/reflux; (iv) 2:1 EtOH/H2O/cHCl/reflux 6-Methyl-N$^4$-(3-nitrophenyl)pyrimidine-2,4-diamine (E1). To a suspension of 2-amino-4-chloro-6-methyl-pyrimidine (A8) [10.04 g, 69.93 mmol] and 3-nitroaniline 99.95 g, 72.02 mmol) in 2-ethoxyethanol (300 mL) was added c.HCl (30 mL), and the resulting solution was refluxed for ~16 h. After this time, the reaction mixture was allowed to cool to room temperature, and then diluted with brine and H$_2$O. The resulting suspension was filtered through a Celite pad, and the solid material thus collected re-dissolved in MeOH, and filtered through a pad of Celite. Solvent was removed under reduced pressure to give diamine E1 as an amorphous beige solid, which was used without further purification: $^1$H NMR (400 MHz, DMSO): δ 12.97 (br s, 1H, pyrimidinyl-N$^+$—H), 11.03 (s, 1H, ArNHAr), 8.52 (s, 1H, ArH), 8.31 (d, J=7.83 Hz, 1H, ArH), 7.97 (ddd, J=8.20, 2.19, 0.72 Hz, 1H, ArH), 7.83 (v br s, 2H, ArNH$_2$), 7.66 (t, J=8.21 Hz, 1H, ArH), 6.25 (s, 1H, ArH), 2.31 (s, 3H, ArCH$_3$); LCMS (APCI$^+$): 246 (100%).

N$^4$-(3-Aminophenyl)-6-methylpyrimidine-2,4-diamine (E2). To a refluxing suspension of diamine E1 in 2:1 EtOH:H$_2$O (500 mL) were sequentially added Fe dust (15.6 g, 4 molar equivalents wrt 1) and c.HCl (10 mL), and the resulting mixture was refluxed overnight. After this time, the hot reaction mixture was filtered through a pad of Celite, and solvent was removed under reduced pressure. The residue was re-dissolved in hot H$_2$O, and the resulting suspension filtered through a pad of Celite. Solvent was removed under reduced pressure, and the residue dried via three MeOH-azeotrope cycles. The resulting residue was reprecipitated from acidified MeOH:EtOAc to give diamine E2 (5.36 g, 30% from A8) as an amorphous tan solid; $^1$H NMR (400 MHz, DMSO): δ 12.90 (v v br s, 1H, pyrimidinyl-N$^+$—H), 11.00 (br s, 1H, ArH), 9.75 (v v br s, 2H, ArNH$_2$), 8.20-7.50 (m, 4H, ArH & ArNH$_2$), 7.37 (t, J=8.05 Hz, 1H, ArH), 6.98 (d, J=7.82 Hz, ArH, 1H), 6.26 (s, 1H, ArH), 2.29 (s, 3H, ArCH$_3$); LCMS (APCI$^+$): 216 (100%), 217 (40%).

N-[3-(2-Amino-6-methylpyrimidin-4-ylamino)phenyl]-4-nitrobenzamide (E3). To a suspension of diamine E2 (5.25 g, 20.85 mmol) and dry pyridine (8.40 mL, 104.26 mmol) in dry dioxane (200 mL) was added 4-nitrobenzoyl chloride (10.79 g, 58.13 mmol), and the resulting solution was refluxed for ~14 h. After this time, the reaction mixture was cooled to room temperature, and then basified by addition of aqueous ammonia solution. The resulting solution was diluted with H$_2$O, and the resulting precipitate collected by filtration to afford amide E3 as an amorphous yellow-brown solid (7.89 g, 94%) [a small sample of this crude material was reprecipitated from acidified MeOH:EtOAc for characterisation, whilst the bulk was used without further purification]; $^1$H NMR (400 MHz, DMSO): δ 12.99 (br s, 1H, pyrimidinyl-N$^+$—H), 10.82 (s, 1H, ArNHAr), 10.76 (br s, 1H, ArC(O)NHAr), 8.35 (dd, J=6.92, 1.99 Hz, 2H, ArH), 8.27 (d, J=6.92, 1.99 Hz, 2H, ArH), 7.90 (v v br s, 2H, ArNH$_2$), 8.20-7.50 (m, 4H, ArH & ArNH$_2$), 7.45-7.10 (m, 2H, ArH), 6.25 (s, 1H, ArH), 2.28 (s, 3H, ArCH$_3$); LCMS (APCI$^+$): 365 (100%).

4-Amino-N-[3-(2-amino-6-methylpyrimidin-4-ylamino)phenyl]-benzamide (E4). To a refluxing suspension of amide E3 (7.89 g, 20.00 mmol) in 2:1 EtOH:H$_2$O (500 mL) were sequentially added Fe dust (4.40 g, 79 mmol) and c.HCl (2% v/v, 10 mL), and the resulting mixture refluxed for ~14 h. After this time, the hot reaction mixture was filtered through a pad of Celite, and the solvent was removed under reduced pressure. The residue was re-dissolved in hot H$_2$O, and the resulting suspension filtered through a pad of Celite. Solvent was removed under reduced pressure, and the residue dried via three MeOH azeotrope cycles. The resulting residue was reprecipitated from acidified MeOH:EtOAc to give amine E4 as an amorphous tan solid (0.95 g, 12%); $^1$H NMR (400 MHz, DMSO): δ 12.71 (br s, 1H, pyrimidinyl-N$^+$—H), 10.55 (br s, 1H, ArC(O)NHAr), 9.95 (s, 1H, ArNHAr), 8.10-7.40 (m, 7H, ArH & ArNH$_2$), 7.32 (m, 1H, ArH), 6.77 (d, J=8.30 Hz, 2H, ArH), 6.18 (s, 1H, ArH), 2.28 (s, 3H, ArCH$_3$); LCMS (APCI$^+$): 335 (100%).

N-[3-(2-Amino-6-methylpyrimidin-4-ylamino)phenyl]-4-(quinolin-4-ylamino)benzamide hydrochloride (Cpd. II). To a solution of amine E4 (0.26 g, 0.63 mmol) in 1:2 EtOH:H$_2$O (30 mL) were sequentially added 4-chloroquinoline (0.62 g, 3.78 mmol) and c.HCl (0.17 mL, 5.67 mmol), and the resulting mixture refluxed for 3 h (reaction progress followed by TLC, eluting with the top phase of a 5:4:1 mixture of n-BuOH:H$_2$O:acetic acid; product R$_f$=0.43, yellow spot after staining with KMnO$_4$). After this time, solvent was removed under reduced pressure, and the residue dried via three MeOH-azeotrope cycles. The residue was re-precipitated from MeOH:EtOAc to give Cpd. II as an amorphous lemon-yellow solid (0.27 g, 79%); mp 251-255° C. (powder-glue); $^1$H NMR (400 MHz, DMSO): δ 14.78 (v br s, 1H, quinolinyl-N$^+$—H), 12.79 (v br s, 1H, pyrimidinyl-N$^+$—H), 11.14 (s, 1H, ArNHAr), 10.64 (br s, 1H, ArC(O)NHAr), 10.52 (s, 1H, ArNHAr), 8.87 (d, J=8.44 Hz, 1H, ArH), 8.61 (d, J=6.94 Hz, 1H, ArH), 8.30-7.45 (m, 12H, ArH & ArNH$_2$), 7.38 (t, J=8.07 Hz, 1H, ArH), 7.00 (d, J=6.94 Hz, 1H, ArH), 6.22 (s, 1H ArH), 2.29 (s, 3H, ArCH$_3$); LCMS (APCI$^+$): 463 (100%); HPLC: 95.4%.

Example JJ

Synthesis of (E)-N-[3-(1-{(diaminomethylene)hydrazono}ethyl)phenyl]-4-[6-(dimethylamino)quinolin-4-ylamino]benzamide dihydrochloride (Cpd. JJ1) and the related compound (Cpd. JJ2)

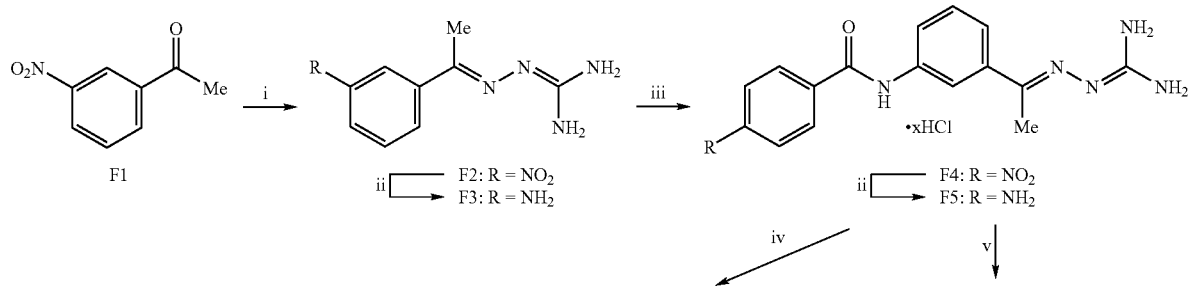

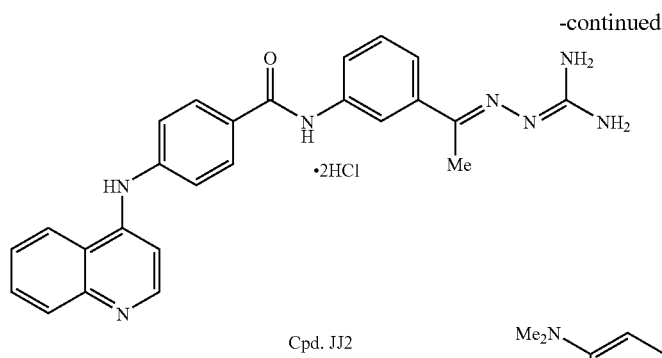

Cpd. JJ2

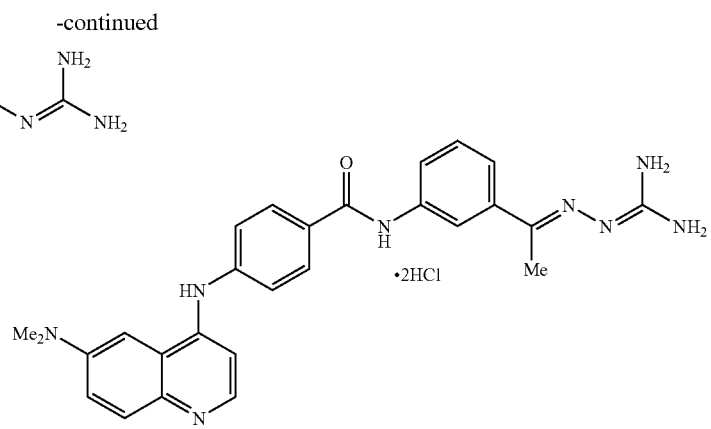

Cpd. JJ1

(i) guanidine sulfate/MeOH/c•HCl/reflux/14 h; (ii) Fe dust, cat. c•HCl, 2:1 EtOH:H₂O, reflux, 14 h; (iii) pyridine, dioxane, reflux, 17 h; (iv) 4-chloroquinoline/1:2 EtOH/H₂O/c•HCl/reflux/20 h; (vi) 4-chloro-6-(dimethylamino)quinoline/1:2 EtOH/H₂O/c•HCl/reflux, 40 h (E)-N-[4-(1-{Diaminomethylene}hydrazono)ethyl]-3-nitrobenzene hydrochloride (F2). To a solution of aminoguanidine sulfate (21.25 g, 80.41 mmol) and 3-nitroacetophenone (F1) (13.53 g, 81.93 mmol) in MeOH (400 mL) was added c.HCl (2.44 mL, 80.42 mmol), and the resulting mixture was refluxed for ~14 h. Solvent was removed from the resulting white suspension to give diamine F2 as an amorphous white solid, which was used without further purification; $^1$H NMR (400 MHz, DMSO): δ 11.00 (v v br s, 1H, hydrazonyl-$N^+$—H), 8.59 (t, J=1.94 Hz, 1H, ArH), 8.39 (d, J=7.87 Hz, 1H, ArH), 8.19 (ddd, J=8.14, 2.18, 0.82 Hz, 1H, ArH), 7.83 (br s, 4H, =C(NH₂)₂), 7.66 (t, J=8.05 Hz, 1H, ArH), 2.40 (s, 3H, Ar(CH₃)=N—); LCMS (APCI$^+$): 222 (100%).

(E)-N-[4-(1-{Diaminomethylene}hydrazono)ethyl]-3-benzamine dihydrochloride (F3). To a refluxing suspension of diamine F2 in 2:1 EtOH:H₂O (500 mL) were sequentially added Fe dust (17.87 g, 320.00 mmol, 4 molar equivalents) and c.HCl (10 mL), and the resulting mixture refluxed for 14 h. After this time, the hot reaction mixture was filtered through a pad of Celite, and the solvent was removed under reduced pressure. The residue was re-dissolved in hot H₂O, and the resulting suspension filtered through a pad of Celite. Solvent was removed under reduced pressure, and the residue dried via three MeOH-azeotrope cycles. The resulting residue was reprecipitated from acidified MeOH/EtOAc to give triamine F3 (10.78 g, 51% over two steps) as an amorphous white solid; $^1$H NMR (400 MHz, DMSO): δ 11.35 (s, 1H, hydrazonyl-$N^+$—H), 9.40 (v v br s, 3H, Ar$NH_3^+$), 7.84 (br m, 5H, ArH & =C(NH₂)₂), 7.75 (s, 1H, ArH), 7.43 (t, J=7.91 Hz, 1H, ArH), 7.27 (d, J=8.27 Hz, 1H, ArH), 2.34 (s, 3H, Ar(CH₃)=N—); LCMS (APCI$^+$): 192 (100%).

(E)-N-[3-(1-{(Diaminomethylene)hydrazono}ethyl)phenyl]-4-nitrobenzamide dihydrochloride (F4). To a suspension of triamine F3 (5.15 g, 19.49 mmol) and dry pyridine (7.85 mL, 97.45 mmol) in dry dioxane (300 mL) was added 4-nitrobenzoyl chloride (10.52 g, 56.69 mmol), and the resulting mixture refluxed for 17 h. After this time, the reaction mixture was cooled to room temperature, and then basified by addition of aqueous ammonia solution. The resulting solution was diluted with H₂O, and the resulting precipitate collected by filtration to afford amide F4 (4.21 g, 51%) as an amorphous creamy yellow solid; $^1$H NMR (400 MHz, DMSO): δ 11.09 (s, 1H, hydrazonyl-$N^+$—H), 10.68 (s, 1H, ArC(O)NHAr), 8.39 (d, J=9.22 Hz, 1H, ArH), 8.29 (m, 3H, ArH), 7.89 (d, J=8.07 Hz, 1H, ArH), 7.82 (d, J=7.89 Hz, 1H, ArH), 7.73 (br s, 4H, =C(NH₂)₂), 7.44 (t, J=7.98 Hz, 1H, ArH), 2.34 (s, 3H, Ar(CH₃)=N—); LCMS (APCI$^+$): 341 (100%).

(E)-4-Amino-N-[3-(1-{(diaminomethylene)hydrazono}ethyl)-phenyl]benzamide dihydrochloride (F5). To a refluxing suspension of amide F4 (2.02 g, 5.36 mmol) in 2:1 EtOH:H₂O (100 mL) were sequentially added Fe dust (1.20 g, 21.44 mmol) and c.HCl (2 mL), and the resulting suspension was refluxed for 14 h. After this time, the hot reaction mixture was filtered through a pad of Celite, and the solvent was removed under reduced pressure. The residue was re-dissolved in hot H₂O, and the resulting suspension filtered through a pad of Celite. Solvent was removed under reduced pressure, and the residue dried via three MeOH-azeotrope cycles. The resulting residue was reprecipitated from acidified MeOH to afford triamine F5 (2.18 g, quantitative) as an amorphous cream solid; $^1$H NMR (400 MHz, DMSO): δ 11.30 (s, 1H, hydrazonyl-$N^+$—H), 10.05 (s, 1H, ArC(O)NHAr), 8.21 (s, 1H, ArH), 8.20-7.55 (m, 8H, ArH & =C(NH₂)₂), 7.36 (t, J=7.90 Hz, 1H, ArH), 6.91 (d, J=7.96 Hz, 1H, ArH), 5.30 (v br s, 3H, Ar$NH_3^+$), 2.35 (s, 3H, Ar(CH₃)=N—); LCMS (APCI$^+$): 311 (100%).

(E)-N-[3-(1-{(Diaminomethylene)hydrazono}ethyl)phenyl]-4-[6-(dimethylamino)quinolin-4-ylamino]benzamide dihydrochloride (Cpd. JJ1). To a solution of triamine F5 (0.22 g, 0.59 mmol) in 1:2 EtOH:H₂O (60 mL) were sequentially added 6-dimethylamino-4-chloroquinoline (0.13 g, 0.64 mmol) and c.HCl (0.16 mL, 5.32 mmol), and the resulting solution was refluxed for 20 h (reaction progress followed by TLC, eluting with the top phase of a 5:4:1 mixture of n-BuOH:H₂O:acetic acid). After this time, solvent was removed under reduced pressure, and the residue dried via two MeOH-azeotrope cycles. The residue was re-precipitated from MeOH:EtOAc to give Cpd. JJ1 (61 mg, 19%) as an amorphous dark brown solid; mp 239-243° C. (powder-glue), 278-282° C. (glue-liquid); $^1$H NMR (400 MHz, DMSO): δ 14.44 (s, 1H, quinolinyl-$N^+$—H), 11.20 (s, 1H, hydrazonyl-$N^+$—H), 10.58 (s, 1H, ArC(O)NHAr), 10.46 (s, 1H, ArNHAr), 8.35 (d, J=6.71 Hz, 1H, ArH), 8.26 (t, J=1.73 Hz, 1H, ArH), 8.22 (d, J=8.61 Hz, 3H, ArH), 7.95 (m, 2H, ArH), 7.79 (m, 5H, ArH & =C(NH₂)₂), 7.69 (d, J=2.52 Hz, 1H, ArH), 7.66 (d, J=8.61 Hz, 2H, ArH), 7.58 (d, J=2.43 Hz, 1H, ArH), 7.43 (t, J=7.98 Hz, 1H, ArH), 6.95 (d, J=6.71 Hz, 1H, ArH), 3.15 (s, 6H, ArN(CH₃)₂), 2.37 (s, 3H, Ar(CH₃)=N—); LCMS (APCI$^+$): 482 (100%); HPLC: 95.8%.

(E)-N-[3-(1-{(Diaminomethylene)hydrazono}ethyl)phenyl]-4-(quinolin-4-ylamino)benzamide dihydrochloride (Cpd. JJ2). To a solution of triamine F5 (0.35 g, 0.91 mmol) in 1:2 EtOH:H₂O (30 mL) were sequentially added 4-chloroquinoline (0.64 g, 3.90 mmol) and c.HCl (0.25 mL, 8.24 mmol), and the resulting solution was refluxed for 20 h (reaction progress followed by TLC, eluting with the top phase of a 5:4:1 mixture of n-BuOH:H₂O:acetic acid; product R$_f$=0.51, yellow spot after staining with KMnO₄). After this time, solvent was removed under reduced pressure, and the residue dried via two MeOH-azeotrope cycles. The residue was re-precipitated from MeOH:EtOAc to give Cpd. JJ2 (91 mg, 20%) as a pale yellow amorphous solid; mp 240-244° C. (powder-glue), 264-268° C. (glue-liquid); $^1$H NMR (400 MHz, DMSO): δ 14.67 (br s, 1H, quinolinyl-N$^+$—H), 11.19 (s, 1H, hydrazonyl-N$^+$—H), 11.07 (s, 1H, ArC(O)NHAr), 10.48 (s, 1H, ArNHAr), 8.72 (d, J=8.52 Hz, 1H, ArH), 8.61 (d, J=6.90 Hz, 1H, ArH), 8.24 (m, 3H, ArH), 8.08 (m, 2H, ArH), 7.95 (d, J=8.10 Hz, 1H, ArH), 7.82 (m, 6H, ArH & =C(NH₂)₂), 7.68 (d, J=8.38 Hz, 2H, ArH), 7.43 (t, J=7.97 Hz, 1H, ArH), 7.01 (d, J=6.90 Hz, 1H, ArH), 2.37 (s, 3H, Ar(CH₃)₂ =N—); LCMS (APCI$^+$): 438 (100%); HPLC: 96.4%.

Example KK

Synthesis of n-[4-(2-amino-6-methylpyrimidin-4-ylamino)phenyl]-4-(6,7,8-trifluoroquinolin-4-ylamino)benzamide dihydrochloride (Cpd. KK)

luoroquinolone acid G2 (3.31 g, 97%) as an amorphous white solid, which was used without further purification; mp 264-268° C.; $^1$H NMR (400 MHz, DMSO): δ 14.20 (v br s, 2H, quinolinyl-N$^+$—H & ArCO₂H), 8.71 (s, 1H, ArH), 8.08 (ddd, J$_{H-F}$=10.17, 7.77, 2.23 Hz, 1H, ArH); LCMS (APCI$^+$): 244 (100%).

6,7,8-Trifluoroquinolin-4(1H)-one (G3). A solution of trifluoroquinolone acid G2 (1.32 g, 5.43 mmol) was refluxed in biphenyl ether (100 mL) for 30 min. After this time, the hot reaction mixture was poured carefully into hexanes, and resulting suspension was allowed to cool to room temperature. The suspension was filtered to give trifluoroquinolone G3 (two batches, 1.32 g total, quantitative) as a very fine amorphous grey-white solid, which was used without further purification; $^1$H NMR (400 MHz, DMSO): δ 12.14 (s, 1H, ArOH), 7.91 (dd, J=6.73, 6.36 Hz, 1H, ArH), 7.80 (ddd, J$_{H-F}$=10.46, 8.11, 2.14 Hz, 1H, ArH), 6.10 (d, J=7.43 Hz, 1H, ArH); LCMS (APCI$^+$): 200 (100%).

4-Chloro-6,7,8-trifluoroquinoline (G4). A solution of quinolone G3 (1.30 g, 6.53 mmol) was refluxed in POCl₃ (50 mL) for 1.3 h, and then excess POCl₃ was removed under reduced pressure. The residue was re-dissolved in CH₂Cl₂, and the resulting solution basified by addition of aqueous ammonia solution. The resulting solution was extracted with CH₂Cl₂, and the combined organic extracts washed sequentially with H₂O and brine, and dried over MgSO₄. Solvent was removed under reduced pressure, and the residue purified by flash chromatography on silica gel, eluting with 100% CH₂Cl₂-1% MeOH:CH₂Cl₂→10% MeOH:CH₂Cl₂), to give

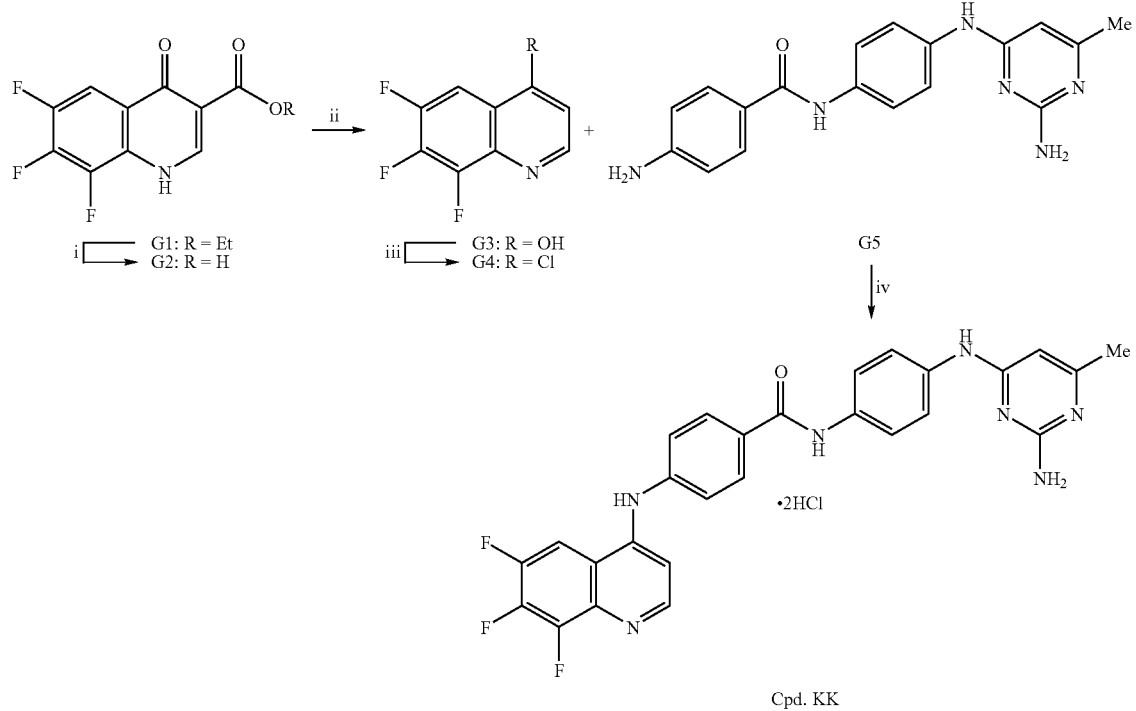

Cpd. KK (i) 1M NaOH/reflux; (ii) Ph₂O/reflux; (iii) POCl₃/reflux; E4/cat. c•HCl/reflux 6,7,8-Trifluoro-4-oxo-1,4-dihydroquinoline-3-carboxylic acid (G2). A solution of trifluoroquinolone ester G1 (3.82 g, 14.09 mmol) was refluxed in 1M NaOH for 14 h, and then cooled to room temperature. The solution was acidified with 1M NaOH, and the resulting suspension filtered to give triftrifluoroquinoline G4 (0.76 g, 54%) as a white crystalline solid; mp 119-121° C.; $^1$H NMR (400 MHz, DMSO): δ 8.93 (d, J=4.73 Hz, 1H, ArH), 8.08 (ddd, J$_{H-F}$=10.23, 7.92, 2.30 Hz, 1H, ArH), 7.95 (d, J=4.73 Hz, 1H, ArH); LCMS (APCI$^+$): 218 (100%), 220 (100%).

N-[4-(2-Amino-6-methylpyrimidin-4-ylamino)phenyl]-4-(6,7,8-trifluoroquinolin-4-ylamino)benzamide dihydrochloride (Cpd. KK). To a solution of amine G5 (0.19 g, 0.46 mmol) in dry MeOH (20 mL) were sequentially added trifluoroquinoline G4 (0.22 g, 1.03 mmol) and c.HCl (~3 drops), and the resulting solution was refluxed for 24 h (reaction progress followed by TLC, eluting with the top phase of a 5:4:1 mixture of n-BuOH:H$_2$O:acetic acid; product R$_f$=0.56, yellow spot after staining with KMnO$_4$. This is same R$_f$ as G5, however, so consumption of G5 was confirmed via LCMS analysis). After this time, solvent was removed under reduced pressure, and the residue dried via three MeOH-azeotrope cycles. The residue was triturated sequentially with MeOH, EtOAc and hexanes, and then dried under high-vacuum to give Cpd. KK (two batches, 214 mg total, 79%) as an amorphous pale/lemon-yellow solid; mp>280° C.; $^1$H NMR (400 MHz, DMSO): δ 12.70 (br s, 1H, pyrimidinyl-N—H$^+$), 10.77 (br s, 1H, ArC(O)NHAr), 10.66 (s, 1H, ArNHAr), 10.39 (s, 1H, ArNHAr), 8.84 (m, 1H, ArH), 8.59 (d, J=6.35 Hz, 1H, ArH), 8.14 (d, J=8.62 Hz, 2H, ArH), 8.06-7.64 (m, 6H, ArH & ArNH$_2$), 7.61 (d, J=8.62 Hz, 2H, ArH), 7.11 (d, J=6.35 Hz, 1H, ArH), 6.19 (s, 1H, ArH), 2.28 (s, 3H, ArCH$_3$) [quinolinyl-N$^+$—H not visible]; LCMS (APCI$^+$): 517 (100%), 518 (40%); HPLC: 98.9%.

Example LL

Synthesis of N-[4-(2-amino-6-methylpyrimidin-4-ylamino)phenyl]-4-(6-chloroquinolin-4-ylamino)benzamide (Cpd. LL)

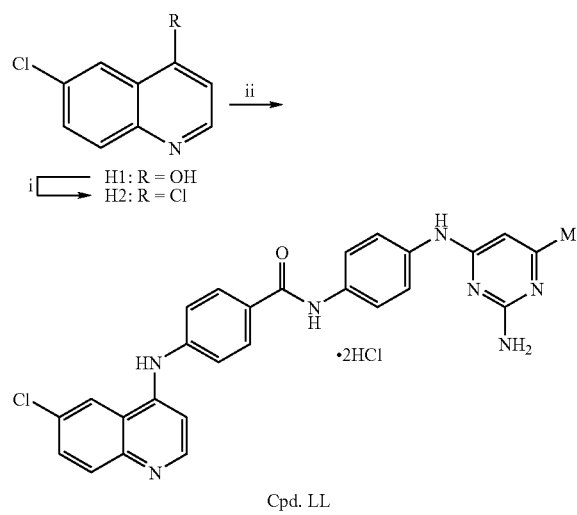

Cpd. LL 4,6-Dichloroquinoline (H2). A solution of 6-chloro-4-quinolone (H1) (1.48 g, 8.22 mmol) in POCl$_3$ (50 mL) was refluxed for 3.5 h, and then excess POCl$_3$ was removed under reduced pressure. The residue was re-dissolved in CH$_2$Cl$_2$, and the resulting solution basified by addition of aqueous ammonia solution. The resulting solution was extracted with CH$_2$Cl$_2$, and the combined organic extracts washed sequentially with H$_2$O and brine, and dried over MgSO$_4$. Solvent was removed under reduced pressure to give dichloroquinoline H2 (1.54 g, 95%) as an amorphous creamy-white solid; mp 101-103° C.; R$_f$=0.83 (5% MeOH:CH$_2$Cl$_2$); $^1$H NMR (400 MHz, DMSO): δ 8.88 (d, J=4.73 Hz, 1H, ArH), 8.21 (d, J=2.33 Hz, 1H, ArH), 8.14 (d, J=8.99 Hz, 1H, ArH), 7.91 (dd, J=8.99, 2.33 Hz, 1H, ArH), 7.84 (d, J=4.73 Hz, 1H, ArH); LCMS (APCI$^+$): 198 (100%), 200 (80%).

N-[4-(2-Amino-6-methylpyrimidin-4-ylamino)phenyl]-4-(6-chloroquinolin-4-ylamino)benzamide (Cpd. LL). To a solution of amine G5 (0.18 g, 0.44 mmol) in dry MeOH (40 mL) were sequentially added dichloroquinoline H2 (0.17 g, 0.88 mmol) and c.HCl (a few drops), and the resulting mixture was refluxed for 2 h. TLC analysis after this time (eluting with the top phase of a 5:4:1 mixture of n-BuOH:H$_2$O:acetic acid) appeared to show H2 had been consumed whilst some E4 remained, thus a further portion of H2 (0.17 g, 0.88 mmol) was added at 3 h. The resulting mixture was refluxed for 14 h, and with no change visible by TLC analysis, solvent was removed under reduced pressure and the residue dried via three MeOH-azeotrope cycles. The residue was triturated with MeOH, and then dried under high-vacuum to give Cpd. LL (2 batches, 0.21 g total, 83%) as an amorphous yellow solid; mp 250-254° C.; $^1$H NMR (400 MHz, DMSO): δ 14.80 (v br s, 1H, pyrimidinyl-N—H$^+$), 12.62 (br s, 1H, quinolinyl-N$^+$—H), 11.07 (s, 1H, ArC(O)NHAr), 10.62 (s, 1H, ArNHAr), 10.44 (s, 1H, ArNHAr), 9.01 (d, J=1.50 Hz, 1H, ArH), 8.63 (d, J=6.90 Hz, 1H, ArH), 8.13 (m, 4H, ArH), 8.05-7.45 (m, 8H, ArH & ArNH$_2$), 7.04 (d, J=6.90 Hz, 1H, ArH), 6.18 (s, 1H, ArH), 2.28 (s, 3H, ArCH$_3$); LCMS (APCI$^+$): 497 (100%), 499 (60%); HPLC: 99.7%.

Example MM

Synthesis of n-[4-(pyridin-4-ylamino)phenyl]-4-(quinolin-4-ylamino)benzamide dihydrochloride (Cpd. MM)

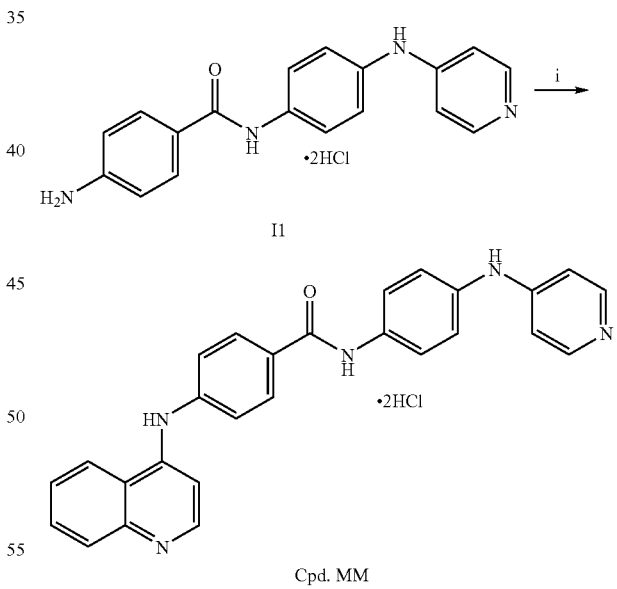

Cpd. MM (i) 4-Chloroquinoline/c•HCl, 1:10 MeOH:EtOH, reflux.

N-[4-(Pyridin-4-ylamino)phenyl]-4-(quinolin-4-ylamino)-benzamide dihydrochloride (Cpd. MM). To a suspension of amine I1 (0.45 g, 1.18 mmol) in 1:10 MeOH:EtOH was sequentially added 4-chloroquinoline (0.97 g, 5.91 mmol), c.HCl (3 mL), and H$_2$O (10 mL), and the resulting mixture was refluxed for ~14 h (reaction progress followed by TLC, eluting with the top phase of a 5:4:1 mixture of n-BuOH:H$_2$O:acetic acid; product R$_f$=0.30, yellow spot after staining with KMnO$_4$). After thus time, solvent was removed under reduced pressure, and the residue dried via three MeOH-azeotrope cycles. The residue was re-precipitated from MeOH:EtOAc, and purified further by preparative HPLC, to give Cpd. MM (0.14 g, 32% brsm) as an amorphous lemon-yellow solid; mp: 148-151° C. (powder-glue), 171-174° C. (glue-liquid); $^1$H NMR (400 MHz, DMSO): δ 13.97 (br s, 2H, pyridinyl-N$^+$—H & quinolinyl-N$^+$—H), 10.83 (br s, 1H, ArC(O)NHAr), 10.49 (s, 1H, ArNHAr), 10.44 (s, 1H, ArNHAr), 8.71 (d, J=8.47 Hz, 1H, ArH), 8.63 (d, J=6.81 Hz, 1H, ArH), 8.27 (d, J=7.14 Hz, 2H, ArH), 8.17 (d, J=8.51 Hz, 2H, ArH), 8.05 (m, 2H, ArH), 7.94 (d, J=8.82 Hz, 2H, ArH), 7.85 (ddd, J=8.32, 5.64, 2.51 Hz, 1H, ArH), 7.67 (d, J=8.51 Hz, 2H, ArH), 7.36 (d, J=8.80 Hz, 2H, ArH), 7.08 (d, J=7.27 Hz, 2H, ArH), 7.03 (d, J=6.81 Hz, 1H, ArH); LCMS (APCI$^+$): 431 (50%), 433 (100%); HPLC: 100%.

Example NN

Synthesis of (E)-N-(4-(1-((Diaminomethylene)hydrazono)ethyl)phenyl)-4-(6-(dimethylamino)quinolin-4-ylamino)benzamide Dihydrochloride (Cpd. NN)

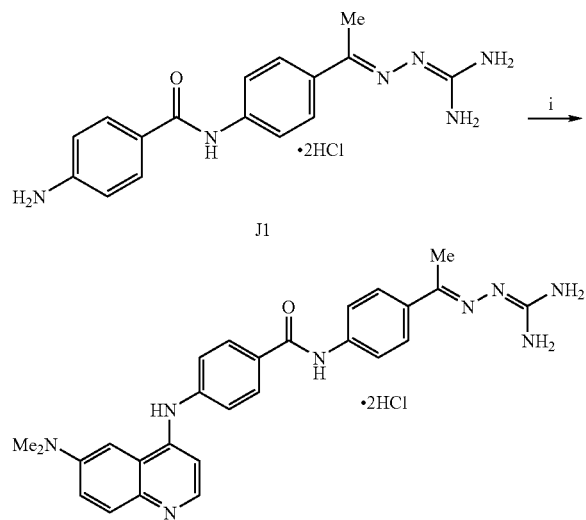

Cpd. NN
(i) 6-(Dimethylamino)-4-chloroquinoline/1:2 EtOH:H$_2$O, c·HCl, reflux, 32 h.

(E)-N-(4-(1-((diaminomethylene)hydrazono)ethyl)phenyl)-4-(6-(dimethylamino)quinolin-4-ylamino)benzamide dihydrochloride (Cpd. NN). To a solution of amine J1 (0.22 g, 0.56 mmol) in 1:2 EtOH:H$_2$O (20 mL) was sequentially added a solution of 6-(dimethylamino)-4-chloroquinoline (0.13 g, 0.61 mmol) in 1:2 EtOH:H$_2$O (10 mL) and c.HCl (0.17 mL, 5.5 mmol). The resulting mixture was refluxed for a few hours, and then allowed to warm to room temperature overnight. After this time (16 h), TLC analysis (eluting with the top phase of a 5:4:1 mixture of n-BuOH:H$_2$O:CH$_3$CO$_2$H) showed some 6 remained in the reaction mixture, so another equivalent of J1 (0.22 g, 0.56 mmol) was added, and the mixture refluxed for a further 16 h. After this time, TLC analysis showed almost complete consumption of the quinoline, so solvent was removed under reduced pressure, and the residue was dried via three MeOH-azeotrope cycles. The residue was reprecipitated from MeOH (acidified with 1.25 methanolic HCl):EtOAc, and further purified via preparative HPLC, to give Cpd. NN as an amorphous yellow-brown solid (18 mg, 6%); mp (MeOH:EtOAc)>280° C.; $^1$H NMR [(CD$_3$)$_2$SO]: δ 2.33 [s, 3H, ArC(CH$_3$)=N—], 3.11 [s, 6H, ArN(CH$_3$)$_2$], 7.00 (s, 1H, ArH), 7.41 [s, 1H, ArH], 7.57-7.90 [m, 8H, ArH & =C(NH$_2$)$_2$], 7.99 [d, J=8.45 Hz, 2H, ArH], 8.12 [d, J=7.01 Hz, 2H, ArH], 8.35 [br s, 1H, ArH], 9.86 [br s, 1H, ArH], 10.40 [s, 1H, ArH], 10.86 [br s, 1H, ArNHAr] {3 remaining exchangeable H signals not visible}; LCMS (APCI$^+$): 482 (100%); HPLC: 98.7%.

Example OO

Synthesis of 6-(dimethylamino)-4-[4-({3-[(1-methyl-4-pyridiniumyl)amino]benzoyl}amino)anilino]-quinolinium dichloride (Cpd. OO1) and the related compound (Cpd. OO2)

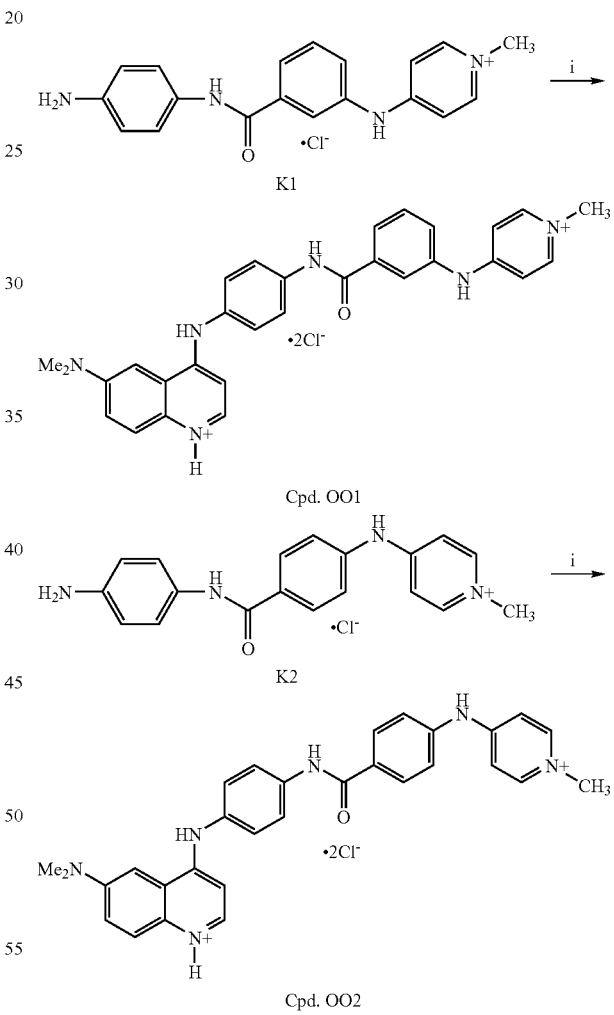

(i) 6-(dimethylamino)-4-chloroquinoline/EtOH/H$_2$O (2:1)/c·HCl/Reflux 6-(Dimethylamino)-4-[4-({3-[(1-methyl-4-pyridiniumyl)amino]-benzoyl}amino)anilino]-quinolinium dichloride Sg EPG 133(Cpd. OO1). To a solution of amine K1 (151 mg, 0.43 mmol) in ethanol (28 mL) and water (14 mL) was added 6-(dimethylamino)-4-chloro quinoline (107 mg, 0.52 mmol) in ethanol (5 mL) and two drops of c.HCl. The reaction mixture was refluxed for 3 days, diluted with EtOAc (150 mL), brought to boil and allowed it to cool to 20° C. The resulting precipitate was filtered, washed with more EtOAc and dried to give a yellow solid 194 mg, which was purified by prep. HPLC (TFA/CH₃CN) and then recrystallized from MeOH/EtOAC to give Cpd. OO1 (80 mg, 33%); mp (MeOH/EtOAc) 17-173° C. (dec); ¹H NMR [(CD₃)₃SO] δ13.88 (bs, 1 H, N⁺H), 10.64 (s, 1 H, NH), 10.53 (s, 1 H, NH), 10.25 (bs, 1 H, NH), 8.32 (d, J=d, J=7.5 Hz, 2 H, ArH), 8.27 (d, J=6.5 Hz, 1 H, ArH), 7.98 (d, J=8.9 Hz, 2 H, ArH), 7.94 (d, J=8.0 Hz, 1 H, ArH), 7.90 (bs, 1 H, ArH), 7.84 (d, J=9.4 Hz, 1 H, ArH), 7.69 (t, J=7.9 Hz, 1 H, ArH), 7.64 (dd, J=9.4, 2.6 Hz, 1 H, ArH), 7.58 (dd, J=8.0, 1.3 Hz, 1 H, ArH), 7.48-7.45 (m, 3 H, ArH), 7.22 (d, J=7.5 Hz, 2 H, ArH), 6.68 (s, 1 H, ArH), 3.99 (s, 3 H, N⁺CH₃), 3.12 [s, 6 H, N(CH₃)₂]; APCI ve⁺ 489.

6-(Dimethylamino)-4-[4-({4-[(1-methyl-4-pyridiniumyl)amino]benzoyl}amino)-anilino]quinolinium dichloride SG EPG 134 (Cpd. OO2). To a solution of amine K2 (162 mg, 0.46 mmol) in ethanol (28 mL) and water (14 mL) was added 6-(dimethylamino)-4-chloro quinoline (114 mg, 0.55 mmol) in ethanol (5 mL) and two drops of c.HCl. The reaction mixture was refluxed for 2 days, diluted with EtOAc (150 mL), brought to boil and allowed it to cool to 20° C. The resulting precipitate was filtered, washed with more EtOAc and dried to give a yellow solid 161 mg, which was purified by prep. HPLC (TFA/CH₃CN) and then recrystallized from MeOH/EtOAC to give Cpd. OO2 (80 mg, 31%); mp (MeOH/EtOAc) 156° C. (dec); ¹H NMR [(CD₃)₂SO] δ13.90 (bs, 1 H, N⁺H), 10.73 (s, 1 H, NH), 10.48 (s, 1 H, NH), 10.29 (bs, 1 H, NH), 8.36 (d, J=7.5 Hz, 2 H, ArH), 8.28 (d, J=6.7 Hz, 1H, ArH), 8.11 (d, J=8.6 Hz, 2 H, ArH), 8.00 (d, J=8.8 Hz, 2 H, ArH), 7.84 (d, J=9.4 Hz, 1 H, ArH), 7.65 (dd, J=9.4, 2.2 Hz, 1 H, ArH), 7.52-7.45 (m, 5 H, ArH), 7.28 (d, J=7.5 Hz, 2 H, ArH), 6.68 (d, J=6.8 Hz, 1 H, ArH), 4.01 (s, 3 H, N⁺CH₃), 3.12 [s, 6 H, N(CH₃)₂] APCI ve⁺ 489.

Example PP

Preparation of 4-[(1E)-N-(diaminomethylene)ethanehydrazonoyl]-N-(4-{[6-(dimethylamino)-4-quinolinyl]amino}phenyl)benzamide dihydrochloride (Cpd. PP)

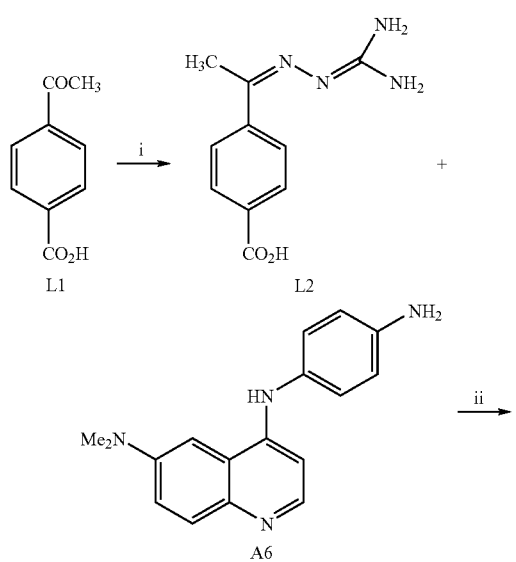

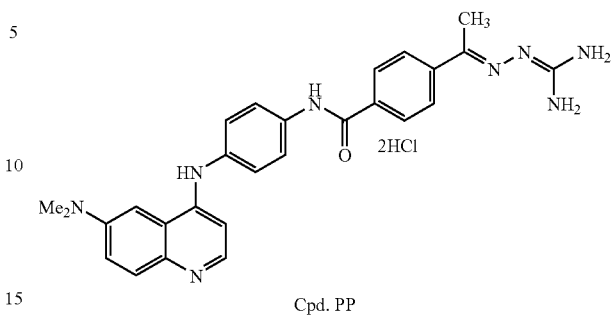

Cpd. PP (i): c•HCl/MeOH/reflux/ H₂NN=C(NH₂)₂; (ii) EDCl/DMAP/DMF/RT

4-[(1E)-N-(Diaminomethylene)ethanehydrazonoyl]benzoic acid hydrochloride (L2). 4-Acetylbenzoic acid (L1) (1.041 g, 6.34 mmol), amino guanidine bicarbonate (1.12 g, 8.2 mmol, 1.3 eq) and c.HCl (0.7 ml, 7.0 mmol) in MeOH (30 mL) was refluxed for 1 h. The reaction mixture was diluted with EtOAc cooled to 20° C. and the resulting precipitate was filtered and recrytallized from MeOH/EtOAc to give L2 (887 mg, 55%), mp (MeOH/EtOAc)>300° C.; ¹H NMR ([(CD₃)₂SO] δ7.97-7.89 (m, 4 H, ArH), 6.75 (br, 4 H, 2×NH₂), 2.25 (s, 3 H, CH₃), mass APCI⁺ 221.

4-[(1E)-N-(Diaminomethylene)ethanehydrazonoyl]-N-(4-{[6-(dimethylamino)-4-quinolinyl]amino}phenyl)benzamide dihydrochloride (Cpd. PP). N⁴-(4-Aminophenyl)-N6,N⁶-dimethyl-4,6-quinolinediamine (A6) (108 mg, 0.34 mmol), L2 (107 mg, 0.34 mmol), EDCI (160 mg, 0.68 mmol) and DMAP (101 mg, 0.68 mmol) in DMF (10 mL) were stirred at 20° C. for 72 h. The solvent was evaporated under reduced pressure at 55° C. The residue was diluted with water and basified with aq NH₃. The resulting precipitate was filtered washed with water, air dried and chromatographed (SiO₂/DCM/MeOH/aq NH₃ 0-7% 2% NH₃). The fractions containing correct mass were combined and evaporated to dryness to give 120 mg of a yellow solid. This was converted to HCl salt by adding few drops of 4N HCl in 1,4-dioxane to a suspension in MeOH, then the solvent was evaporated to dryness. The resulting residue was recrystallized from MeOH/EtOAc to give a crude product (107 mg) containing two main compounds by HPLC. This was purified by prep. HPLC (HCOO⁻N⁺H₄) to give Cpd. PP (52 mg, 27%); m.p (MeOH/EtOAc)>300° C.; ¹H NMR [(CD₃)₂SO] δ14.09 (br s, 1 H, N⁺H), 11.21 (s, 1 H, NH), 10.56 (s, 1 H, NH), 10.40 (s, 1 H, NH), 8.27 (d, J=6.8 Hz, 1 H, ArH), 8.13 (d, J=8.6 Hz, 2 H, ArH), 8.06-8.01 (m, 4 H, ArH), 7.88 (d, J=9.4 Hz, 1 H, ArH), 7.83 (br, 4 H, 2×NH₂), 7.65 (dd, J=9.4, 2.3 Hz, 1 H, ArH), 7.53 (d, J=2.3 Hz, 1 H, ArH), 7.47 (d, J=8.9 Hz, 2 H, ArH), 6.67 (d, J=6.8 Hz, 1 H, ArH), 3.13 [s, 6 H, [N(CH₃)₂], 2.41 (s, 3 H, CH₃); mass APCI⁺ 481.

Example QQ

Preparation of 4-[4-({3-[(1E)-N-(diaminomethylene)ethanehydrazonoyl]-benzoyl}amino)anilino]-6-(dimethylamino)quinolinium chloride (Cpd. QQ)

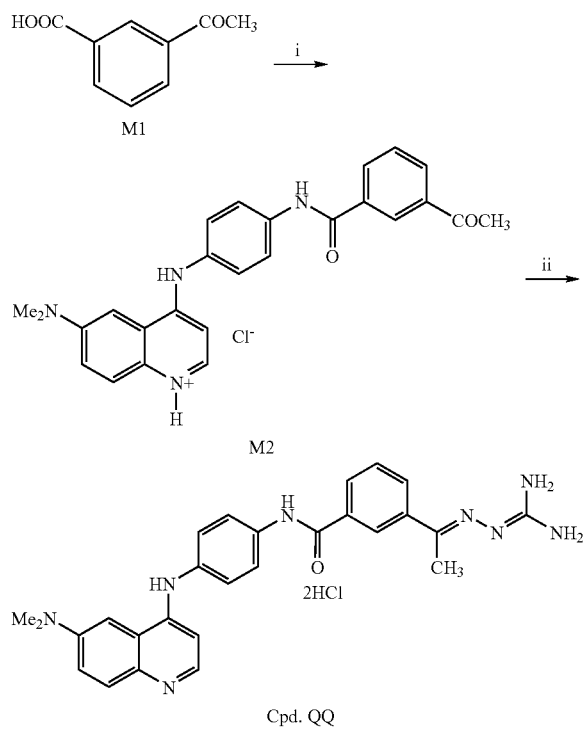

Cpd. QQ
(i) EDCl/DMAP/DMF/20° C.; (ii) MeOH/HCl/reflux

4-{4-[(3-acetylbenzoyl)amino]anilino}-6-(dimethylamino)-quinolinium chloride (M2). A mixture of $N^4$-(4-Aminophenyl)-$N6,N^6$-dimethyl-4,6-quinolinediamine (181 mg, 0.58 mmol), 3-acetylbenzoic acid (M1) (97 mg, 0.58 mmol) and EDCI (220 mg, 0.1.16 mmol) in DMF (5 mL) was stirred at 20° C. for 5 min. Then DMAP (140 mg, 1.16 mmol) was added and the reaction mixture was stirred at 20° C. for 24 h. The solvent was removed under reduced pressure and residue was stirred in aqueous $NaHCO_3$ for 1 h. The resulting precipitate was filtered and purified by chromatography in $SiO_2$ eluting with a gradient (0-7.5%) of MeOH/DCM to give M2 (113 mg, 42%); mp (DCM/MeOH)>280° C.; $^1$HNMR [$(CD_3)_2SO$] δ14.02 (br, 1 H, $N^+H$), 10.66 (s, 1 H, NH), 10.31 (s, 1 H, NH), 8.53 (t, J=1.6 Hz, 1 H, ArH), 8.28 (d, J=6.7 Hz, 1 H, ArH), 8.24 (td, J=8.1, 1.5 Hz, 1 H, ArH), 8.19 (td, J=7.8, 2.8 Hz, 1 H, ArH), 8.00 (d, J=6.8 Hz, 2 H, ArH), 7.87 (d, J=9.4 Hz, 1 H, ArH), 7.78 (t, J=7.8 Hz, 1 H, ArH), 7.64 (dd, J=9.4, 2.6 Hz, 1 H, ArH), 7.51 (d, J=2.5 Hz, 1 H, ArH), 7.47 (d, J=8.8 Hz, 2 H, ArH), 6.69 (d, J=6.7 Hz, 1 H, ArH), 3.09 [s, 6 H, $(NCH_3)_2$], 2.68 (s, 3 H, $COCH_3$); APCI$^+$ve 425.

4-[4-({3-[(1E)-N-(diaminomethylene)ethanehydrazonoyl]benzoyl}amino)anilino]-6-(dimethyl-amino)quinolinium chloride (Cpd. QQ). A mixture of M2 (94 mg, 0.20 mmol), aminoguanidine bicarbonate (42 mg, 0.3 mmol) and c.HCl (0.02 mL, 0.022 mmol) in MeOH 10 mL) was refluxed for 2 hr diluted with EtOAc, some of the MeOH was boiled off and cooled to 20° C. The resulting precipitate was filtered, washed with more EtOAc and recrystallized from MeOH/EtOAc to give Cpd. QQ (109 mg 100%) as a yellow solid; mp (MeOH/EtOAC)>280° C.; $^1$H NMR [$(CD_3)_2SO$] δ 14.13 (br 1 H, $N^+H$), 11.25 (s, 1 H, NH), 10.67 (s, 1 H, NH), 10.42 (s, 1 H, NH), 8.48 (t, J=1.5 Hz, 1 H, ArH), 8.27 (d, J=6.8 Hz, 1 H, ArH), 8.22 (t, d, J=7.9, 1.4 Hz, 1 H, ArH), 8.05-8.01 (m, 3 H, ArH), 7.89 (d, J=9.6 Hz, 1 H, ArH), 7.85 (br, 4 H, $2×NH_2$), 7.66-7.59 (m, 2 H, ArH), 7.54 (d, J=2.3 Hz, 1 H, ArH), 7.47 (d, J=8.8 Hz, 2 H, ArH), 6.67 (d, J=6.8 Hz, 1 H, ArH), 3.13 [s, 3, 6 H, $(NCH_3)_2$], 2.45 (s, 3 H, $CH_3$); APCI$^+$ve 481.

Example RR

Preparation of 3-[(2,6-diamino-4-pyrimidinyl)amino]-N-{4-[(6-nitro-4-quinolinyl)amino]phenyl}benzamide dihydrochloride (Cpd. RR1) and the related compounds (Cpd. RRR2 and Cpd. RRR3)

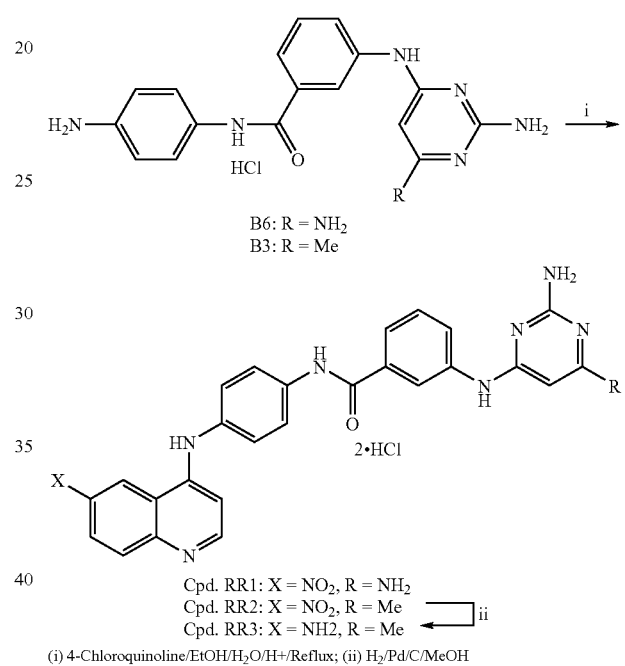

Cpd. RR1: X = $NO_2$, R = $NH_2$
Cpd. RR2: X = $NO_2$, R = Me
Cpd. RR3: X = $NH_2$, R = Me (i) 4-Chloroquinoline/EtOH/$H_2O$/H+/Reflux; (ii) $H_2$/Pd/C/MeOH 3-[(2,6-diamino-4-pyrimidinyl)amino]-N-{4-[(6-nitro-4-quinolinyl)amino]phenyl}benzamide dihydrochloride (Cpd. RRR1). To a solution of amine B6 (204 mg, 0.55 mmol) in EtOH (20 mL) and $H_2O$ (10 mL) was added 4-chloro-6-nitroquinoline (126 mg, 0.61 mmol) and stirred until it dissolved, then 2 drops of c.HCl was added. The reaction mixture was refluxed for 4 h, diluted with EtOAc, brought to boil and cool to 20° C. The resulting precipitate was filtered and recrystallized from MeOH/EtOAc to give Cpd. RRR1 (224 mg 70%); m.p. (MeOH/EtOAc)>300° C.; $^1$H NMR [$(CD_3)_2SO$] δ 14.75 (br, 1 H, $N^+H$), 11.50 (br, 1 H, $N^+H$), 11.10 (br, 1 H, NH), 10.50 (s, 1 H, NH), 9.88 (s, 1 H, NH), 9.77 (s, 1 H, NH), 9.76 (s, 1 H, ArH), 8.66 (d, J=9.3 Hz, 1 H, ArH), 8.60 (d, J=6.8 Hz, 1 H, ArH), 8.19 (d, J=9.3 Hz, 1 H, ArH), 8.25 (d, J=8.8 Hz, 2 H, ArH), 7.94 (br s 2 H, $NH_2$), 7.71 (d, J=7.6 Hz, 1 H, ArH), 7.56-7.42 (m, 6 H, $NH_2$ & 4×ArH), 6.91 (d, J=6.8 Hz, 1 H, ArH), 5.44 (s, 1 H, ArH). HRMS (FAB$^+$) calc. for $C_{26}H_{22}N_9O_3$ ($M^{+1}$) m/z 508.1846, found 508.1841.

3-[(2-amino-6-methyl-4-pyrimidinyl)amino]-N-{4-[(6-nitro-4-quinolinyl)amino]phenyl}benzamide dihydrochloride (Cpd. RRR2). To a solution of amine B3 (205 mg, 0.55 mmol) in EtOH (20 mL) and $H_2O$ (10 mL) was added 4-chloro-6-nitroquinoline (135 mg, 0.64 mmol) and stirred until it dissolved, then 2 drops of c.HCl was added. The reaction mixture was refluxed for 5 h, diluted with EtOAc, brought to boil and cool to 20° C. The resulting precipitate was filtered and recrystallized from MeOH/EtOAc to give Cpd. RRR2 (217 mg 68%); m.p. (MeOH/EtOAc)>300° C.; $^1$H NMR [(CD$_3$)$_2$SO] δ 13.00 (br, 2 H, 2×N$^+$H), 10.99 (br, 1 H, NH), 10.75 (br s, 1 H, NH), 10.53 (s, 1 H, NH), 9.75 (d, J=1.9 Hz, 1 H, ArH), 8.64 (br d, J=7.4 Hz, 1 H, ArH), 8.60 (d, J=6.7 Hz, 1 H, ArH), 8.17 (d, J=9.3 Hz, 1 H, ArH), 8.15 (br, 1 H, NH), 8.07 (br s, 1 H, NH), 7.99 (d, J=8.8 Hz, 2 H, ArH), 7.79 (br d, J=7.5 Hz, 3 H, ArH), 7.57 (t, J=7.9 Hz, 1 H, ArH), 7.48 (d, J=8.8 Hz, 2 H, ArH), 6.91 (d, J=6.7 Hz, 1 H, ArH), 6.22 (d, J=0.6 Hz, 1 H, ArH), 2.30 (s, 3 H. CH$_3$); HRMS (FAB$^+$) calc. for C$_{27}$H$_{23}$N$_8$O$_3$ (M$^{+1}$) m/z 507.1893, found 507.1888.

3-[(2-Amino-6-methyl-4-pyrimidinyl)amino]-N-{4-[(6-amino-4-quinolinyl)amino]phenyl}benzamide dihydrochloride (Cpd. RRR3). Compound Cpd. RRR2 (146 mg, 146 mg, 0.25 mmol) was dissolved in MeOH (30 ml) and hydrogenated with 10% Pd/C (20 mg) at 30 Hg mm for 3 h. The reaction mixture was filtered through a pad of celite. The filtrate was evaporated to dryness. The resulting residue was dissolved in MeOH (10 mL) stirred with 1.25 M HCl in MeOH (0.5 mL), then precipitated by adding EtOAc, filtered and dried to give 120 mg of Cpd. RRR3. This was 90% clean by HPLC. This was then converted to free base by stirring in aq NH$_3$ filtered, air dried and chromatographed on neutral alumina eluting with a gradient (0-10%) of MeOH/DCM containing 1% aq NH$_3$ to give 83 mg of clean free base. This was then converted to HCl salt by dissolving in MeOH and adding 1.25 M HCl in MeOH. Evaporated to dryness and the residue was recrystallized from MeOH/EtOAc to give Cpd. RRR3 (88 mg, 64%), mp (MeOH/EtOAc) 280-284° C.; $^1$H NMR [(CD$_3$)$_2$SO] δ 14.0 (d, J=5.4 Hz, 1 H, N$^+$H), 12.78 (br s, 1 H, N$^+$H), 10.79 (br s, 1 H, NH), 10.50 (s, 1 H, NH), 10.19 (s, 1 H, NH), 8.22 (t, J=6.4 Hz, 2 H, ArH), 8.16-8.07 (br, 2 H, NH$_2$)7.96 (d, J=8.9 Hz, 2 H, ArH), 7.80 (br s, 1 H, ArH), 7.78 (d, J=9.0 Hz, 2 H, ArH), 7.56 (t, J=8.0 Hz, 1 H, ArH), 7.47 (br d, J=2.1 Hz, 1 H, ArH), 7.43 (d, J=8.7 Hz, 2 H, ArH), 7.39 (dd, J=9.0, 2.2 Hz, 1 H, ArH), 6.67 (d, J=6.8 Hz, 1 H, ArH), 6.23 (s, 1 H, ArH), 5.9 (v. br, 2 H, NH$_2$), 2.31 (s, 3 H, CH$_3$).

Example SS

Preparation of 4-[(2,6-diamino-4-pyrimidinyl)amino]-N-(4-{[6-(dimethylamino)-4-quinolinyl]amino}phenyl)benzamide dihydrochloride (Cpd. SS)

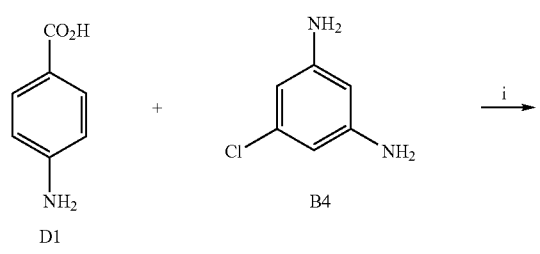

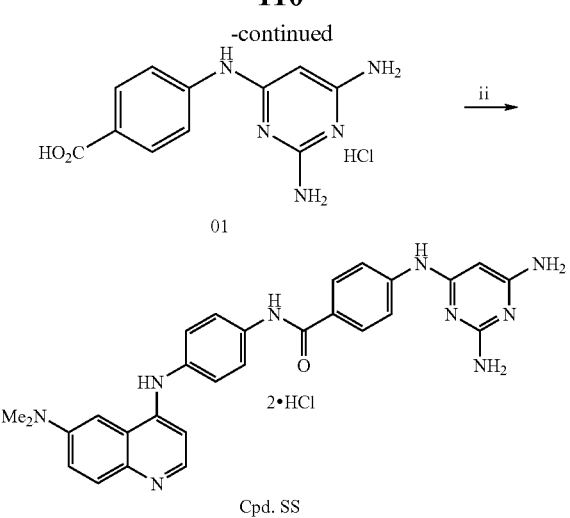

(i) Ethanol/H$^+$/Reflux; (ii) A3/EDCI/DMAP/N-Methylpyrrolidinone

4-[(2,6-Diamino-4-pyrimidinyl)amino]benzoic acid (O$_1$). 4-amino-benzoic acid (D1) (2.0 g, 14.55 mmol), and 2,6-diamino-4-chloropyrimidine (B4) (2.013 g, 14.55 mmol) were dissolved in 2-ethoxyethanol (20 mL). 2 drops of c.HCl was added to this mixture and refluxed for 20 h. The reaction mixture was cooled to 20° C. and the resulting precipitate was filtered and recrystallized from MeOH/EtOAc to give compound O$_1$ (3.12 g, 56%), mp (MeOH/EtOAc)° C.; $^1$H NMR [(CD$_3$)$_2$SO] δ 12.65 (br, 1 H, COOH or N$^+$H), 11.84 (br s, 1 H, N$^+$H or COOH), 10.07 (s, 1 H, NH), 7.86 (br d, J=8.7 Hz, 2 H, ArH), 7.75 (v.br d, J=7.8, 2 H, ArH), 7.64 (br, 2 H, NH$_2$), 7.51 (br, 2 H, NH$_2$), 5.50 (s, 1 H, ArH).

4-[(2,6-Diamino-4-pyrimidinyl)amino]-N-(4-{[6-(dimethylamino)-4-quinolinyl]amino}phenyl)benzamide dihydrochloride (Cpd. SS). Compound O1 (101.4 mg, 0.36 mmol), EDCI (138 mg, 0.72 mmol) and DMAP (88 mg, 0.36 mmol) in N-methylpyrrolidinone (5 mL) was stirred at 20° C. for 5 min. Then N$^4$-(4-Aminophenyl)-N6,N$^6$-dimethyl-4,6-quinolinediamine (100 mg, 0.36 mmol) and Et$_3$N (0.2 mL, 1.44 mmol) was added and stirred 20 h. The tlc of a small sample (Al$_2$O$_3$/DCM/MeOH 5% and/aqNH$_3$) showed still presence of N$^4$-(4-Aminophenyl)-N6,N$^6$-dimethyl-4,6-quinolinediamine, therefore more EDCI (138 mg 0.72 mmol) was added and stirred 72 h. The reaction mixture was then diluted with H$_2$O and stirred for 1 h. The resulting precipitate was filtered, washed with water, air dried and chromatographed on neutral alumina eluting with a gradient of 0-5% of DCM/MeOH, to remove impurity of unreacted N$^4$-(4-Aminophenyl)-N6,N$^6$-dimethyl-4,6-quinolinediamine then adding 1% aq. NH$_3$ to elute the product Cpd. SS. Evaporation of the fractions containing the product gave compound Cpd. SS (75 mg). This was dissolved in a small amount of MeOH and stirred with 1.25 M HCl in MeOH (0.5 mL), solvent was evaporated and the residue recrystallized from MeOH/EtOAc to give Cpd. SS (84 mg, 40%), mp (MeOH/EtOAc) 283-287° C.; $^1$H NMR [(CD$_3$)$_2$SO] δ 14.14 (d, J=4.7 Hz, 1 H, N$^+$H), 11.81 (br, 1 H, N$^+$H), 10.42 (s, 1 H, NH), 10.39 (s, 1 H, NH), 10.09 (s, 1 H, NH), 8.26 (t, J=6.4 Hz 1 H, ArH), 8.02-7.98 (m, 4 H, ArH), 7.89 (d, J=8.7 Hz, 1 H, ArH), 7.80 (br d, 2 H, ArH), 7.68 (br, 2 H, NH$_2$), 7.64 (dd, J=9.4, 2.5 Hz, 1 H, ArH), 7.53 (dd, J=9.3, 2.5 Hz, 1 H, ArH), 7.52 (br s, 2 H, NH$_2$), 7.45 (d, J=8.9 Hz, 2 H, ArH), 6.66 (d, J=6.8 Hz, 1H, ArH), 5.51 (s, 1 H, ArH), 3.12 [s, 6 H, N(CH$_3$)$_3$].

Example TT

Preparation of 4-[(2,6-diamino-4-pyrimidinyl)amino]-N-[4-(4-quinolinylamino)phenyl]benzamide dihydrochloride (Cpd. TT)

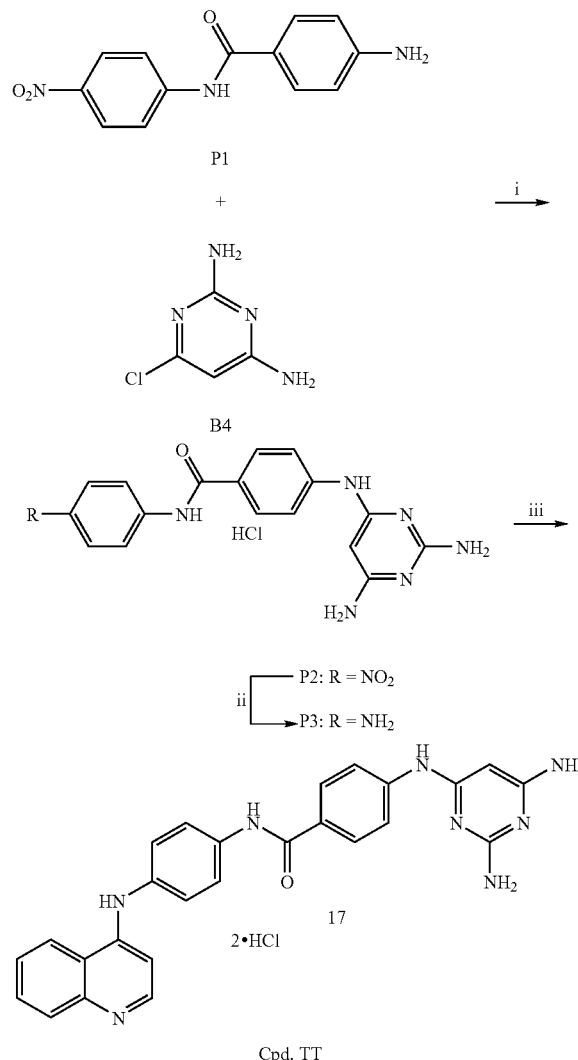

(i) MeOH/HCl/Reflux; (ii) H₂/Pd/C/MeOH; (iii) 4-chloroquinoline/2:1 EtOH/H₂O/H⁺Reflux 4-[(2,6-Diamino-4-pyrimidinyl)amino]-N-(4-nitrophenyl)-benzamide hydrochloride (P2). Amine P1 (1.0 g, 3.89 mmol) and chloropyrimidine B4 (1.12 g, 7.78 mmol) were dissolved in MeOH (200 mL) by heating then c.HCl (3 drops) were added and refluxed for 5 days. The reaction mixture was cooled to 20° C. and the precipitate was filtered washed with more MeOH and dried to give essentially pure compound P2 (814 mg 52%), $^1$H NMR [(CD$_3$)$_2$SO] δ 11.84 (s, 1 H, N⁺H), 10.75 (s, 1 H, NH), 10.12 (s, 1 H, NH), 8.28-8.24 (m, 2 H, ArH), 8.11-8.07 (m, 2 H, ArH), 8.24 (br d, J=8.7 Hz, 2 H, ArH), 7.83 (br, 2 H, ArH), 7.68 (br, 2 H, NH$_2$), 7.54 (br, 2 H, NH$_2$), 5.51 (s, 1 H, ArH). HRMS (FAB⁺) calc. for C$_{15}$H$_{16}$N$_7$O$_3$ (M⁺¹) m/z 366.1315, found 366.1306.

N-(4-Aminophenyl)-4-[(2,6-diamino-4-pyrimidinyl)amino]-benzamide dihydrochloride (P3). A suspension of compound P2 (811 mg, 2.01 mmol) in MeOH 100 (mL) was hydrogenated with 10% Pd/C (100 mg) at 40 Hg mm H$_2$ pressure for 20 h. The resulting new suspension was stirred with 1.25 M HCl in MeOH (5 mL) to dissolve the product and this was then filtered through a pad of Celite to remove Pd residues. The filtrate was evaporated to dryness and the residue was recrystallized from MeOH/EtOAc to give compound P3 (785 mg, 100%), $^1$H NMR [(CD$_3$)$_2$SO] δ 10.02 (s, 1 H, NH), 9.88 (s, 1 H, NH), 7.91 (d, J=8.7 Hz, 2 H, ArH), 7.74 (d, J=8.5 Hz, 2 H, ArH), 7.62 (br, 2 H, NH$_2$), 7.68 (br s, 2 H, NH$_2$), 7.47 (d, J=8.8 Hz, 2 H, ArH), 6.71 (d, J=8.7 Hz, 2 H, ArH), 5.45 (s, 1 H, ArH).

4-[(2,6-Diamino-4-pyrimidinyl)amino]-N-[4-(4-quinolinylamino)-phenyl]benzamide dihydrochloride (Cpd. TT). To a solution of compound P3 (128 mg, 0.34 mmol) in EtOH (20 mL) and H$_2$O (10 mL) was added 4-chloroquinoline (127 mg, 0.51 mmol) and stirred until it dissolved, then 2 drops of c.HCl was added. The reaction mixture was refluxed for 4 h, diluted with EtOAc, brought to boil and cool to 20° C. The resulting precipitate was filtered and recrystallized from MeOH/EtOAc to give Cpd. TT (151 mg, 83%); m.p. (MeOH/EtOAc) 263-267° C.; $^1$HNMR [(CD$_3$)$_2$SO] δ14.10 (br, 1 H, N⁺H), 11.90 (br, 1 H, N⁺H), 10.89 (s, 1 H, NH), 10.40 (s, 1 H, NH), 10.04 (s, 1 H, NH), 8.77 (d, J=8.7 Hz, 1 H, ArH), 8.51 (d, J=7.0 Hz, 1 H, ArH), 8.06-7.98 (m, 6 H, ArH), 7.83-7.79 (m, 3 H, ArH & NH$_2$), 7.61 (br, 2 H, NH$_2$), 7.47 (d, J=8.9 Hz, m, 2 H, ArH), 6.78 (d, J=7.0 Hz, 1 H, ArH), 5.45 (s, 1H, ArH).

Example UU

Preparation of N-{4-[(6-amino-4-quinolinyl)amino]phenyl}-3-[(2,6-diamino-4-pyrimidinyl)amino]benzamide dihydrochloride (Cpd. UU)

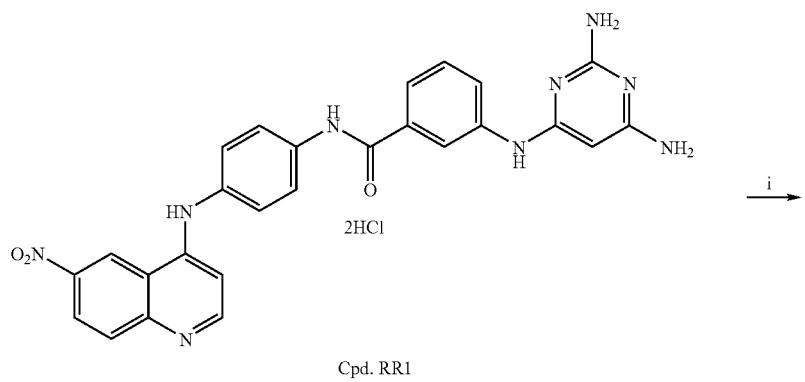

Cpd. RR1

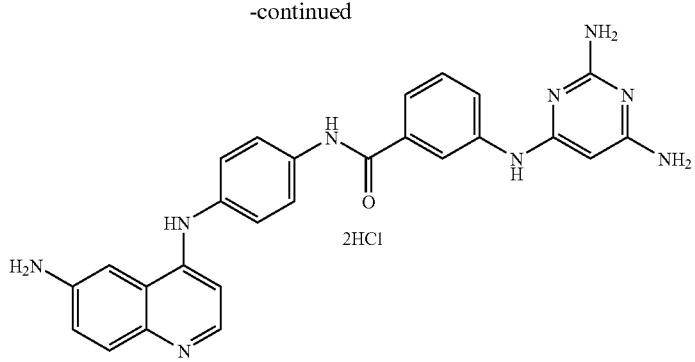

Cpd. UU (i) H₂Pd/C/MeOH

N-{4-[(6-Amino-4-quinolinyl)amino]phenyl}-3-[(2,6-diamino-4-pyrimidinyl)amino]benzamide dihydrochloride (Cpd. UU). 3-[(2,6-Diamino-4-pyrimidinyl)amino]-N-{4-[(6-nitro-4-quinolinyl)amino]phenyl}benzamide dihydrochloride (Cpd. RRR1) (148 mg, 0.25 mmol) was dissolved in MeOH (30 ml) and hydrogenated with 10% Pd/C (20 mg) at 30 Hg mm for 20 h. The reaction mixture was filtered through a pad of celite. The filtrate was evaporated to dryness. The resulting residue was dissolved in MeOH (10 mL) stirred with 1.25 M HCl in MeOH (0.5 mL). then precipitated by adding EtOAc, filtered and dried to give 90 mg of compound UU. This was 78% clean by HPLC. This was then converted to free base by stirring in aq NH₃ filtered, air dried and chromatographed on neutral alumina eluting with a gradient(0-7%) of MeOH/DCM containing 1.5% aq NH₃ to give 51 mg of clean free base of Cpd. UU (51 mg, 43%). This was then converted to HCl salt by dissolving in MeOH and adding 1.25 M HCl in MeOH. Evaporated to dryness and the residue was recrystallized from MeOH/EtOAc to give Cpd. UU, mp (MeOH/EtOAc) 250-255° C.; ¹H NMR [(CD₃)₂SO] δ 14.15 (d, J=6.1 Hz, 1 H, N⁺H), 11.70 (br 1 H, N⁺H), 10.48 (s, 1 H, NH), 10.46 (s, 1 H, NH, 10.21 (S, 1 H, NH), 8.22 (t, J=6.5 Hz, 1 H, ArH), 8.05-7.89 (m, 4 H, ArH), 7.79 (d, J=9.1 Hz, 1 H, ArH), 7.71 (br d, J=7.5 Hz, 1 H, ArH), 7.59 (br, 2 H, NH₂), 7.53-7.38 (m, 8 H, ArH & NH₂), 6.67 (d, J=6.7 Hz, 1 H, ArH), 5.45 (s, 1 H, ArH). HPLC purity %. HRMS (FAB⁺), calc. for $C_{26}H_{23}N_9O$ (M⁺¹) m/z 478.2104, found, 478.2103.

Example VV

Preparation of D [(2,6-diamino-4-pyrimidinyl)amino]-N-{4-[(6-nitro-4-quinolinyl)amino]phenyl}benzamide dihydrochloride (Cpd. VV1) and the related compound (Cpd. VV2)

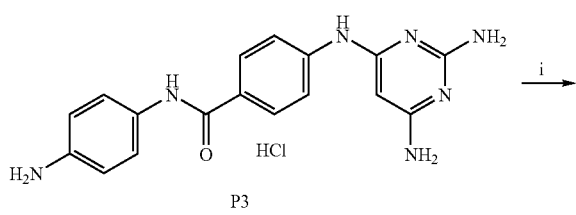

P3

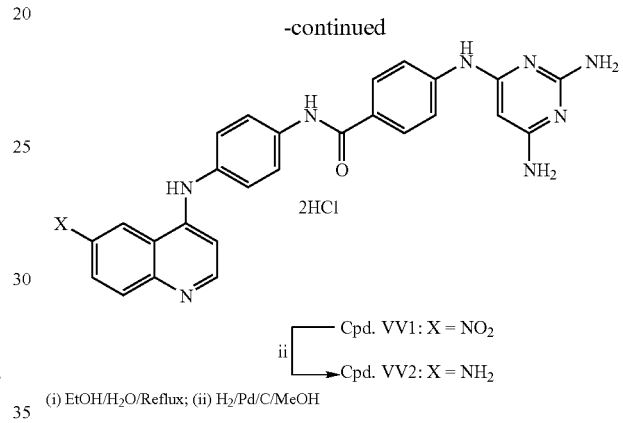

Cpd. VV1: X = NO₂
Cpd. VV2: X = NH₂

(i) EtOH/H₂O/Reflux; (ii) H₂/Pd/C/MeOH

4-[(2,6-Diamino-4-pyrimidinyl)amino]-N-{4-[(6-nitro-4-quinolinyl)amino]phenyl}benzamide dihydrochloride (Cpd. VV1). To a solution of compound P3 (288 mg, 0.76 mmol) in EtOH (20 mL) and H₂O (10 mL) was added 4-chloro-6-nitroquinoline (196 mg, 0.94 mmol) and stirred until it dissolved, then 2 drops of c.HCl was added. The reaction mixture was refluxed for 4 h, diluted with EtOAc, brought to boil and cool to 20° C. The resulting precipitate was filtered and recrystallized from MeOH/EtOAc to give Cpd. VV1 (445 mg 99%); m.p. (MeOH/EtOAc) 260-265° C.; ¹HNMR [(CD₃)₂SO] δ 11.38 (brs, 1 H, N⁺H), 10.43 (s, 1 H, NH), 10.10 (s, 1 H, NH), 9.81 (d, J=2.1 Hz, 1 H, NH), 8.78 (dd, J=9.3, 2.2 Hz, 1 H, ArH), 8.84 (d, J=7.2 Hz, 1 H, ArH), 8.24 (d, J=9.3 Hz, 1 H, NH), 8.04-7.98 (m, 4 H, ArH), 7.81 (br d, J=7.4 Hz, 2 H, ArH), 7.68 (br s, 2 H, NH₂), 7.53 (br s, 2 H, NH₂), 7.48 (d, J=8.9 Hz, 2 H, ArH), 6.90 (d, J=7.0 Hz, 1 H, ArH), 5.52 (s, 1 H, ArH). HPLC purity 100%; HRMS (FAB⁺) calc for $C_{26}H_{21}N_9O_3$ (M⁺¹) m/z 508.1846, found 508.1844; Anal. Calc. for $C_{26}H_{23}Cl_2N_9O_3 \cdot 4H_2O$: C, 47.9; H, 4.2; N, 19.3; Cl, 10.9; found C, 48.0; H, 4.4; N, 19.2; Cl, 11.1%.

N-{4-[(6-Amino-4-quinolinyl)amino]phenyl}-4-[(2,6-diamino-4-pyrimidinyl)amino]benzamide dihydrochloride (Cpd. VV2). A solution of Cpd. VV1 (211 mg, 0.36 mmol) was dissolved in MeOH (30 ml) and hydrogenated with 10% Pd/C (20 mg) at 30 Hg mm for 5 h. The reaction mixture was filtered through a pad of celite. The filtrate was evaporated to dryness. The resulting residue was dissolved in MeOH (10 mL) stirred with 1.25 M HCl in MeOH (0.5 mL), then MeOH was evaporated to dryness. Residue was redissolved in MeOH and evaporated to dryness, and then recrystallized from MeOH/EtOAc to give 178 mg of the product; this was only 93% clean by HPLC. This was then converted to free base by stirring in aq $NH_3$ filtered, air dried and chromatographed on neutral alumina eluting with a gradient(0-7.5%) of MeOH/DCM containing 1.5% aq $NH_3$ to give clean free base of Cpd. VV2. This was then converted to HCl salt by dissolving in MeOH and adding 1.25 M HCl in MeOH. Evaporated to dryness and the residue was recrystallized from MeOH/EtOAc to give Cpd. VV2 (138 mg, 70%), mp (MeOH/EtOAc) 262-266° C.; $^1$H NMR [$(CD_3)_2SO$] δ 14.11 (br s, 1 H, $N^+H$), 11.81 (br, 1 H, $N^+H$), 10.36 (s, 1 H, NH), 10.19 (s, 1 H, NH), 10.08 (s, 1 H, NH), 8.21 (t, J=6.0 Hz, 1 H, ArH), 8.00-7.96 (m, 4 H, ArH), 7.79 (br s, 2 H, $NH_2$), 7.78 (d, J=9.1 Hz, 1 H, ArH), 7.67 (br s, 2 H, $NH_2$), 7.53 (br s, 2 H, $NH_2$), 7.48 (br s, 1 H, ArH), 7.42-7.38 (m, 3 H, ArH), 6.66 (d, J=6.7 Hz, 1 H, ArH), 6.00 (v.br, 2 H, $NH_2$), 5.51 (s, 1 H, ArH). HPLC purity 99.7%; HRMS (FAB$^+$) calc. for $C_{26}H_{24}N_9O$ ($M^{+1}$) m/z 478.2104 found 478.2107.

Example WW

Preparation of N-methyl-N-[4-(pyridin-4-ylamino) phenyl]-4-(quinolin-4-ylamino)benzamide hydrochloride (Cpd. WW)

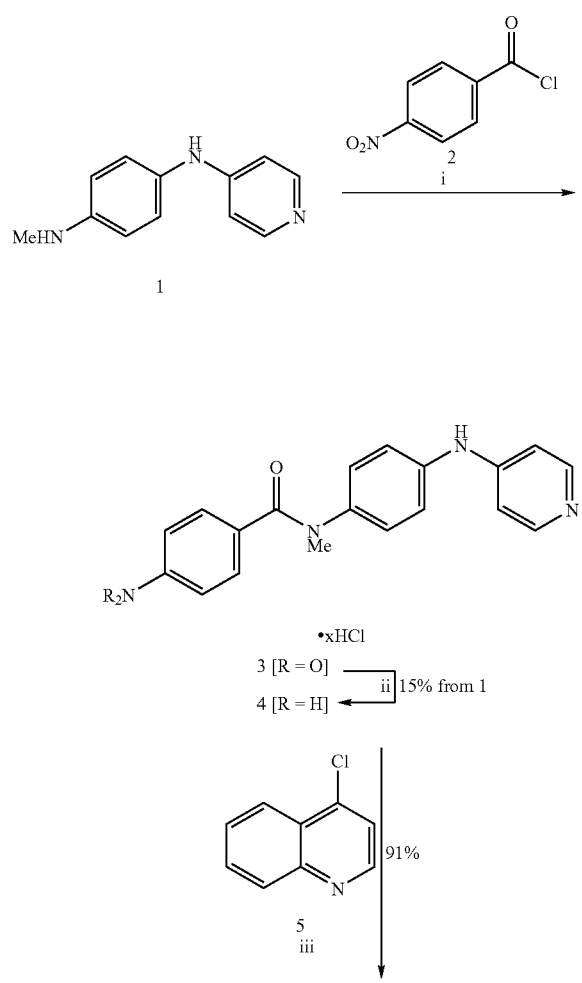

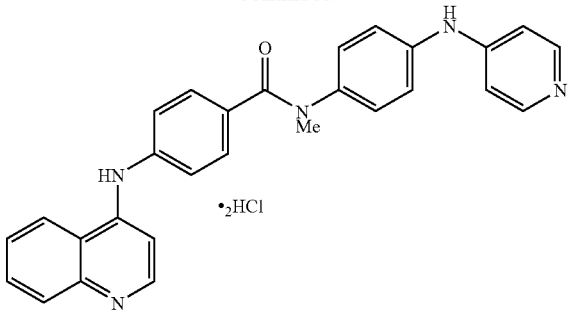

Cpd. WW

Reagent and conditions: (i) pyridine, dioxane, reflux, 60 h; (ii) 10% Pd/C, $H_2$, MeOH, r.t., 24 h; (iii) 20% aq. EtOH, c•HCl, reflux, 16 h.

N-Methyl-4-nitro-N-[4-(pyridin-4-ylamino)phenyl]benzamide hydrochloride (3). To a solution of amine 1 (0.82 g, 4.10 mmol) in dry dioxane (70 mL) were sequentially added dry pyridine (1.65 mL, 20.50 mmol) and acid chloride 2 (2.08 g, 11.19 mmol), and the resulting mixture was refluxed for ~60 h. After this time, the reaction mixture was cooled to room temperature, and the resulting solid collected by filtration. The filtrate was basified by addition of aqueous $NH_3$, and the resulting second batch of solid collected by filtration. Batches of solid were combined to give amide 3 as an amorphous yellow solid (3.46 g), which was analyzed by $^1$H NMR and MS, and used without further purification. $^1$H NMR: 8.88 (dd, J=6.32, 1.32 Hz, 4H, ArC(O)N(CH$_3$)Ar & ArNHAr), 8.32 (ddd, J=9.17, 4.31, 2.27 Hz, 4H, ArH), 8.17 (ddd, J=9.17, 4.31, 2.28), 7.98 (dd, J=7.59, 6.50 Hz, 4H, ArH) [pyridyl-$N^+$—H not visible]; LCMS (APCI$^+$): 349 (100%).

4-Amino-N-methyl-N-[4-(pyridin-4-ylamino)phenyl] benzamide hydrochloride (4). To a solution of amide 3 (3.46 g, 8.99 mmol) in MeOH (~40 mL) was added a spatula tipful of 10% Pd/C, and the resulting suspension hydrogenated at 40 psi for 16 h. After this time, the reaction mixture was filtered through a pad of Celite, and solvent removed under reduced pressure. The residue was reprecipated from MeOH-EtOAc to give amine 4 as an amorphous cream solid (0.25 g, 15% from 1); mp 235-238° C. (powder -tar), 245-249° C. (gas evolved); $^1$H NMR: 13.85 (v br s, 1H, pyridine-$N^+$—H), 10.75 (s, 1H, ArNHAr), 8.28 (d, J=7.23 Hz, 2H, ArH), 7.25 (s, 4H, ArH), 7.16 (d, J=8.44 Hz, 2H, ArH), 7.07 (d, J=7.03 Hz, 2H, ArH), 6.73 (d, J=7.79 Hz, 2H, ArH), 3.36 (s, ArC(O)N(CH$_3$)Ar) [ArN$^+$H$_3$ not visible]; HRMS (EI) calc. for $C_{19}H_{18}N_4O$ m/z 318.1481, found 318.1481.

N-Methyl-N-[4-(pyridin-4-ylamino)phenyl]-4-(quinolin-4-ylamino)-benzamide hydrochloride Cpd. WW. To a solution of amine 4 (0.23 g, 0.58 mmol) in 20% aqueous EtOH (40 mL) were sequentially added quinoline 5 (0.22 g, 1.36 mmol) and c.HCl (0.17 mL, 5.60 mmol), and the resulting mixture was refluxed for ~16 h. After this time, solvent was removed under reduced pressure, and the residue re-precipitated from MeOH:EtOAc to give Cpd. WW as a pale yellow amorphous solid (0.27 g, 91%), mp 287-292° C. (tar-liquid); $^1$H NMR: 14.6 (v br s, 1H, quinolinyl-$N^+$—H), 13.84 (v br s, 1H, pyridinyl-$N^+$—H, 1H), 11.02 (s, 1H, ArNHAr), 10.95 (s, 1H, ArNHAr), 8.80 (d, J=8.49 Hz, 1H, ArH), 8.58 (d, J=6.95 Hz, 1H, ArH), 8.28 (d, J=7.28 Hz, 2H, ArH), 8.06 (m, 2H, ArH), 7.79 (ddd, J=8.31, 6.80, 1.30 Hz, 1H, ArH), 7.49 (d, J=8.50 Hz, 1H, ArH), 7.40 (d, J=8.53 Hz, 1H, ArH), 7.36 (d, J=8.78 Hz, 1H, ArH), 7.31 (m, 4H), 7.13 (d, J=7.10 Hz, 2H, ArH), 6.76 (d, J=6.94 Hz, 1H, ArH), 3.44 (s, 3H, ArC(O)N(CH$_3$)Ar); HRMS (FAB$^+$): calc. for $C_{28}H_{24}N_5O$ (MH+) m/z 446.1981, found 446.1985; HPLC: 96.3%.

Example XX

Preparation of N-{4-[(2-amino-6-methyl-4-pyrimidinyl)amino]phenyl}-5-(4-quinolinylamino)-2-pyridinecarboxamide dihydrochloride (Cpd. XX)

N-{4-[(2-amino-6-methyl-4-pyrimidinyl)amino]phenyl}acetamide hydrochloride (16): To a mixture of 4-aminoacetanilide 14 (3.55 g, 23.64 mmol) and 2-amino-4-chloro-6-methylpyrimidine 15 (3.73 g, 26 mmol) in ethanol (50 mL) was added. C.HCl (2 drops). The reaction mixture was stirred under reflux conditions for 2 h, cooled to 20° C. and the

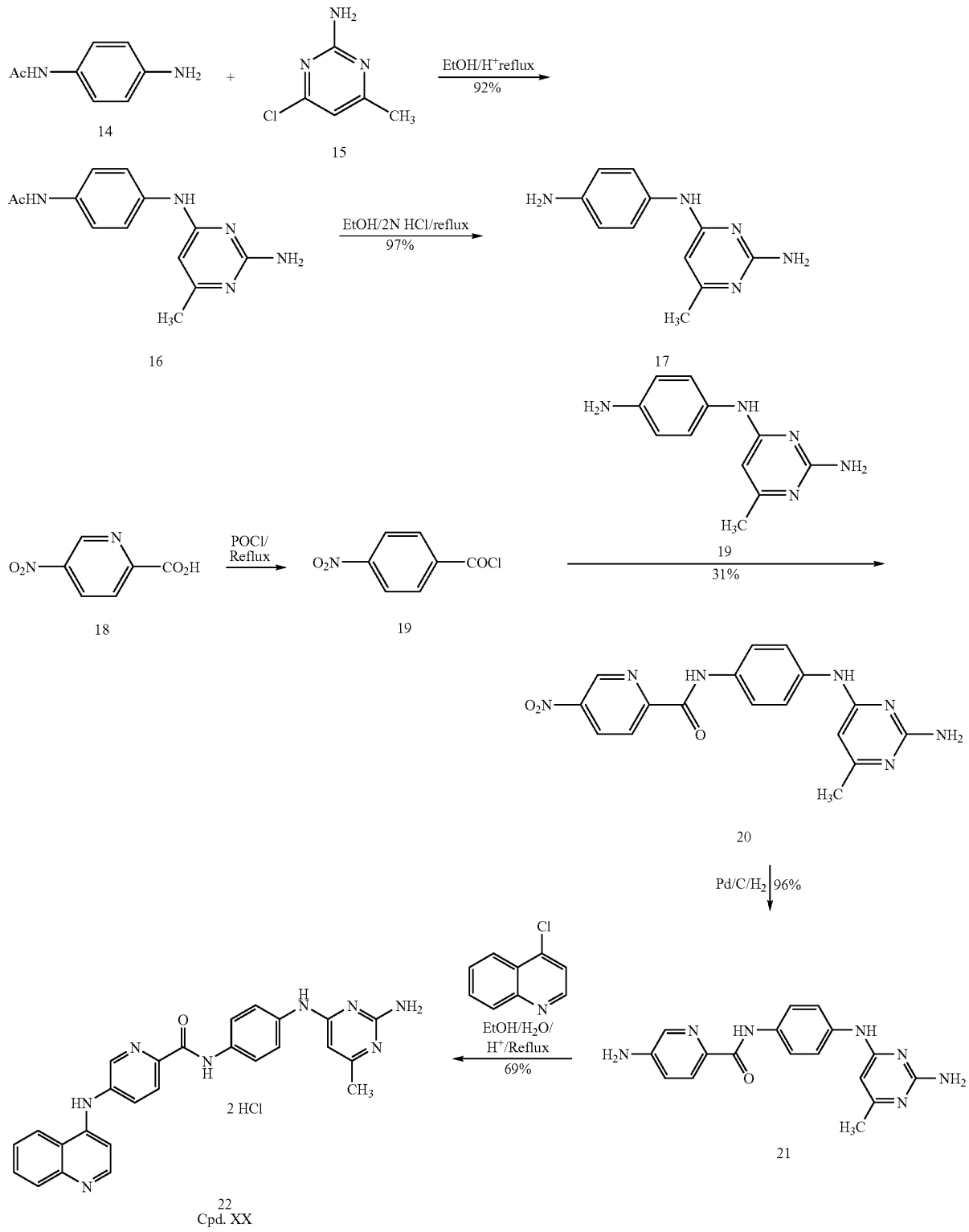

product was filtered washed with more ethanol and dried to give essentially pure 16 (6.38 g, 92%); mp (EtOH) 203-207° C.; $^1$H NMR [(CD$_3$)$_2$SO] δ 12.60 (br, 1 H, N$^+$H), 10.50 (br 1 H, NH), 10.02 (s, 1 H, NH), 7.60-7.58 (br m, 6 H, NH$_2$ & ArH), 6.13 (s, 1 H, H-5"), 2.26 (s, 3 H, CH$_3$), 2.04 (s, 3 H, CH$_3$); HRMS (FAB$^+$), calc. for C$_{13}$H$_{16}$N$_5$O (M$^{+1}$) m/z 258.1355, found 258.1346.

N$^4$-(4-aminophenyl)-6-methyl-2,4-pyrimidinediamine hydrochloride (17): To a suspension of 16 (6.0 g, 20 mmol) was added 2N HCl (40 mL) and the mixture was refluxed for 20 h. The solvents were evaporated to dryness, residue boiled in MeOH and diluted with EtOAc. The resulting precipitate was filtered and washed with EtOAc and dried to give essentially pure 17 (5.0 g, 97%); mp (MeOH/EtOAc) 275-280° C.; $^1$H NMR [(CD$_3$)$_2$SO] δ 12.50 (br, 1 H, N$^+$H), 10.75 (br s, 1 H, NH), 9.75 (br s, 2 H, NH$_2$), 7.85 (br s, 4 H, NH$_2$ & ArH)), 7.34 (d, J=8.6 Hz, 2 H, ArH), 6.24 (br s, 1 H, ArH), 2.79 (s, 3 H, CH$_3$), HRMS (FAB$^+$) calc. for C$_{11}$H$_{14}$N$_5$ (M$^{+1}$) m/z 216.1249, found 216.1247.

N-{4-[(2-amino-6-methyl-4-pyrimidinyl)amino]phenyl}-5-nitro-2-pyridinecarboxamide 20. 5-Nitropyridine-2-carboxylic acid 18 (1.06 g, 6.31 mmol) was refluxed in POCl$_3$ (10 mL) for 1 h. (clear solution obtained), cooled to 20° C. and excess POCl$_3$ was removed under vacuum. The resulting residue was dissolved in 1,4-dioxane ((20 mL) and added slowly to a suspension of 17 (1.44 g, 5.72 mmol) and N,N-diethylaniline (2.0 mL, 12.62 mmol) in 1,4-dioane (20 mL). The reaction mixture was stirred at 20° C. for 3 days. The resulting white precipitate was filtered and washed with more 1,4-dioxane. The solid was stirred in aqueous NH$_3$ (20 mL) and the resulting red precipitate was filtered, washed with water and recrystallized from MeOH to give 20 (708 mg, 31%); mp (MeOH)>290° C.; $^1$H NMR ([(CD$_3$)$_2$SO] δ 10.74 (1 H, NH), 9.43 (dd, J=2.6, 0.5 Hz, 1 H, H-6), 8.96 (s, 1 H, NH), 8.81 (dd, J=8.6, 2.6 Hz, 1 H, H-4), 8.38 (dd, J=8.6, 0.6 Hz, 1 H, H-3), 7.81 (d, J=9.0 Hz, 2 H, H-2' H-6'), 7.70 (d, J=9.1 Hz, 2 H, H-3',5'), 6.09 (s, 2 H, NH$_2$), 5.87 (s, 1 H, H-5"), 2.09 (s, 3 H, CH$_3$); HRMS (FAB$^+$) calc. for C$_{17}$H$_{16}$N$_7$O$_3$ (M$^{+1}$) m/z 366.1315, found 366.1314; Anal. calc. for C$_{17}$H$_{15}$N$_7$O$_3$.0.25 MeOH: C, 55.5; H, 4.4: N, 26.3; found, C, 55.7; H, 4.5; N, 26.2%.

5-amino-N-{4-[(2-amino-6-methyl-4-pyrimidinyl)amino]phenyl}-2-pyridinecarboxamide (21): To a suspension of 20 (523 mg, 1.43 mmol) was suspended in 1:1 MeOH/THF (100 ml) was added 10% Pd/C (100 mg) and hydrogenated at 55 Hg mm. for 5 h. The reaction mixture was filtered and evaporated to dryness and recrystallized from DCM/Pet.ether to give 21 (649 mg, 96%); mp (DCM/Pet.ether)>290° C.; $^1$H NMR [(CD$_3$)$_2$SO] δ 10.05 (s, 1 H, NH), 8.85 (s, 1 H, NH), 8.25 (d, J=2.5 Hz, 1 H, H-6), 7.82 (d, J=8.6 Hz, 1 H, H-3), 7.73 (d, J=9.0 Hz, 2 H, H-2',6'), 7.60 (d, J=9.0 Hz, 2 H, H-3',5'), 7.03 (dd, J=8.5, 2.7 Hz, 1 H, H-4), 6.04 (brs, 2 H, NH$_2$), 6.03 (brs, 2 H, NH$_2$), 5.85 (s, 1 H, H-5"), 2.08 (s, 3 H, CH$_3$); Anal. calc. for C$_{17}$H$_{17}$N$_7$).0.25H$_2$O C, 60.1; H, 5.2; N, 28.9; found, C, 60.0; H, 5.2; N, 28.7%.

N-{4-[(2-amino-6-methyl-4-pyrimidinyl)amino]phenyl}-5-(4-quinolinylamino)-2-pyridinecarboxamide dihydrochloride (22) (Cpd. XX). To a solution of 21 (270 mg, 0.81 mmol) in EtOH (30 mL) and H$_2$O (15 mL) was added few drops of c.HCl, followed by 4-chloroquinoline (264 mg, 1.62 mmol, 2 eq) and stirred at 20° C. until dissolved. The reaction mixture was refluxed for 2 h, then more 4-chloroquinoline (264 mg, 1.62 mmol) was added and refluxed for 20 h. The reaction mixture was diluted with EtOAc, boiled and cooled to 20° C. The resulting precipitate was filtered to give a pale yellow solid (95% clean by HPLC). This solid was stirred in aqueous NH$_3$. The resulting precipitate was filtered washed with water, dried and recrystallized from MeOH to give freebase of the product (300 mg). (This was 98% clean by HPLC.) Then the free base was converted to HCl salt by adding 1.25M HCl in MeOH (2.5 mL), stirred 30 min, and evaporated to dryness. The residue was recrystallized from MeOH/EtOAc to give 22 (Cpd. XX) (297 mg 69%); HPLC 99.2%; mp (MeOH/EtOAc)> 290° C.; $^1$H NMR [(CD$_3$)$_2$SO] δ 15.00 (br, 1 H, N$^+$H), 12.50 (br, 1 H, N$^+$H), 11.23 (brs, 1 H, NH), 10.74 (s, 1 H, NH), 10.65 (brs, 1 H, NH), 8.92 (d, J=2.3 Hz, 1 H, ArH), 8.89 (d, J=8.5 Hz, 1 H, ArH), 8.66 (d, J=6.8 Hz, 1 H, ArH), 8.31 (d, J=8.5 Hz, 1 H, ArH), 8.22 (dd, J=8.4, 2.5 Hz, 1 H, ArH), 8.15 (d, J=7.9 Hz, 1 H, ArH), 8.08 (t, J=7.9 Hz, 1 H, ArH), 7.96 (d, J=8.9 Hz, 2 H, ArH), 7.87 (t, J=7.6 Hz, 1 H, ArH), 7.77 (br, 3 H, ArH & NH$_2$), 7.13 (d, J=6.8 Hz, 1 H, ArH), 6.18 (s, 1 H, ArH), 2.28 (s, 3 H, CH$_3$) one of the aromatic CH signals was not observed; Anal. calc. for C$_{26}$H$_{24}$Cl$_2$N$_8$O 0.5 H$_2$O: C, 57.4; H, 4.6; N, 20.6; Cl, 13.0; found, C, 57.3; H, 4.8; N, 20.7; Cl, 12.7%.

Example YY

Preparation of N-{6-[(2-amino-6-methyl-4-pyrimidinyl)amino]-3-pyridinyl}-4-(4-quinolinylamino)benzamide dihydrochloride (Cpd. YY)

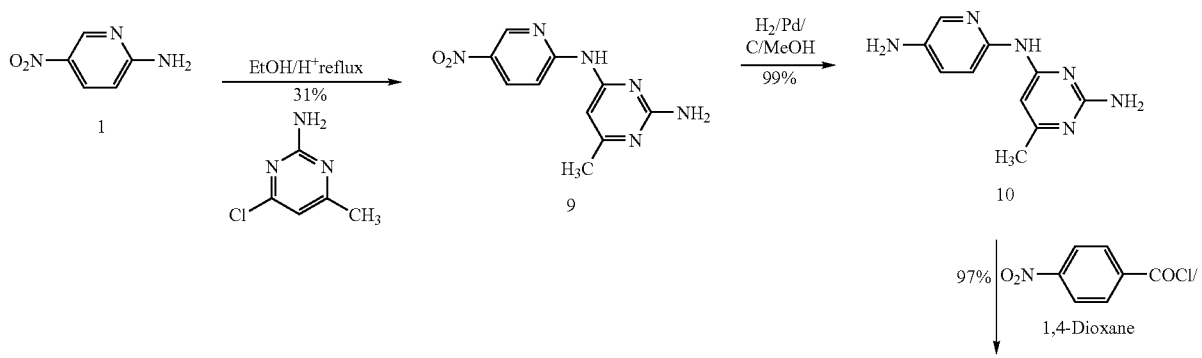

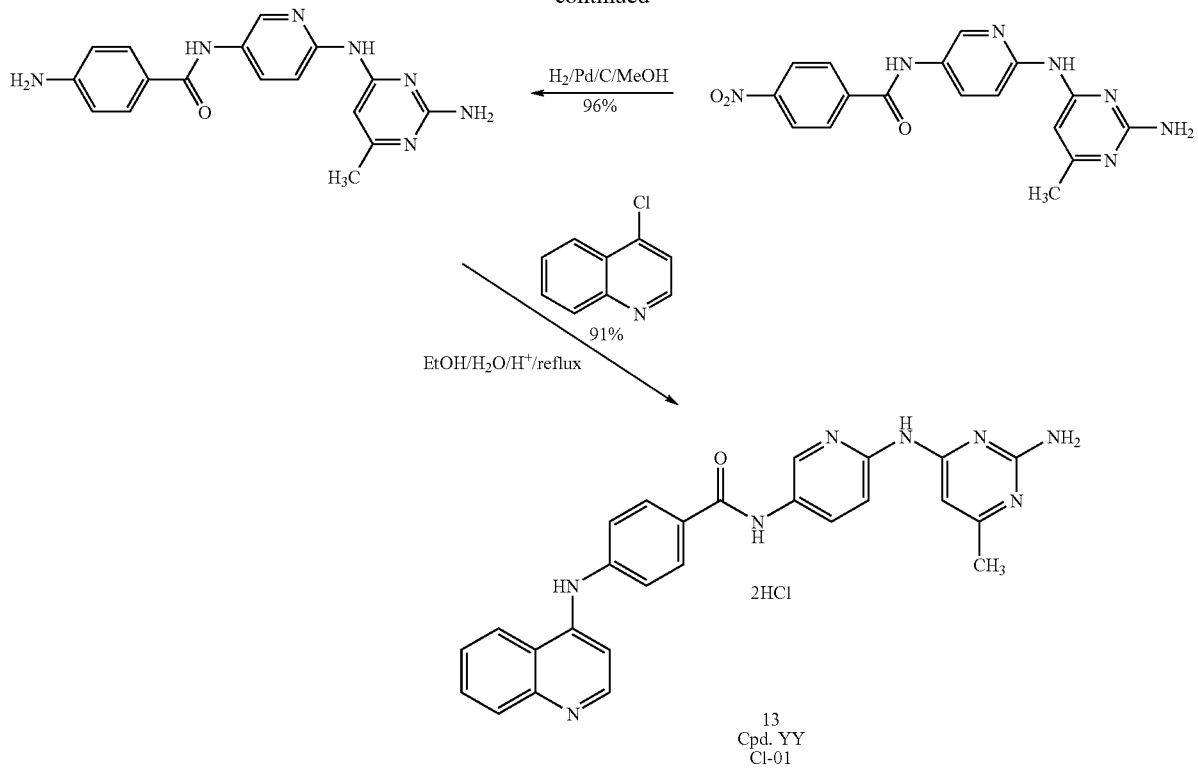

6-Methyl-N$^4$-(5-nitro-2-pyridinyl)-2,4-pyrimidinediamine (9). To a solution of 2-Amino-5-nitropyridine 1 (1.23 g, 8.84 mmol) and 2-amino-4-chloro-6-methylpyrimidine (1.40, g, 9.72 mmol) in ethanol (30 mL) was added few drops of c.HCl. The reaction mixture was refluxed for 2 days, cooled to 20° C. and ethanol was evaporated to dryness. The resulting brown glue was stirred in MeOH to obtain a filterable precipitate. This was filtered and washed with more MeOH give the product as the hydrochloride salt. The $^1$H NMR showed this was not completely clean. This material was converted to free base by stirring in aqueous NH$_3$, filtered and recrystallized to give 9 (682 mg, 31%); mp (MeO)>300° C.; $^1$H NMR [(CD$_3$)$_2$SO] δ 10.47 (s, 1 H, NH), 9.10 (dd, J=2.8, 0.4 Hz, 1 H, H-6'), 8.39 (dd, J=9.4, 2.8 Hz, 1 H, H-4'), 8.28 (dd, J=9.3, 0.3 Hz, 1 H, H-3'), 6.63 (s, 1 H, H-5), 6.39 (s, 2 H, NH$_2$), 2.18 (s, 3 H, CH$_3$); HRMS (EI$^+$) calc. for C$_{10}$H$_{10}$N$_6$O$_2$ (M$^+$) m/z 246.0865, found 246.0866; Anal. calc. for C$_{10}$H$_{10}$N$_6$O$_2$: C, 48.8; H, 4.1; N, 34.1; found C, 48.7; H, 4.2; N, 34.1%.

N$^4$-(5-amino-2-pyridinyl)-6-methyl-2,4-pyrimidinediamine (10). Compound 9 (634 mg, 246 mmol) was hydrogenated in MeOH (50 mL) with 10% Pd/C (100 mg) at 45 Hg mm. for 20 h. The reaction mixture was filtered and evaporated to dryness to give 10 (550 mg, 99%); mp (MeOH) 230-233° C.; $^1$H NMR [(CD$_3$)$_2$SO] δ 8.96 (s, 1 H, NH), 7.70 (d, J=8.7 Hz, 1 H, H-3'), 7.65 (d, J=2.5 Hz, 1 H, H-6'), 6.95 (dd, J=8.8, 2.9 Hz, H-4'), 6.30 (s, 1 H, H-5), 5.94 (s, 2 H, NH$_2$), 4.84 (s, 2 H, NH$_2$), 2.07 (s, 3H, CH$_3$); HRMS (FAB$^+$) calc. for C$_{10}$H$_{13}$N$_6$ (M$^{+1}$) m/z 217.1202, found 217.1202; Anal. calc. for C$_{10}$H$_{12}$N$_6$; C, 55.5; H, 5.6; N, 38.9; found C, 55.3; H, 5.7; N, 38.6%.

N-{6-[(2-amino-6-methyl-4-pyrimidinyl)amino]-3-pyridinyl}-4-nitrobenzamide (11). To a suspension of 10 (500 mg, 2.31 mmol) and N,N-diethylaniline (1 ml, 1.5 eq) in 1,4-dioxane (20 ml) at 0° C. was added dropwise a solution of p-nitrobenzoylchloride (429 mg, 12.31 mmol). The reaction mixture was stirred at 20° C. for 2 h. TLC and mass spectrum showed still presence of 10. Therefore more p-nitrobenzoylchloride (43 mg, 0.1 eq) was added and stirred for 20 h. The resulting precipitate was filtered and washed with more 1,4-dioxane. The collected solid was stirred in aqueous NH$_3$, filtered washed with water and dried to give essentially pure 11 (821 mg, 97%); mp (MeOH)>300° C.; $^1$H NMR [(CD$_3$)$_2$SO] δ 10.58 (s, 1 H, NH), 9.56 (s, 1 H, NH), 8.65 (d, J=2.5 Hz, 1 H, H-2'), 8.38 (d, J=8.9 Hz, 2 H, H-3,5), 8.20 (d, J=9.2 Hz, 2 H, H-2,6), 8.17 (d, J=9.1 Hz, 1 H, H-5'), 8.02 (dd, J=9.0, 2.6 Hz, 1H, H-4'), 6.45 (s, 1 H, H-5"), 6.15 (s, 2 H, NH$_2$), 2.12 (s, 3 H, CH$_3$); HRMS (FAB$^+$) (M$^{+1}$) m/z calc. for C$_{17}$H$_{16}$N$_7$O$_3$ (M$^{+1}$) m/z, 366.1315, found 366.1314; Anal. calc. for C$_{17}$H$_{15}$N$_7$O$_3$: C, 55.9; H, 4.1; N, 26.8, found C, 55.6; H, 4.2; N, 26.8%.

4-amino-N-{6-[(2-amino-6-methyl-4-pyrimidinyl)amino]-3-pyridinyl}benzamide 12. To a suspension of 11 (790 mg, 2.16 mmol) in 1:1 MeOH/THF (100 ml) was added 10% Pd/C (100 mg) and hydrogenated at 45 Hg mm. for 20 h. The reaction mixture was filtered and evaporated to dryness and recrystallized from DCM/Pert.ether to give 12 (695 mg, 96%); mp (DCM/pet.ether)>300° C.; $^1$H NMR [(CD$_3$)$_2$SO] δ 9.78 (s, 1 H, NH), 9.45 (s, 1 H, NH), 8.63 (dd, J=2.4, 0.3 Hz, 1 H, H-2'), 8.09 (d, J=9.0 Hz, 1 H, H-5'), 7.98 (dd, J=9.0, 2.6 Hz, 1 H, H-4'), 7.72 (d, J=8.7 Hz, 2 H, H-2,6), 6.61 (d, J=8.7 Hz, 2 H, H-3,5), 6.43 (s, 1 H, H-5"), 6.13 (s, 2 H, NH$_2$), 5.73 (s, 2 H, NH$_2$), 2.12 (s, 3 H, CH$_3$); HRMS (FAB$^+$) calc. for C$_{17}$H$_{18}$N$_7$O (M$^{+1}$) m/z 336.1573, found 336.1578; Anal. calc. for C$_{17}$H$_{17}$N$_7$O-0.25H$_2$O: C, 60.1; H, 5.2; N, 28.9; C, 60.2; N, 5.3; N, 29.0%.

N-{6-[(2-amino-6-methyl-4-pyrimidinyl)amino]-3-pyridinyl}-4-(4-quinolinylamino)benzamide dihydrochloride

(13) (Cpd. YY). To a solution of 12 (250 mg, 0.75 mmol) in EtOH (40 mL) and H$_2$O (20 mL) was added few drops of c.HCl, followed by 4-chloroquinoline (159 mg, 0.98 mmol, 1.3 eq) and stirred at 20° C. until dissolved. The reaction mixture was refluxed for 4 h, then more 4-chloroquinoline (100 mg) was added and refluxed for 20 h. The reaction mixture was diluted with EtOAc, boiled and cooled to 20° C. The resulting precipitate was filtered to give a pale yellow solid. (75% clean by HPLC) This solid was stirred in aqueous NH$_3$. The resulting precipitate was filtered washed with water and dried to give freebase of the product. This was 96% clean by HPLC. Then the free base was converted to HCl salt by adding 1.25M HCl in MeOH (2.5 mL), stirred 30 min, and evaporated to dryness. The residue was stirred in MeOH (10 mL), filtered and dried to give 13 (Cpd. YY) (365 mg 91%); HPLC 98.9%; mp (MeOH)>290° C.; $^1$H NMR [(CD$_3$)$_2$SO] δ 14.70 (br 1 H, N$^+$H), 12.98 (br, 1 H, N$^+$H), 11.12 (s, 1 H, NH), 11.01 (s, 1 H, NH), 10.68 (s, 1 H, NH), 8.88 (d, J=3.0 Hz, 1 H, ArH), 8.84 (d, J=8.6 Hz, 1 H, ArH), 8.62 (d, J=6.9 Hz, 1 H, ArH), 8.26 (dd, J=9.0, 2.6 Hz, 1 H, ArH), 8.22 (d, J=8.6 Hz, 2 H, ArH), 8.15-8.05 (m, 2 H, ArH), 7.86 (ddd, J=7.6, 6.8, 1.5 Hz, 1 H, ArH), 7.70 (d, J=8.6 Hz, 2 H, ArH), 7.01 (d, J=6.9 Hz, 1 H, ArH), 7.02 (v.br, 1 H, ArH), 2.32 (s, 3 H, CH$_3$), the signals for NH$_2$ and one of aromatics were not observed; HRMS (FAB$^+$) calc. for C$_{26}$H$_{23}$N$_8$O (M$^{+1}$) m/z 463.1995, found 463.1996; Anal. calc for C$_{26}$H$_{24}$N$_8$Cl$_2$O.HCl.0.25H$_2$O:, C, 54.2; H, 4.5; N, 19.4; Cl, 18.5; found C, 54.2; H, 4.5; N, 19.3; Cl, 17.7%.

Example ZZ

Preparation of N-{5-[(2-amino-6-methyl-4-pyrimidinyl)amino]-2-pyridinyl}-4-(4-quinolinylamino)benzamide dihydrochloride (Cpd. ZZ)

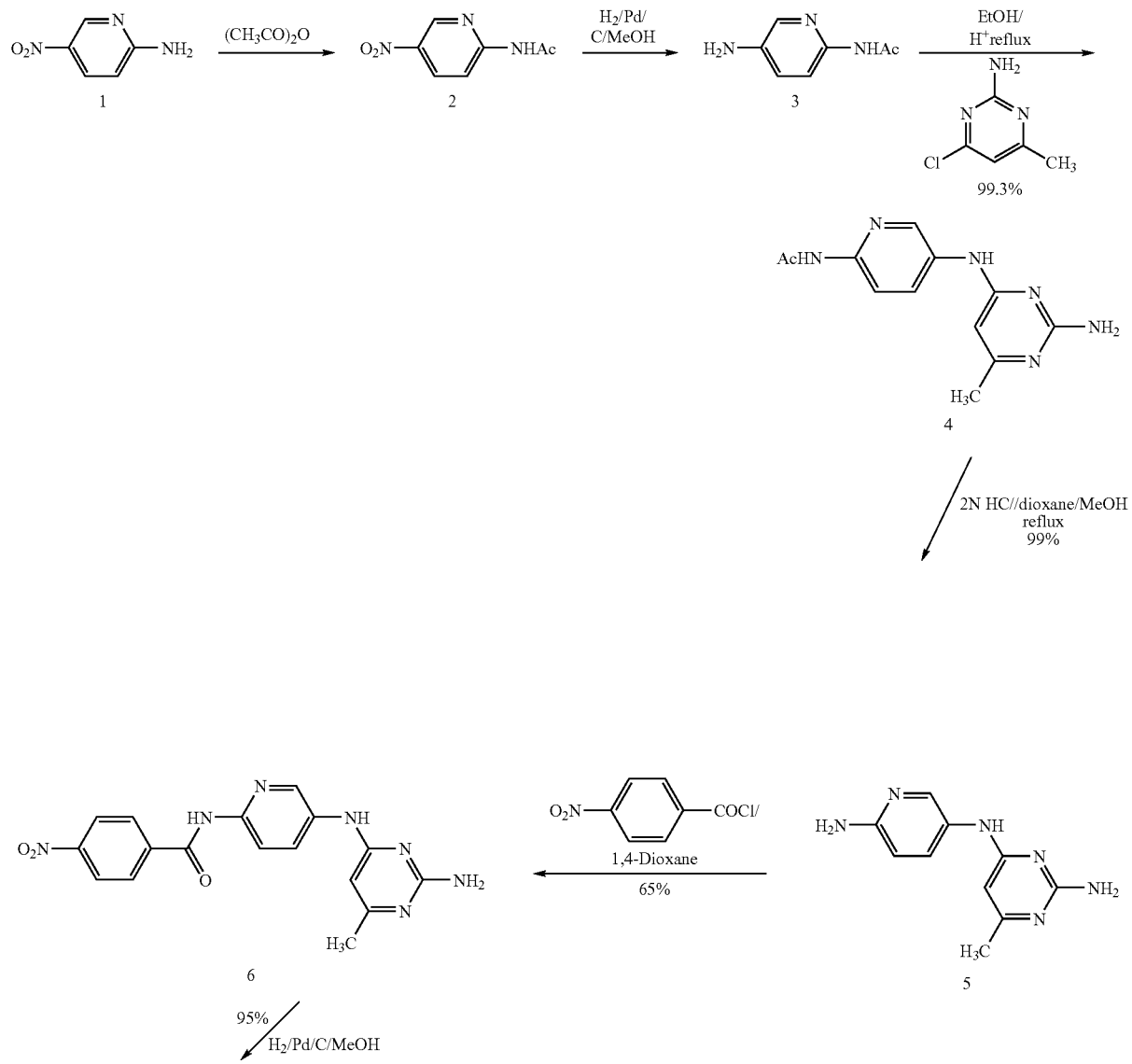

-continued

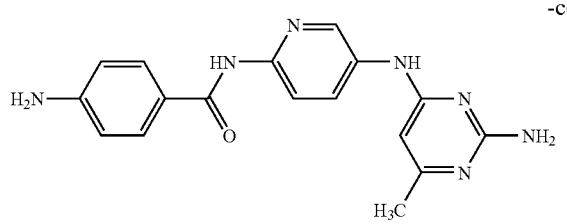

7

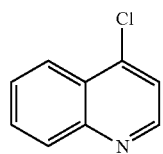

58%

EtOH/H₂O/H⁺/reflux

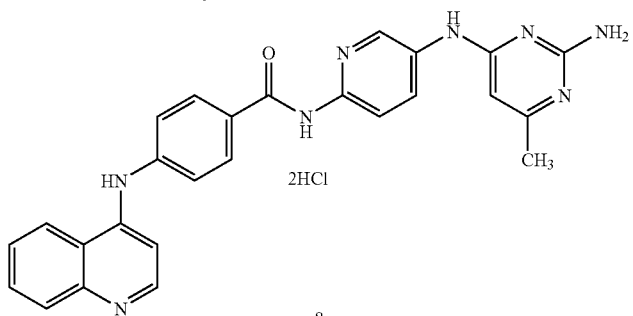

8
Cpd. ZZ
Cl-01

N-[5-[(2-amino-6-methyl-4-pyrimidinyl)amino]-2-pyridinyl]-acetamide (4). To a solution of N-(5-amino-2-pyridinyl)acetamide 2(1.04 g, 6.88 mmol), and 2-amino-4-chloro-6-methylpyrimidine (1.09 g, 7.57 mmol) in EtOH (30 mL) was added 2 drops c.HCl. The reaction mixture was refluxed for 2 h, cooled to 20° C. The resulting precipitate was filtered washed with more ethanol and dried to give (1.85 g, ) further material (165 mg) was isolated from mother liquor concentration. Total yield of 4 99.3%. mp (MeOH/EtOAc)>300° C. $^1$H NMR [(CD₃)₂SO] δ 12.77 (br, 1 H, NH), 10.72 (br, 1 H, NH), 10.44 (s, 1 H, NH), 8.63 (br s, 1 H, ArH), 8.13-8.06 (m, 2 H, ArH), 7.79 (v. br, 2 H, NH₂), 6.18 (s, 1 H, ArH), 2.30 (s, 3 H, COCH₃), 2.09 (s, 3 H, CH₃); HRMS (FAB⁺) calc. for C₁₂H₁₅N₆O (M⁺¹) m/z 259.1307, found 259.1304; Anal. Calc. for Cl₂H₁₅ClN₆O.H₂O: C, 46.1; H, 5.5; N, 26.9; Cl, 11.3; found C, 45.9; H, 5.5; N, 26.4; Cl, 11.45%.

N⁴-(6-amino-3-pyridinyl)-6-methyl-2,4-pyrimidinediamine (5). A suspension of 4 (1.53 g, 5.19 mmol), in 1,4-dioxane/MeOH (1:1, 100 mL) and 2 N HCl [10 mL, H₂O mL+c.HCl 2 mL)] was refluxed 24 h. The solvents were evaporated to dryness and the residue was basified with aq NH₃. The resulting solution was extracted with EtOAc (110× 50 mL), dried (Na₂SO₄) and evaporation of the solvent gave 5 (1.11 g, 99%). A small sample was recrystallized from DCM/Pet.ether; mp (DCM/Pet.ether) 183-186° C.; $^1$H NMR [(CD₃)₂SO] δ 8.41 (s, 1 H, NH), 8.01 (d, J=2.5 Hz, 1 H, H-2'), 7.56 (dd, J=8.7, '), 6.42 (d, 2.6 Hz, 1 H, H-4 J=8.8 Hz, 1 H, H-5'), 5.90 (s, 2 H, NH₂), 5.67 (s, 1 H, H-5), 5.59 (s, 2 H, NH₂H, CH), 2.03 (s, 33) HRMS (EI⁺) calc. for C₁₀H₁₂N₆ (M⁺) m/z 216.1123, found 216.1124; Anal. Calc. for C₁₀H₁₂N₆.0.25H₂O: C, 54.4; H, 5.7; N, 38.1; found, C, 54.4; H, 5.7; N, 37.9%.

N-{5-[(2-amino-6-methyl-4-pyrimidinyl)amino]-2-pyridinyl}-4-nitrobenzamide) (6). To a suspension of 5 (830 mg, 3.84 mmol) and N,N-diethylaniline (1.0 mL, 5.76 mmol) in 1,4-dioxane (20 mL) at 0° C. was added dropwise a solution of 4-nitrobenzoylchloride (720 mg, 3.88 mmol) in 1,4-dioxane (20 mL). After the addition was completed the reaction mixture was stirred at 20° C. for 1 h, then dioxane was removed under vacuum. The residue was stirred in H₂O (50 mL) and the resulting precipitate was filtered washed with aqueous NH₃, H₂O, and pet.ether. The residue was boiled in MeOH and the insoluble red solid was collected. This process was repeated 3 more times to give essentially pure 6 (903 mg, 65%), [if repeating the product should be filtered off from dioxane to avoid extra steps]; mp (MeOH) 294-297° C.; $^1$H NMR [(CD₃)₂SO] 10.99 (s, 1 H, NH), 9.14 (s, 1 H, NH), 8.68 (d, J=2.5 Hz, 1 H, H-6'), 8.32 (d, J=8.9 Hz, 2 H, H-3&5), 8.27 (dd, J=9.0, 2.7 Hz, 1 H, H-4'), 8.23 (d, J=8.9 Hz, 2 H, H-2&H-6), 8.08 (d, J=9.0 Hz, 1 H, H-3'), 6.18 (s, 2 H, NH₂), 5.88 (s, 1 H, H-5"), 2.11 (s, 3 H, CH₃); HRMS (FAB⁺), calc. for C₁₇H₁₆N₇O₃ (M⁺¹) m/z 366.1315, found 366.1312; Anal. calc. for C₁₇H₁₅N₇O₃.CH₃OH: C, 54.4; H, 4.8; N, 24.7; found C, 54.5; H, 4.8; N, 24.7%.

4-amino-N-{5-[(2-amino-6-methyl-4-pyrimidinyl)amino]-2-pyridinyl}benzamide (7). To a suspension of 6 (802 mg, 2.19 mmol) in 1:1 MeOH/THF (100 ml) was added 10% Pd/C (100 mg) and hydrogenated at 45 Hg mm. for 20 h. The reaction mixture was filtered and evaporated to dryness and recrystallized from DCM/Pert.ether to give 7 (697 mg, 95%); mp (DCM/pet.ether) 157-161° C.; $^1$H NMR [(CD₃)₂SO] δ 9.98 (s, 1 H, NH), 9.03 (s, 1 H, NH), 8.59 (d, J=2.4 Hz, 1 H, H-6'), 8.16 (dd, J=9.0, 2.7 Hz, 1 H, H-4'), 8.04 (d, J=8.9 Hz, 1 H, H-3'), 7.77 (d, J=8.7 Hz, 2 H, H-2,6), 6.57 (d, J=8.7 Hz, 2 H, H-3,5), 6.13 (s, 2 H, NH₂), 5.13 (s, 1 H, H-5"), 5.74 (s, 2 H, NH₂), 2.10 (s, 3 H, CH₃); HRMS (FAB⁺) calc. for C₁₇H₁₈N₇O (M⁺¹) m/z 336.1573, found 366.1574; Anal. calc. for C₁₇H₁₇N₇O.2H₂O: C, 55.0; H, 5,7; N, 26.4; found C, 55.2; H, 5.7; N, 26.3%.

N-{5-[(2-amino-6-methyl-4-pyrimidinyl)amino]-2-pyridinyl}-4-(4-quinolinylamino)benzamide dihydrochloride (8) (Cpd. ZZ). To a solution of 7 (241 mg, 0.72 mmol) in EtOH (20 mL) and $H_2O$ (10 mL) was added 4-chloroquinoline (153 mg, 0.94 mmol, 1.3 eq) and stirred at 20° C. until dissolved. Then c.HCl few drops were added and refluxed for 24 h. The reaction mixture was diluted with EtOAc, boiled and cooled to 20° C. The resulting precipitate was filtered to give a pale yellow solid, this was recrystallized from MeOH/EtOAc to give 350 mg of the product this was 84% clean by HPLC. This solid was stirred in aqueous $NH_3$ to convert to free base of the product, resulting precipitate was filtered washed with water and dried to give 204 mg. This was 98% clean by HPLC. The free base was converted to HCl salt by adding 1.25M HCl in MeOH (1 mL). stirred 30 min, filtered and dried to give 8 (Cpd. ZZ) (224 mg 58%); HPLC 100%; mp (MeOH)>295° C.; $^1$H NMR [$(CD_3)_2SO$] δ 14.75 (br, 1 H, $N^+H$), 12.89 (bs, 1 H, $N^+H$), 11.14 (s, 1 H, NH), 10.99 (bs, 1 H, NH), 10.94 (s, 1 H, NH), 8.87 (d, J=8.5 Hz, 1 H, ArH), 8.77 (br 1 H, ArH), 8.61 (d, J=6.9 Hz, 1 H, ArH), 8.31 (br, 1 H, ArH), 8.23 (d, J=8.6 Hz, 2 H, ArH), 8.13 (dd, J=8.0, 0.9 Hz, 1 H, ArH), 8.07 (td, J=7.7, 0.9 Hz, 1 H, ArH), 7.85 (td, J=7.7, 1.2 Hz, 1 H, ArH), 7.67 (d, J=8.6 Hz, 2 H, ArH), 7.02 (d, J=6.9 Hz, 1 H, ArH), 6.26 (s, 1 H, ArH), 2.31 (s, 3 H, $CH_3$); HRMS ($FAB^+$), calc. for $C_{26}H_{23}N_8O$ ($M^{+1}$) m/z 4631995, found 463.1994; Anal. calc. for $C_{26}H_{24}Cl_2N_{80}.HCl.H_2O$: C, %2.9; H, 4.6; N, 19.0; Cl, 18.0; Found C. 53.1; H, 4.6; N, 19.2; Cl, 17.9%.

Example AAA

Preparation of N-[4-(pyridin-4-ylthio)phenyl]-4-(quinolin-4-ylamino)benzamide hydrochloride (Cpd. AAA)

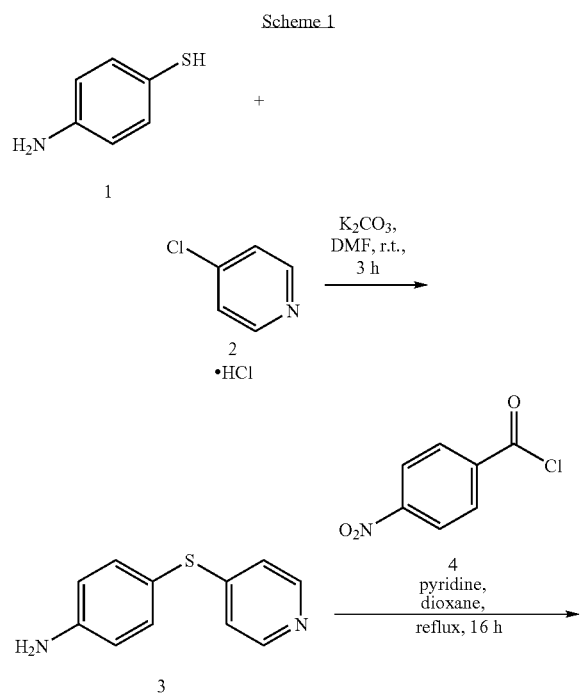

4-(Pyridin-4-ylthio)aniline (3). To a solution of 4-aminobenzenethiol 1 (5.10 g, 40.74 mmol) in dry DMF (90 mL) were sequentially added 4-chloropyridine hydrochloride 2 (6.41 g, 42.68 mmol) and anhydrous $K_2CO_3$ (14.70 g, 106.34 mmol), and the resulting suspension was stirred vigorously at room temperature for ~3 h. After this time, the reaction mixture was diluted with EtOAc (100 mL) and $H_2O$ (100 mL), and the organic layer separated. The aqueous layer was extracted further with EtOAc (100 mL×2), and the organic extracts were then combined, washed with brine, and finally dried over anhydrous $MgSO_4$. Solvent was removed under reduced pressure, and washing of the resulting residue with 1:1 $Et_2O$:hexanes (300 mL) afforded amine 3 as fine grey-white crystalline solid (4.64 g, 56%), mp (MeOH:EtOAc) 171-173° C.; $^1$H NMR [$(CD_3)_2SO$]: δ 5.64 (s, 2H, $NH_2$), 6.67 (ddd, J=9.40, 4.78, 2.81 Hz, 2H, ArH), 6.90 (dd, J=4.61, 1.59 Hz, 2H, ArH), 7.20 (ddd, J=9.40, 4.78, 2.81 Hz, 2H, ArH), 8.29 (dd, J=4.61, 1.59 Hz, 2H, ArH); HRMS: Calc. for $C_{11}H_{11}N_2S$ ($M^+$) 203.0643, found 203.0641.

4-Nitro-N-[4-(pyridin-4-ylthio)phenyl]benzamide (5). To a solution of amine 3 (2.03 g, 10.06 mmol) in dry dioxane (70 mL) were sequentially added dry pyridine (4.05 mL, 50.28 mmol) and 4-nitrobenzoyl chloride 4 (3.19 g, 17.18 mmol, as solution in 30 mL of dry dioxane), and the resulting mixture was stirred at ~50° C. for 14 h. After this time, the resultant yellow solid was isolated by filtration, and washed sequentially with dioxane, EtOAc, and hexanes. The resulting solid was re-dissolved in MeOH (~5 L), and this solution was filtered through Celite to remove undissolved impurities, and then concentrated to a smaller volume under reduced pressure. The resulting solid was collected by filtration, then re-suspended in and washed sequentially with EtOH, MeOH, and EtOAc, and finally collected again by filtration. The resulting material was washed with hexanes and dried under high-vacuum to afford amide 5 as an amorphous yellow powdery solid, mp 295-298° C.; $^1$H NMR [(CD$_3$)$_2$SO]: δ 7.38 (d, J=6.15 Hz, 2H, ArH), 7.55 (ddd, J=9.42, 4.45, 2.59 Hz, 2H, ArH), 8.07 (m, 2H, ArH), 8.24 (ddd, J=9.21, 4.32, 2.31 Hz, 2H, ArH), 8.39 (dd, J=6.92, 1.97 Hz, 2H, ArH), 8.53 (d, J=6.6 Hz, 2H, ArH), 10.97 (s, 1H, —C(O)NH—); HRMS: Calc. for C$_{18}$H$_{14}$N$_3$O$_3$S (M$^+$) 352.0756, found 352.0755.

4-Amino-N-[(4-(pyridin-4-ylthio)phenyl]benzamide (6). To a refluxing solution of nitro compound 5 (0.54 g, 1.53 mmol) in 2:1 EtOH:H$_2$O (100 mL) were sequentially added Fe dust (0.54 g, 9.72 mmol) and c.HCl (2 mL), and the resulting suspension was refluxed for 1 h. After this time, the hot reaction mixture was filtered through a pad of Celite, and solvent was removed under reduced pressure. The residue was redissolved in MeOH, and the resulting solution stirred with Celite overnight. The resulting suspension was filtered through a pad of Celite, and the filtrate acidified with 1.25 M methanolic HCl. The solution was concentrated to a smaller volume under reduced pressure, and the resulting solid removed by filtration through a pad of Celite. The filtrate was re-acidified and treated as before (twice), finally affording an amorphous ochre solid (0.38 g, 77%) which was used without further purification; $^1$H NMR [(CD$_3$)$_2$SO]: δ 5.79 (s, 2H, —NH$_2$), 6.62 (d, J=8.58 Hz, 2H, ArH), 6.98 (d, J=5.96 Hz, 2H, ArH), 7.53 (d, J=8.61 Hz, 2H, ArH), 7.74 (d, J=8.58 Hz, 2H, ArH), 7.96 (d, J=8.61 Hz, 2H, ArH), 8.34 (d, J=5.35 Hz, 2H, ArH), 10.02 (s, 1H, —C(O)NH—); LCMS (APCI$^+$): 322 (100%).

N-[4-(pyridin-4-ylthio)phenyl]-4-(quinolin-4-ylamino) benzamide hydrochloride (Cpd. AAA). To a solution of amine 5 (0.31 g, 0.97 mmol) in 20% aq. EtOH (100 mL) were sequentially added 4-chloroquinoline 7 (0.33 g, 2.02 mmol) and c.HCl (0.20 mL, 8.71 mmol), and the resulting suspension refluxed for 15 h. After this time, solvent was removed under reduced pressure, and the residue dried via two MeOH azeotrope cycles. The resulting solid was purified by column chromatography (twice) on silica gel, eluting with 5%→10%→20% MeOH:CH$_2$Cl$_2$, to afford a solid residue which was re-precipitated from MeOH:methanolic HCl: EtOAc to give Cpd. AAA as an amorphous yellow solid (0.15 g, 29%), mp (EtOAc:MeOH) 306-310° C.; $^1$HNMR [(CD$_3$)$_2$SO]: δ 7.01 (d, J=6.94 Hz, 1H, ArH), 7.45 (d, J=6.77 Hz, 2H, ArH), 7.70 (m, 4H), 7.86 (m, 1H), 8.11 (m, 4H), 8.22 (dd, J=6.82, 1.79 Hz, 2H, ArH), 8.55 (d, J=6.77 Hz, 2H, ArH), 8.62 (d, J=6.94 Hz, 1H, ArH), 8.89 (d, J=8.35 Hz, 1H, ArH), 10.78 (s, 1H, ArNHAr), 11.19 (s, 1H, —C(O)NH—), 14.72 (br s, 1H, pyridinium-N$^+$—H) [quinolinium N$^+$—H not visible]; HRMS: Calc. for C$_{27}$H$_{21}$N$_4$OS (M$^+$) 449.1436, found 449.1441; HPLC: 99.3%.

Example BBB

Preparation of N-[4-(2-aminopyridin-4-ylthio)phenyl]-4-(quinolin-4-ylamino)benzamide hydrochloride (Cpd. BBB)

Scheme 2

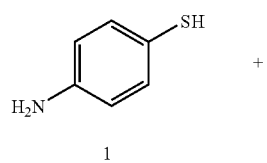

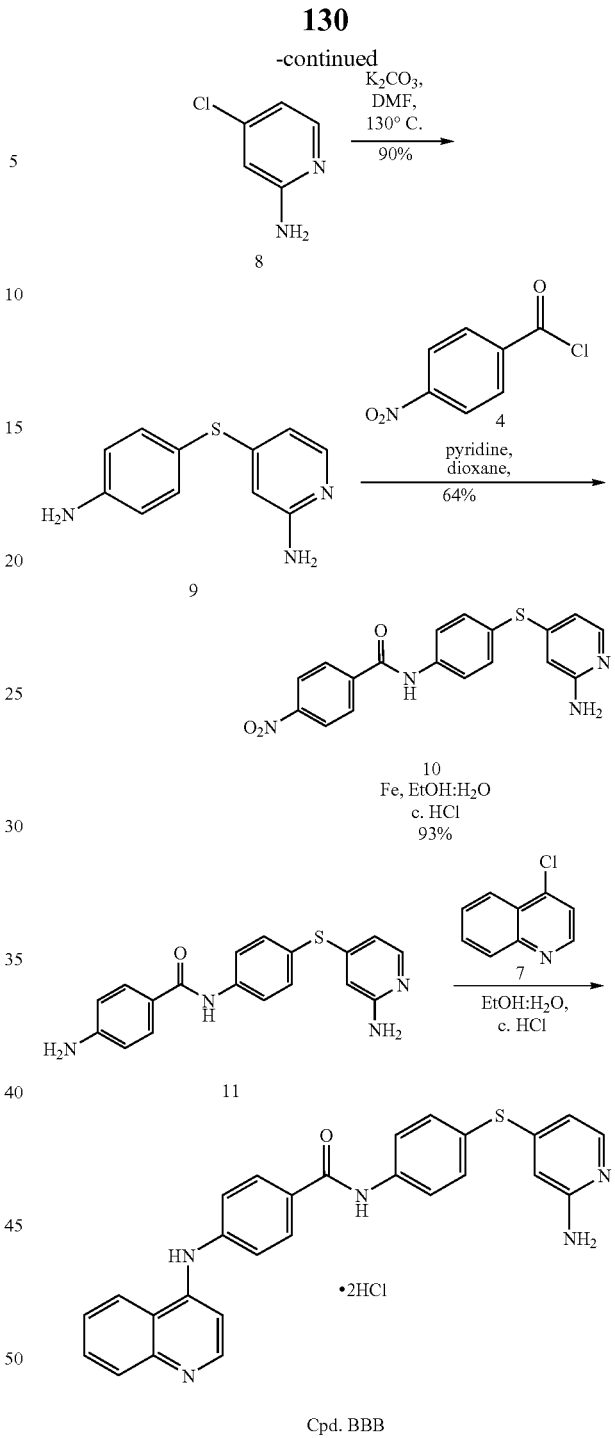

4-(4-Aminophenylthio)pyridin-2-amine (9). To a solution of 4-aminobenzene thiol 1 (9.49 g, 75.77 mmol) in dry DMF (54 mL) were sequentially added 4-chloro-2-aminopyridine 8 (3.70 g, 28.80 mmol) and dry K$_2$CO$_3$ (10.70 g, 107.97 mmol), and the resulting yellow suspension stirred at ~120° C. (bath temperature) for ~45 min. After this time, the resultant brown-black suspension was cooled to room temperature, and then diluted with H$_2$O and EtOAc. The resulting mixture was extracted with EtOAc (×2), and the organic fractions were combined and washed with brine, and then dried over MgSO$_4$. Solvent was removed under reduced pressure, and the residue was then re-dissolved in a small amount of MeOH, and filtered though a pad of silica gel. Solvent was removed under reduced pressure to afford amine 9 (5.66 g, 90%) as an amorphous creamy-purple solid, mp: 141-143° C.; $^1$H NMR [(CD$_3$)$_2$SO]: δ 5.56 (br s, 2H, NH$_2$), 5.76 (br s, 2H, NH$_2$), 5.94 (d, J=1.22 Hz, 1H, ArH), 6.10 (dd, J=5.46, 1.68 Hz, 1H, ArH), 6.64 (ddd, J=9.37, 4.78, 2.79 Hz, 2H, ArH), 7.17 (ddd, J=9.38, 4.74, 2.79 Hz, 2H, ArH), 7.65 (d, J=5.44 Hz, 1H, ArH); HRMS: Calc. for C$_{11}$H$_2$N$_3$S (MH+) m/z 218.0753, found 218.0750.

N-[4-(2-Aminopyridin-4-ylthio)phenyl]-4-nitrobenzamide (10). To a solution of amine 9 (1.09 g, 5.01 mmol) in dry dioxane (30 mL) were sequentially added dry pyridine (2.08 mL, 25.04 mmol) and 4-nitrobenzoyl chloride 4 (1.60 g, 8.60 mmol; added as a solution in 20 mL of dry DMF), and the resulting mixture was stirred at 55-60° C. (bath temperature) for ~4 h. After this time, the resultant solid was collected by filtration, and washed sequentially with dioxane, EtOAc, and hexanes. The crude product was re-precipitated from MeOH:methanolic HCl:EtOAc to afford nitro compound 10 as an amorphous yellow solid (1.19 g, 64%), mp>300° C.; $^1$H NMR [(CD$_3$)$_2$SO]: δ 13.35 (br s, 1H, quinoline-N$^+$—H), 10.97 (s, 1H, ArC(O)NHAr), 8.39 (ddd, J=9.25, 4.40, 2.37 Hz, 2H, ArH), 8.23 (ddd, J=9.20, 4.34, 2.31 HZ, 2H, ArH), 8.06 (ddd, J=9.43, 4.53, 2.62 Hz, 2H, ArH), 7.81 (m, 3H, ArH & ArNH$_2$), 7.66 (ddd, J=9.41, 4.52, 2.61 Hz, 2H, ArH), 6.65 (dd, J=6.87, 1.91 Hz, 1H, ArH), 6.29 (d, J=1.73 Hz, 1H, ArH); HRMS: Calc. for C$_{18}$H$_{15}$N$_4$O$_3$S (MH+) m/z 367.0865, found 367.0865.

4-Amino-N-[4-(2-aminopyridin-4-ylthio)phenyl]benzamide hydrochloride (11). Nitro compound 10 (0.83 g, 2.07 mmol) was suspended in 2:1 EtOH:H$_2$O (100 mL) and the resulting suspension brought to reflux. To this mixture was sequentially added Fe dust (0.54 g, 9.59 mmol) and c.HCl (2 mL), and the resulting dark orange suspension was refluxed for 1 h. After this time, the resulting yellow suspension was filtered hot through a pad of Celite, and the solvent removed under reduced pressure. The residue was re-suspended on H$_2$O, to which was added a quantity of Celite, and the resulting suspension was stirred overnight. After this time, the suspension was filtered through a pad of Celite, and solvent was removed under reduced pressure to afford crude amine 11 as an amorphous off-white solid (0.65 g, 93%), which was used without further purification. $^1$H NMR [(CD$_3$)$_2$SO]: δ 9.98 (s, 1H, ArC(O)NHAr), 7.91 (ddd, J=9.40, 4.48, 2.58 Hz, 2H, ArH), 7.72 (m, 3H, ArH), 7.48 (ddd, J=9.37, 4.39, 2.55 Hz, 2H, ArH), 6.61 (d, J=7.85 Hz, 2H, ArH), 6.18 (dd, J=5.46, 1.68 Hz, 1H, ArH), 5.82 (d, J=1.36 Hz, 1H, ArH), 6.01 (br s, 2H, ArNH$_2$), 5.82 (br s, 2H, ArNH$_2$); HRMS: Calc. for C$_{18}$H$_{17}$N$_4$OS (MH+) m/z 337.1123, found 337.1126.

N-[4-(2-aminopyridin-4-ylthio)phenyl]-4-(quinolin-4-ylamino)-benzamide hydrochloride (Cpd. BBB). 4-Chloroquinoline 7 (0.66 g, 4.01 mmol) and c.HCl (0.52 mL, 17.13 mmol) were sequentially added to a solution of amine 11 (0.63 g, 1.88 mmol) in 20% aq. EtOH (100 mL), and the resulting mixture refluxed for 3 h. After this time, solvent was removed under reduced pressure, and the residue was dried via two MeOH azeotrope cycles. The residue was then re-precipitated twice from MeOH:methanolic HCl:EtOAc to give Cpd. BBB (0.55 g, 54%) as an amorphous yellow solid, mp 225-239° C.; $^1$H NMR [(CD$_3$)$_2$SO]: δ 14.10 (v v br s, 2H, quinolinyl-N$^+$—H & pyridinyl-N$^+$H), 11.14 (s, 1H, ArNHAr), 10.75 (s, 1H, ArC(O)NHAr), 8.87 (d, J=8.48 Hz, 1H, ArH), 8.62 (d, J=6.92 Hz, 1H, ArH), 8.20 (d, J=8.61 Hz, 2H, ArH), 8.09 (m, 4H, ArH), 7.82 (m, 4H, ArH & ArNH$_2$), 7.68 (m, 4H, ArH), 7.01 (d, J=6.91 Hz, 1H, ArH), 6.66 (dd, J=6.88, 1.87 Hz, 1H, ArH), 6.31 (d, J=1.74 Hz, 1H, ArH); HRMS: Calc. for C$_{27}$H$_{22}$N$_5$OS (MH$^+$) m/z 464.1541, found 464.1541; HPLC: 97.4%.

Example CCC

Preparation of N-[4-(2-hydroxypyridin-4-ylthio)phenyl]-4-(quinolin-4-ylamino)benzamide hydrochloride (Cpd. CCC)

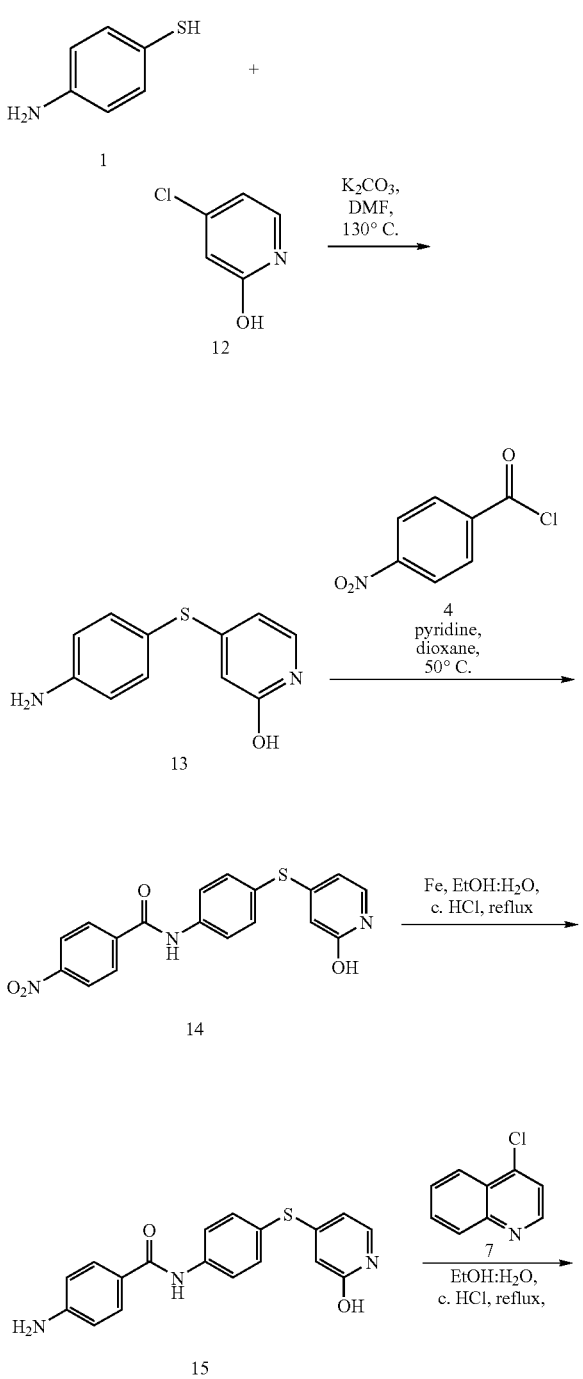

Scheme 3

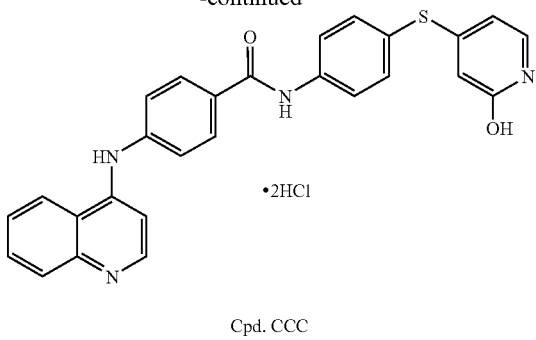

Cpd. CCC 4-(4-Aminophenylthio)pyridin-2-ol (13). To a solution of 4-aminobenzene thiol 1 (3.68 g, 29.40 mmol) in dry DMF (54 mL) were sequentially added 4-chloro-2-hydroxypyridine 12 (0.49 g, 3.81 mmol) and dry $K_2CO_3$ (10.70 g, 107.97 mmol), and the resulting yellow suspension stirred at ~120° C. (bath temperature) for ~1 h. LCMS analysis of the reaction mixture after this time showed that there was still much 12 present, thus a further quantity of 1 (1.28 g, 10.22 mmol) was added (as a solution in 10 mL of dry DMF). After 1 h, LCMS and TLC analysis showed the reaction to be complete, so the reaction mixture was cooled to room temperature, diluted with $H_2O$, and extracted with EtOAc(×3). The combined organic extracts were washed with brine, dried over anhydrous $MgSO_4$, and solvent was removed under reduced pressure. The reside was purified by column chromatography on silica gel, eluting with 1%→10% MeOH:$CH_2Cl_2$, to afford amine 13 as an amorphous off-white solid (0.47 g, 56%), which was used without further purification; $^1H$ NMR [$(CD_3)_2$ SO]: δ 11.20 (br s, 1H, ArOH), 7.18 (m, 3H, ArH), 6.66 (ddd, J=9.38, 4.76, 2.80 Hz, 2H, ArH), 5.89 (dd, J=6.95, 1.92 Hz), 5.64 (br s, 2H, ArNH$_2$), 5.55 (d, J=1.79 Hz, 1H, ArH); HRMS: Calc. for C11H1N$_2$OS (MH+) m/z 219.0592, found 219.0591.

N-[4-(2-hydroxypyridin-4-ylthio)phenyl]-4-nitrobenzamide (14). To a solution of amine 13 (0.47 g, 2.13 mmol) in dry dioxane (120 mL) were sequentially added dry pyridine (0.86 mL, 10.65 mmol) and 4-nitrobenzoyl chloride 4 (0.70 g, 3.76 mmol, added as solution in 20 mL of dry DMF), and the resulting mixture was stirred at ~50° C. (bath temperature) overnight. After this time, the reaction mixture was cooled to room temperature, and then combined with a quantity of silica. Solvent was removed under reduced pressure, and the resulting silica adsorbate was purified by column chromatography on silica gel, eluting with 1%→20% MeOH:$CH_2Cl_2$ (with 0.5% aq.$NH_3$), to afford cleaner 14. This material was washed with MeOH, and the undissolved solid filtered off and dried, to afford a first batch of nitro compound 14 (0.27 g). The filtrate was concentrated under reduced pressure, and the residue washed with a small amount of MeOH, and then dried, affording a further quantity of 14 (0.30 g, overall 68%), mp 255-260° C. (dark powder-tar); $^1H$ NMR [$(CD_3)_2$SO]: δ 10.86 (s, 1H, ArC(O)NHAr), 8.38 (ddd, J=9.22, 4.34, 2.33 Hz, 2H ArH), 8.22 (ddd, J=9.24, 4.32, 2.31 Hz, 2H, ArH), 7.98 (ddd, J=9.40, 4.48, 2.57 Hz, 2H ArH), 7.61 (ddd, J=9.33, 4.46, 2.56 Hz, 2H, ArH), 7.38 (d, J=6.95 Hz, 1H, ArH), 6.05 (dd, J=6.94, 1.93 Hz, 1H, ArH), 5.73 (d, J=1.78 Hz, 1H, ArH) [—OH signal very broad around 5.6 ppm]; HRMS: Calc. for $C_{18}H_{14}N_3O_4S$ (MH+) m/z 368.0705, found 368.0711.

4-Amino-N-[4-(2-hydroxypyridin-4-ylthio]phenyl)benzamide (15). Nitro compound 14 (0.48 g, 1.18 mmol) was suspended in 2:1 EtOH:$H_2O$ (100 mL) and the resulting suspension brought to reflux. To this mixture was sequentially added Fe dust (0.30 g, 9.59 mmol) and c.HCl (2 mL), and the resulting suspension refluxed for 15 min. TLC and LCMS analysis at this time showed that the reaction was incomplete, thus further quantities of Fe dust (0.80 g, 14.29 mmol) and c.HCl (10 mL) were added, and the mixture refluxed for a further 50 min. After this time, the reaction was complete, and thus the reaction mixture was filtered hot through a pad of Celite, and solvent was removed under reduced pressure. The residue was dried via two MeOH-azeotrope cycles, and then re-dissolved in MeOH and stirred overnight with Celite and activated charcoal. The resulting slurry was filtered through a pad of Celite, and solvent was removed under reduced pressure. The residue was re-dissolved in MeOH and adsorbed onto a quantity of silica gel, and the resulting silica adsorbate was purified by column chromatography on silica gel, eluting with 1%→20% MeOH:$CH_2Cl_2$ (with 0.5% aq.$NH_3$), to afford crude 15. This material was purified further by re-precipitation from MeOH:methanolic HCl:EtOAc, to afford amine 15 as an amorphous cream solid (15 mg, 3%—presumably much material lost by adsorption to activated charcoal,; latter was extracted several times, to little avail); $^1H$ NMR [$(CD_3)_2$SO]: δ 11.40 (v v br s, 1H, quinolinyl-N$^+$—H), 10.08 (s, 1H, ArH), 7.94 (ddd, J=9.40, 4.51, 2.59 Hz, 2H, ArH), 7.78 (d, J=8.67 Hz, 2H, ArH), 7.52 (ddd, J=9.40, 4.49, 2.61 Hz, 2H, ArH), 7.27 (d, J=6.95 Hz, 1H, ArH), 6.71 (d, J=8.52 Hz, 2H, ArH), 5.96 (dd, J=6.96, 1.93 Hz, 1H, ArH) [ArOH & ArNH$_2$ not visible]; LCMS (APCI$^+$): 338 (100%), 423 (60%), 169 (40%).

N-[4-(2-Hydroxypyridin-4-ylthio)phenyl]-4-(quinolin-4-ylamino)-benzamide hydrochloride (Cpd. CCC). 4-Chloroquinoline 7 (12 mg, 0.07 mmol) and c.HCl (30 μL, 17.13 mmol) were sequentially added to a solution of amine 15 (13 mg, 0.032 mmol) in 20% aq. EtOH (6 mL), and the resulting mixture refluxed for 18 h. After this time, solvent was removed under reduced pressure, and the residue was dried via two MeOH-azeotrope cycles. The resulting material was re-dissolved in MeOH and adsorbed onto a quantity of silica gel, and the resulting silica adsorbate was purified by column chromatography on silica gel, eluting with 1% p10% MeOH:$CH_2Cl_2$ (with 0.5% aq.$NH_3$), to afford cleaner material. This material was purified further by re-precipitation from MeOH:methanolic HCl:EtOAc, to afford Cpd. CCC as an amorphous yellow solid (7 mg, 41%), mp 209-214° C.; $^1H$ NMR [$(CD_3)_2$SO]: δ 14.42 (br s, 1H, 1H, quinolinyl-N$^+$—H), 11.34 (br s, 1H, pyridinyl-N$^+$—H), 10.99 (s, 1H, ArNHAr), 10.61 (s, 1H, ArC(O)NHAr), 8.77 (d, J=8.60 Hz, 1H, ArH), 8.62 (d, J=6.90 Hz, 1H, ArH), 8.19 (d, J=8.60 Hz, 2H, ArH), 8.07 (m, 2H), 8.00 (dd, J=6.88, 1.83 Hz, 2H, ArH), 7.87 (septet, J=11.29, 8.36, 5.40, 2.76 Hz, 1H, ArH), 7.69 (d, J=8.55 Hz, 2H, ArH), 7.60 (d, J=8.60 Hz, 2H, ArH), 7.27 (d, J=6.97 Hz, 1H, ArH), 7.06 (d, J=6.94 Hz, 1H, ArH), 5.97 (d, J=6.96, 1.88 Hz), 1H, ArH), 5.63 (d, J=1.76 Hz, 1H, ArH) [ArOH not visible]; HRMS: Calc. for $C_{27}H_{21}N_4O_2S$ (MH$^+$) m/z 465.1385, found 465.1389; HPLC: 93.5%.

Unless specified otherwise, all solvents and reagents used in the following Examples DDD, EEE, FFF and GGG below were available from Sigma-Aldrich (St. Louise, Mo.) or VWR International (West Chester, Pa.) and used as supplied or purified by standard laboratory methods as required. NMR spectra were recorded on a Varian Unity at 400 MHz ($^1H$) at 25° C. Chemical shifts are reported in ppm and referenced internally to residual CHCl$_3$ for (d 7.26) or CH$_3$OH for (d 3.33). Low resolution mass spectrometry was performed by The Mass Spectrometry and Proteomics Core facility at the University of Utah. Flash chromatography was performed on Combifalsh (Yamazen) with normal phase silica gel column

Example DDD

Preparation of 4-(4-(4-(quinolin-4-ylamino)benzamido)phenylthio)pyrrolidine-2-carboxylic acid (Cpd. DDD)

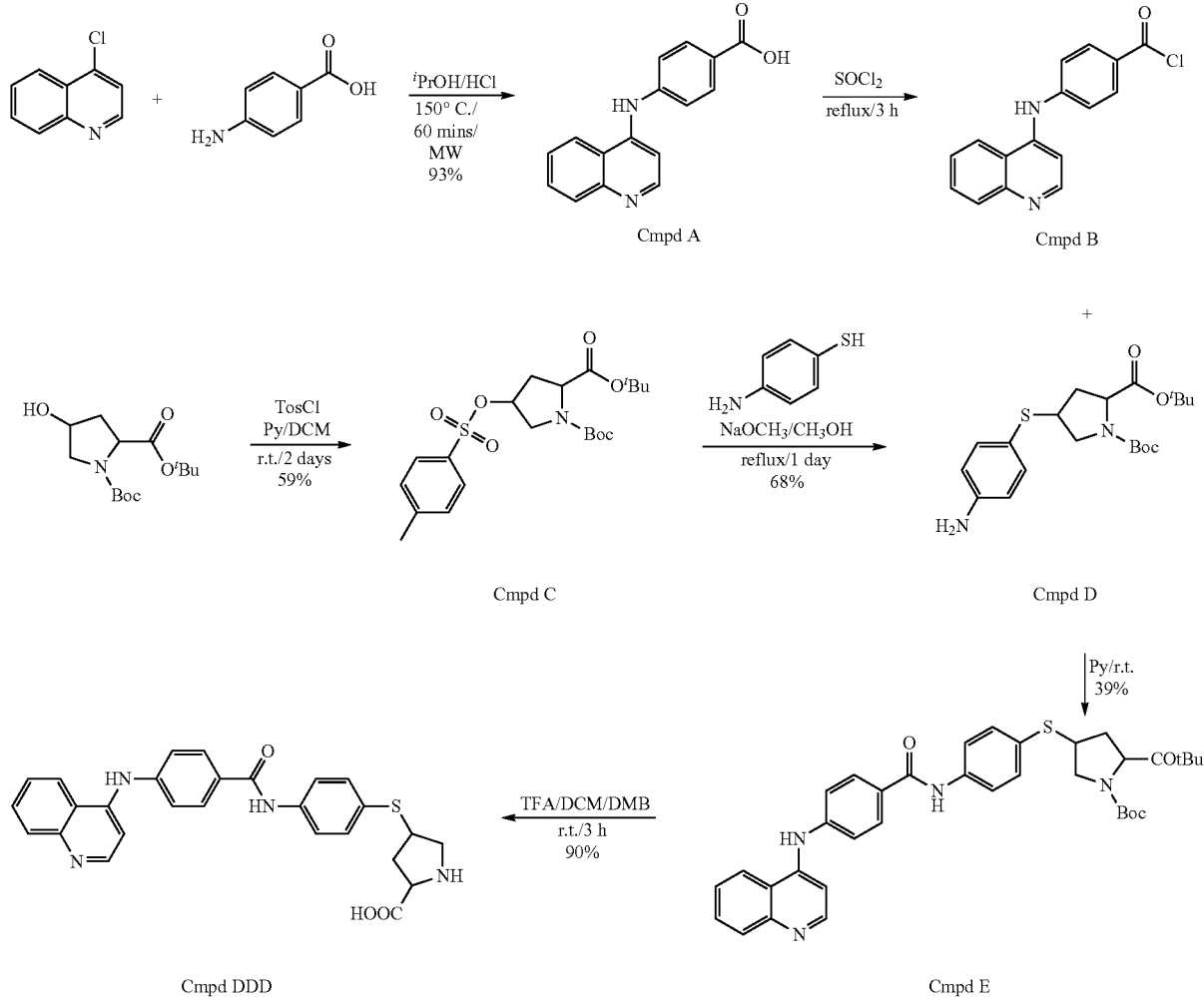

4-(Quinolin-4-ylamino)benzoic acid (Cpd A). To a mixture of 4-chloroquinoline (0.5 g, 3.06 mmol) and 4-aminobenzoic acid (0.419 g, 3.06 mmol) in anhydrous $^i$PrOH 10 mL was added concentrated HCl 0.1 mL and heat to 150° C. in microwave for 1 h. The resulting reaction mixture was cooled down to r.t. White precipitate formed and the crude product was filtered and washed with $^i$PrOH 3 mL×3. The crude product was dried and analyzed with TLC. Single spot was detected and it was sufficiently pure (Cpd A) for the next step. Spectral Data: $^1$H-NMR (DMSO-$d_6$/400 MHz): 15.05 (s, 1H), 11.24 (s, 1H), 8.91 (d, J=8.3 Hz, 1H), 8.57 (d, J=7.0 Hz, 1H), 8.15 (d, J=7.4 Hz, 1H), 8.06 (m, 3H), 7.83 (m, 1H), 7.78 (m, 2H), 7.03 (d, J=6.9 Hz, 1H). MS (ES+, m/z): 265.1 (M$^+$+1, 100.0).

4-(Quinolin-4-ylamino)benzoic acid (Cpd B). Cpd A (0.099 g, 0.294 mmol) in anhydrous thionyl chloride 3 mL was refluxed for 3 h, then evaporated the solution and got white crude product. The crude product, Cpd B, was used for the next step directly.

Di-tert-butyl 4-(tosyloxy)pyrrolidine-1,2-dicarboxylate (Cpd C). To a stirred solution of Boc-Hyp-OtBu (0.5 g, 1.74 mmol) in DCM (20 mL) were added pyridine (0.550 g, 6.96 mmol) and p-toluenesulfonyl chloride (0.663 g, 3.48 mmol) at r.t. After being stirred at r.t. for 24 h, the reaction mixture was quenched with 1M HCl and extracted with DCM. The organic layer was successively washed with 1M HCl, water, brine, dried over Na$_2$SO$_4$, and concentrated in vacuo. The crude product was purified by chromatography on silica gel and provided pure product, Cpd C (yellow solid). Spectral Data: $^1$H-NMR (CDCl$_3$/400 MHz): 7.82 (d, J=8.3 Hz, 2H), 7.40 (d, J=8.3 Hz, 2H), 5.05 (m, 1H), 4.28 (m, 1H), 3.59 (m, 2H), 2.49 (s, 3H), 2.57 (m, 1H), 2.13 (m, 1H), 1.47 (s, 9H), 1.45 (s, 9H). MS (ES+, m/z): 442.2 (M$^+$+1, 30.0).

Di-tert-butyl 4-(4-aminophenylthio)pyrrolidine-1,2-dicarboxylate (Cpd D). To a stirred solution of 4-aminothiophenol (0.072 g, 0.579 mmol) in anhydrous methanol (10 mL) were added sodium methoxide (0.039 g, 0.724 mmol) and Cpd C (0.213 g, 0.482 mmol) at r. t. After being stirred for 16 h at 80° C., the reaction mixture was quenched with saturated NH$_4$Cl and extracted with DCM. The organic layer was successively washed with water, brine, dried over Na$_2$SO$_4$, and concentrated in vacuo. The product was purified by chromatography (0% AE in Hexane) and provide pure compound, Cpd D. Spectral Data: $^1$H-NMR (CDCl$_3$/400 MHz): 7.30 (d, J=8.3 Hz, 2H), 6.64 (d, J=8.3 Hz, 2H), 4.20 (m, 1H), 3.90 (m, 1H), 3.40 (m, 2H), 2.59 (m, 1H), 1.95 (m, 1H), 1.49 (s, 9H), 1.45 (s, 9H). MS (ES+, m/z): 395.2 (M$^+$+1, 40.0).

Di-tert-butyl 4-(4-(4-(quinolin-4-ylamino)benzamido) phenylthio)-pyrrolidine-1,2-dicarboxylate (Cpd F). Dissolved Cpd B (0.090 g, 0.253 mmol) and Cpd D (0.100 g, 0.253 mmol) in anhydrous pyridine 5 mL and stirred at r.t. for overnight. Then the solvent was evaporated, and the resulting reaction mixture was concentrated and the pure product, Cpd F, was obtained as a colorless oil by column chromatography using methanol/DCM, 0-5% ration solvent system. Spectral Data: $^1$H-NMR (CDCl$_3$/400 MHz): 9.06 (s, 1H), 8.68 (s, 1H), 8.09 (m, 1H), 7.96 (m, 3H), 7.77 (d, J=8.3 Hz, 2H), 7.65 (m, 1H), 7.42 (m, 1H), 7.36 (m, 2H), 7.25 (d, J=8.3 Hz, 2H), 6.76 (m, 1H), 4.21 (m, 1H), 3.84 (m, 1H), 3.58 (m, 1H), 3.28 (m, 1H), 2.66 (m, 1H), 1.95 (m, 1H), 1.49 (s, 9H), 1.45 (s, 9H). MS (ES+, m/z): 641.3 (M$^+$+1, 100.0).

4-(4-(4-(Quinolin-4-ylamino)benzamido)phenylthio)pyrrolidine-2-carboxylic acid (Cpd DDD). To a solution of Cpd E (0.020 g, 0.032 mmol) in anhydrous DCM 4 mL was added 0.5 mL 1,3-dimethoxybenzene and 2 mL of TFA at 0° C. The resulting reaction mixture was stirred at r.t. for 2 h. The solvent was evaporated and neutralized with NH$_3$ in methanol, then acidified with HCl in dioxane. The crude product was purified with preparative TLC by using 20% methanol in DCM. Cpd DDD was obtained in white solid. Spectral Data: $^1$H-NMR (CD$_3$OD/400 MHz): 8.64 (d, , J=8.4 Hz, 1H), 8.47 (d, , J=6.6 Hz, 1H), 8.13 (d, J=8.4 Hz, 2H), 8.03 (m, 2H), 7.84 (m, 3H), 7.67 (d, , J=8.3 Hz, 2H), 7.52 (d, J=8.3 Hz, 2H), 7.14 (d, J=8.3 Hz, 1H), 4.10 (t, , J=7.8 Hz, 1H), 3.92 (t, , J=7.8 Hz, 1H), 3.62 (m, 2H), 2.74 (m, 1H), 2.11 (m, 1H). MS (ES+, m/z): 485.1 (M$^+$+1, 50.0).

Example EEE

Preparation of 3-(4-(4-(quinolin-4-ylamino)benzamido)phenylthio)pyrrolidine (Cpd. EEE)

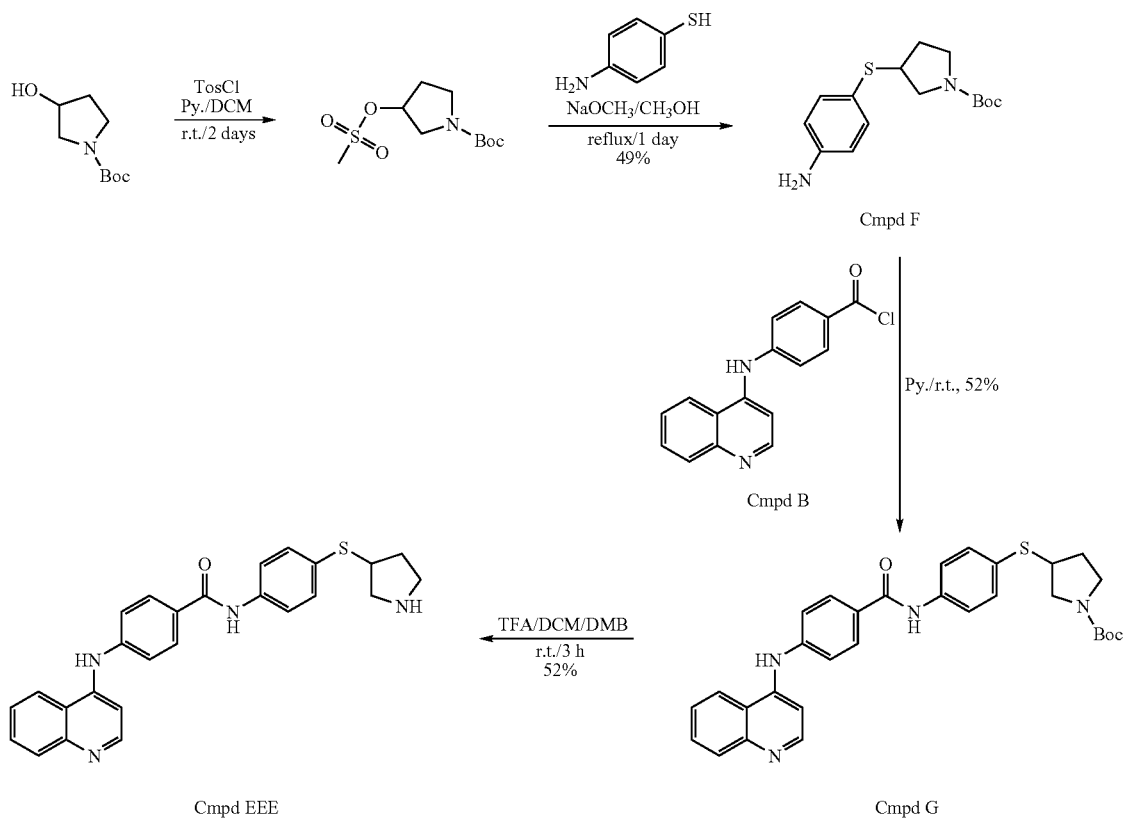

Tert-butyl 3-(4-aminophenylthio)pyrrolidine-1-carboxylate (Cpd F). To a stirred solution of 4-aminothiphenol (0.220 g, 1.757 mmol) in methanol (10 mL) were added sodium methoxide (0.119 g, 2.197 mmol) and N-Boc-3-MsO-pyrrolidine (0.389 g, 1.464 mmol) at r.t. Then refluxed for 1d. After cooled to r.t., the reaction mixture was quenched with saturated NH$_4$Cl and extracted with DCM. The organic layer was successively washed with water, brine, dried over Na$_2$SO$_4$, and concentrated in vacuo. FC with AE/HE 10-30% provided pure product, Cpd F. Spectral Data: $^1$H-NMR (CDCl$_3$/400 MHz): 7.30 (d, J=6.3 Hz, 2H), 6.64 (d, J=6.3 Hz, 2H), 3.82 (br, 2H), 3.52 (m, 2H), 3.34 (m, 2H), 2.13 (m, 2H), 1.88 (m, 1H), 1.49 (s, 9H). MS (ES+, m/z): 295.2 (M$^+$+1, 40.0).

Tert-butyl 4-(4-(4-(quinolin-4-ylamino)benzamido)phenylthio)-pyrrolidine-carboxylate (Cpd G). Dissolved Cpd B (0.181 g, 0.509 mmol) and Cpd. F (0.150 g, 0.509 mmol) in anhydrous pyridine 5 mL and stirred at r.t. for overnight. Then the solvent was evaporated, and the crude product was purified by methanol and DCM mixture 5-10% to yield Cpd G. Product, white solid. Spectral Data: $^1$H-NMR (CDCl$_3$/400 MHz): 8.72 (d, J=5.1 Hz, 1H), 8.13 (d, J=9.5 Hz, 1H), 7.99 (m, 3H), 7.65 (m, 3H), 7.48 (m, 2H), 7.36 (d, J=8.3 Hz, 2H), 7.27 (d, J=8.3 Hz, 2H), 6.95 (br, 1H), 3.69 (m, 1H), 3.56 (m, 1H), 3.37 (m, 2H), 2.19 (m, 1H), 1.93 (m, 1H), 1.49 (s, 9H). MS (ES+, m/z): 514.2 (M$^+$+1, 100.0).

3-(4-(4-(Quinolin-4-ylamino)benzamido)phenylthio)pyrrolidine (Cpd EEE). To the solution of Cpd G (0.100 g, 0.185 mmol) in 5 mL anhydrous DCM was added 0.5 mL 1,3-dimethoxybenzene and 2 mL TFA at 0° C. The reaction mixture was stirred at r.t. for overnight. Then the solvent was evaporated, and the crude product was neutralized with NH$_3$ in methanol. After removed the solvent, the reaction mixture was acidified with HCl in dioxane. The crude product was purified by methanol and DCM mixture 20% on preparative TLC to yield Cpd EEE. Spectral Data: $^1$H-NMR (CD$_3$OD/ 400 MHz): 8.47 (m, 2H), 8.08 (d, J=9.5 Hz, 2H), 7.92 (m, 2H), 7.72 (m, 2H), 7.58 (m, 1H), 7.56 (d, J=8.3 Hz, 2H), 7.46 (d, J=8.3 Hz, 2H), 7.15 (d, J=8.3 Hz, 1H), 4.40 (m, 1H), 3.56 (m, 1H), 3.32 (m, 2H), 2.42 (m, 1H), 2.02 (m, 1H). MS (ES+, m/z): 441.2 (M$^+$, 60.0).

Example FFF

Preparation of N-(4-(piperidin-4-ylthio)phenyl)-4-(Quinolin-4-ylamino)-benzamide (Cpd. FFF)

solution was diluted with dichloro-methane, washed 2× with 1M hydrochloric acid, with brine, 3× with 1M sodium hydroxide, with brine and dried with sodium sulfate. Solvent was removed under reduced pressure to give 5.25 g of almost colorless oil. It was treated with ~50 mL of hexanes—crystallization started. Crystals were filtered off, washed 3× with hexanes and dried in vacuo to give Cpd A as white crystals. Purity (HPLC): 100%. It was immediately used for the next step.

Tert-butyl 4-(4-aminophenylthio)piperidine-1-carboxylate (Cpd. B). To a stirred solution of Cpd A (1.066 g, 3.0 mmol) in DMF (15 mL) potassium carbonate (2.488 g, 18.0 mmol, 6 eq.), followed by a solution of 4-aminothiophenol (0.789 g, 6.3 mmol, 2.1 eq.) in DMF (15 mL) was added. The suspension was stirred and heated at 70° C. (bath temperature) overnight. The mixture was partitioned between water and ethyl acetate. Aqueous layer was additionally extracted 2× with ethyl acetate. Extracts were combined and washed 2× with 1M sodium hydroxide then 2× with brine. The solution was dried over sodium sulfate and the solvent was removed under reduced pressure to yield 1.36 g of pale brown thick oil. It was purified by MPLC (24g silica column, gradient 0-30% AcOEt in hexanes) to give a brown oil which solidified in

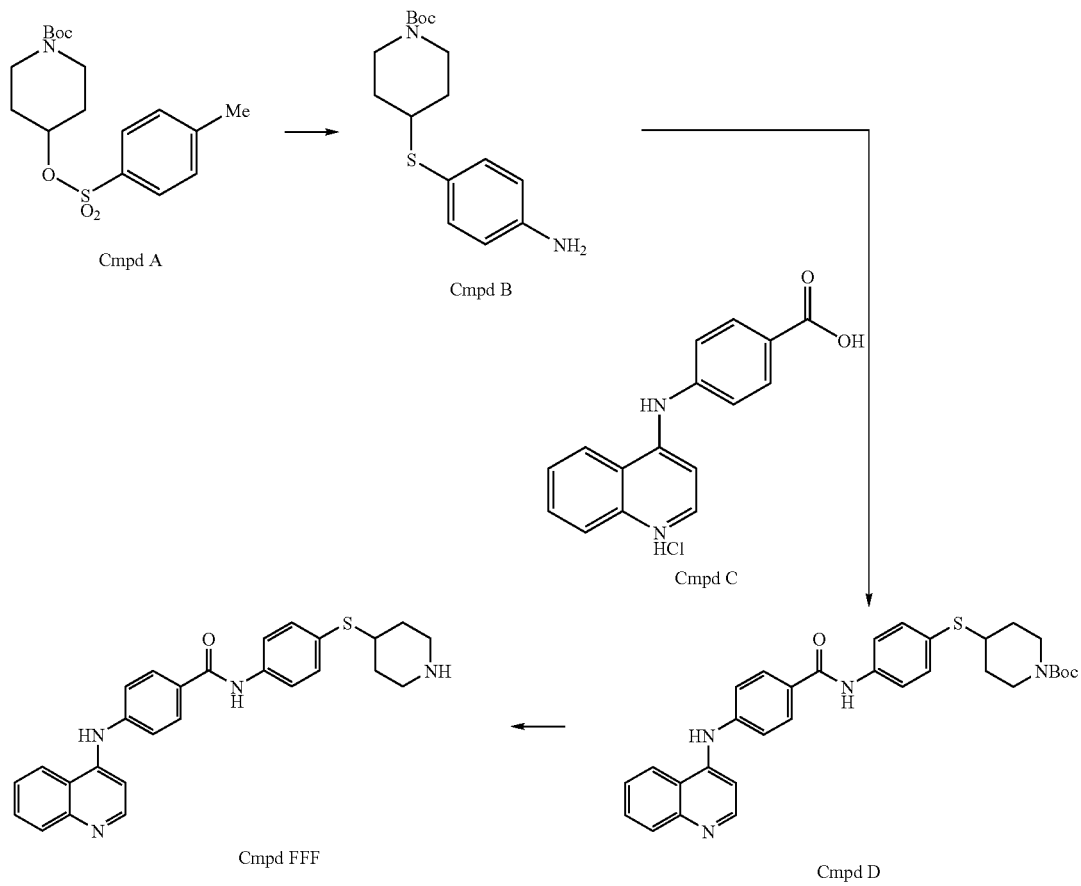

Tert-butyl 4-(tosyloxy)piperidine-1-carboxylate (Cpd A). To a cooled in an ice bath solution of 1-Boc-4-hydroxypiperidine (2.013 g, 10.0 mmol) in dichloromethane (25 mL) pyridine (4 mL, 50 mmol), followed by a solution of p-tosyl chloride (3.810 g, 20.0 mmol) in dichloromethane (25 mL) was added. The solution was stirred for 5 days. Colorless vacuo to give Cpd B (0.730g, 79%). Purity (HPLC): 98%. MS (ES+): calc. for C16H24N2O2SNa (MNa+) 331.1, found 331.3

4-(quinolin-4-ylamino)benzoic acid hydrochloride (Cpd C). To a suspension of 4-chloroquinoline (0.500 g, 3.06 mmol) and 4-aminobenzoic acid (0.419 g, 3.06 mmol) in 2-propanol (10 mL) 3 drops of concentrated hydrochloric acid were added and mixture was microwave irradiated at 150° C. for 1 hour. After cooling solid was filtered off, washed with 2-propanol and dried in vacuo to give Cpd C as a yellow powder. Purity (HPLC): 100%. $^1$H NMR (DMSO-$d_6$): 7.05 (d, J=6.9 Hz, 1H), 7.64-7.67 (m, 2H), 7.80-7.85 (m, 1H), 8.02-8.17 (m, 5H), 8.59 (d, J=7.2 Hz, 1H), 8.92 (d, J=8.1 Hz, 1H), 11.26 (s, 1H). MS (ES+): calc. for $C_{16}H_{13}N_2O_2$ (MH+) 265.1, found 265.1.

Tert-butyl 4-(4-(4-(quinolin-4-ylamino)benzamido)phenylthio)-piperidine-1-carboxylate (Cpd D). Solution of Cpd C (0.256 g, 0.85 mmol, 1.1 eq.) in thionyl chloride (5 mL) was refluxed for 3 hours. Excess of thionyl chloride was removed under reduced pressure and residual yellow acid chloride was dissolved in pyridine (5 mL). Solution of Cpd B (0.239 g, 0.78 mmol) in pyridine (5 mL) was added and red solution was stirred overnight at room temperature. The mixture was partitioned between ethyl acetate and 1M sodium hydroxide. Aqueous layer was additionally extracted 2× with ethyl acetate. The extracts were combined, washed 2× with 1M sodium hydroxide then with brine and dried over sodium sulfate. The solvent was removed under reduced pressure and residue was co-evaporated with toluene to remove the remaining pyridine to give 0.458 g of a red solid. It was triturated with DCM to give Cpd D as beige powder (0.235 g, 55%). Purity (HPLC): 88%. $^1$H NMR (DMSO-d6): 1.39 (s, 9H), 1.25-1.45 (m, 2H), 1.80-1.92 (m, 2H), 2.70-3.00 (m, 1H), 3.25-3.40 (m, 2H), 3.78-3.88 (m, 2H), 7.23 (d, J=4.5 Hz, 1H), 7.41-7.63 (m, 5H), 7.72-7.84 (m, 3H), 7.92-8.05 (m, 3H), 8.39 (d, J=8.1 Hz, 1H), 8.59 (d, J=4.5 Hz, 1H), 9.30 (bs, 1H), 10.27 (s, 1H).

N-(4-(piperidin-4-ylthio)phenyl)-4-(quinolin-4-ylamino)-benzamide (Cpd FFF). Suspension of Cpd D (0.235 g, 0.424 mmol) in a mixture of 1,3-dimethoxybenzene (2 mL) and dichloromethane (5 mL) was cooled down in an ice bath and trifluoroacetic acid (3 mL) was added in one portion. Solids dissolved immediately and in ~5 min. solution turned green. Bath was removed and solution was left at room temperature overnight. Solvents from brown solution were removed under reduced pressure, residual oil was partitioned between ethyl acetate and diluted (1:2) concentrated hydrochloric acid. Aqueous layer was additionally extracted 2× with ethyl acetate, basified with conc. sodium hydroxide and extracted 3× with ethyl acetate. Extracts were combined, washed with brine, dried with sodium sulfate and solvent was removed under reduced pressure to give almost white solid of Cpd FFF. Purity (HPLC): 97%. $^1$H NMR (DMSO-d6): 1.25-1.45 (m, 2H), 1.72-1.92 (m, 2H), 2.76-3.44 (m, 5H), 7.22 (d, J=5.1 Hz, 1H), 7.30-8.05 (m, 11H), 8.38 (d, J=8.7 Hz, 1H), 8.57 (d, J=5.1 Hz, 1H), 9.25 (bs, 1H), 10.21 (s, 1H). MS (ES+): calc. for C27H27N4OS (MH+) 455.2, found 455.4.

Example GGG

Preparation of N-(4-(piperidin-3-ylthio)phenyl)-4-(quinolin-4-ylamino)-benzamide (Cpd. GGG)

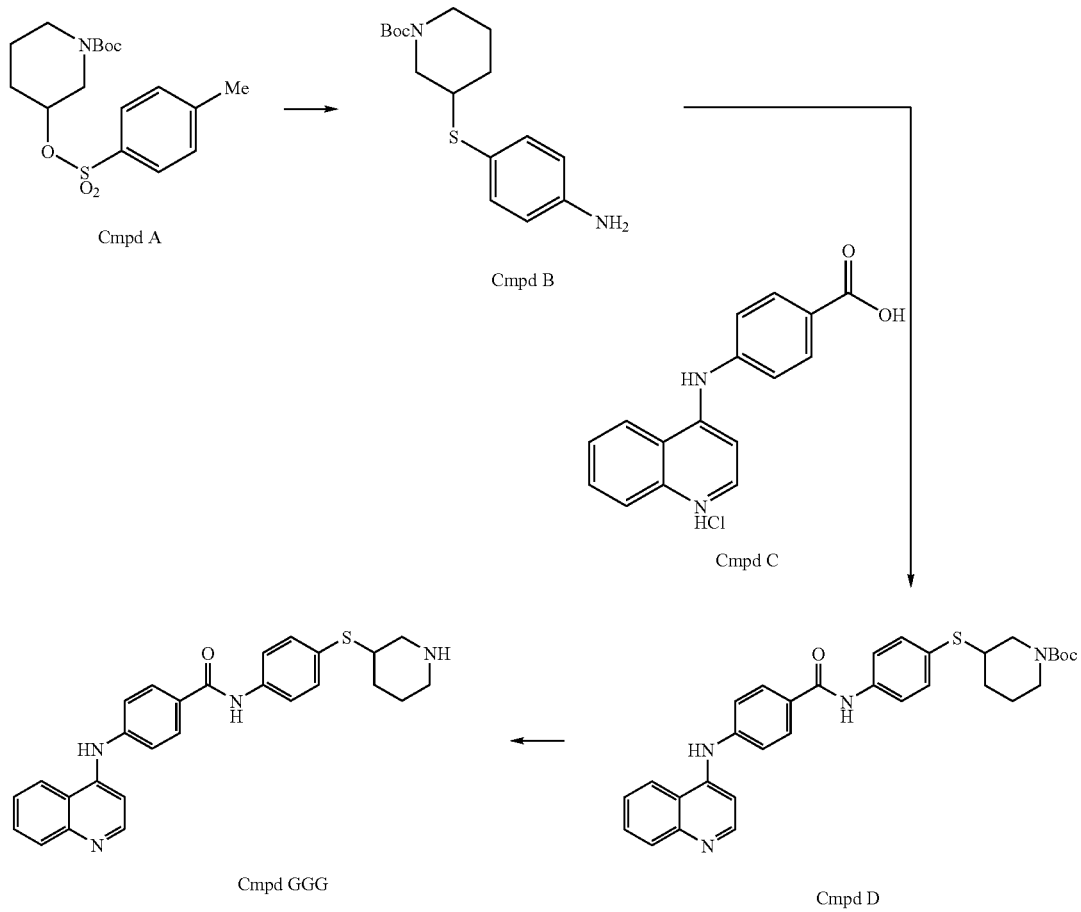

Tert-butyl 3-(tosyloxy)piperidine-1-carboxylate (Cpd A). To a cooled in an ice bath solution of 1-Boc-3-hydroxypiperidine (1.006 g, 5.0 mmol) in dichloromethane (15 mL) pyridine (2 mL, 25 mmol), followed by a solution of p-tosyl chloride (1.906 g, 10.0 mmol) in dichloromethane (10 mL) was added. The solution was stirred for 5 days. Colorless solution was diluted with dichloromethane, washed 2× with 1M hydrochloric acid, with brine, 3× with 1M sodium hydroxide, with brine and dried with sodium sulfate. Solvent was removed under reduced pressure to give 2.56 g of almost colorless oil. It was purified by MPLC (24g silica column, gradient 0-30% AcOEt in hexanes) to give Cpd A as a colorless thick oil. It was immediately used for the next step.

Tert-butyl 3-(4-aminophenylthio)piperidine-1-carboxylate (Cpd B). To a stirred solution of Cpd A (1.487 g, 4.18 mmol) in DMF (20 mL) potassium carbonate (3.47 g, 25.1 mmol, 6 eq.), followed by a solution of 4-aminothiophenol (1.100g, 8.79 mmol, 1.1 eq.) in DMF (10 mL) was added. The suspension was stirred and heated at 70° C. (bath temperature) overnight. The mixture was partitioned between water and ethyl acetate. Aqueous layer was additionally extracted 2× with ethyl acetate. Extracts were combined and washed 2× with 1M sodium hydroxide then 2× with brine. The solution was dried over sodium sulfate and the solvent was removed under reduced pressure to yield 1.452 g of yellow oil. It was purified by MPLC (24g silica column, gradient 0-30% AcOEt in hexanes) to give Cpd B as an off white solid. Purity (HPLC): 100%. $^1$H NMR (CDCl$_3$): 1.42 (s, 9H), 1.60-1.80 (m, 1H), 2.00-2.10 (m, 1H), 2.70-2.92 (m, 3H), 3.70-4.30 (m, 4H), 6.64 (d, J=8.4 Hz, 2H), 7.30 (d, J=8.1 Hz, 2H).

4-(quinolin-4-ylamino)benzoic acid hydrochloride (Cpd C). To a suspension of 4-chloroquinoline (0.500 g, 3.06 mmol) and 4-aminobenzoic acid (0.419 g, 3.06 mmol) in 2-propanol (10 mL) 3 drops of concentrated hydrochloric acid were added and mixture was microwave irradiated at 150° C. for 1 hour. After cooling solid was filtered off, washed with 2-propanol and dried in vacuo to give Cpd C as a yellow powder. Purity (HPLC): 100%. $^1$H NMR (DMSO-d$_6$): 7.05 (d, J=6.9 Hz, 1H), 7.64-7.67 (m, 2H), 7.80-7.85 (m, 1H), 8.02-8.17 (m, 5H), 8.59 (d, J=7.2 Hz, 1H), 8.92 (d, J=8.1 Hz, 1H), 11.26 (s, 1H). MS (ES+): calc. for $C_{16}H_{13}N_2O_2$ (MH+) 265.1, found 265.1.

Tert-butyl 3-(4-(4-(quinolin-4-ylamino)benzamido)phenylthio)-piperidine-1-carboxylate (Cpd D). Solution of Cpd C (0.331 g, 1.1 mmol, 1.1 eq.) in thionyl chloride (5 mL) was refluxed for 3 hours. Excess of thionyl chloride was removed under reduced pressure and residual yellow acid chloride was dissolved in pyridine (5 mL). Solution of Cpd B (0.308 g, 1.0 mmol) in pyridine (5 mL) was added and red solution was stirred overnight at room temperature. The mixture was partitioned between ethyl acetate and 1M sodium hydroxide. Aqueous layer was additionally extracted 2× with ethyl acetate. The extracts were combined, washed 2× with 1M sodium hydroxide then with brine and dried over sodium sulfate. The solvent was removed under reduced pressure and residue was co-evaporated with toluene to remove the remaining pyridine to give 0.541 g of a yellow solid. It was dissolved in small amount of boiling ethyl acetate and diluted with -equal volume of hexanes. After cooling precipitate was filtered off, washed with AcOEt-hexanes (1:1), with hexanes and dried in vacuo to give Cpd D as a pale yellow powder. Purity (HPLC): 96%.

N-(4-(piperidin-3-ylthio)phenyl)-4-(quinolin-4-ylamino)benzamide (Cpd GGG). Suspension of Cpd D (0.314 g, 0.566 mmol) in a mixture of 1,3-dimethoxybenzene (2 mL) and dichloromethane (5 mL) was cooled down in an ice bath and trifluoroacetic acid (3 mL) was added in one portion. Solids dissolved immediately and in ~5 min. solution turned green. Bath was removed and solution was left at room temperature overnight. Solvents from brown solution were removed under reduced pressure, residual oil was partitioned between ethyl acetate and diluted (1:2) concentrated hydrochloric acid. Aqueous layer was additionally extracted 2× with ethyl acetate, basified with conc. sodium hydroxide and extracted 3× with ethyl acetate. Extracts were combined, washed with brine, dried with sodium sulfate and solvent was removed under reduced pressure to give almost white solid (0.246 g, 96%). It was triturated with ethyl acetate to give Cpd GGG as a pale yellow solid. Purity (HPLC): 97%. $^1$H NMR (DMSO-d$_6$): 1.30-1.65 (m, 2H), 1.65-1.80 (m, 1H), 1.95-2.10 (m, 1H), 2.50-2.65 (m, 2H), 2.90-3.05 (m, 1H), 3.05-3.30 (m, 2H), 7.23 (d, J=5.4 Hz, 1H), 7.42-7.62 (m, 5H), 7.23-7.84 (m, 3H), 7.93-8.04 (m, 3H), 8.41 (d, J=8.4 Hz, 1H), 8.59 (d, J=5.4 Hz, 1H), 9.32 (bs, 1H), 10.29 (s, 1H). MS (ES+): calc. for C27H27N4OS (MH+) 455.2, found 455.3.

Example HHH

Biological Activity of Compounds of the Invention

Test for the selective depletion of DNMT1 by 4-anilinoquinolines was performed with highly specific antibodies against all three enzymes, as described by Ghoshal et al. [*Mol. Cell. Biol.* 2005, 11, 4727-41.]. For DNMT1, commercially available antibodies from Santa Cruz or New England Biolabs were used. Antibodies against DNMT3a and 3b with high titre, which did not cross-react with each other in Western blot or immunoprecipitation analysis, were prepared fresh. Protein extracts (equivalent to 100 μg) were isolated from HCT116 cells (colon cancer cells that express all three DNMTs at a relatively high level) that have been treated with 4-anilinoquinolines at concentrations 5, 10 and 100 μM. As shown in Table 3, of the compounds screened, nine compounds at 100 μM, thirteen at 10 μM, and eleven at 5 μM were able to induce DNMT1 degradation greater than 60% (DNMT1 level less than 40%). Four compounds (Cpd. E, Cpd. EEE2, Cpd. II, and Cpd. FF1) were able to induce DNMT1 degradation greater than 94% (DNMT1 level less than 6%) at 10 μM, exhibiting a level of potency on the order of that achieved by decitabine.

The demethylating activity of non-bis-quaternary 4-anilinoquinolines were tested in a cell-based GFP (green fluorescent protein) assay. This assay has a GFP gene regulated by the CMV promoter and is sensitive to the methylation of CpG sites within the promoter. A decrease in methylation resulting from exposure to a methylation inhibitor leads to GFP expression and is readily scored. Specifically, the CMV-EE210 cell line containing the epigenetically silenced GFP transgene was used to assay for reactivation of GFP expression by flow cytometry. CMV-EE210 was made by transfecting NIH 3T3 cells with the pTR-UF/UF1/UF2 plasmid (Zolotuhin et al., 1996), which is comprised of pBS(+) (Stratagene, Inc.) containing a cytomegalovirus (CMV) promoter driving a humanized GFP gene adapted for expression in mammalian cells. After transfection, high-level GFP expressing cells were initially selected by FACS analysis and sorting using a MoFlo cytometer (Cytomation, Inc.). Decitabine, potent inhibitor of mammalian DNMT1, was used as a positive control. To screen for reactivation of CMV-EE210, decitabine (at 11 M) or a test compound (at a concentration of 30-50 μM) was added to complete medium (phenol red free DMEM (Gibco, Life Technologies) supplemented with 10% fetal bovine serum (Hyclone)). Cells were then seeded to 30% confluence (~5000 cell/well) in 96 well plate containing the test compounds and grown for three days in at 37° C. in 5% $CO_2$. The plates were examined under a fluorescent microscope using a 450-490 excitation filter (13 filter cube, Leica, Deerfield Ill.). Wells were scored g1 positive if 10% of viable cells express GFP, g2 positive if 30% of viable cells express GFP and g3 if greater than 75% of the viable cells express GFP. GFP IC 50 is the concentration of an inhibitor that (like an $IC_{50}$) is the dose at which the GFP expression level goes from g3 to g1/2. As shown in Table 3, of the compounds tested, six compounds (Cpd. O, Cpd. BB, Cpd. P, Cpd. Q, Cpd. Z, and Cpd. CC) reactivated transcription of the GFP gene at greater than 75% level. In addition, they are less than one-half as toxic as decitabine.

TABLE 3

SUMMARY OF DEMETHYLATING ACTIVITY AND INDUCTION OF DNMT1 DEGRADATION OF SELECT COMPOUNDS OF THE PRESENT INVENTION

| Compound | % DNMT1 Level | | | GFP Expression Level | $IC_{50}$ (μM) | $TD_{50}$ (μM) |
|---|---|---|---|---|---|---|
| | 5 μM | 10 μM | 100 μM | | | |
| Untreated Control | 100 | — | — | — | — | — |
| Decitabine | 0-5 | — | — | g3 | 0.39 | 12.5 |
| A | 99 | 117 | 119 | ND | — | 12.5 |
| V | 112 | 110 | 124 | ND | — | 12.5 |
| K | 98 | 92 | 37 | ND | — | 12.5 |
| L | 144 | 145 | 128 | g2 | 50 | 50 |
| O | 84 | 150 | 142 | g3 | 12.5 | 50 |
| N | 160 | 152 | 130 | g2 | 100 | 50 |
| F | 145 | 210 | 155 | ND | — | 25 |
| R | 160 | 170 | 165 | ND | — | 25 |
| Y | 93 | 63 | 77 | g1 | 100 | 25 |
| S | 87 | 101 | 69 | ND | — | 25 |
| AA | 136 | 101 | 32 | g2 | 100 | 25 |
| J | 101 | 89 | 59 | ND | — | 12.5 |
| T | 64 | 69 | 85 | ND | — | 25 |
| D | 131 | 103 | 74 | g1 | — | 12.5 |
| C | 31 | 33 | 34 | g1 | 50 | 25 |
| U | 97 | 53 | 32 | ND | — | 25 |
| M | 30 | 40 | 43 | ND | — | 25 |
| X | 49 | 98 | 73 | g2 | 50 | 25 |
| BB | 106 | 76 | 32 | g3 | 100 | 25 |
| P | 57 | 91 | 11 | g3 | 50 | 25 |
| H | 132 | 25 | 24 | ND | — | 12.5 |
| Q | 219 | 93 | 10 | g3 | 12.5 | 25 |
| Z | 83 | 115 | 87 | g3 | 1.0 | 25 |
| B | 102 | 98 | 81 | ND | — | 25 |
| DD | 90 | 74 | 52 | ND | — | 25 |
| CC | 65 | 81 | 26 | g3 | 6.0 | 25 |
| E | 11 | 0.5 | — | g1 | 12.0 | 25 |
| I | 27 | 80 | 48 | ND | — | 25 |
| G | 95 | 95 | 100 | — | — | — |
| EE | 30 | 10 | — | — | — | — |
| W | 45 | 75 | — | — | — | — |
| OO2 | 50 | 95 | — | — | — | — |
| NN | 70 | 70 | — | — | — | — |
| OO1 | 25 | 15 | — | — | — | — |
| QQ | 60 | 50 | — | — | — | — |
| EEE2 | 3 | 0 | — | — | — | — |
| PP | 60 | 70 | — | — | — | — |
| GG1 | 25 | 20 | — | — | — | — |
| GG2 | 85 | 52 | — | — | — | — |
| JJ1 | 75 | 70 | — | — | — | — |
| JJ2 | 147 | 130 | — | — | — | — |
| GG3 | 110 | 10 | — | — | — | — |
| II | 25 | 0 | — | — | — | — |
| FF1 | 15 | 5 | — | — | — | — |
| FF2 | 85 | 83 | — | — | — | — |
| LL | 70 | 15 | — | — | — | — |
| KK | 82 | 20 | — | — | — | — |
| HH | — | 90 | — | — | — | — |
| GG4 | — | 90 | — | — | — | — |
| GG5 | — | 90 | — | — | — | — |
| RR1 | — | 100 | — | — | — | — |
| RR2 | — | 100 | — | — | — | — |
| RR3 | — | 100 | — | — | — | — |

ND - No activity detected;
$TD_{50}$ - Dose at which cells are >50% viable

RT-PCR Assay for Gene Expression

RKO and HCT-116 cells were treated with Cpd. AAA, Cpd. BBB, and Cpd. CCC at varying concentrations. After a forty eight hour incubation cells were harvested for RNA isolation using the Qiagen RNeasy Mini kit. RNA was quantified using a spectrophotometer and 1 μg of RNA was used for cDNA synthesis using the Bio-Rad iScript cDNA Synthesis Kit. RTPCR was performed using SYBER GreenER qPCR SuperMix for iCycler according to the manufacturer's protocol. Primer sequences used are as follows p16 5'-atgtc-ctgccttttaacgta-3' (SEQ ID NO: 2) and 5'-gtgctcactcca-gaaaactc-3' (SEQ ID NO: 3), MLH-1 5'-tgaggaagggaacct-gattg-3' (SEQ ID NO: 4) and 5'-tcttcgtcccaattcacctc-3' (SEQ ID NO:5), p15 5'-caccatgaagcgaaacacag-3' (SEQ ID NO: 6) and 5'-tccatcggaagattcgtagc-3' (SEQ ID NO: 7), GAPDH 5'-attgccctcaacgaccactt-3' (SEQ ID NO:8) and 5'-ggtccaccac-cctgttgc-3' (SEQ ID NO:9), and B-actin 5'-ctggaacggtgaag-gtgaca-3' (SEQ ID NO: 10) and 5'-aagggacttcctgtaacaacgca-3' (SEQ ID NO:11). Samples were analyzed on the iQ5 Multicolor Real-Time PCR Detection System from Bio-Rad. Data analysis was performed using the iQ5 Optical System Software version 2.0, Threshold Cycle (CT) and CT mean values were determined from this software. For each sample there are at least four reactions, two for p16 and two for GAPDH the housekeeping control. The mean CT value from the GAPDH reactions was subtracted from each of the corresponding p16 samples CT giving a value termed Delta CT. Then the Delta CT for the untreated p16 sample is subtracted from all treated Delta CT values giving another value termed Delta Delta CT. The Relative Expression value equals two to the power of the negative Delta Delta CT value (=2^−Delta Delta CT). The duplicate samples are averaged together to get an average Relative Expression for each treatment and the Standard Error is calculated. Relative expression values for p15 and MLH-1 were calculated using the same method.

As seen in FIG. 1, Cpd. AAA, Cpd. BBB, and Cpd. CCC were able to increase the RNA expression levels of p16. Cpd. AAA at the concentration of 0.11 M caused the greatest re-expression of p16 over no treatment. Because the higher levels of p16 seemed to have less effect in causing re-expression of p16 there may be some issues with drug solubility or toxicity at the higher concentrations tested.

Cell-Based Growth Assays

Cell culture-based assays can be used to evaluate the ability of compounds of the invention to inhibit one or more cellular activities, such as cancer cell growth and/or survival. Numerous cancer cell lines can be obtained from the American Type Culture Collection (ATCC) and other sources. Briefly, cells are seeded into 96-well, tissue-culture treated, opaque white plates (Thermo Electron, Vantaa, Finland), at between 5000 and 10000 cells per well, depending on the speed of cell proliferation, in 100 μl of appropriate growth medium (determined by the ATCC). Cells are then exposed to the appropriate concentration of drug or an equal amount of DMSO (drug diluent) and allowed to grow in its presence for 96 hours. Following this, 100 μl of Cell-Titer-Glo (CTG) reagent (Promega, Inc., Madison, Wis.) is added to each well. Plates are then shaken for 2 minutes at room temperature to allow for cell lysis and incubated for 10 minutes at room temperature to stabilize the luminescent signal. Similar to the Kinase-Glo assay reagent from Promega, this reagent contains both luciferase enzyme and its substrate luciferin. Luciferase, activated by ATP in the cell lysate, catalyzes the conversion of luciferin to oxyluciferin, a reaction which produces light. The amount of light produced is proportionate to the amount of ATP in the cell lysate, which is itself proportional to cell number and gives an index of cellular proliferation. $IC_{50}$ values for representative compounds are set forth in Table 4 below.

TABLE 4

| | $IC_{50}$ Values CTG | | |
| --- | --- | --- | --- |
| Cell line | Cpd. AAA. Cl | Cpd. BBB. Cl | Cpd. CCC. Cl |
| HCT-116 | 6.15 μM | 0.67 μM | ND |
| RKO | 1.22 μM | 0.74 μM | 6.60 μM |
| Panc-1 | 1.80 μM | 1.00 μM | ND |

DNMT1 Inhibition Assay

The DNMT1 Activity/Inhibition kit from Epigentek Inc. (Brooklyn, N.Y.) was used in this experiment (Catalog No. P-3006). In general terms, this assay utilizes an active DNMT1 enzyme incubated with S-adenosylmethionine (SAM) in 96-well plates upon which unmethylated DNA has been immobilized onto the surface of each well. After incubation the reaction wells are washed and probed with a primary anti-methylcytosine antibody, which will bind to methylated DNA. A secondary antibody is then used to detect the primary antibody and creates a signal that is proportional to the amount of methylated DNA in the well. Uninhibited DNMT1 produces a well with high levels of methylated DNA (high signal), whereas inhibited DNMT1 produces a well with low levels of methylation (low signal). The final concentrations of reagents used in this DNMT1 assay were as follows: 100 μM SAM and 2.2 μg/ml DNMT1 enzyme, with inhibitor concentrations typically ranging from 100 μM to 0.781 μM.

More specifically, test compounds were resuspended in 100% DMSO at 3 mM and serially diluted 1:2 in DMSO 8 times. A volume of 100 μl of 1× assay buffer was combined with 12 μl of 1 mM SAM solution and 4 μl of 66.7 μg/mL DNMT1 enzyme in the presence of 4 μl of test compound diluted in DMSO. Controls include enzyme only (no inhibitor, but containing 3.3% DMSO), no enzyme, and compounds having inhibitory activity. A volume of 30 μl of the mixed solution was then added to the substrate-coated wells in triplicate and incubated at 37° C. for 2 hours. Reaction wells are then washed 3× with 150 μl of DNMT wash buffer. The primary antibody (anti-methylcytosine) was diluted 1:1000 in wash buffer, added to each well (50 μl) and incubated at room temperature for 1 hour. Reaction wells were washed again. The secondary antibody was diluted 1:1000 in wash buffer, added to each well (50 μl) and incubated at room temperature for 30 min. The wells were washed for the last time. The developing solution was added to each well (100 μl) and incubated at room temperature for 4 minutes. The stop solution was added (50 μl) and the plate was immediately read on a plate reader at 450 nm absorbance. Compounds DDD, EEE and GGG were tested by this assay and gave values of 1.6 μM, 5.5 μM and 0.31 μM, respectively.

While this invention has been described with reference to certain embodiments and examples, it is to be appreciated that further modifications and variations can be made to embodiments and examples without departing from the spirit or scope of the invention.

What is claimed is:

1. A compound selected from the group consisting of 4-(4-(4-(quinolin-4-ylamino)benzamido)phenylthio)pyrrolidine-2-carboxylic acid; 3-(4-(4-(quinolin-4-ylamino)benzamido)phenylthio)pyrrolidine; N-(4-(piperidin-4-ylthio)phenyl)-4-(quinolin-4-ylamino)-benzamide; and N-(4-(piperidin-3-ylthio)phenyl)-4-(quinolin-4-ylamino)-benzamide, or a pharmaceutically acceptable salt thereof.

2. The compound of claim 1, wherein the compound is 4-(4-(4-(quinolin-4-ylamino)benzamido)phenylthio)pyrrolidine-2-carboxylic acid, or a pharmaceutically acceptable salt thereof.

3. The compound of claim 1, wherein the compound is 3-(4-(4-(quinolin-4-ylamino)benzamido)phenylthio)pyrrolidine, or a pharmaceutically acceptable salt thereof.

4. The compound of claim 1, wherein the compound is N-(4-(piperidin-4-ylthio)phenyl)-4-(quinolin-4-ylamino)-benzamide, or a pharmaceutically acceptable salt thereof.

5. The compound of claim 1, wherein the compound is N-(4-(piperidin-3-ylthio)phenyl)-4-(quinolin-4-ylamino)-benzamide, or a pharmaceutically acceptable salt thereof.

6. The compound of claim 1, wherein the pharmaceutically acceptable salt is formed with an acid selected from the group consisting of hydrochloric acid, hydrobromic acid, sulfuric acid, phosphoric acid, acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, glutamic acid, aspartic acid, phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglyceric acid, glucose-6-phosphoric acid, N cyclohexylsulfamic acid, and ascorbic acid.

7. The compound of claim 1, wherein the pharmaceutically acceptable salt is a sodium, calcium, lithium, potassium, ammonium, or trialkylammonium salt.

8. A pharmaceutical composition comprising a compound of claim 1, or a pharmaceutically acceptable salt thereof, and a pharmaceutically acceptable carrier.

9. The pharmaceutical composition of claim 8, wherein the pharmaceutical composition is in a solid form.

10. The pharmaceutical composition of claim 8, wherein the pharmaceutical composition is in an oral dosage form.

11. The pharmaceutical composition of claim 8, wherein the pharmaceutical composition is in an injectable dosage form.

12. The pharmaceutical composition of claim 8, wherein the pharmaceutical composition is in a topical dosage form.

13. A method for inhibiting DNA methylation in a cell, comprising contacting the cell with a compound of claim 1, or a pharmaceutically acceptable salt thereof, such that DNA methylation activity of the cell is inhibited.

14. A method for inhibiting DNA methylation in a cell, comprising contacting the cell with a compound of claim 1, or a pharmaceutically acceptable salt thereof, such that DNA methytransferase activity in the cell is inhibited.

15. The method of claim 14, wherein DNA methyltransferase activity is inhibited via degradation of DNA methyltransferase DNMT1.

16. The method of claim 14, wherein the step of contacting the cell includes contacting the cell with a biologically effective amount of a compound of claim 1, or a pharmaceutically acceptable salt thereof, such that at least 50% of the activity of DNA methyltransferase DNMT1 in the cell is inhibited.

17. The method of claim 14, wherein the step of contacting the cell includes contacting the cell with a biologically effective amount of a compound of claim 1, or a pharmaceutically acceptable salt thereof, such that at least 25% of the activity of DNA methyltransferase DNMT1 in the cell is inhibited.

* * * * *

SEQUENCE LISTING

```
<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Inhibitor of non-receptor tyrosine
      kinase from the Syk/ZAP-70 family.

<400> SEQUENCE: 1

Lys Leu Ile Leu Phe Leu Leu Leu
 1               5

<210> SEQ ID NO 2
<211> LENGTH: 20
<212> TYPE: DNA
<213> ORGANISM: Artificial Sequence
<220> FEATURE:
<223> OTHER INFORMATION: PCR primer sequence

<400> SEQUENCE: 2
atgtcctgcc ttttaacgta                                               20

<210> SEQ ID NO 3
```

```
<211> LENGTH: 20
<212> TYPE: DNA
<213> ORGANISM: Artificial Sequence
<220> FEATURE:
<223> OTHER INFORMATION: PCR primer sequence

<400> SEQUENCE: 3
gtgctcactc cagaaaactc                                                    20

<210> SEQ ID NO 4
<211> LENGTH: 20
<212> TYPE: DNA
<213> ORGANISM: Artificial Sequence
<220> FEATURE:
<223> OTHER INFORMATION: PCR primer sequence

<400> SEQUENCE: 4
tgaggaaggg aacctgattg                                                    20

<210> SEQ ID NO 5
<211> LENGTH: 20
<212> TYPE: DNA
<213> ORGANISM: Artificial Sequence
<220> FEATURE:
<223> OTHER INFORMATION: PCR primer sequence

<400> SEQUENCE: 5
tcttcgtccc aattcacctc                                                    20

<210> SEQ ID NO 6
<211> LENGTH: 20
<212> TYPE: DNA
<213> ORGANISM: Artificial Sequence
<220> FEATURE:
<223> OTHER INFORMATION: PCR primer sequence

<400> SEQUENCE: 6
caccatgaag cgaaacacag                                                    20

<210> SEQ ID NO 7
<211> LENGTH: 20
<212> TYPE: DNA
<213> ORGANISM: Artificial Sequence
<220> FEATURE:
<223> OTHER INFORMATION: PCR primer sequence

<400> SEQUENCE: 7
tccatcggaa gattcgtagc                                                    20

<210> SEQ ID NO 8
<211> LENGTH: 20
<212> TYPE: DNA
<213> ORGANISM: Artificial Sequence
<220> FEATURE:
<223> OTHER INFORMATION: PCR primer sequence

<400> SEQUENCE: 8
attgccctca acgaccactt                                                    20

<210> SEQ ID NO 9
<211> LENGTH: 18
<212> TYPE: DNA
<213> ORGANISM: Artificial Sequence
<220> FEATURE:
<223> OTHER INFORMATION: PCR primer sequence

<400> SEQUENCE: 9
```

-continued

```
ggtccaccac cctgttgc                                                    18

<210> SEQ ID NO 10
<211> LENGTH: 20
<212> TYPE: DNA
<213> ORGANISM: Artificial Sequence
<220> FEATURE:
<223> OTHER INFORMATION: PCR primer sequence

<400> SEQUENCE: 10
ctggaacggt gaaggtgaca                                                  20

<210> SEQ ID NO 11
<211> LENGTH: 23
<212> TYPE: DNA
<213> ORGANISM: Artificial Sequence
<220> FEATURE:
<223> OTHER INFORMATION: PCR primer sequence

<400> SEQUENCE: 11
aagggacttc ctgtaacaac gca                                              23
```